(12) United States Patent
Gao et al.

(10) Patent No.: US 11,851,657 B2
(45) Date of Patent: *Dec. 26, 2023

(54) ANTI-ANGIOGENIC MIRNA THERAPEUTICS FOR INHIBITING CORNEAL NEOVASCULARIZATION

(71) Applicant: University of Massachusetts, Boston, MA (US)

(72) Inventors: Guangping Gao, Westborough, MA (US); Yi Lu, Shanghai (CN); Qiang Zheng, Chengdu (CN); Xun Xu, Shanghai (CN); Phillip D. Zamore, Northborough, MA (US); Phillip Tai, Worcester, MA (US)

(73) Assignee: University of Massachusetts, Boston, MA (US)

( * ) Notice: Subject to any disclaimer, the term of this patent is extended or adjusted under 35 U.S.C. 154(b) by 134 days.

This patent is subject to a terminal disclaimer.

(21) Appl. No.: 17/342,587

(22) Filed: Jun. 9, 2021

(65) Prior Publication Data

US 2021/0380981 A1 Dec. 9, 2021

Related U.S. Application Data

(63) Continuation of application No. 16/076,881, filed as application No. PCT/US2017/017469 on Feb. 10, 2017, now Pat. No. 11,060,088.

(60) Provisional application No. 62/294,362, filed on Feb. 12, 2016.

(51) Int. Cl.

| | | |
|---|---|---|
| *C07H 21/04* | (2006.01) | |
| *C12N 15/113* | (2010.01) | |
| *C12N 15/86* | (2006.01) | |
| *C12N 15/11* | (2006.01) | |
| *A61P 27/02* | (2006.01) | |
| *A61K 9/00* | (2006.01) | |
| *A61K 48/00* | (2006.01) | |

(52) U.S. Cl.
CPC .......... *C12N 15/113* (2013.01); *A61K 9/0019* (2013.01); *A61K 9/0048* (2013.01); *A61P 27/02* (2018.01); *C12N 15/111* (2013.01); *C12N 15/86* (2013.01); *A61K 48/00* (2013.01); *C12N 2310/113* (2013.01); *C12N 2310/141* (2013.01); *C12N 2320/32* (2013.01); *C12N 2330/51* (2013.01); *C12N 2750/14122* (2013.01); *C12N 2750/14143* (2013.01)

(58) Field of Classification Search
None
See application file for complete search history.

(56) References Cited

U.S. PATENT DOCUMENTS

| | | |
|---|---|---|
| 5,478,745 A | 12/1995 | Samulski et al. |
| 5,871,982 A | 2/1999 | Wilson et al. |
| 6,177,403 B1 | 1/2001 | Stedman |
| 6,251,677 B1 | 6/2001 | Wilson et al. |
| 6,485,966 B2 | 11/2002 | Gao et al. |
| 6,544,786 B1 | 4/2003 | Xiao et al. |
| 6,953,690 B1 | 10/2005 | Gao et al. |
| 7,022,519 B2 | 4/2006 | Gao et al. |
| 7,198,951 B2 | 4/2007 | Gao et al. |
| 7,235,393 B2 | 6/2007 | Gao et al. |
| 7,427,396 B2 | 9/2008 | Arbetman et al. |
| 7,456,015 B2 | 11/2008 | Bohn et al. |
| 7,906,111 B2 | 3/2011 | Wilson et al. |
| 8,222,221 B2 | 7/2012 | Corey et al. |
| 8,524,446 B2 | 9/2013 | Gao et al. |
| 8,734,809 B2 | 5/2014 | Gao et al. |
| 9,217,155 B2 | 12/2015 | Gao et al. |
| 9,249,424 B2 | 2/2016 | Wolf et al. |
| 11,060,088 B2 | 7/2021 | Gao et al. |
| 2001/0016355 A1 | 8/2001 | Samulski et al. |
| 2002/0164783 A1 | 11/2002 | Feldhaus |
| 2002/0173025 A1 | 11/2002 | Lazarus et al. |
| 2002/0192823 A1 | 12/2002 | Bartlett |
| 2003/0103939 A1 | 6/2003 | Engelhardt et al. |
| 2003/0110526 A1 | 6/2003 | Brown et al. |
| 2003/0138772 A1 | 7/2003 | Gao et al. |
| 2004/0101514 A1 | 5/2004 | Liu et al. |
| 2004/0219528 A1 | 11/2004 | Morris et al. |
| 2005/0032219 A1 | 2/2005 | Aubourg et al. |
| 2005/0037988 A1 | 2/2005 | Zamore et al. |
| 2005/0137153 A1 | 6/2005 | McSwiggen et al. |
| 2005/0197313 A1 | 9/2005 | Roelvink et al. |
| 2005/0255086 A1 | 11/2005 | Davidson et al. |
| 2005/0255089 A1 | 11/2005 | Chiorini et al. |

(Continued)

FOREIGN PATENT DOCUMENTS

| | | |
|---|---|---|
| EP | 2261242 A1 | 12/2010 |
| EP | 2468891 A2 | 6/2012 |

(Continued)

OTHER PUBLICATIONS

Mao et al. (Human Gene Therapy 22: 1525-1535 (Dec. 2011)).*

(Continued)

*Primary Examiner* — Kimberly Chong

(74) *Attorney, Agent, or Firm* — Wolf, Greenfield & Sacks, P.C.

(57) ABSTRACT

The disclosure relates, in some aspects, to compositions and methods for treating corneal disease (e.g., corneal neovascularization. In some embodiments, the disclosure relates to rAAV-mediated delivery of an cornea-associated transgene to a subject. In some embodiments, the rAAV transduces the corneal tissue of a subject.

4 Claims, 55 Drawing Sheets

Specification includes a Sequence Listing.

(56) References Cited

U.S. PATENT DOCUMENTS

| | | |
|---|---|---|
| 2005/0287122 A1 | 12/2005 | Bartlett et al. |
| 2006/0063174 A1 | 3/2006 | Turner et al. |
| 2006/0093589 A1 | 5/2006 | Warrington et al. |
| 2006/0153826 A1 | 7/2006 | Arnould et al. |
| 2006/0189564 A1 | 8/2006 | Burright et al. |
| 2006/0228800 A1 | 10/2006 | Lin et al. |
| 2006/0292117 A1 | 12/2006 | Loiler et al. |
| 2007/0036760 A1 | 2/2007 | Wilson et al. |
| 2007/0243526 A1 | 10/2007 | Kay et al. |
| 2007/0292410 A1 | 12/2007 | Cashman et al. |
| 2008/0199509 A1 | 8/2008 | Nick et al. |
| 2009/0042828 A1 | 2/2009 | Xu et al. |
| 2009/0111766 A1 | 4/2009 | Atkinson et al. |
| 2009/0149409 A1 | 6/2009 | Bohn et al. |
| 2009/0239240 A1 | 9/2009 | Chu |
| 2010/0186103 A1 | 7/2010 | Gao et al. |
| 2010/0227909 A1 | 9/2010 | Cleary et al. |
| 2010/0323001 A1 | 12/2010 | Pachuk |
| 2011/0171262 A1 | 7/2011 | Bakker et al. |
| 2011/0172293 A1 | 7/2011 | Fish et al. |
| 2011/0212520 A1 | 9/2011 | Davidson et al. |
| 2011/0258716 A1 | 10/2011 | Baltimore et al. |
| 2012/0077870 A1 | 3/2012 | Blanks et al. |
| 2012/0137379 A1 | 5/2012 | Gao et al. |
| 2012/0164106 A1 | 6/2012 | Schaffer et al. |
| 2012/0270930 A1 | 10/2012 | Van Der Maarel et al. |
| 2012/0309050 A1 | 12/2012 | Kumon et al. |
| 2013/0101558 A1 | 4/2013 | Gao et al. |
| 2013/0109742 A1 | 5/2013 | Hewitt et al. |
| 2013/0142861 A1 | 6/2013 | Tsou et al. |
| 2013/0195801 A1 | 8/2013 | Gao et al. |
| 2013/0281516 A1 | 10/2013 | Gao et al. |
| 2013/0323226 A1 | 12/2013 | Wilson et al. |
| 2014/0142161 A1 | 5/2014 | Flotte et al. |
| 2014/0142288 A1 | 5/2014 | Davidson et al. |
| 2014/0179770 A1 | 6/2014 | Zhang et al. |
| 2014/0201857 A1 | 7/2014 | Fahrenkrug et al. |
| 2014/0335054 A1 | 11/2014 | Gao et al. |
| 2015/0065560 A1 | 3/2015 | Bjorklund et al. |
| 2015/0258180 A1 | 9/2015 | Mahuran et al. |
| 2016/0017005 A1 | 1/2016 | Asokan et al. |
| 2016/0060624 A1 | 3/2016 | Davidson et al. |
| 2016/0076054 A1 | 3/2016 | Auricchio et al. |
| 2016/0153005 A1 | 6/2016 | Zhang et al. |
| 2016/0185832 A1 | 6/2016 | Drivas et al. |
| 2016/0194374 A1 | 7/2016 | Wijnholds et al. |
| 2016/0272976 A1 | 9/2016 | Kaspar |
| 2017/0029785 A1 | 2/2017 | Zhao et al. |
| 2017/0114340 A1 | 4/2017 | Mueller et al. |
| 2017/0165377 A1 | 6/2017 | Gao et al. |

FOREIGN PATENT DOCUMENTS

| | | |
|---|---|---|
| WO | WO 1993/025670 A1 | 12/1993 |
| WO | WO 2003/042397 A2 | 5/2003 |
| WO | WO 2004/108922 A2 | 12/2004 |
| WO | WO 2005/033321 | 4/2005 |
| WO | WO 2006/031267 A2 | 3/2006 |
| WO | WO 2006/066066 A2 | 6/2006 |
| WO | WO 2006/119432 A2 | 11/2006 |
| WO | WO 2007/000668 A2 | 1/2007 |
| WO | WO 2007/027775 A2 | 3/2007 |
| WO | WO 2007/127264 A2 | 11/2007 |
| WO | WO 2008/091703 A2 | 7/2008 |
| WO | WO 2008/125846 A2 | 10/2008 |
| WO | WO 2008/147839 A1 | 12/2008 |
| WO | WO 2008/150897 A2 | 12/2008 |
| WO | WO 2009/043936 A1 | 4/2009 |
| WO | WO 2009/109665 A1 | 9/2009 |
| WO | WO 2009/137807 A2 | 11/2009 |
| WO | WO 2009/146178 A1 | 12/2009 |
| WO | WO 2010/027446 A2 | 3/2010 |
| WO | WO 2010/034314 A1 | 4/2010 |
| WO | WO 2010/071454 A1 | 6/2010 |
| WO | WO 2010/099383 A2 | 9/2010 |
| WO | WO 2010/129021 A1 | 11/2010 |
| WO | WO 2010/138263 A2 | 12/2010 |
| WO | WO 2011/094198 A1 | 8/2011 |
| WO | WO 2011/133890 A1 | 10/2011 |
| WO | WO 2012/123430 A1 | 9/2012 |
| WO | WO 2013/055865 A1 | 4/2013 |
| WO | WO 2013/123503 A1 | 8/2013 |
| WO | WO 2013/170078 A1 | 11/2013 |
| WO | WO 2013/190059 A1 | 12/2013 |
| WO | WO 2014/140051 A1 | 9/2014 |
| WO | WO 2014/160092 A1 | 10/2014 |
| WO | WO 2014/186746 A1 | 11/2014 |
| WO | WO 2014/197748 A2 | 12/2014 |
| WO | WO 2015/121501 A1 | 8/2015 |
| WO | WO 2015/138426 A1 | 9/2015 |
| WO | WO 2015/164786 A1 | 10/2015 |
| WO | WO 2015/168666 A2 | 11/2015 |
| WO | WO 2016/065001 A1 | 4/2016 |
| WO | WO 2017/023724 A1 | 2/2017 |

OTHER PUBLICATIONS

Extended European Search Report for Application No. 22162624.5, dated Jan. 11, 2023.
Park et al., microRNA-184 regulates angiogenic factors to maintain corneal avascularity. ARVO Annual Meeting Abstract. Investigative Ophthalmology & Visual Science. Jun. 2015;56(7): 4495.
Takahashi et al., Functional Role of MicroRNA-184 In Diabetic Retinopathy. ARVO Annual Meeting Abstract. Investigative Ophthalmology & Visual Science. Jun. 2015; 56(7): 5169.
Takahashi et al., MicroRNA-184 modulates canonical Wnt signaling through the regulation of frizzled-7 expression in the retina with ischemia-induced neovascularization. FEBS Lett. Apr. 28, 2015;589(10):1143-1149. doi: 10.1016/j.febslet.2015.03.010. Epub Mar. 18, 2015.
Zong et al., Down-Regulation of MicroRNA-184 Is Associated With Corneal Neovascularization. Invest Ophthalmol Vis Sci. Mar. 2016;57(3):1398-407. doi: 10.1167/iovs.15-17417.
Partial Supplementary European Search Report for Application No. EP 17750871.0, dated Jul. 18, 2019.
Extended European Search Report for Application No. EP 17750871.0, dated Oct. 22, 2019.
International Search Report and Written Opinion for Application No. PCT/US2017/01746, dated Jun. 15, 2017.
International Preliminary Report on Patentability for Application No. PCT/US2017/017469, dated Aug. 23, 2018.
Aartsma-Rus et al., New insights in gene-derived therapy: the example of Duchenne muscular dystrophy. Ann N Y Acad Sci. Dec. 2010;1214:199-212. doi: 10.1111/j.1749-6632.2010.05836.x. Epub Dec. 1, 2010.
Adachi et al., Drawing a high-resolution functional map of adeno-associated virus capsid by massively parallel sequencing. Nat Commun. 2014;5:3075. doi: 10.1038/ncomms4075.
Afione et al., In vivo model of adeno-associated virus vector persistence and rescue. J Virol. May 1996;70(5):3235-41.
Ahmed et al., A Single Intravenous rAAV Injection as Late as P20 Achieves Efficacious and Sustained CNS Gene Therapy in Canavan Mice. Mol Ther. Jul. 2, 2013. doi: 10.1038/mt.2013.138. [Epub ahead of print].
Akache et al., The 37/67-kilodalton laminin receptor is a receptor for adeno-associated virus serotypes 8, 2, 3, and 9. J Virol. Oct. 2006;80(19):9831-6.
Alisky et al., Gene therapy for amyotrophic lateral sclerosis and other motor neuron diseases. Hum Gene Ther. Nov. 20, 2000;11(17):2315-29.
Arbetman et al., Novel caprine adeno-associated virus (AAV) capsid (AAV-Go.1) is closely related to the primate AAV-5 and has unique tropism and neutralization properties. J Virol. Dec. 2005;79(24):15238-45.
Arbuthnot et al., Hepatic delivery of RNA interference activators for therapeutic application. Curr Gene Ther. Apr. 2009;9(2):91-103.
Askou, Development of gene therapy for treatment of age-related macular degeneration. Acta Ophthalmol. 2014;92 Thesis3:1-38. doi:10.1111/aos.12452.

(56) References Cited

OTHER PUBLICATIONS

Asokan et al., The AAV vector toolkit: poised at the clinical crossroads. Mol Ther. Apr. 2012;20(4):699-708. doi: 10.1038/mt.2011.287. Epub Jan. 24, 2012.
Azzouz et al., VEGF delivery with retrogradely transported lentivector prolongs survival in a mouse ALS model. Nature. May 27, 2004;429(6990):413-7.
Baek et al., AAV-mediated gene delivery in adult GM1-gangliosidosis mice corrects lysosomal storage in CNS and improves survival. PLoS One. Oct. 18, 2010;5(10):e13468. doi: 10.1371/journal.pone.0013468.
Berns et al., Biology of adeno-associated virus. Curr Top Microbiol Immunol. 1996;218:1-23.
Beutler et al., AAV for pain: steps towards clinical translation. Gene Ther. Apr. 2009;16(4):461-9. Epub Mar. 5, 2009.
Boillée et al., Onset and progression in inherited ALS determined by motor neurons and microglia. Science. Jun. 2, 2006;312(5778):1389-92.
Bourdenx et al., Systemic gene delivery to the central nervous system using Adeno-associated virus. Front Mol Neurosci. Jun. 2, 2014;7:50. doi: 10.3389/fnmol.2014.00050. eCollection 2014.
Brantly et al., Phase I trial of intramuscular injection of a recombinant adeno-associated virus serotype 2 alpha1-antitrypsin (AAT) vector in AAT-deficient adults. Hum Gene Ther. Dec. 2006;17(12):1177-86.
Brown et al., A microRNA-regulated lentiviral vector mediates stable correction of hemophilia B mice. Blood. Dec. 15, 2007;110(13):4144-52. Epub Aug. 28, 2007.
Brown et al., Endogenous microRNA can be broadly exploited to regulate transgene expression according to tissue, lineage and differentiation state. Nat Biotechnol. Dec. 2007;25(12):1457-67. Epub Nov. 16, 2007.
Brown et al., Endogenous microRNA regulation suppresses transgene expression in hematopoietic lineages and enables stable gene transfer. Nat Med. May 2006;12(5):585-91. Epub Apr. 23, 2006.
Buning et al., Receptor targeting of adeno-associated virus vectors. Gene Ther. Jul. 2003;10(14):1142-51.
Bussing et al., let-7 microRNAs in development, stem cells and cancer. Trends Mol Med. Sep. 2008;14(9):400-9. doi: 10.1016/j.molmed.2008.07.001. Epub Jul. 31, 2008.
Calcedo et al., Worldwide epidemiology of neutralizing antibodies to adeno-associated viruses. J Infect Dis. Feb. 1, 2009;199(3):381-90.
Carter et al., Adeno-associated virus gene expression and regulation. CRC Handbook of parvoviruses. 1990;227-54.
Carter, in "Handbook of Parvoviruses", ed., P. Tijsser, CRC Press, pp. 155-168 (1990).
Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.
Chadderton et al., Improved retinal function in a mouse model of dominant retinitis pigmentosa following AAV-delivered gene therapy. Mol Ther. Apr. 2009;17(4):593-9. Epub Jan. 27, 2009.
Chang et al., miR-122, a mammalian liver-specific microRNA, is processed from her mRNA and may downregulate the high affinity cationic amino acid transporter CAT-1. RNA Biol. Jul. 2004;1(2):106-13. Epub Jul. 1, 2004.
Chen et al., Efficient transduction of vascular endothelial cells with recombinant adeno-associated virus serotype 1 and 5 vectors. Hum Gene Ther. Feb. 2005;16(2):235-47.
Chen et al., Molecular signatures of disease brain endothelia provide new sites for CNS-directed enzyme therapy. Nat Med. Oct. 2009;15(10):1215-8. doi: 10.1038/nm.2025. Epub Sep. 13, 2009.
Chen et al., Regulation of immune responses and tolerance: the microRNA perspective. Immunol Rev. May 2013;253(1):112-28. doi:10.1111/imr.12060.
Cheng et al., Development of optimized AAV3 serotype vectors: mechanism of high-efficiency transduction of human liver cancer cells. Gene Ther. Apr. 2012;19(4):375-84. doi: 10.1038/gt.2011.105. Epub Jul. 21, 2011.

Chiorini et al., Cloning and characterization of adeno-associated virus type 5. J Virol. Feb. 1999;73(2):1309-19.
Choudhury et al., Identification of Novel vectors capable of CNS transduction in adult mice after single round selection using DNA shuffled AAV capsid library. Mol Ther. May 1, 2013;21(1):S1.
Christensen et al., A let-7 microRNA-binding site polymorphism in the KRAS 3' UTR is associated with reduced survival in oral cancers. Carcinogenesis. Jun. 2009;30(6):1003-7. doi: 10.1093/carcin/bgp099. Epub Apr. 20, 2009.
Conlon et al., Efficient hepatic delivery and expression from a recombinant adeno-associated virus 8 pseudotyped alpha1-antitrypsin vector. Mol Ther. Nov. 2005;12(5):867-75. Epub Aug. 8, 2005.
Conlon et al., Ribozyme Approaches towards Down-Regulation of Pi*Z Mutant Human a-1 Anti-Trypsin. Mol. Therapy. 2004;9:S333. Abstract 875.
Conrad et al., Safety of single-dose administration of an adeno-associated virus (AAV)-CFTR vector in the primate lung. Gene Ther. Aug. 1996;3(8):658-68.
Coulouarn et al., Loss of miR-122 expression in liver cancer correlates with suppression of the hepatic phenotype and gain of metastatic properties. Oncogene. Oct. 8, 2009;28(40):3526-36. doi: 10.1038/onc.2009.211. Epub Jul. 20, 2009.
Cruz et al., In vivo post-transcriptional gene silencing of alpha-1 antitrypsin by adeno-associated virus vectors expressing siRNA. Lab Invest. Sep. 2007;87(9):893-902. Epub Jun. 25, 2007.
Cruz et al., The promise of gene therapy for the treatment of alpha-1 antitrypsin deficiency. Pharmacogenomics. Sep. 2007;8(9):1191-8.
Csak et al., microRNA-122 regulates hypoxia-inducible factor-1 and vimentin in hepatocytes and correlates with fibrosis in diet-induced steatohepatitis. Liver Int. Feb. 2015;35(2):532-41. doi: 10.1111/liv.12633. Epub Jul. 28, 2014.
Czech, MicroRNAs as therapeutic targets. N Engl J Med. Mar. 16, 2006;354(11):1194-5.
Davidoff et al., Sex significantly influences transduction of murine liver by recombinant adeno-associated viral vectors through an androgen-dependent pathway. Blood. Jul. 15, 2003;102(2):480-8. Epub Mar. 13, 2003.
Daya et al., Gene therapy using adeno-associated virus vectors. Clin Microbiol Rev. Oct. 2008;21(4):583-93. doi: 10.1128/CMR.00008-08.
Di Giorgio et al., Non-cell autonomous effect of glia on motor neurons in an embryonic stem cell-based ALS model. Nat Neurosci. May 2007;10(5):608-14. Epub Apr. 15, 2007.
Duque et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.
Eberling et al., Results from a phase I safety trial of hAADC gene therapy for Parkinson disease. Neurology. May 20, 2008;70(21):1980-3. doi: 10.1212/01.wnl.0000312381.29287.ff. Epub Apr. 9, 2008.
Ebert et al., MicroRNA sponges: competitive inhibitors of small RNAs in mammalian cells. Nat Methods. Sep. 2007;4(9):721-6. Epub Aug. 12, 2007.
Elmén et al., Antagonism of microRNA-122 in mice by systemically administered LNA-antimiR leads to up-regulation of a large set of predicted target mRNAs in the liver. Nucleic Acids Res. Mar. 2008;36(4):1153-62. Epub Dec. 23, 2007.
Elmén et al., LNA-mediated microRNA silencing in non-human primates. Nature. Apr. 2008;452(17): 896-900.
Esau et al., miR-122 regulation of lipid metabolism revealed by in vivo antisense targeting. Cell Metab. Feb. 2006;3(2):87-98.
Fabani et al., miR-122 targeting with LNA/2'-O-methyl oligonucleotide mixmers, peptide nucleic acids (PNA), and PNA-peptide conjugates. RNA. Feb. 2008;14(2):336-46. Epub Dec. 11, 2007.
Fechner et al., Cardiac-targeted RNA interference mediated by an AAV9 vector improves cardiac function in coxsackievirus B3 cardiomyopathy. J Mol Med (Berl). Sep. 2008;86(9):987-97. doi: 10.1007/s00109-008-0363-x. Epub Jun. 12, 2008.
Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.

(56) References Cited

OTHER PUBLICATIONS

Fischer et al., Successful transgene expression with serial doses of aerosolized rAAV2 vectors in rhesus macaques. Mol Ther. Dec. 2003;8(6):918-26.
Fisher et al., Transduction with recombinant adeno-associated virus for gene therapy is limited by leading-strand synthesis. J Virol. Jan. 1996;70(1):520-32.
Flotte et al., Gene therapy for alpha-1 antitrypsin deficiency. Hum Mol Genet. Apr. 15, 2011;20(R1):R87-92. doi: 10.1093/hmg/ddr156. Epub Apr. 16, 2011.
Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.
Flotte, Recombinant adeno-associated virus (AAV) gene therapy vectors for, cystic fibrosis (CF), alpha-1-antitrypsin deficiency (AAT) and fatty oxidation disorders (FAO). Umass Medical School. Interdisciplinary Graduate Program. Last accessed at http://www.umassmed.edu/igp/faculty/flotte.cfm?start=0& on Aug. 27, 2009.
Forman et al., A search for conserved sequences in coding regions reveals that the let-7 microRNA targets Dicer within its coding sequence. Proc Natl Acad Sci U S A. Sep. 30, 2008;105(39):14879-84. doi: 10.1073/pnas.0803230105. Epub Sep. 23, 2008.
Foust et al., Intravascular AAV9 preferentially targets neonatal-neurons and adult-astrocytes. Nature Biotechnology, 27; 59-65 2009.
Foust et al., Over the barrier and through the blood: to CNS delivery we go. Cell Cycle. Dec. 15, 2009;8(24):4017-8.
Fraldi et al., Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.
Gadalla et al., Improved survival and reduced phenotypic severity following AAV9/MECP2 gene transfer to neonatal and juvenile male Mecp2 knockout mice. Mol Ther. Jan. 2013;21(1):18-30. doi:10.1038/mt.2012.200. Epub Sep. 25, 2012.
Gao et al., Erythropoietin gene therapy leads to autoimmune anemia in macaques. Blood. May 1, 2004;103(9):3300-2. Epub Dec. 24, 2003.
Gao et al., Inadvertent gene transfer of co-packaged rep and cap sequences during the production of AAV vector and its potential impact on vector performance. Molecular Therapy. May 2008;16(Suppl. 1):S105-S106. Abstract 279.
Gao et al., Novel adeno-associated viruses from rhesus monkeys as vectors for human gene therapy. Proc Natl Acad Sci U S A. Sep. 3, 2002;99(18):11854-9. Epub Aug. 21, 2002.
Gao et al., RAAV-mediated targeting in adult mice and its potential in generating animal models of tissue-specific somatic transgenics or knock down. Molecular Therapy. May 2008;16(1):S118-S119. Abstract 316.
Gentner et al., Stable knockdown of microRNA in vivo by lentiviral vectors. Nat Methods. Jan. 2009;6(1):63-6. doi: 10.1038/nmeth.1277. Epub Nov. 30, 2008.
Girard et al., miR-122, a paradigm for the role of microRNAs in the liver. J Hepatol. Apr. 2008;48(4):648-56. doi: 10.1016/j.jhep.2008.01.019. Epub Feb. 12, 2008.
Gramantieri et al., Cyclin G1 is a target of miR-122a, a microRNA frequently down-regulated in human hepatocellular carcinoma. Cancer Res. Jul. 1, 2007;67(13):6092-9.
Grimm et al., Fatality in mice due to oversaturation of cellular microRNA/short hairpin RNA pathways. Nature. May 25, 2006;441(7092):537-41.
Grimm, Small silencing RNAs: state-of-the-art. Adv Drug Deliv Rev. Jul. 25, 2009;61(9):672-703. doi: 10.1016/j.addr.2009.05.002. Epub May 7, 2009.
Haraguchi et al., Vectors expressing efficient RNA decoys achieve the long-term suppression of specific microRNA activity in mammalian cells. Nucleic Acids Res. Apr. 2009;37(6):e43. doi: 10.1093/nar/gkp040. Epub Feb. 17, 2009.

Haussecker et al., miR-122 continues to blaze the trail for microRNA therapeutics. Mol Ther. Feb. 2010;18(2):240-2. doi: 10.1038/mt.2009.313.
Hernandez et al., Latent adeno-associated virus infection elicits humoral but not cell-mediated immune responses in a nonhuman primate model. J Virol. Oct. 1999;73(10):8549-58.
Horwich et al., Design and delivery of antisense oligonucleotides to block microRNA function in cultured *Drosophila* and human cells. Nat Protoc. 2008;3(10):1537-49. doi: 10.1038/nprot.2008.145.
Hsu et al., Essential metabolic, anti-inflammatory, and anti-tumorigenic functions of miR-122 in liver. J Clin Invest. Aug. 2012;122(8):2871-83. doi:10.1172/JCI63539. Epub Jul. 23, 2012.
Hutvágner et al., Sequence-specific inhibition of small RNA function. PLoS Biol. Apr. 2004;2(4):E98. Epub Feb. 24, 2004.
Iida et al., Systemic Delivery of Tyrosine-Mutant AAV Vectors Results in Robust Transduction of Neurons in Adult Mice. BioMed Res Int. 2013;2013.
Ishida et al., Dynamic changes of microRNAs in the eye during the development of experimental autoimmune uveoretinitis. Invest Ophthalmol Vis Sci. 2011;52(1):611-617. Published Feb. 1, 2011. doi:10.1167/iovs.10-6115.
Iwamoto et al., Global diffuse distribution in the brain and efficient gene delivery to the dorsal root ganglia by intrathecal injection of adeno-associated viral vector serotype 1. J Gene Med. Jun. 2009;11(6):498-505. doi: 10.1002/jgm.1325.
Jakobsson et al., Lentiviral vectors for use in the central nervous system. Mol Ther. Mar. 2006;13(3):484-93. Epub Jan. 3, 2006.
Janson et al., Clinical protocol. Gene therapy of Canavan disease: AAV-2 vector for neurosurgical delivery of aspartoacylase gene (ASPA) to the human brain. Hum Gene Ther. Jul. 20, 2002;13(11):1391-412.
Johnson et al., RAS is regulated by the let-7 microRNA family. Cell. Mar. 11, 2005;120(5):635-47.
Kaspar et al., Retrograde viral delivery of IGF-1 prolongs survival in a mouse ALS model. Science. Aug. 8, 2003;301(5634):839-42.
Kota et al., AAV8-Mediated Delivery of miR-26a inhibits cancer cell proliferation and induces tumor-specific apoptosis in a liver cancer model. Mol. Therapy. May 2009. 17(1):S300. Abstract 783.
Kota et al., Therapeutic microRNA delivery suppresses tumorigenesis in a murine liver cancer model. Cell. Jun. 12, 2009;137(6):1005-17. doi: 10.1016/j.cell.2009.04.021.
Kotin et al., Organization of adeno-associated virus DNA in latently infected Detroit 6 cells. Virology. Jun. 1989;170(2):460-7.
Kotin et al., Site-specific integration by adeno-associated virus. Proc Natl Acad Sci U S A. Mar. 1990;87(6):2211-5.
Krützfeldt et al., Silencing of microRNAs in vivo with 'antagomirs'. Nature. Dec. 1, 2005;438(7068):685-9. Epub Oct. 30, 2005.
Kumar et al., Lack of aspartoacylase activity disrupts survival and differentiation of neural progenitors and oligodendrocytes in a mouse model of Canavan disease. J Neurosci Res. Nov. 15, 2009;87(15):3415-27. doi: 10.1002/jnr.22233.
Kutay et al., Downregulation of miR-122 in the rodent and human hepatocellular carcinomas. J Cell Biochem. Oct. 15, 2006;99(3):671-8.
Lanford et al., Therapeutic silencing of microRNA-122 in primates with chronic hepatitis C virus infection. Science. Jan. 8, 2010;327(5962):198-201. Epub Dec. 3, 2009.
Lawlor et al., Efficient gene delivery and selective transduction of glial cells in the mammalian brain by AAV serotypes isolated from nonhuman primates. Mol Ther. Oct. 2009;17(10):1692-702. doi :; 10.1038/mt.2009.170.
Lebherz et al., Gene therapy with novel adeno-associated virus vectors substantially diminishes atherosclerosis in a murine model of familial hypercholesterolemia. J Gene Med. Jun. 2004;6(6):663-72.
Leone et al., Aspartoacylase gene transfer to the mammalian central nervous system with therapeutic implications for Canavan disease. Ann Neurol. Jul. 2000;48(1):27-38. Erratum in: Ann Neurol Sep. 2000;48(3):398. Bilianuk L [corrected to Bilaniuk L].
Lewis et al., Conserved seed pairing, often flanked by adenosines, indicates that thousands of human genes are microRNA targets. Cell. Jan. 14, 2005;120(1):15-20.

(56) References Cited

OTHER PUBLICATIONS

Lewis et al., Prediction of mammalian microRNA targets. Cell. Dec. 26, 2003;115(7):787-98.

Li et al., Efficient and Targeted Transduction of Nonhuman Primate Liver With Systemically Delivered Optimized AAV3B Vectors. Mol Ther. Dec. 2015;23(12):1867-76. doi: 10.1038/mt.2015.174. Epub Sep. 25, 2015.

Li et al., Ex vivo transduction and transplantation of bone marrow cells for liver gene delivery of alpha1-antitrypsin. Mol Ther. Aug. 2010;18(8):1553-8. Epub Jun. 15, 2010.

Li et al., Intronic microRNA: discovery and biological implications. DNA Cell Biol. Apr. 2007;26(4):195-207.

Li et al., Protein trans-splicing as a means for viral vector-mediated in vivo gene therapy. Hum Gene Ther. Sep. 2008;19(9):958-64. doi: 10.1089/hum.2008.009.

Liu et al., Comparative biology of rAAV transduction in ferret, pig and human airway epithelia. Gene Ther. Nov. 2007;14(21):1543-8. Epub Aug. 30, 2007.

Liu et al., Species-specific differences in mouse and human airway epithelial biology of recombinant adeno-associated virus transduction. Am J Respir Cell Mol Biol. Jan. 2006;34(1):56-64. Epub Sep. 29, 2005.

Ljubimov et al., Progress in corneal wound healing. Prog Retin Eye Res. Nov. 2015; 49: 17-45. EPub Jul. 18, 2015. doi: 10.1016/j.preteyeres.2015.07.002.

Loiler et al., Targeting recombinant adeno-associated virus vectors to enhance gene transfer to pancreatic islets and liver. Gene Ther. Sep. 2003;10(18):1551-8.

Lomas et al., The mechanism of Z alpha 1-antitrypsin accumulation in the liver. Nature. Jun. 18, 1992;357(6379):605-7.

Lowenstein, Crossing the rubicon. Nat Biotechnol. Jan. 2009;27(1):42-4.

Loya et al., Transgenic microRNA inhibition with spatiotemporal specificity in intact organisms. Nat Methods. Dec. 2009;6(12):897-903. doi: 10.1038/nmeth.1402. Epub Nov. 15, 2009.

Lux et al., Green fluorescent protein-tagged adeno-associated virus particles allow the study of cytosolic and nuclear trafficking. J Virol. Sep. 2005;79(18):11776-87.

Lynn, Meta-regulation: microRNA regulation of glucose and lipid metabolism. Trends Endocrinol Metab. Nov. 2009;20(9):452-9. doi: 10.1016/j.tem.2009.05.007. Epub Sep. 30, 2009.

Ma et al., Therapeutic silencing of miR-10b inhibits metastasis in a mouse mammary tumor model. Nat Biotechnol. Apr. 2010;28(4):341-7. doi: 10.1038/nbt.1618. Epub Mar. 28, 2010.

Madhyastha et al., MicroRNA signature in diabetic wound healing: promotive role of miR-21 in fibroblast migration. Int Wound J. 2012;9(4):355-361. doi:10.1111/j.1742-481X.2011.00890.x.

Maguire et al., Gene therapy for the nervous system: challenges and new strategies. Neurotherapeutics. Oct. 2014;11(4):817-39. doi: 10.1007/s13311-014-0299-5.

Mandel et al., Recombinant adeno-associated viral vectors as therapeutic agents to treat neurological disorders. Mol Ther. Mar. 2006;13(3):463-83. Epub Jan. 18, 2006.

Mao et al., Persistent suppression of ocular neovascularization with intravitreal administration of AAVrh.10 coding for bevacizumab. Hum Gene Ther. Dec. 2011;22(12):1525-35. doi: 10.1089/hum.2011.090. Epub Oct. 27, 2011.

Matalon et al., Adeno-associated virus-mediated aspartoacylase gene transfer to the brain of knockout mouse for canavan disease. Mol Ther. May 2003;7(5 Pt 1):580-7.

Mattan et al., Aspartoacylase deficiency affects early postnatal development of oligodendrocytes and myelination. Neurobiol Dis. Nov. 2010;40(2):432-43. doi: 10.1016/j.nbd.2010.07.003. Epub Jul. 14, 2010.

McBride et al., Artificial miRNAs mitigate shRNA-mediated toxicity in the brain: implications for the therapeutic development of RNAi. Proc Natl Acad Sci U S A. Apr. 15, 2008;105(15):5868-73. Epub Apr. 8, 2008.

McCarty et al., Adeno-associated virus terminal repeat (TR) mutant generates self-complementary vectors to overcome the rate-limiting step to transduction in vivo. Gene Ther. Dec. 2003;10(26):2112-8.

McCarty et al., Integration of adeno-associated virus (AAV) and recombinant AAV vectors. Annu Rev Genet. 2004;38:819-45.

McCarty et al., Self-complementary recombinant adeno-associated virus (scAAV) vectors promote efficient transduction independently of DNA synthesis. Gene Ther. Aug. 2001;8(16):1248-54.

McCarty, Self-complementary AAV vectors; advances and applications. Mol Ther. Oct. 2008;16(10):1648-56. Epub Aug. 5, 2008.

McCurdy et al., Sustained normalization of neurological disease after intracranial gene therapy in a feline model. Sci Transl Med. Apr. 9, 2014;6(231):231ra48. doi: 10.1126/scitranslmed.3007733.

McLean et al., Gene targeted therapeutics for liver disease in alpha-1 antitrypsin deficiency. Biologics. 2009;3:63-75. Epub Jul. 13, 2009.

Meijer et al., Controlling brain tumor growth by intraventricular administration of an AAV vector encoding IFN-beta. Cancer Gene Ther. Aug. 2009;16(8):664-71. doi: 10.1038/cgt.2009.8. Epub Feb. 6, 2009.

Meister et al., Sequence-specific inhibition of microRNA- and siRNA-induced RNA silencing. RNA. Mar. 2004;10(3):544-50.

Moffett et al., N-Acetylaspartate in the CNS: from neurodiagnostics to neurobiology. Prog Neurobiol. Feb. 2007;81(2):89-131. Epub Jan. 5, 2007.

Moss et al., Repeated adeno-associated virus serotype 2 aerosol-mediated cystic fibrosis transmembrane regulator gene transfer to the lungs of patients with cystic fibrosis: a multicenter, double-blind, placebo-controlled trial. Chest. Feb. 2004;125(2):509-21.

Mueller et al., Development of Simultaneous Gene Augmentation and Reduction of Mutant Gene Expression with a Single Recombinant AAV for Alpha-1 Antitrypsin Disease. Molecular Therapy May 2009;17(1):S391-S392. Abstract 1030.

Mueller et al., In Vivo AAV Delivered Allele Specific shRNA for the Knockdown of Alpha-1 Antitrypsin. Molecular Therapy May 2010;18(1):S22. Abstract 53.

Mueller et al., In Vivo Allele Specific Knockdown of Mutant Alpha-1 Antitrypsin Using Recombinant AAV Delivered shRNA. Molecular Therapy May 2009;17(1):S313. Abstract 817.

Mueller et al., Sustained miRNA-mediated knockdown of mutant AAT with simultaneous augmentation of wild-type AAT has minimal effect on global liver miRNA profiles. Mol Ther. Mar. 2012;20(3):590-600. Epub Jan. 17, 2012.

Mueller et al., The pros and cons of immunomodulatory IL-10 gene therapy with recombinant AAV in a Cftr-/- -dependent allergy mouse model. Gene Ther. Feb. 2009;16(2):172-83. Epub Sep. 25, 2008.

Mueller et al., Using rAAV Delivered miRNAs to Knockdown Misfolded Human Alpha 1 Antitrypsin in a Transgenic Mouse Model. Molecular Therapy May 2010;18(1):S21. Abstract 51.

O'Reilly et al., RNA interference-mediated suppression and replacement of human rhodopsin in vivo. Am J Hum Genet. Jul. 2007;81(1):127-35. Epub May 23, 2007.

Parikh et al., A Path towards restoration of vision using ocular gene therapy: An opthalmic review. In J Pharm Biomed Sci. 2012;3(3):140-7.

Passini et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.

Pertin et al., Efficacy and specificity of recombinant adeno-associated virus serotype 6 mediated gene transfer to drg neurons through different routes of delivery. Poster sessions. Eur J. Pain. 2009;13:S74. Abstract 229.

Raghunath et al., Micro-RNAs and their roles in eye disorders. Ophthalmic Res. 2015;53(4):169-186. doi: 10.1159/000371853.

Ralph et al., Silencing mutant SOD1 using RNAi protects against neurodegeneration and extends survival in an ALS model. Nat Med. Apr. 2005;11(4):429-33. Epub Mar. 13, 2005.

Raoul et al., Lentiviral-mediated silencing of SOD1 through RNA interference retards disease onset and progression in a mouse model of ALS. Nat Med. Apr. 2005;11(4):423-8. Epub Mar. 13, 2005.

(56) References Cited

OTHER PUBLICATIONS

Schattgen et al., Cutting Edge: DNA in the Lung Microenvironment during Influenza Virus Infection Tempers Inflammation by Engaging the DNA Sensor AIM2. J Immunol. Jan. 1, 2016;196(1):29-33. doi: 10.4049/jimmunol.1501048.

Schnepp et al., Characterization of adeno-associated virus genomes isolated from human tissues. J Virol. Dec. 2005;79(23):14793-803.

Sen et al., Micromanaging vascular biology: tiny microRNAs play big band. J Vasc Res. 2009;46(6):527-40. doi: 10.1159/000226221. Epub Jun. 30, 2009.

Sivasothy et al., Pathogenic alpha 1-antitrypsin polymers are formed by reactive loop-beta-sheet A linkage. J Biol Chem. Oct. 27, 2000;275(43):33663-8.

Snyder et al., Comparison of adeno-associated viral vector serotypes for spinal cord and motor neuron gene delivery. Hum Gene Ther. Sep. 2011;22(9):1129-35. doi: 10.1089/hum.2011.008. Epub Jul. 25, 2011.

Song et al., Intramuscular administration of recombinant adeno-associated virus 2 alpha-1 antitrypsin (rAAV-SERPINA1) vectors in a nonhuman primate model: safety and immunologic aspects. Mol Ther. Sep. 2002;6(3):329-35.

Stoica et al., Targeting Human SOD1 Using AAV mediated RNAi in a mouse model of amyotrophic lateral sclerosis. Mol ther. Jun. 2013;21(1):S149.

Storek et al., Intrathecal long-term gene expression by self-complementary adeno-associated virus type 1 suitable for chronic pain studies in rats. Mol Pain. Jan. 30, 2006;2:4.

Storkebaum et al., Treatment of motoneuron degeneration by intracerebroventricular delivery of VEGF in a rat model of ALS. Nat Neurosci. Jan. 2005;8(1):85-92. Epub Nov. 28, 2004.

Tanimizu et al., Downregulation of miR122 by grainyhead-like 2 restricts the hepatocytic differentiation potential of adult liver progenitor cells. Development. Dec. 2014;141(23):4448-56. doi:10.1242/dev.113654. Epub Nov. 18, 2014.

Tenenbaum et al., Recombinant AAV-mediated gene delivery to the central nervous system. J Gene Med. Feb. 2004;6 Suppl 1:S212-22.

Tokumaru et al., let-7 regulates Dicer expression and constitutes a negative feedback loop. Carcinogenesis. Nov. 2008;29(11):2073-7. doi: 10.1093/carcin/bgn187. Epub Aug. 11, 2008.

Tomar et al., Use of adeno-associated viral vector for delivery of small interfering RNA. Oncogene. Aug. 28, 2003;22(36):5712-5.

Towne et al., Systemic AAV6 delivery mediating RNA interference against SOD1: neuromuscular transduction does not alter disease progression in fALS mice. Mol Ther. Jun. 2008;16(6):1018-25. doi: 10.1038/mt.2008.73. Epub Apr. 15, 2008.

Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.

Tsai et al., MicroRNA-122, a tumor suppressor microRNA that regulates intrahepatic metastasis of hepatocellular carcinoma. Hepatology. May 2009;49(5):1571-82. doi: 10.1002/hep.22806.

Vandenberghe et al., Heparin binding directs activation of T cells against adeno-associated virus serotype 2 capsid. Nat Med. Aug. 2006;12(8):967-71. Epub Jul. 16, 2006.

Vandenberghe et al., Tailoring the AAV vector capsid for gene therapy. Gene Ther. Mar. 2009;16(3):311-9. Epub Dec. 4, 2008.

Vandendriessche et al., Efficacy and safety of adeno-associated viral vectors based on serotype 8 and 9 vs. lentiviral vectors for hemophilia B gene therapy. J Thromb Haemost. Jan. 2007;5(1):16-24. Epub Sep. 26, 2006.

Vaucheret et al., The action of ARGONAUTE1 in the miRNA pathway and its regulation by the miRNA pathway are crucial for plant development. Genes Dev. May 15, 2004;18(10):1187-97. Epub May 6, 2004.

Vermeulen et al., Double-stranded regions are essential design components of potent inhibitors of RISC function. RNA. May 2007;13(5):723-30. Epub Mar. 30, 2007.

Virella-Lowell et al., Enhancing rAAV vector expression in the lung. J Gene Med. Jul. 2005;7(7):842-50.

Vulchanova et al., Differential adeno-associated virus mediated gene transfer to sensory neurons following intrathecal delivery by direct lumbar puncture. Mol Pain. May 28, 2010;6:31. doi: 10.1186/1744-8069-6-31.

Waldman et al., Applications of microRNA in cancer: Exploring the advantages of miRNA. Clin Transl Sci. Jun. 2009;2(3):248-9. doi: 10.1111/j.1752-8062.2009.00110.x.

Wang et al., Neuroprotective effects of glial cell line-derived neurotrophic factor mediated by an adeno-associated virus vector in a transgenic animal model of amyotrophic lateral sclerosis. J Neurosci. Aug. 15, 2002;22(16):6920-8.

Wang et al., Rescue and replication of adeno-associated virus type 2 as well as vector DNA sequences from recombinant plasmids containing deletions in the viral inverted terminal repeats: selective encapsidation of viral genomes in progeny virions. J Virol. Mar. 1996;70(3):1668-77.

Wang et al., Somatically Repairing Compound Heterozygous Recessive Mutations by Chromosomal Cut-and-Paste for in Vivo Gene Therapy. May 2016. 24(1):S289. Abstract 733.

Wang et al., Sustained correction of disease in naive and AAV2-pretreated hemophilia B dogs: AAV2/8-mediated, liver-directed gene therapy. Blood. Apr. 15, 2005;105(8):3079-86. Epub Jan. 6, 2005.

Wang et al., The design of vectors for RNAi delivery system. Curr Pharm Des. 2008;14(13):1327-40.

Wang et al., The potential of adeno-associated viral vectors for gene delivery to muscle tissue. Expert Opin Drug Deliv. Mar. 2014;11(3):345-64. doi: 10.1517/17425247.2014.871258. Epub Jan. 3, 2014.

Wang et al., Therapeutic gene silencing delivered by a chemically modified small interfering RNA against mutant SOD1 slows amyotrophic lateral sclerosis progression. J Biol Chem. Jun. 6, 2008;283(23):15845-52. doi: 10.1074/jbc.M800834200. Epub Mar. 26, 2008.

Wang et al., Widespread spinal cord transduction by intrathecal injection of rAAV delivers efficacious RNAi therapy for amyotrophic lateral sclerosis. Hum Mol Genet. Feb. 1, 2014;23(3):668-81. doi: 10.1093/hmg/ddt454. Epub Sep. 18, 2013.

Watson et al., Intrathecal administration of AAV vectors for the treatment of lysosomal storage in the brains of MPS I mice. Gene Ther. Jun. 2006;13(11):917-25.

Weismann et al., Systemic AAV9 gene transfer in adult GM1 gangliosidosis mice reduces lysosomal storage in CNS and extends lifespan. Hum Mol Genet. Aug. 1, 2015;24(15):4353-64. doi: 10.1093/hmg/ddv168. Epub May 10, 2015.

Weismann, Approaches and Considerations Towards a Safe and Effective Adena-Associated Virus Mediated Therapeutic Intervention for GM 1-Gangliosidosis: A Dissertation. University Massachusetts Medical School. Aug. 5, 2014.

Xia et al., Allele-specific RNAi selectively silences mutant SOD1 and achieves significant therapeutic benefit in vivo. Neurobiol Dis. Sep. 2006;23(3):578-86. Epub Jul. 20, 2006.

Xie et al., Characterization of positioning effect of pol III-shRNA transcription unit in scAAV vector genome on the packaging efficiency and functionality of shRNA silencing. Molecular Therapy. May 2010;18(1): S262. Abstract 671.

Xie et al., MicroRNA regulated tissue specific transduction by rAAV vector. Molecular Therapy. May 2009;17(1): S279. Abstract 732.

Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.

Xie et al., rAAV-mediated delivery of micro RNA scavengers leads to efficient and stable knockdown of cognate micro RNAs, upregulation of their natural target genes and phenotypic changes in mice. Molecular Therapy. May 2010;18(1): S140. Abstract362.

Xu et al., Delivery of MDR1 small interfering RNA by self-complementary recombinant adeno-associated virus vector. Mol Ther. Apr. 2005;11(4):523-30.

Yamanaka et al., Astrocytes as determinants of disease progression in inherited amyotrophic lateral sclerosis. Nat Neurosci. Mar. 2008;11(3):251-3. doi: 10.1038/nn2047. Epub Feb. 3, 2008.

(56) References Cited

OTHER PUBLICATIONS

Yang et al., The muscle-specific microRNA miR-1 regulates cardiac arrhythmogenic potential by targeting GJA1 and KCNJ2. Nat Med. Apr. 2007;13(4):486-91. Epub Apr. 1, 2007. Erratum in: Nat Med. Dec. 2011;17(12):1693.
Yu et al., let-7 regulates self renewal and tumorigenicity of breast cancer cells. Cell. Dec. 14, 2007;131(6):1109-23.
Zabner et al., Adeno-associated virus type 5 (AAV5) but not AAV2 binds to the apical surfaces of airway epithelia and facilitates gene transfer. J Virol. Apr. 2000;74(8):3852-8.
Zhang et al., Characterization of 12 AAV vectors for intravascular delivery to target CNS and detarget non-CNS tissues by mirna regulation: implications in treatment of canavan disease. Molecular Therapy. May 2010;18(1): S174. Abstract 450.
EP 17750871.0, Jul. 18, 2019, Partial Supplementary European Search Report.
EP 17750871.0, Oct. 22, 2019, Extended European Search Report.
PCT/US2017/01746, Jun. 15, 2017, International Search Report and Written Opinion.
PCT/US2017/01746, Aug. 23, 2018, International Preliminary Report on Patentability.

* cited by examiner

Genomic copy mRNA expression

\*: p<0.05; \*\*: p<0.01; \*\*\*: p<0.001; \*\*\*\*: p<0.0001

*: p<0.05; : p<0.01; *: p<0.001; ****: p<0.0001

ANTI-ANGIOGENIC MIRNA THERAPEUTICS FOR INHIBITING CORNEAL NEOVASCULARIZATION

RELATED APPLICATIONS

This application is a continuation under 35 U.S.C. § 120 of U.S. application Ser. No. 16/076,881, filed Aug. 9, 2018, which is a National Stage Application of PCT/US2017/017469, filed Feb. 10, 2017, entitled "ANTI-ANGIOGENIC MIRNA THERAPEUTICS FOR INHIBITING CORNEAL NEOVASCULARIZATION", which claims the benefit under 35 U.S.C. § 119(e) of U.S. Provisional Application 62/294,362, filed on Feb. 12, 2016, entitled "ANTIANGIOGENIC MIRNA THERAPEUTICS FOR INHIBITING CORNEAL NEOVASCULARIZATION", the entire contents of each application are incorporated herein by reference.

GOVERNMENT SUPPORT

This invention was made with government support under NS07699 and AI100263 awarded by the National Institutes of Health. The government has certain rights in the invention.

BACKGROUND OF INVENTION

Cornea, the transparent and avascular tissue of the anterior ocular segment, is the major refractive surface of the eye, as well as a protective barrier to physical and pathogenic injury. Corneal opacities due to disease, infection or injury, is one of the leading causes of blindness worldwide (5.1%). Corneal neovascularization (NV), one of the most common pathological processes in corneal diseases, is a significant and underestimated cause of unilateral blindness, leading to between 1.5 and 2 million new cases each year. Although a variety of treatments are available in clinic, including steroid hormone drugs, non-steroidal anti-inflammatory drugs (NSAIDs), cyclosporine, peroxisome proliferator activated receptor (PPARγ) agonists, and anti-VEGF therapies, a safe and effective therapy for corneal visual impairment remains to be an unmet medical challenge, especially the most severe cases, for which corneal transplantation is required. However, even in developed countries, access to this surgery is very difficult for lack of donors.

SUMMARY OF INVENTION

Adeno-associated virus (AAV) is a single-stranded DNA virus, and recombinant AAV (rAAV) vectors possess many advantages in gene therapy applications, including low immunogenicity and genotoxicity, broad tissue tropism and high transduction efficiency in vivo, and long-term transgene expression. Aspects of the invention are related to the discovery that rAAV vectors comprising capsid proteins having a certain serotype, including, but not limited to, AAV5, AAV6, AAV6.2, AAV7, AAV8, AAV9, AAVrh.8, AAVrh.10, AAVrh.39, and AAVrh.43, mediate delivery of transgenes to ocular tissue (e.g., corneal tissue) more efficiently than other vectors (e.g., rAAV vectors comprising other capsid protein serotypes).

Accordingly in some aspects, the disclosure provides a method for delivering a transgene to ocular tissue (e.g., corneal tissue), e.g., for treating or preventing eye diseases, such as corneal neovascularization. In some embodiments, methods provided herein comprise administering to ocular (e.g., corneal) tissue of a subject an effective amount of rAAV, wherein the rAAV comprises (i) a capsid protein having a selected serotype (e.g., selected from the group consisting of AAV5, AAV6, AAV6.2, AAV7, AAV8, AAV9, AAVrh.8, AAVrh.10, AAVrh.39, and AAVrh.43), and (ii) a nucleic acid comprising a promoter operably linked to a transgene.

In some aspects, the disclosure provides a method of treating an ocular (e.g., corneal) disease. In some embodiments, the methods comprise: administering to a subject having or suspected of having an ocular (e.g., corneal) disease an effective amount of rAAV, wherein the rAAV comprises (i) a capsid protein having a selected serotype (e.g., selected from the group consisting of AAV5, AAV6, AAV6.2, AAV7, AAV8, AAV9, AAVrh.8, AAVrh.10, AAVrh.39, and AAVrh.43), and (ii) a nucleic acid comprising a promoter operably linked to a transgene.

Aspects of the invention relate, in part, to the discovery that certain genes are highly up-regulated or highly down-regulated (e.g., SEQ ID NOs: 1-3) in a subject having an ocular disease (e.g., a subject having a corneal disease) and modulation of such genes confers a therapeutic benefit to the subject. Accordingly, in some aspects the disclosure provides a method of treating an ocular disease (e.g., a corneal disease) comprising administering to ocular (e.g., corneal) tissue of a subject an effective amount of rAAV, wherein the rAAV comprises (i) a capsid protein, and (ii) a nucleic acid comprising a promoter operably linked to a transgene, wherein the transgene encodes a gene associated with an ocular (e.g., corneal) disease.

In some aspects, the disclosure provides compositions for use in the methods described herein. In some aspects, the disclosure provides a recombinant adeno-associated virus comprising: (i) a capsid protein having a serotype selected from the group consisting of AAV5, AAV6, AAV6.2, AAV7, AAV8, AAV9, AAVrh.8, AAVrh.10, AAVrh.39, and AAVrh.43; and, (ii) a nucleic acid comprising a promoter operably linked to a transgene.

In some aspects, the disclosure provides a recombinant adeno-associated virus (rAAV) comprising: (i) a capsid protein; and, (ii) a nucleic acid comprising a promoter operably linked to a transgene, wherein the transgene encodes a gene associated with an ocular (e.g., corneal) disease.

In some embodiments, the capsid protein of an rAAV described by the disclosure comprises an amino acid sequence that is at least 70%, at least 80%, at least 90%, at least 95%, or at least 99% identical to any one of SEQ ID NO: 7-16. In some embodiments, the capsid protein comprises an amino acid sequence as set forth in SEQ ID NO: 7-16. In some embodiments, the capsid protein is AAVrh.10 capsid protein (SEQ ID NO: 14), or AAVrh.39 capsid protein (SEQ ID NO: 15).

In some embodiments, the transgene encodes a gene associated with an ocular (e.g., corneal) disease. In some embodiments, the ocular (e.g., corneal) disease is selected from corneal neovascularization (NV), corneal dystrophy, corneal inflammation, and corneal fibrosis. In some embodiments, the gene encodes a miRNA, an antagomir, or a miRNA mimic. In some embodiments, the gene encodes a miRNA, optionally a TuD miRNA or a pri miRNA. In some embodiments, the transgene comprises a region of complementarity to a sequence selected from the group consisting of SEQ ID NO: 1, 2, 3, 27, 28, and 29. In some embodiments, the transgene comprises SEQ ID NO: 4, SEQ ID NO: 5, or SEQ ID NO: 6.

In some embodiments, the administration occurs by injection. In some embodiments, the injection is intrastromal injection (intrastromal injection into ocular tissue). In some embodiments, the administration is topical administration (e.g., topical administration to an eye).

In some embodiments, the administration results in transduction of an ocular (e.g., corneal) cell type selected from the group consisting of keratocytes, corneal endothelial cells, corneal basal cells, corneal wing cells, and corneal squamous cells. In some embodiments, the administration results in transduction of keratocytes.

In some embodiments, the rAAV further comprises two AAV inverted terminal repeats (ITRs), wherein the ITRs flank the transgene. In some embodiments, the AAV ITRs are ITRs of one or more serotypes selected from: AAV2, AAV3, AAV4, AAV5, and AAV6.

In some embodiments of methods described herein, the subject is a mammal, optionally a human.

In some aspects, the disclosure provides a composition comprising a recombinant adeno-associated virus as described herein.

Each of the limitations of the disclosure can encompass various embodiments of the disclosure. It is, therefore, anticipated that each of the limitations of the disclosure involving any one element or combinations of elements can be included in each aspect of the disclosure. This disclosure is not limited in its application to the details of construction and the arrangement of components set forth in the following description or illustrated in the drawings. The disclosure is capable of other embodiments and of being practiced or of being carried out in various ways.

BRIEF DESCRIPTION OF DRAWINGS

FIG. 1A shows corneal neovascularization (NV) was observed for 15 days after alkali burn, and the corneas of four time points (before and days 5, 10 and 15 after alkali burn) were harvested for RNA extraction. Nanostring technology was used to detect 618 miRNAs, and the analysis of the results is showed as the heatmap. The color represents the expression fold of miRNA in neovascularized corneas compared to normal corneas. FIG. 1B shows miRNA expression results using nanostring technology is further verified by qRT-PCR. Sample results are showed. (n=8/group). FIG. 1C shows the top 3 miRNAs (miR-21, miR-184 and miR-204) with over 10-fold expression change were selected as gene therapy candidates. The pri/TuD miRNA constructs, which overexpress or inhibit the target miRNA expression, were cloned and verified. The rAAV genome of the three constructs are showed.

FIG. 2A shows the gene transfer efficiency of 14 rAAV serotypes (AAV1, AAV2, AAV3b, AAV4, AAV5, AAV6, AAV6.2, AAV7, AAV8, AAV9, AAVrh.8, AAVrh.10, AAVrh.39, and AAVrh.43) with EGFP were assessed in mouse corneas delivered by intrastromal injection. rAAVrh.8, rh.10, rh.39 and rh.43 showed stronger EGFP signals in whole corneal flat-mounts. 25×, scale bar=250 µm. Left lower: high magnification images of central cornea, 100×. FIG. 2B shows gene transfer efficiency of rAAVrh.8, rh.10, rh.39 and rh.43 were further evaluated by topical administration with or without corneal epithelium removed. rAAVrh.10 and rh.39 showed stronger EGFP signals in whole corneal flat-mounts when delivered by topical administration in the condition that the corneal epithelium was removed. 25×, scale bar=250 µm. Left lower: high magnification images of central cornea, 100×. FIG. 2C shows in vivo observation of EGFP expression mediated by rAAVrh.10 and rh.39. EGFP signals could be detected from 1 week till 4 weeks after intrastromal injection or topical administration. FIG. 2D shows confocal images of mouse corneas transduced by rAAVrh.10 and rh.39 EGFP vectors. Corneal stromal cells (keratocytes) were stained as red (keratocan positive). 630×, scale bar=50 µm.

FIG. 3A shows an overview of the experimental schedule. FIG. 3B shows CD31-stained whole corneal flat-mounts harvested at day 15 post alkali burn. Blood vessels in corneal stroma were stained as red. No blood vessels were detected in corneas without alkali burn (group of normal). TuD miR-21, pri miR-184 and pri miR-204 inhibited corneal NV when compared to control groups of PBS, Gluc and TuD scramble. Yellow dash circle: avascular areas (area without blood vessels). Gluc: backbone plasmid of all the three miRNA constructs, TuD scramble: same backbone as other miRNA constructs with scramble TuD sequence. 25×, scale bar=1 mm. FIG. 3C shows corneal NV was observed and measured in vivo at days 3, 5, 7, 10 and 14 after alkali burn. The in vivo results showed that the inhibitory effects of TuD miR-21, pri miR-184 and pri miR-204 started from day 5 till day 14 after alkali burn. FIG. 3D shows quantification analysis of NV area percentage among CD31-stained whole corneal flat-mounts indicated that all the three constructs effectively inhibited corneal NV. NV: neovascularization. $p<0.01$, $*p<0.001$ compared to PBS group.

FIG. 4A shows an overview of the experimental schedule. FIG. 4B shows CD31-stained whole corneal flat-mounts harvested at day 15 post alkali burn. Blood vessels in corneal stroma were stained as red. No blood vessels were detected in corneas without alkali burn (group of normal). TuD miR-21, pri miR-184 and pri miR-204 could not inhibit corneal NV at day 15 when compared to control groups of PBS, Gluc and TuD scramble (whole corneas were covered by blood vessels). Yellow dash circle: avascular areas (area without blood vessels). 25×, scale bar=1 mm. FIG. 4C shows corneal NV was observed and measured in vivo at days 3, 5, 7, 10 and 14 after alkali burn. The in vivo results showed that TuD miR-21, pri miR-184 and pri miR-204 could partially suppress the corneal NV at days 7 and 10 after alkali burn. However, the inhibitory effects disappeared till the day 14 post alkali burn. FIG. 4D shows quantification analysis of NV area percentage among CD31-stained whole corneal flat-mounts indicated that no inhibitory effect was found among any of the three miRNA therapeutics. NV: neovascularization. $*p<0.05$, $p<0.01$, $*p<0.001$ compared to PBS group.

FIG. 5A shows an overview of the experimental schedule. FIG. 5B shows CD31-stained whole corneal flat-mounts harvested at day 15 post alkali burn. Blood vessels in corneal stroma were stained as red. No blood vessels were detected in corneas without alkali burn (group of normal). TuD miR-21, pri miR-184 and pri miR-204 inhibited corneal NV when compared to control groups of PBS, Gluc and TuD scramble. Whole cornea of Gluc group was covered by blood vessels. Yellow dash circle: avascular areas (area without blood vessels). 25×, scale bar=1 mm. FIG. 5C shows corneal NV was observed and measured in vivo at days 3, 5, 7, 10 and 14 after alkali burn. The in vivo results showed that the inhibitory effects of pri miR-184 and pri miR-204 started from day 5, while TuD miR-21 from day 10, and continued till day 14 after alkali burn. FIG. 5D shows quantification analysis of NV area percentage among CD31-stained whole corneal flat-mounts indicated that all the three constructs effectively inhibited corneal NV. NV: neovascularization. *p<0.05, p<0.01, *p<0.001 compared to PBS group.

FIG. 6A shows an intra-stromal injection. A small incision in the corneal epithelium was first created, and a 33-gauge needle attached to a 5 µL Hamilton microliter syringe was then introduced through the incision into the corneal stroma and $2.4 \times 10^{10}$ genomic copies (GC) of rAAV vectors in 4 µL PBS were injected. In vivo imaging was conducted at weeks 1, 2, 3 and 4 after injection. Corneas were harvested at 4 weeks post-injection. FIG. 6B shows topical administration (eye drop). rAAV transduction through topical administration was conducted with or without corneal epithelium removed. For epithelium removal, alcohol soaked filter membrane was applied on each cornea for 20 seconds and epithelium was removed by gentle scraping. One drop of rAAV vectors ($2.4 \times 10^{10}$ GC) in 4 µL PBS was directly applied to the intact cornea or the corneal stroma after epithelium removed.

FIG. 7A shows the gene transfer efficiency of fourteen rAAV serotypes with EGFP was assessed in mouse corneas delivered by intra-stromal injection. rAAVrh.8, rh.10, rh.39 and rh.43 showed stronger EGFP signals in the immunofluorescence images of whole corneal flat-mounts at the fourth week after injection. Magnification: 25×, scale bar=250 µm. Lower left: images of central cornea under high magnification, 100×. FIG. 7B shows the percentage of EGFP positive area from whole corneal flat-mount area. Nearly 80% of the whole cornea areas were efficiently transduced by rAAVrh.8, rh.10 and rh.39 vectors. FIG. 7C shows quantification of EGFP fluorescence intensity of whole corneal flat-mounts presented in arbitrary unit (a.u.). The EGFP intensity in the four rhesus serotype groups of rAAVrh.8, rh.10, rh.39 and rh.43 were almost four folds over other rAAV serotypes tested. : p<0.01, *: p<0.001 compared to PBS group (n=3/group).

FIG. 8A shows the gene transfer efficiency of rAAVrh.8, rh.10, rh.39 and rh.43 were further evaluated by topical eye-drop administration without (left column) or with (middle column) corneal epithelium removed. Groups of rAAVrh.10 and rh.39 showed stronger EGFP signals in immunofluorescence images of whole corneal flat-mounts when delivered by topical administration in the condition that the corneal epithelium was removed. Intra-stromal injection (right column) was set as a positive control. Magnification: 25×, scale bar=250 µm. Lower left: images of central cornea under high magnification, 100×. FIG. 8B shows percentage of EGFP positive area from whole corneal flat-mount area. FIG. 8C shows quantification of EGFP fluorescence intensity of whole corneal flat-mounts presented in arbitrary unit (a.u.) (n=3/group).

FIG. 9A shows in vivo observation of EGFP expression delivered by rAAVrh.10 and rh.39. EGFP signals were detected from 1 to 4-weeks after intra-stromal injection or topical administration (with corneal epithelium removed). FIG. 9B shows quantification of rAAV genome copies in mouse corneas harvested 4-weeks after topical administration or intra-stromal injection. For both serotypes, the intra-stromal injected groups showed higher genome copies than the topical administration groups. Liver DNA from mice that received an intravenous injection of rAAV9 EGFP vectors ($1 \times 10^{12}$ genomic copies) was used as positive control. FIG. 9C shows quantification of EGFP mRNA expression in mouse corneas harvested 4-weeks after topical administration or intra-stromal injection. Higher EGFP expression was detected with intra-stromal injection than topical administration in both serotypes. : p<0.01, *: p<0.001. (n=5/group).

FIG. 10A shows representative immunofluorescence images of mouse corneas transduced by rAAVrh.10 and rh.39 EGFP vectors. Corneal stromal cells (keratocytes) were stained as red (keratocan positive). Magnification: 630×, scale bar=50 µm. Squared regions indicate the locations of high magnification images shown on the right. FIG. 10B shows quantification of the percentage of EGFP positive cells among keratocytes. Higher percentage of EGFP positive keratocytes was found in intra-stromal injection groups than topical administration groups of both serotypes. : p<0.01, *: p<0.001 (n=3/group).

FIG. 12A shows miRNA profiling of alkali-burn induced mouse corneal NV. FIG. 12B shows signaling systems.

FIG. 26A shows a dendrogram of gene expression profiles between untreated corneas (day 0), corneas from 5 days post-treatment with alkali burn (day 5), and corneas from 15 days post-treatment (day 15). FIG. 26B shows volcano plots comparing fold-change (log 2 of fold-change) vs. significance values ($-\log_{10}$ of p-value) between day 0 and day 5 (left plot), day 0 and day 15 (middle plot), and day 5 and day 15 (right plot). Lighter shaded data points denote genes that show significant fold-change between compared conditions. FIG. 26C shows a heat map display of the fold-change in alkali-burn treated corneas. The shading scale is displayed to the right. Fold-change is shown as log 2 difference over day-0 values ($\log_2$(FPKM/day 0)).

FIG. 27A shows a heat map of fold-change in expression of miR-204 predicted genes in corneas 5 days and 15 days post-alkali-burn treatment. The shading scale is displayed to the right. Fold-change is shown as log 2 difference over day 0 values ($\log_2$(FPKM/day 0)). FIG. 27B shows K-means clustering of miR-204 predicted target gene expression profiles in alkali-burn treated corneas. Three distinct groups were defined: genes with little or no change (left plot, group 1); down-regulated genes (center plot, group 2); and up-regulated genes (right plot, group 3). FIG. 27C shows a gene ontology (GO) network map for the group 3 genes. Genes that enrich for selected terms are displayed as small nodes that connect to the larger GO-term nodes. The relative sizes of the GO-term nodes also reflect their significance levels.

DETAILED DESCRIPTION OF INVENTION

Figure 1A:
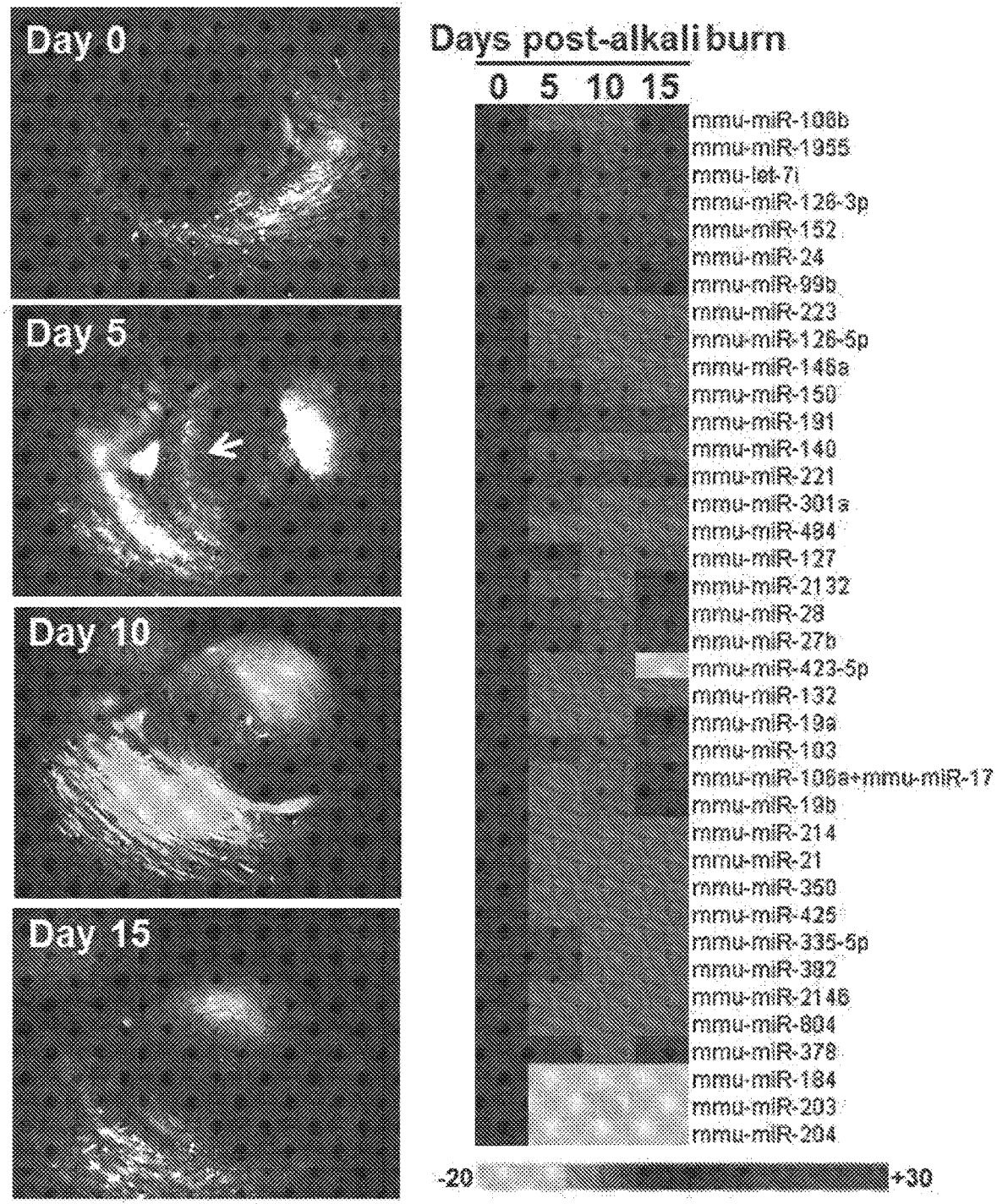
FIGS. 1A-1C show the miR profile of corneal neovascularization in an alkali burn induced mouse model.

The disclosure relates in some aspects to compositions and methods for tissue-specific delivery of a transgene by a recombinant adeno-associated virus (rAAV). The invention relates, in part, to the discovery that rAAV vectors comprising a capsid protein(s) having a certain serotype (e.g., AAV5, AAV6, AAV6.2, AAV7, AAV8, AAV9, AAVrh.8, AAVrh.10, AAVrh.39, and AAVrh.43) mediate delivery of transgenes to ocular tissue (e.g., corneal tissue) more efficiently than other vectors (e.g., rAAV vectors comprising other capsid protein serotypes). In some embodiments, the disclosure relates to the discovery of 35 miRNA-encoding genes that are expressionally up-regulated, and 3 miRNA-encoding genes that are expressionally down-regulated, in response to ocular injury (e.g., corneal trauma).

Methods and Compositions for AAV-Mediated Delivery of a Transgene to Ocular Tissue Methods for delivering a transgene to ocular (e.g., corneal) tissue in a subject are provided herein. The methods typically involve administering to a subject an effective amount of a rAAV comprising a nucleic acid for expressing a transgene in the subject. An "effective amount" of a rAAV is an amount sufficient to infect a sufficient number of cells of a target tissue in a subject. In some embodiments, a target tissue is ocular (e.g., corneal) tissue. An effective amount of a rAAV may be an amount sufficient to have a therapeutic benefit in a subject, e.g., to extend the lifespan of a subject, to improve in the subject one or more symptoms of disease, e.g., a symptom of ocular disease (e.g., corneal neovascularization (NV)). In some cases, an effective amount of a rAAV may be an amount sufficient to produce a stable somatic transgenic animal model. The effective amount will depend on a variety of factors such as, for example, the species, age, weight, health of the subject, and the ocular tissue to be targeted, and may thus vary among subject and tissue.

An effective amount may also depend on the rAAV used. The invention is based, in part on the recognition that rAAV comprising capsid proteins having a particular serotype (e.g., AAV5, AAV6, AAV6.2, AAV7, AAV8, AAV9, AAVrh.8, AAVrh.10, AAVrh.39, and AAVrh.43) mediate more efficient transduction of ocular (e.g., corneal) tissue that rAAV comprising capsid proteins having a different serotype. Thus in some embodiments, the rAAV comprises a capsid protein of an AAV serotype selected from the group consisting of: AAV5, AAV6, AAV6.2, AAV7, AAV8, AAV9, AAVrh.8, AAVrh.10, AAVrh.39, and AAVrh.43 (SEQ ID NO: 7-16). In some embodiments, the rAAV comprises a capsid protein of AAVrh.10 serotype (SEQ ID NO: 14) or AAVrh.39 serotype (SEQ ID NO: 15). In some embodiments, the capsid protein comprises an amino acid sequence that is at least 70%, at least 80%, at least 90%, at least 95%, or at least 99% identical to any one of SEQ ID NO: 7-16. In some embodiments, the capsid protein is AAVrh.10 capsid protein (SEQ ID NO: 14) or AAVrh.39 capsid protein (SEQ ID NO: 15).

In certain embodiments, the effective amount of rAAV is $10^{10}$, $10^{11}$, $10^{12}$, $10^{13}$, or $10^{14}$ genome copies per kg. In certain embodiments, the effective amount of rAAV is $10^{10}$, $10^{11}$, $10^{12}$, $10^{13}$, $10^{14}$, or $10^{15}$ genome copies per subject.

An effective amount may also depend on the mode of administration. For example, targeting an ocular (e.g., corneal) tissue by intrastromal administration or subcutaneous injection may require different (e.g., higher or lower) doses, in some cases, than targeting an ocular (e.g., corneal) tissue by another method (e.g., systemic administration, topical administration). The invention is based, in part, on the recognition that intrastromal injection (IS) of rAAV having certain serotypes (e.g., AAV5, AAV6, AAV6.2, AAV7, AAV8, AAV9, AAVrh.8, AAVrh.10, AAVrh.39, and AAVrh.43) mediates efficient transduction of ocular (e.g., corneal) cells. Thus, in some embodiments, the injection is intrastromal injection (IS). In some embodiments, the injection is topical administration (e.g., topical administration to an eye). In some cases, multiple doses of a rAAV are administered.

Generally, the anatomy of an eye (e.g., a mammalian eye) comprises a sclera, choroid, retina, vitreous body, macula, fovea, optic disc, lens, pupil, iris, aqueous fluid, cornea, conjunctiva ciliary body, and optic nerve. The cornea is a transparent, multilayered (e.g., comprising four, five, or six layers) tissue that covers the iris, pupil, and anterior chamber of the eye. Layers of the cornea include, but are not limited to, corneal epithelium, Bowman's layer (e.g., anterior limiting membrane), corneal stroma (e.g., substantia propria), Descemet's membrane (e.g., posterior limiting membrane), and corneal endothelium. Administration of compositions described by the disclosure may result in transduction of one of the foregoing corneal layers, or more than one corneal layer (e.g., 2, 3, 4, 5, or 6 corneal layers). Corneal layers can comprise a single cell type, or multiple cell types. In some embodiments, administration of an rAAV as described herein results in transduction of an ocular (e.g., corneal) cell type selected from the group consisting of keratocytes, corneal endothelial cells, corneal basal cells, corneal wing cells, and corneal squamous cells. In some embodiments, the administration results in transduction of keratocytes.

Ocular (e.g., corneal) tissue can be healthy ocular (e.g., corneal) tissue (e.g., ocular tissue not having a disease, or at risk of developing an ocular disease, such as a corneal disease) or diseased ocular tissue (e.g., ocular tissue having corneal neovascularization (NV), corneal dystrophy, corneal inflammation, and corneal fibrosis). As used herein, "at risk of developing an ocular disease" refers to a subject having an increased probability of developing an ocular disease (e.g., corneal disease) than the general population due to the presence of a risk factor. Examples categories of risk factors for developing ocular disease include, but are not limited to: exposure to certain microbial pathogens (e.g., *Pseudomonas aeruginosa, Staphylococcus aureus*), contact lens wear, ocular trauma, prior ocular surgery, age, race, and family history (e.g., positive family history of ocular disease, high cholesterol, high blood pressure, or diabetes).

Without wishing to be bound by any particular theory, efficient transduction of ocular (e.g., corneal) cells by rAAV described herein may be useful for the treatment of a subject having an ocular disease (e.g., corneal disease). Accordingly, methods and compositions for treating ocular disease are also provided herein. In some aspects, the disclosure provides a method for treating an ocular disease (e.g., corneal disease), the method comprising: administering to a subject having or suspected of having an ocular disease (e.g., corneal disease) an effective amount of rAAV, wherein the rAAV comprises (i) a capsid protein having a serotype selected from the group consisting of AAV5, AAV6, AAV6.2, AAV7, AAV8, AAV9, AAVrh.8, AAVrh.10, AAVrh.39, and AAVrh.43, and (ii) a nucleic acid comprising a promoter operably linked to a transgene.

As used herein, an "ocular disease" is a disease or condition of the eye. In some embodiments, an ocular disease is a corneal disease (e.g., a disease affecting the cornea or corneal cells). Non-limiting examples of ocular diseases include, but are not limited to, amblyopia, astigmatism, blepharitis, cataract, chalazion, conjunctivitis, diabetic retinopathy, dry eye, glaucoma, keratitis, keratonconus, macular degeneration, ocular hypertension, pinquecula, pterygium, retinitis pigmentosa, and ocular cancer (e.g., retinoblastoma, melanoma of the eye, lymphoma of the eye, medulloepithelioma, squamous cell cancer of the conjunctiva). Examples of corneal diseases include, but are not limited to, corneal neovascularization (NV), corneal dystrophy, corneal inflammation, corneal abrasion, and corneal fibrosis.

Ocular Disease-Associated Transgenes

In some aspects, an rAAV described by the disclosure comprises a nucleic acid encoding a transgene (e.g., miR-21, pri miR-184, pri miR-204) associated with ocular disease (e.g., corneal disease, such as corneal neovascularization). Without wishing to be bound by any particular theory, rAAV-based delivery of a transgene encoding a gene associated with a ocular disease is useful for treatment of subjects having an ocular disease (e.g., corneal disease). As used herein, "gene associated with an ocular disease" refers to any gene, wherein expression of that gene that provides a therapeutic benefit in a subject, e.g., to improve in the subject one or more symptoms of disease, e.g., a symptom of ocular disease (e.g., corneal neovascularization (NV), corneal dystrophy, corneal inflammation, corneal abrasion, and corneal fibrosis, etc.).

A gene associated with ocular disease can be a protein, polypeptide, antibody or fragment thereof (e.g., ScFv), toxin, or interfering RNA (e.g., siRNA, dsRNA, miRNA, artificial miRNA (ami-RNA), antagomir). Examples of genes associated with ocular disease include, but are not limited to Frizzled 4 (Fzd4; SEQ ID NO: 27), angiopoietin-1 (Angpt1, isoform 1 and/or isoform 2; SEQ ID NOs: 28-29, respectively), associated with corneal trauma; transforming growth factor β (TGF-β), Smad and mitogen-activated protein kinases (e.g., MAPK), associated with fibrotic disorders of the eye; IL-1α, IL-1β, IL-6, TNFα, interferon γ, transforming growth factor β1, and CD4, associated with traumatic corneal injury (e.g., alkali burn), protein p27, Cytokeratin 13, interleukin-like growth factor 2 (ILGF-2), junB, Metallothionein hMT-Ie, keratin 6 (e.g., KRT6), and beta 2-microglobulin, associated with corneal disease; and, connective tissue growth factor (CTGF) and vascular endothelial growth factor (VEGF).

In some aspects, the disclosure relates to the discovery that 3 genes encoding miRNA are significantly down-regulated (e.g., miR-184, miR-203, and miR-204) in response to ocular injury (e.g., corneal trauma). Without wishing to be bound by any particular theory, increasing the expression of down-regulated miRNA may provide a useful therapeutic benefit in a subject. Thus, in some embodiments, a rAAV described by the disclosure comprises a nucleic acid that encodes a micro-RNA (miRNA) that is down-regulated in response to ocular injury (e.g., corneal injury) or ocular disease, such as miR-184, miR-203, or miR-204. MicroRNAs are transcribed by RNA polymerase II as large RNA precursors called pri-miRNAs. In some embodiments, a rAAV described by the disclosure comprises a transgene encoding a pri-miRNA. In some embodiments, the pri-miRNA is pri-miRNA-184 or pri-miRNA-204.

In some aspects, the disclosure relates to the discovery that 35 genes encoding miRNA are significantly up-regulated (e.g., miR-21) in response to ocular injury (e.g., corneal trauma). Without wishing to be bound by any particular theory, decreasing the expression of up-regulated miRNA may provide a useful therapeutic benefit in a subject. Overexpression of miRNA can be reduced by using a "sponge design", for example a Tough Decoy (TuD) scaffold, as disclosed by Haraguchi et al., Nucleic Acids Res, 37: e43 (2009). A TuD is an ~60-bp long hairpin-shaped RNA with an internal loop exposing two miRNA binding sites. In some embodiments, a rAAV described by the disclosure comprises a transgene that encodes a TuD miRNA (e.g., miR-21 TuD miRNA).

In some embodiments, the gene associated with ocular disease (e.g., corneal disease) is selected from the group consisting of miR-106b, miR-1955, let-7i, miR-126-3p, miR-152, miR-24, miR99b, miR223, miR126-5p, miR146a, miR-150, miR191, miR-140, miR-221, miR301a, miR-484, miR-327, miR-2132, miR-28, miR-27b, miR-423-5p, miR-132, miR-19a, miR-1-3, miR-1-6, miR-17, miR-19b, miR-214, miR-21, miR-350, miR-425, miR-335-5p, miR-382, miR-2146, miR-804, miR-378, miR-184, miR-203, and miR-204.

In some embodiments the molecule that modulates miRNA activity (e.g., antagomir) modulates the activity of a miRNA selected from the group consisting of miR-106b, miR-1955, let-7i, miR-126-3p, miR-152, miR-24, miR99b, miR223, miR126-5p, miR146a, miR-150, miR191, miR-140, miR-221, miR301a, miR-484, miR-327, miR-2132, miR-28, miR-27b, miR-423-5p, miR-132, miR-19a, miR-1-3, miR-1-6, miR-17, miR-19b, miR-214, miR-21, miR-350, miR-425, miR-335-5p, miR-382, miR-2146, miR-804, miR-378, miR-184, miR-203, and miR-204.

In some aspects, the disclosure relates to the discovery that AAV-mediated delivery of molecules (e.g., miR-184, miR-204) that target certain ocular-disease associated genes (e.g., Fzd4, Angpt1) are useful for treatment of corneal disease, such as corneal neovascularization (NV). Thus, in some embodiments, a rAAV described by the disclosure comprises a nucleic acid encoding a transgene that has a region of complementarity to Fzd4 or Angpt1. A "region of complementarity" refers to a region on a nucleic acid antisense strand (e.g., miRNA) that is substantially complementary (e.g., 60%, 70%, 80%, 90%, 95%, 99%, or 100% complementary) to a sequence, for example a target sequence (e.g., Fzd4, Angpt1). A region of complementarity can be 1, 2, 3, 4, 5, 6, 7, 8, 9, 10, 15, 16, 17, 18, 19, 20, 21, 22, 23, 24, 25, 26, 27, 28, 29, 30, 40, or 50 nucleotides in length. In some embodiments, a region of complementarity is greater than 50 nucleotides in length. In some embodiments, a rAAV described by the disclosure comprises transgene, wherein the transgene comprises a region of complementarity to a sequence selected from the group consisting of SEQ ID NO: 1, 2, 3, 27, 28, and 29.

Recombinant Adeno-Associated Viruses (rAAVs)

In some aspects, the disclosure provides isolated AAVs. As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a nuclease and/or transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected.

In some aspects, the disclosure provides an rAAV having a capsid appropriate for targeting ocular tissue (e.g., corneal tissue). In some embodiments, the capsid has a serotype selected from the group consisting of AAV5, AAV6, AAV6.2, AAV7, AAV8, AAV9, AAVrh.8, AAVrh.10, AAVrh.39, and AAVrh.43. In some embodiments, the capsid has an AAVrh.10 serotype (e.g., SEQ ID NO: 14) or an AAVrh.39 serotype (e.g., SEQ ID NO: 15). The skilled artisan also recognizes that rAAV described herein may comprise variants of AAV5, AAV6, AAV6.2, AAV7, AAV8, AAV9, AAVrh.8, AAVrh.10, AAVrh.39, and AAVrh.43 serotype capsid proteins. In some embodiments, the capsid protein comprises an amino acid sequence that is at least 70%, at least 80%, at least 90%, at least 95%, or at least 99% identical to any one of SEQ ID NO: 7-16.

Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the instant disclosure relates to a host cell containing a nucleic acid that comprises a coding sequence encoding a gene associated with an ocular disease (e.g., corneal disease). In some embodiments, the instant disclosure relates to a composition comprising the host cell described above. In some embodiments, the composition comprising the host cell above further comprises a cryopreservative.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al, J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or functional RNA (e.g., guide RNA, miRNA) from a transcribed gene.

The foregoing methods for packaging recombinant vectors in desired AAV capsids to produce the rAAVs of the disclosure are not meant to be limiting and other suitable methods will be apparent to the skilled artisan.

Isolated Nucleic Acids

A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

The skilled artisan will also realize that conservative amino acid substitutions may be made to provide functionally equivalent variants, or homologs of the capsid proteins. In some aspects the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides disclosed herein.

Recombinant AAV Vectors (rAAV Vectors)

"Recombinant AAV (rAAV) vectors" of the disclosure are typically composed of, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., gRNA) or other gene product, of interest. The nucleic acid coding sequence is operatively linked to regulatory components in a manner which permits transgene transcription, translation, and/or expression in a cell of a target tissue.

In some embodiments, the instant disclosure relates to a recombinant AAV (rAAV) vector comprising a nucleic acid sequence including a promoter operably linked to a transgene, wherein the transgene is a gene associated with an ocular disease (e.g., corneal disease). In some embodiments, a rAAV vector further comprises nucleic acid sequences encoding one or more AAV inverted terminal repeat sequences (ITRs), for example AAV2 ITRs. In some embodiments, a rAAV vector further comprises nucleic acid sequences encoding one or more AAV ITRs selected from the group consisting of AAV3, AAV4, AAV5, and AAV6.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types (e.g., AAV2, AAV3, AAV4, AAV5, or AAV6 ITR sequences).

In addition to the major elements identified above for the recombinant AAV vector, the vector also includes control elements necessary which are operably linked to the transgene in a manner which permits its transcription, translation and/or expression in a cell transfected with the plasmid vector or infected with the virus produced by the disclosure. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence (e.g., coding sequence) and regulatory sequences are said to be "operably" linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., gRNA, miRNA).

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and/or other vector elements may be performed, as appropriate, and many such sequences are available [see, e.g., Sambrook et al, and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, P et al., Human Gene Therapy, 2000; 11: 1921-1931; and Klump, H et al., Gene Therapy, 2001; 8: 811-817).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter is an enhanced chicken β-actin promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 268:1766-1769 (1995), see also Harvey et al, Curr. Opin. Chem. Biol., 2:512-518 (1998)), the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: an eye-specific retinoschisin promoter or K12 promoter, a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

In some embodiments, one or more bindings sites for one or more of miRNAs are incorporated in a transgene of a rAAV vector, to inhibit the expression of the transgene in one or more tissues of an subject harboring the transgene. The skilled artisan will appreciate that binding sites may be selected to control the expression of a transgene in a tissue specific manner. For example, binding sites for the liver-specific miR-122 may be incorporated into a transgene to inhibit expression of that transgene in the liver. The target sites in the mRNA may be in the 5' UTR, the 3' UTR or in the coding region. Typically, the target site is in the 3' UTR of the mRNA. Furthermore, the transgene may be designed such that multiple miRNAs regulate the mRNA by recognizing the same or multiple sites. The presence of multiple miRNA binding sites may result in the cooperative action of multiple RISCs and provide highly efficient inhibition of expression. The target site sequence may comprise a total of 5-100, 10-60, or more nucleotides. The target site sequence may comprise at least 5 nucleotides of the sequence of a target gene binding site.

Recombinant AAV Administration Methods

The rAAVs may be delivered to a subject in compositions according to any appropriate methods known in the art. The rAAV, preferably suspended in a physiologically compatible carrier (i.e., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments, a host animal does not include a human.

Delivery of the rAAVs to a mammalian subject may be by, for example, intraocular injection or topical administration (e.g., eye drops). In some embodiments, the intraocular injection is intrastromal injection, subconjunctival injection, or intravitreal injection. In some embodiments, the injection is not topical injection. Combinations of administration methods (e.g., topical administration and intrastromal injection) can also be used.

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

In some embodiments, a composition further comprises a pharmaceutically acceptable carrier. Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAVs are administered in sufficient amounts to transfect the cells of a desired tissue (e.g., ocular tissue, such as corneal tissue) and to provide sufficient levels of gene transfer and expression without undue adverse effects. Examples of pharmaceutically acceptable routes of administration include, but are not limited to, direct delivery to the selected organ (e.g., intrastromal delivery to the eye), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of the rAAV is generally in the range of from about 1 ml to about 100 ml of solution containing from about $10^9$ to $10^{16}$ genome copies. In some cases, a dosage between about $10^{11}$ to $10^{13}$ rAAV genome copies is appropriate. In certain embodiments, $10^{10}$ or $10^{11}$ rAAV genome copies is effective to target ocular tissue (e.g., corneal tissue). In some cases, stable transgenic animals are produced by multiple doses of an rAAV.

In some embodiments, a dose of rAAV is administered to a subject no more than once per calendar day (e.g., a 24-hour period). In some embodiments, a dose of rAAV is administered to a subject no more than once per 2, 3, 4, 5, 6, or 7 calendar days. In some embodiments, a dose of rAAV is administered to a subject no more than once per calendar week (e.g., 7 calendar days). In some embodiments, a dose of rAAV is administered to a subject no more than bi-weekly (e.g., once in a two calendar week period). In some embodiments, a dose of rAAV is administered to a subject no more than once per calendar month (e.g., once in 30 calendar days). In some embodiments, a dose of rAAV is administered to a subject no more than once per six calendar months. In some embodiments, a dose of rAAV is administered to a subject no more than once per calendar year (e.g., 365 days or 366 days in a leap year).

In some embodiments, rAAV compositions are formulated to reduce aggregation of AAV particles in the composition, particularly where high rAAV concentrations are present (e.g., ~$10^{13}$ GC/ml or more). Appropriate methods for reducing aggregation of may be used, including, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments, rAAVs in suitably formulated pharmaceutical compositions disclosed herein are delivered directly to target tissue, e.g., direct to ocular tissue (e.g., corneal tissue) However, in certain circumstances it may be desirable to separately or in addition deliver the rAAV-based therapeutic constructs via another route, e.g., subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by intrastromal injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a suitable sterile aqueous medium may be employed. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500.ANG., containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

Kits and Related Compositions

The agents described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

In some embodiments, the instant disclosure relates to a kit for producing a rAAV, the kit comprising a container housing an isolated nucleic acid encoding an AAV capsid protein selected from any one of SEQ ID NO: 7-16. In some embodiments, the kit further comprises instructions for producing the rAAV. In some embodiments, the kit further comprises at least one container housing a recombinant AAV vector, wherein the recombinant AAV vector comprises a transgene (e.g., a gene associated with ocular disease, such as corneal disease).

In some embodiments, the instant disclosure relates to a kit comprising a container housing a recombinant AAV having an isolated AAV capsid protein having an amino acid sequence as set forth in SEQ ID NO: 14 or SEQ ID NO: 15.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit.

As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for producing specific somatic animal models.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The instructions included within the kit may involve methods for detecting a latent AAV in a cell. In addition, kits of the disclosure may include, instructions, a negative and/or positive control, containers, diluents and buffers for the sample, sample preparation tubes and a printed or electronic table of reference AAV sequence for sequence comparisons.

EXAMPLES

Figure 1B:
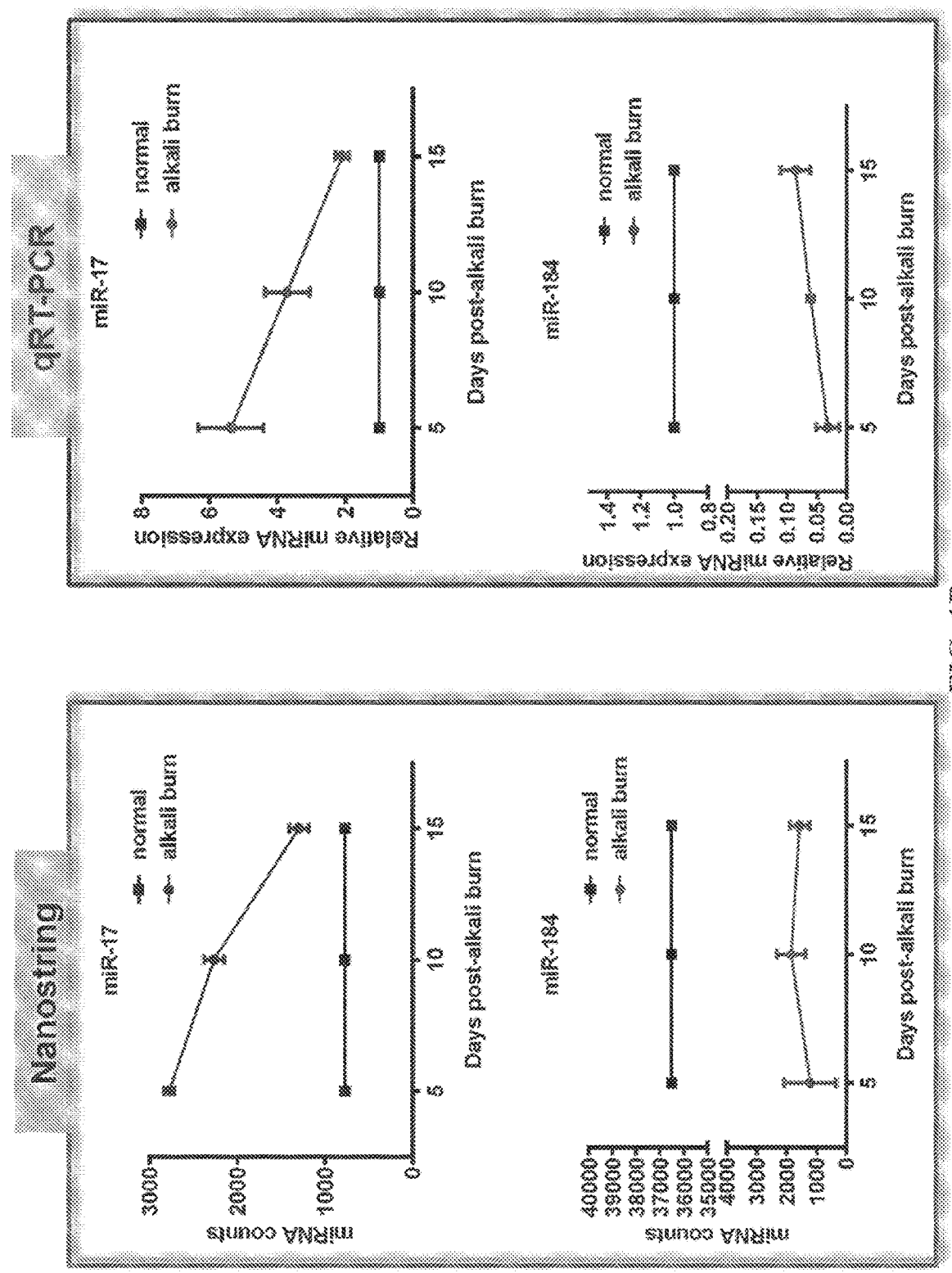
Figure 1C:
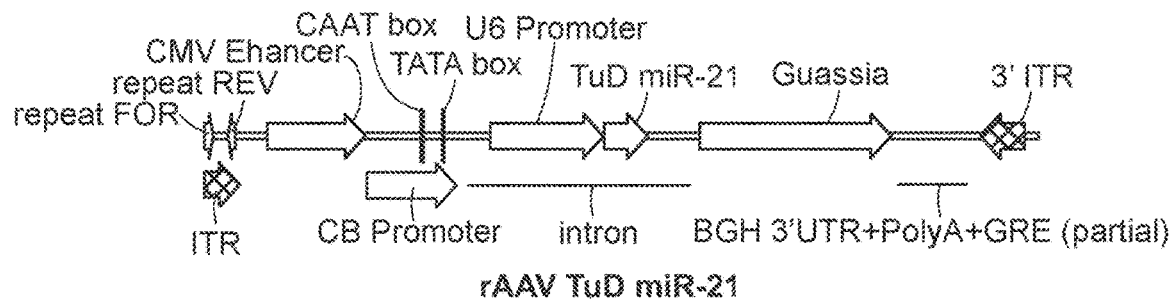
Figure 1C:
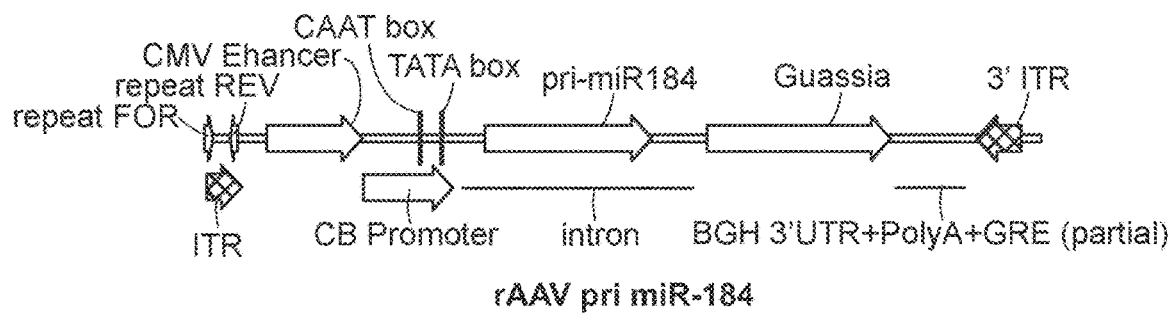
Figure 1C:
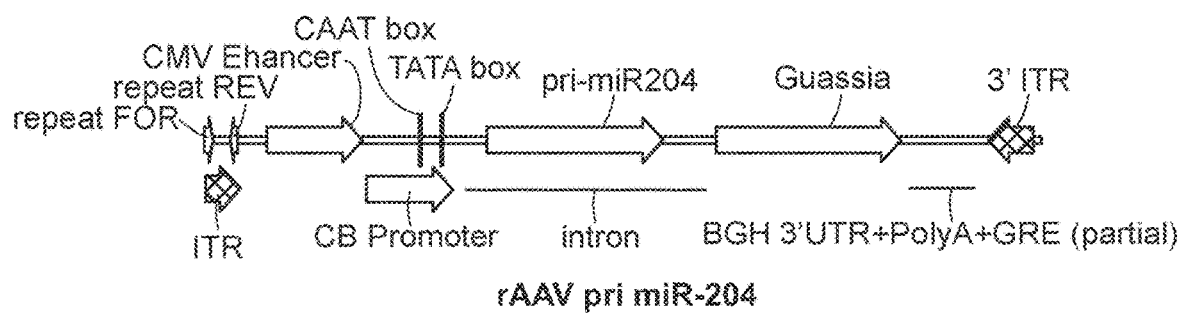
Figure 2A:
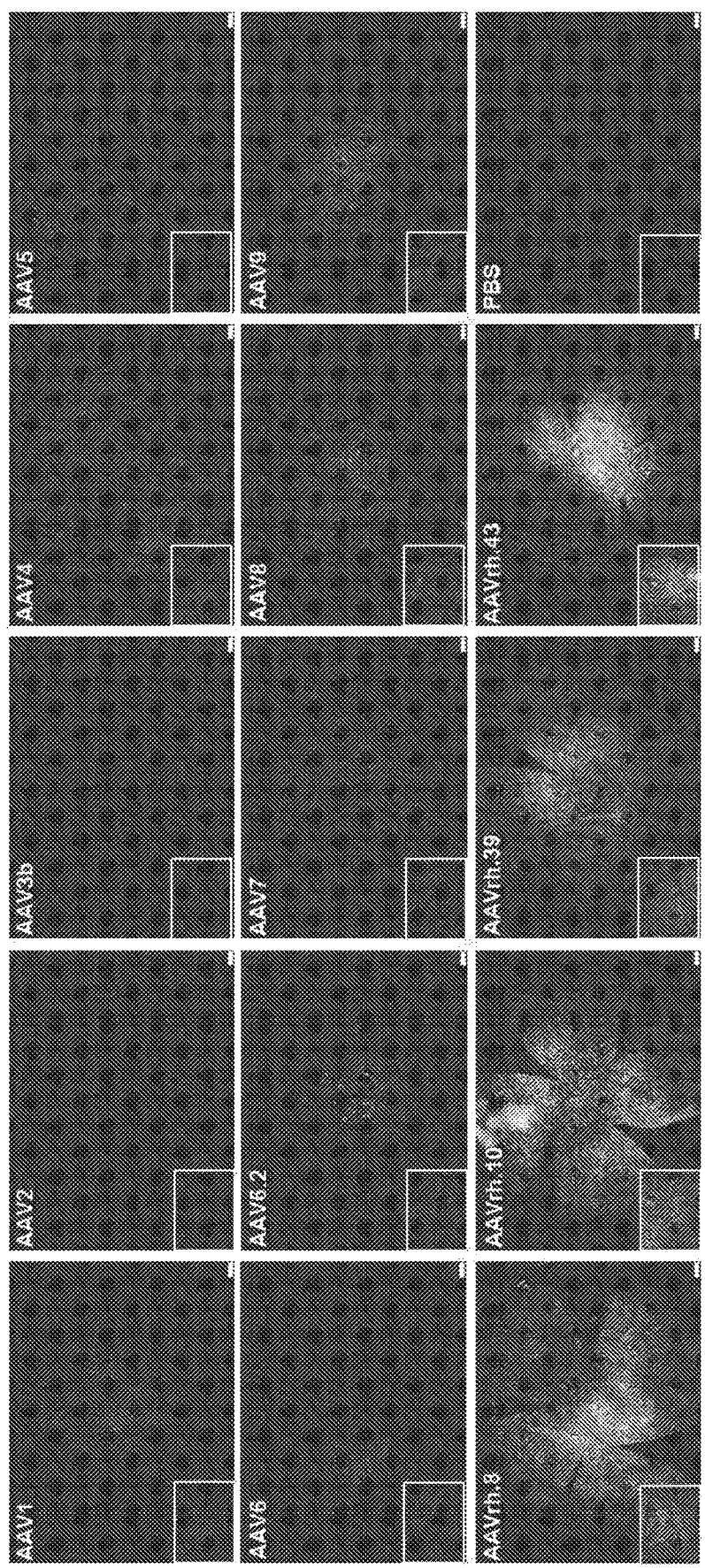
FIGS. 2A-2D show rAAV serotype screening for gene transfer to mouse cornea.
Figure 2B:
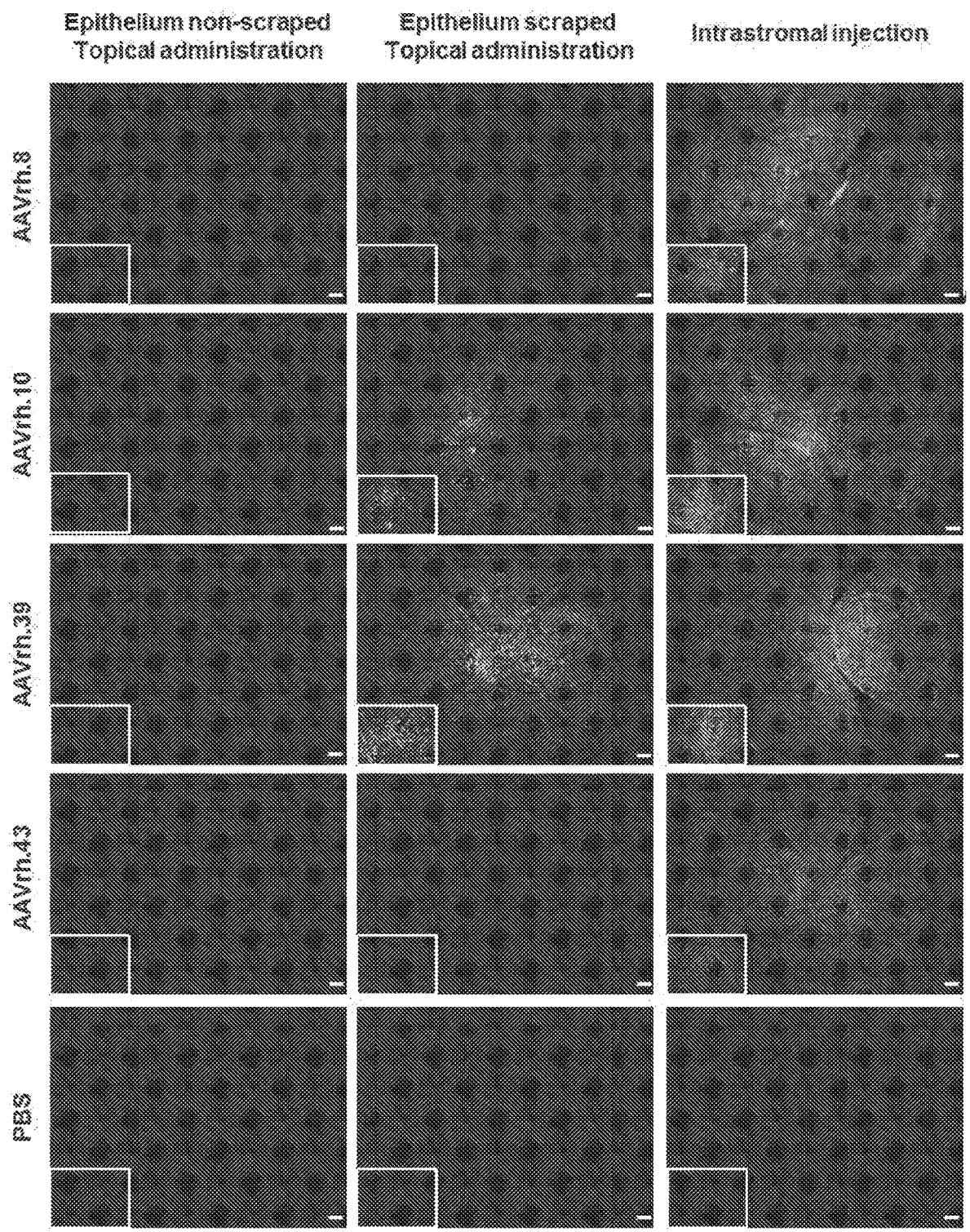
Figure 2C:
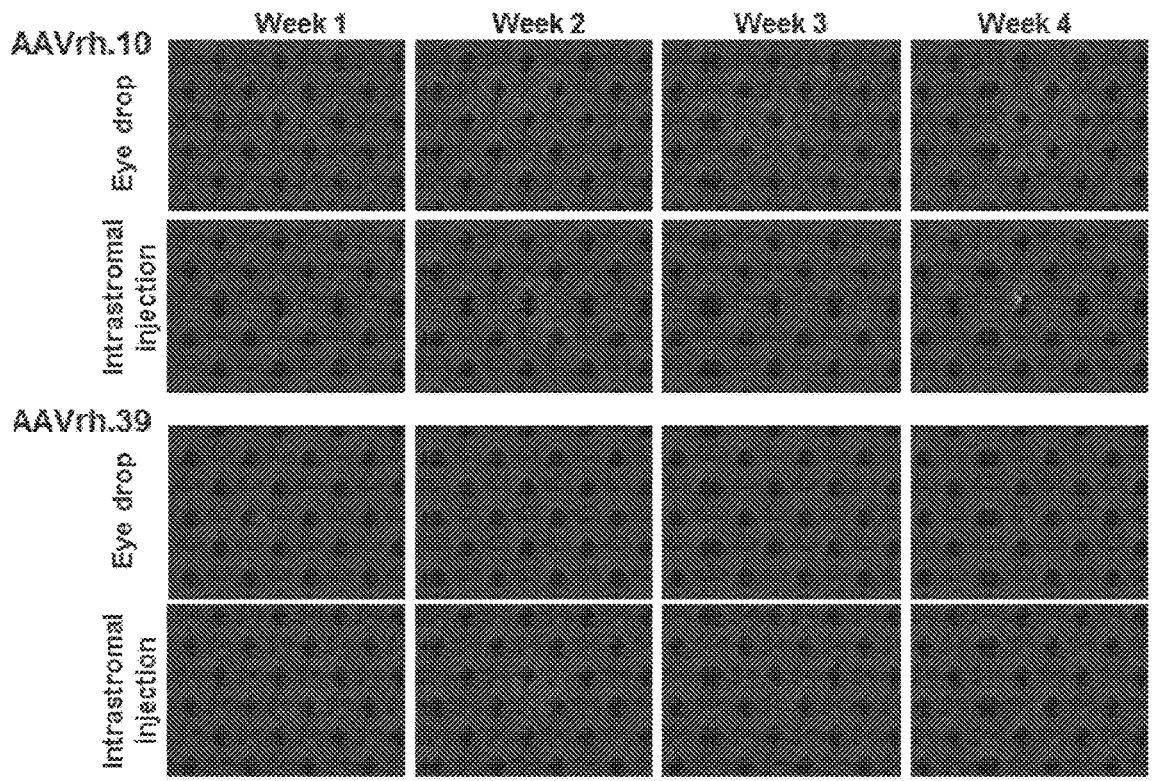
Figure 2D:
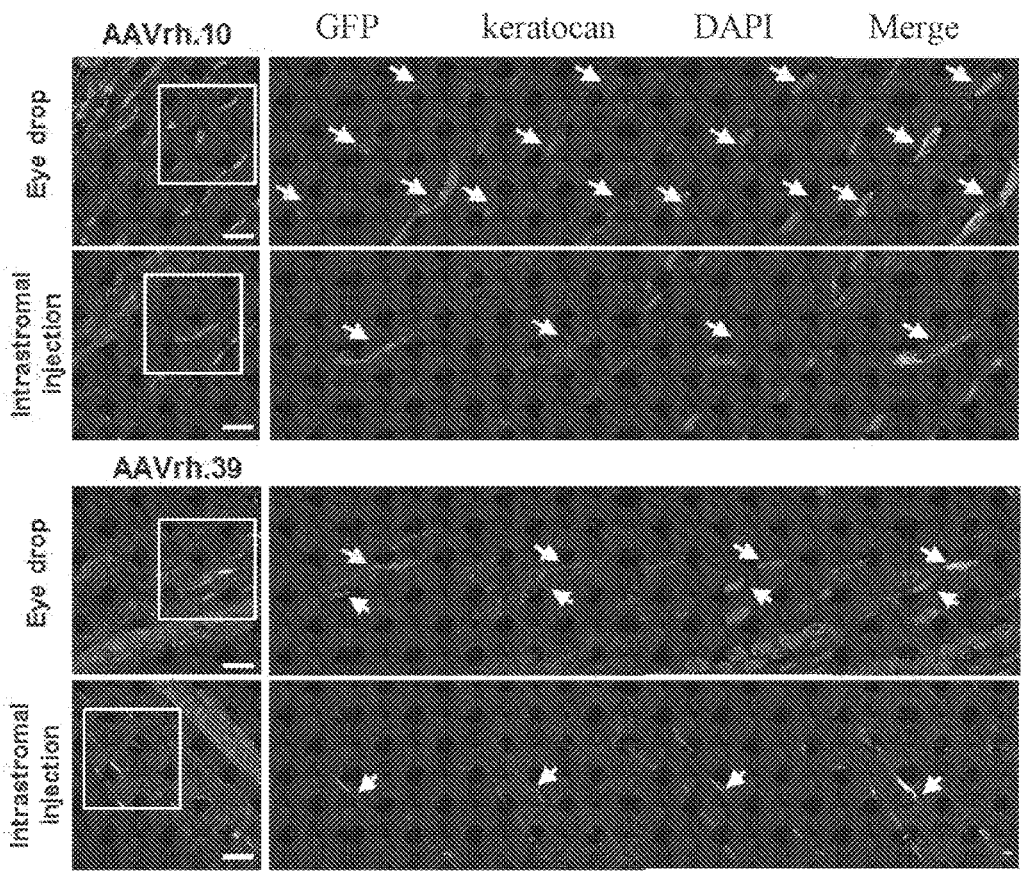

Example 1. Anti-Angiogenic miRNA Therapeutics for the Prevention and/or Treatment of Corneal NV In this example, anti-angiogenic miRNA therapeutics for the prevention and/or treatment of corneal NV are described. First, target miRNAs that play roles in corneal NV were identified. To date, there has been no report on miRNA expression profile of corneal NV. Using Nanostring technologies and the classic alkali-burn induced corneal NV mouse model, small RNAs prepared from corneal tissues harvested from of study mice were profiled for expression levels of 618 mouse miRNAs before and days 5, 10 and 15 after alkali injury (corneal NV in mouse model begins to regress naturally after 2 weeks post alkali burn). 35 up-regulated and 3 down-regulated miRNAs were identified in the mouse neovascularized corneas (FIG. 1A). The expression profiles of 19 miRNAs were further verified by qRT-PCR; examples of data generated are shown in FIG. 1B. Among them, the top 3 miRNAs (miR-21, miR-184 and miR-204) with over 10-fold expression change were selected as therapeutic candidates. Then, pri/TuD miRNA constructs, which overexpress or inhibit the target miRNA expression, were cloned and verified (FIG. 1C).

rAAV vectors were tested for efficient delivery of candidate miRNA pri-miRNAs or the corresponding TuD RNAs to the corneas of alkali-burn induced corneal NV mice. The potency of the pri-miRNA and TuD RNAs in preventing or treating corneal NV was evaluated. To this end, 14 serotypes of rAAV EGFP (AAV1, AAV2, AAV3b, AAV4, AAV5, AAV6, AAV6.2, AAV7, AAV8, AAV9, AAVrh.8, AAVrh.10, AAVrh.39, AAVrh.43) were assessed for gene transfer efficiency in mouse corneas after delivery by intrastromal injection in order to identify the most efficient AAV serotypes for miRNA therapeutics. Among them, for the first time, rAAVrh.8, rh.10, rh.39 and rh.43 were found to be highly efficient in transgene delivery (FIG. 2A). Transduction efficiency of these four rAAV serotypes (e.g., rh.8, rh.10, rh.39, and rh.43) was tested by topical administration with/without corneal epithelium removed, to further explore the feasibility of using rAAV to deliver transgenes into cornea by eye dropping. Data indicated that rAAVrh.10 and rh.39 showed better gene transfer efficiency through topical administration in the condition that the corneal epithelium was removed (FIG. 2B). The in vivo observation indicated that both rAAVrh.10 and rh.39 EGFP expression started from as early as 1 week after intrastromal injection or topical administration, reached the peak at around the 2$^{nd}$ week, and continued at least for 2 more weeks (FIG. 2C). Moreover, it was observed that rAAVrh.10 and rh.39 efficiently transduced keratocytes, which are the major cells in corneal stroma (FIG. 2D).

Figure 3A:
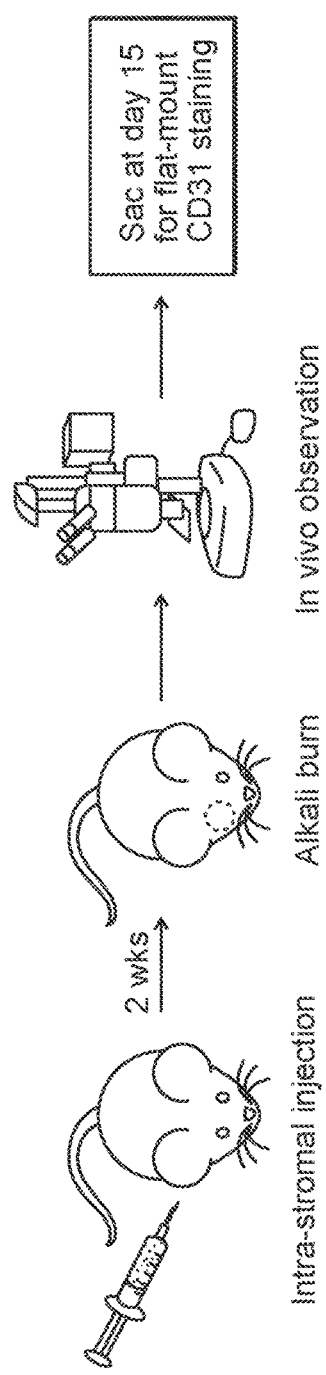
FIGS. 3A-3D show rAAV mediated miRNA therapeutics inhibit corneal NV by intrastromal injection.
Figure 3B:
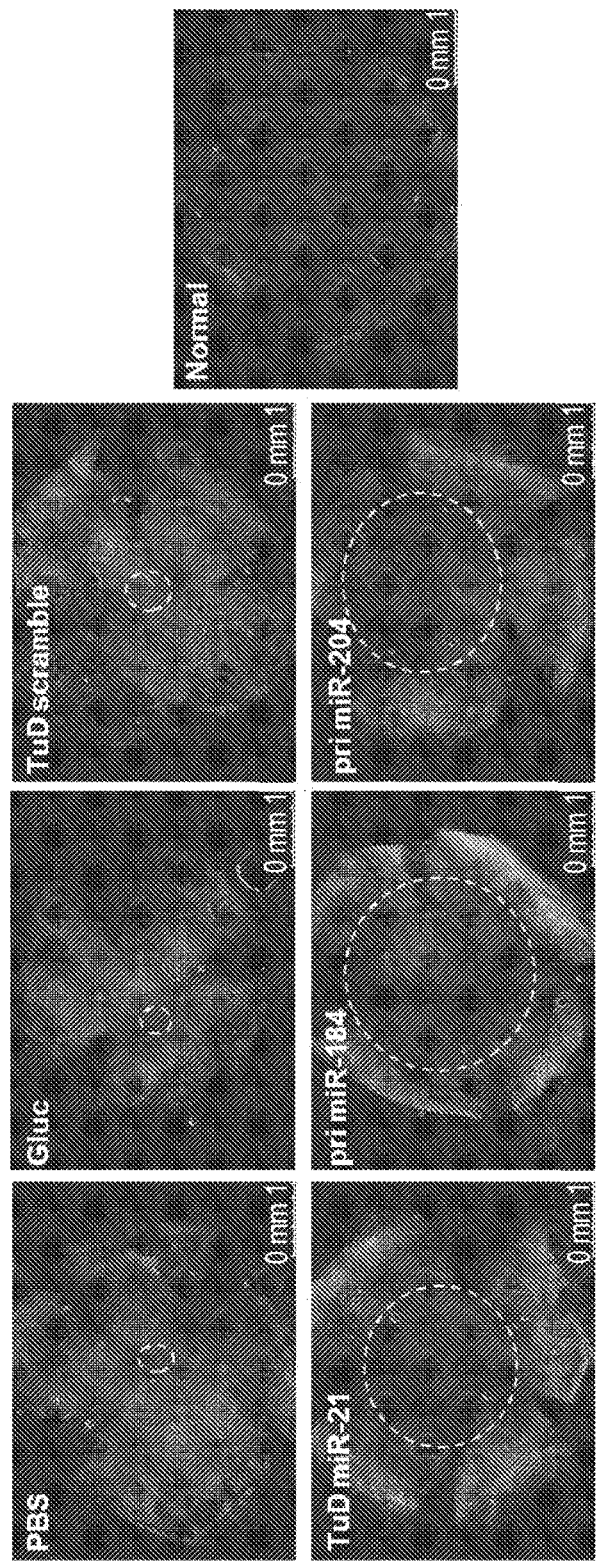
Figure 3C:
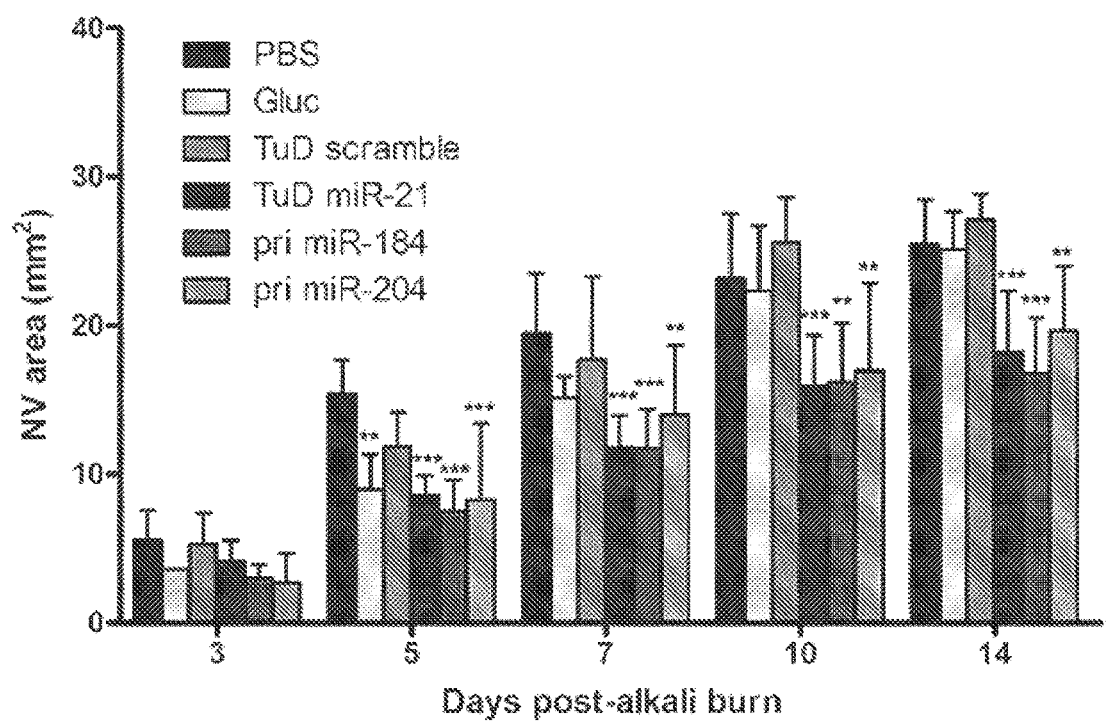
Figure 3D:
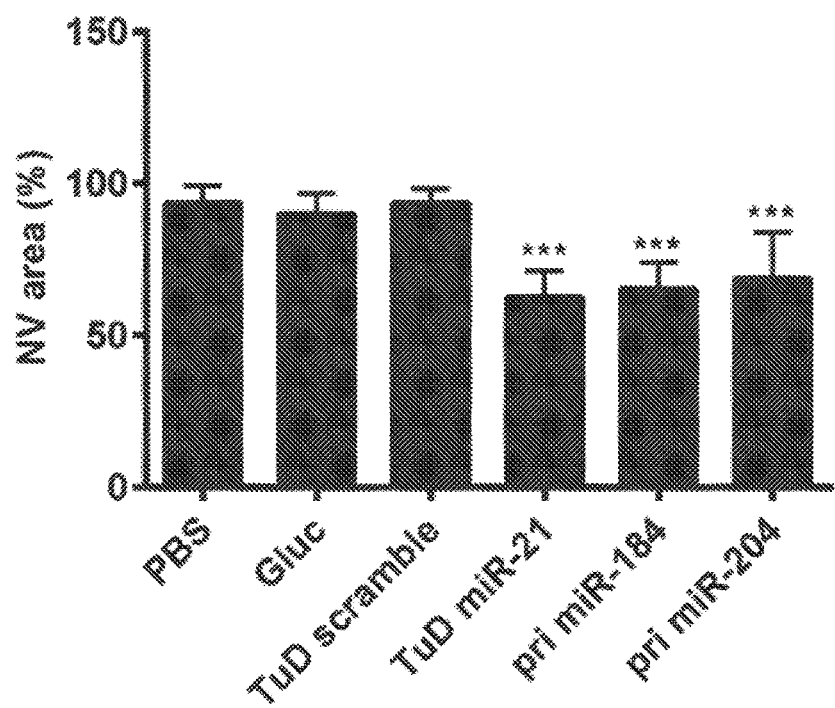
Figure 4A:
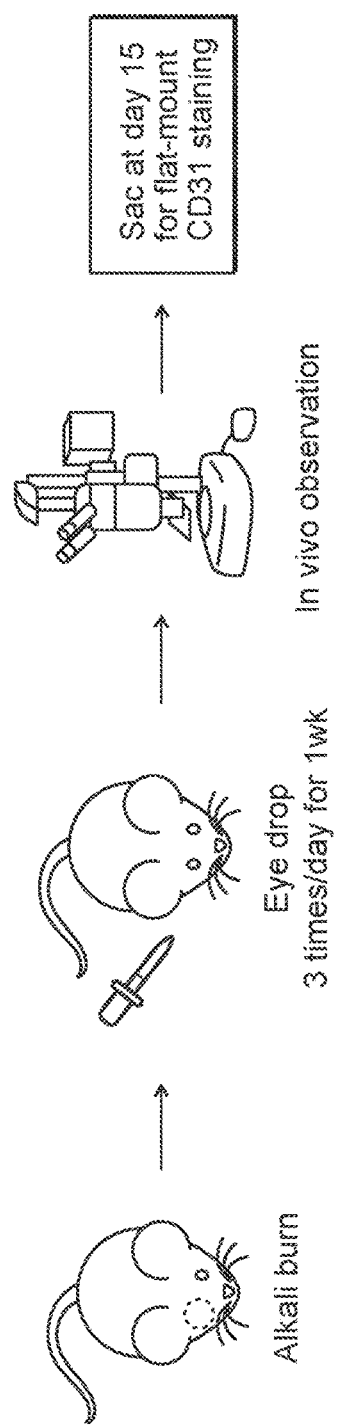
FIGS. 4A-4D show rAAV mediated miRNA therapeutics inhibit corneal NV by topical administration at days 7 and 10 after alkali burn.
Figure 4B:
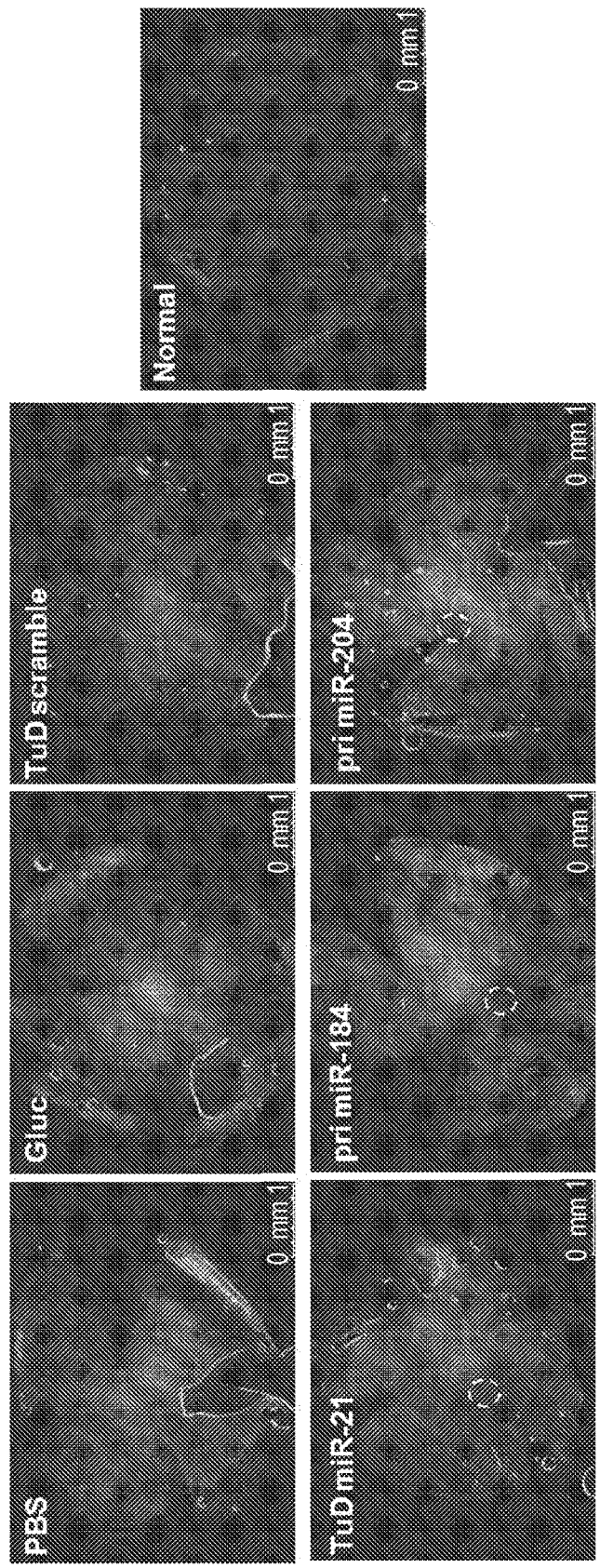
Figure 4C:
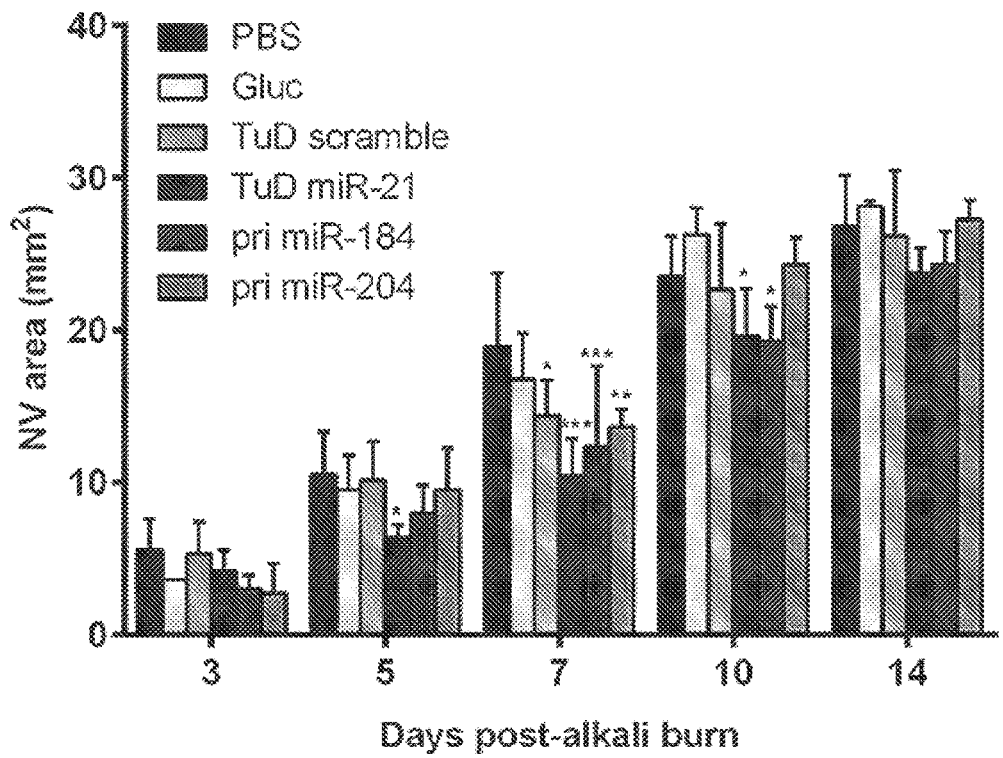
Figure 4D:
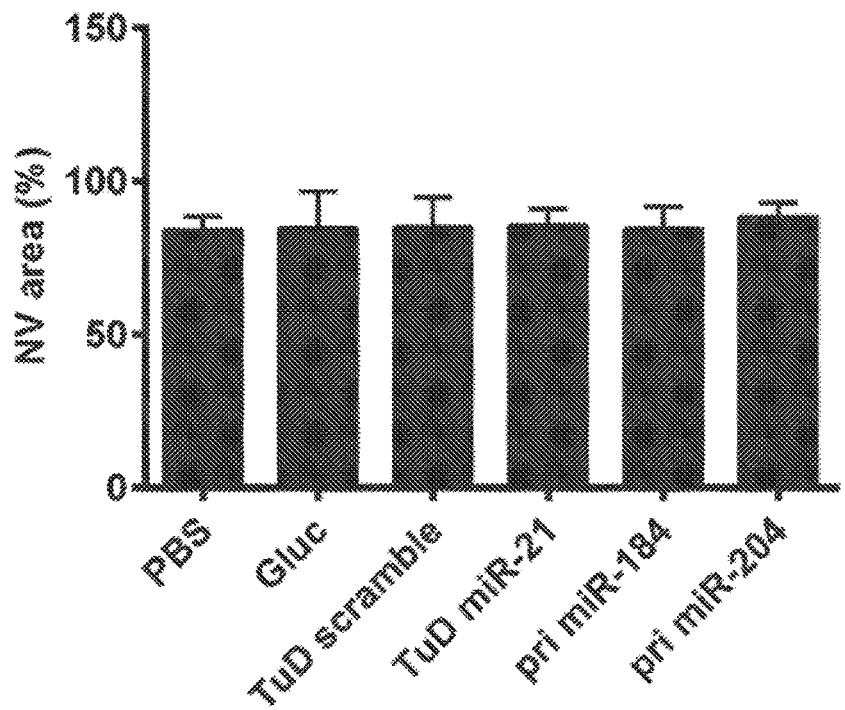
Figure 5A:
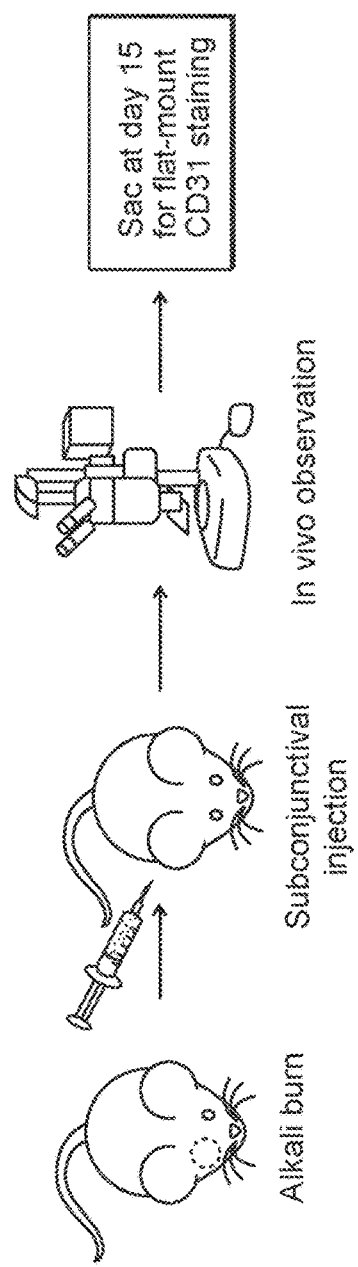
FIGS. 5A-5D show rAAV mediated miRNA therapeutics inhibit corneal NV by subconjunctival injection.
Figure 5B:
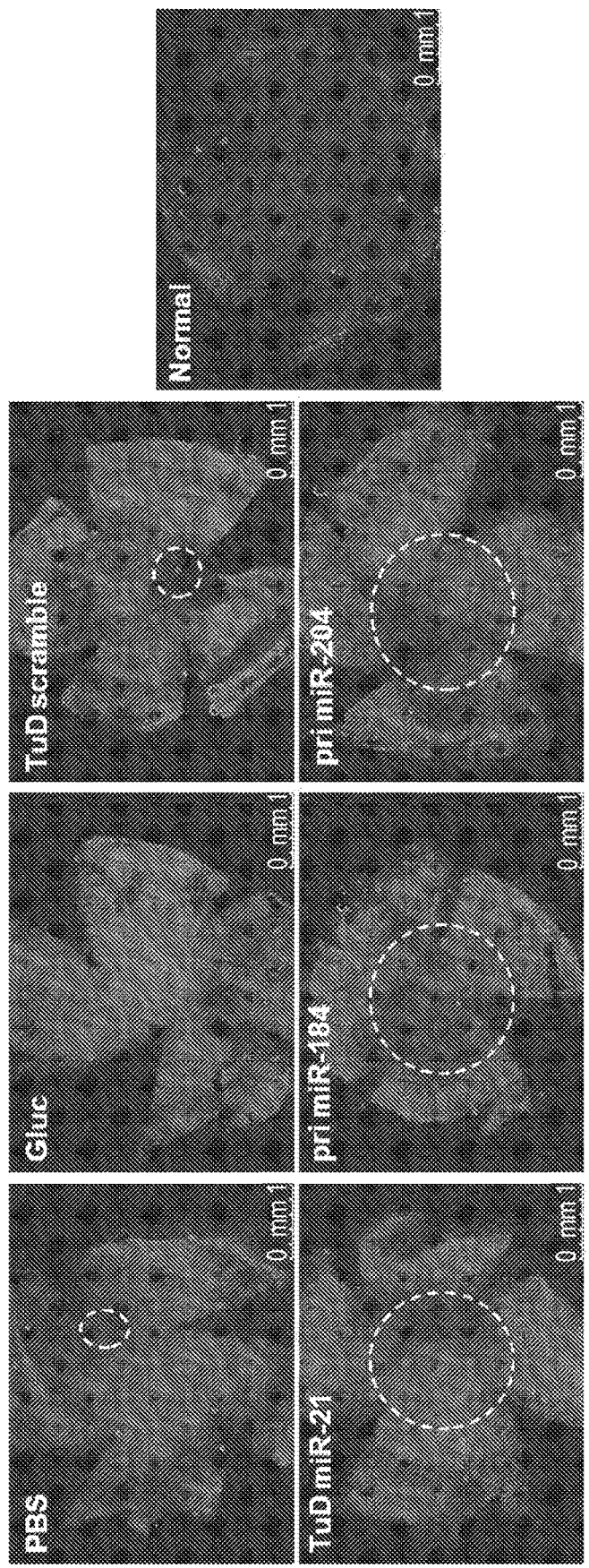
Figure 5C:
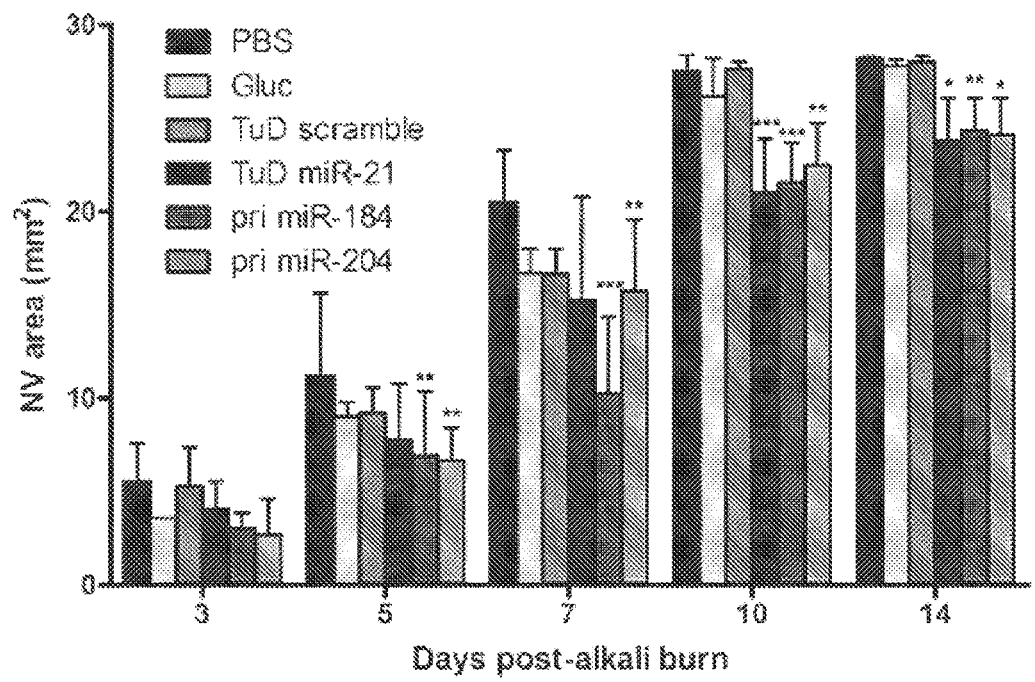
Figure 5D:
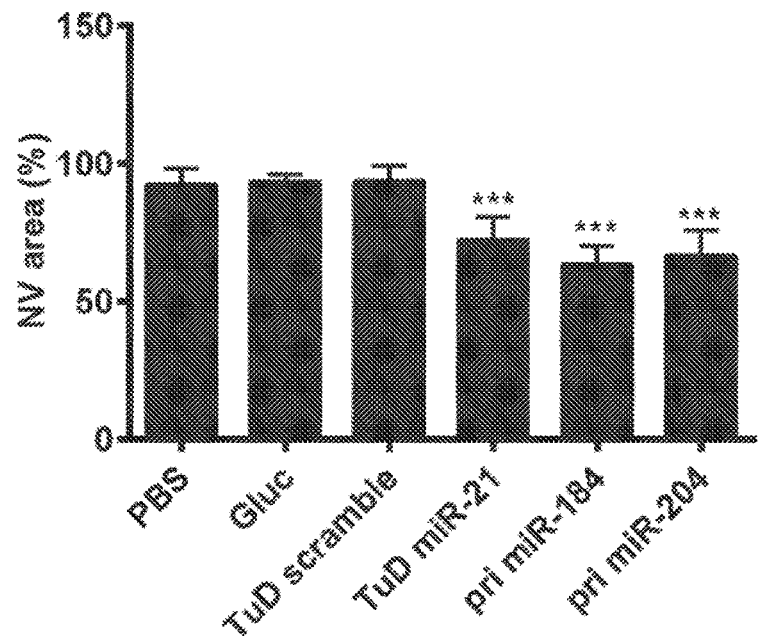

Based on these findings, rAAVrh.10 was selected to deliver candidate pri/TuD miRNAs into corneal stroma by intrastromal injection and topical administration to estimate their effects on corneal NV. Considering the time course of transgene expression delivered by rAAV vector and the feasibility of clinical application, intrastromal injection was used as a prevention strategy, delivering the rAAV vectors into mouse corneal stroma 2 weeks before alkali burn (FIG. 3A). Meanwhile, conducting topical administration right after alkali burn was tested as a treatment for injury induced corneal NV (FIG. 4A). In both experiments, the corneal NV was observed and measured in vivo at days 3, 5, 7, 10 and 14 after alkali burn (FIG. 3C and FIG. 4C), and then the mice were sacrificed on day 15 post alkali burn with the corneas enucleated for whole flat-mount immunofluorescence staining. The cell marker of vascular endothelial cells, CD31 was used to visualize the new blood vessels in corneas (FIG. 3B and FIG. 4B) and the percentage of neovascularized area was quantified using Imaris 8 software (FIG. 3D and FIG. 4D). Data suggested that all three constructs including TuD miR-21, pri miR-184 and pri miR-204, effectively inhibited corneal NV through intrastromal injection; thus serving as a prevention method (FIG. 3). However, none of them showed sustained inhibitory effect (e.g., post day 10) on corneal NV when delivered by topical administration (FIG. 4).

In sum, this example demonstrates that miRNA-targeted therapeutics can be delivered as either rAAV or synthetic nucleic acid drugs (e.g., miRNA mimics and antagomir) to offer an additional clinical option for preventing and treating corneal NV.

Example 2. Efficient Transduction of Corneal Stroma by Adeno-Associated Virus Serotype Vectors for Implications in Gene Therapy of Corneal Diseases Materials and Methods Primary antibody of rabbit anti-mouse keratocan was obtained from Santa Cruz Biotechnology (Dallas, TX, USA). Primary antibody of rabbit anti-mouse GFP, and goat anti rabbit IgG (H+L) secondary antibody Alexa Fluor 488 conjugate, as well as Alexa Fluor 568 conjugate, were purchased from Life Technologies (Grand Island, NY, USA). VECTASHIELD® anti-fade mounting medium with 4',6-diamidino-2-phenylindole (DAPI) was obtained from Vector Laboratories (Burlingame, CA, USA).

Six-to-eight-week old female C57BL/6J mice (Charles River Laboratories) were maintained and used according to the guidelines of the Institutional Animal Care and Use Committee (IACUC) of the University of Massachusetts Medical School. Prior to experimental operation, all animals were anesthetized by an intraperitoneal injection of a ketamine-xylazine (100 mg/kg and 10 mg/kg, respectively) mixture. The right eyes of mice were treated as experimental eyes.

rAAV Vector Production rAAV vectors were generated by triple plasmid transfection of HEK293 cells. The self-complimentary (sc) pAAV-CB-PI-EGFP plasmid was used for packaging with capsids from 14 different serotypes to produce rAAV1, rAAV2, rAAV3b, rAAV4, rAAV5, rAAV6, rAAV6.2, rAAV7, rAAV8, rAAV9, rAAVrh.8, rAAVrh.10, rAAVrh.39 and rAAVrh.43. Viruses were purified with CsCl gradient ultracentrifugation and titered by both quantitative polymerase chain reaction (qPCR) and silver staining of SDS-Page.

rAAV Transduction of Mouse Cornea by Intra-Stromal Injection

Figure 6A:
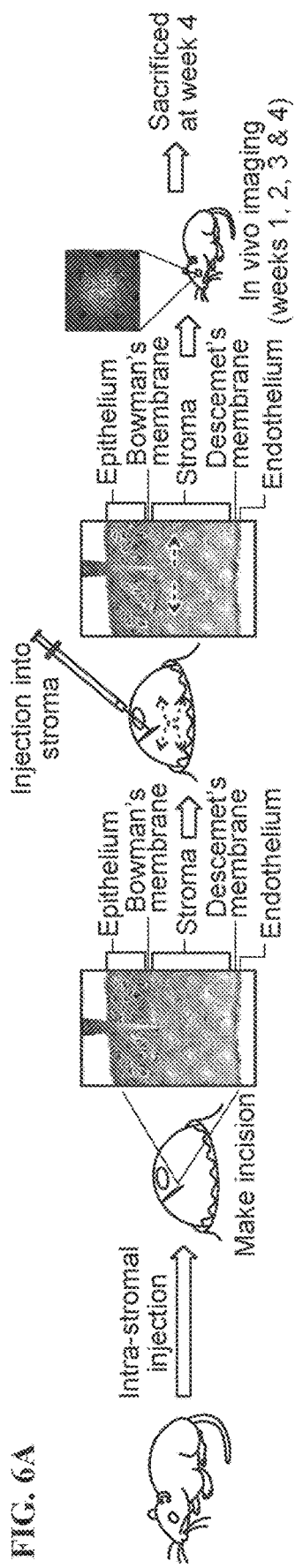
FIGS. 6A-6B show the overview of intra-stromal injection and topical administration of rAAV vectors to cornea.
Figure 6B:
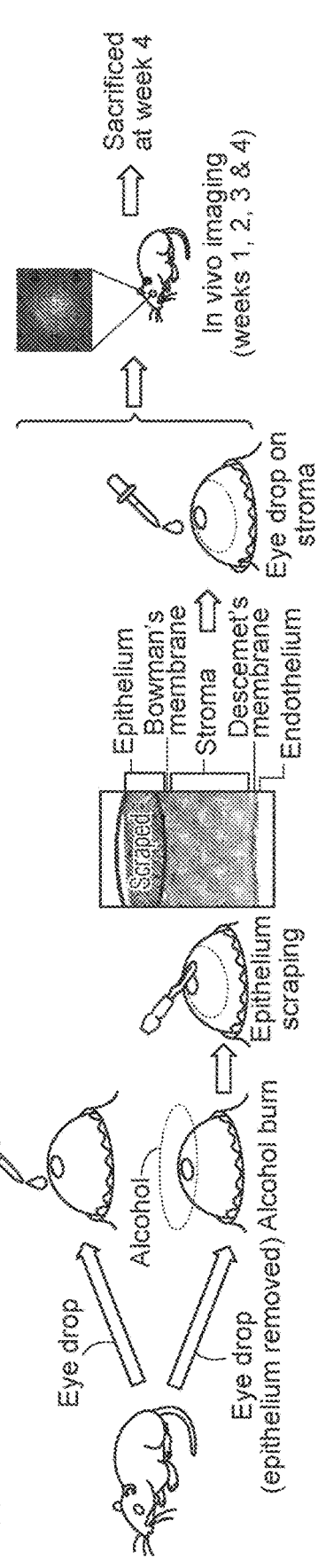

Intra-stromal injection was performed according to the previously published procedure (FIG. 6A). Briefly, a 1.0 mm long incision was first created through the corneal epithelium using the tip of a 26-gauge needle, which was performed equidistant between the cornea-scleral junction and the corneal center. The tip of a 33-gauge needle attached to a 5 µL Hamilton microliter syringe (Hamilton, Reno, NV, USA) was then introduced through the incision into the corneal stroma and $2.4 \times 10^{10}$ genomic copies (GC) of vector in 4 µL of PBS were injected. The antibiotic ointment was applied after injection.

rAAV Transduction of Mouse Cornea by Topical Administration rAAV transduction through topical administration was conducted with or without corneal epithelium removed (FIG. 6B). The corneal epithelium scraping was performed accordingly. Alcohol soaked filter membrane was applied on each cornea for 20 seconds and the whole layer of epithelium covering about 80% corneal area was removed by gentle scraping with a #64 Beaver blade (Beaver Visitec, Waltham, MA, USA) under an operating microscope. $2.4 \times 10^{10}$ GC of virus vectors in 4 µL of PBS were directly applied to the intact cornea or the corneal stroma after epithelium removal and allowed to sit for 2 minutes. After drying the cornea with antiseptic cotton swab, an antibiotic ointment was applied afterwards.

In Vivo Microscopy Studies

Animals of each group were observed in vivo at the 1st, 2nd, 3rd and 4th week after rAAV administration. The image of EGFP expression in the mouse eye was captured utilizing the Micron III camera (Phoenix Research Labs, Pleasanton, CA, USA).

Histological and Immunofluorescence-Histochemical Analysis

Following sacrifice, mouse eyes were enucleated. Eight eyes from each group were fixed in 4% paraformaldehyde. Among them, four corneas with limbus were harvested for corneal flat-mounts, which were blocked in 5% goat serum in PBS and stained with 1:1000 primary antibody of rabbit anti-mouse GFP, followed by 1:1500 secondary antibody of goat anti-rabbit IgG-Alexa Fluor 488. The corneal whole mounts were then mounted for observation and imaging analysis.

The remaining four eyeballs harvested from each group were embedded in O.C.T compound (Fisher Scientific, Pittsburgh, PA, USA) for cryosectioning at a thickness of 10 µm, then blocked in 5% goat serum and stained with 1:50 primary antibody of rabbit anti-mouse keratocan and 1:1500 secondary antibody of goat anti-rabbit IgG-Alexa Fluor 568. All immunofluorescence stained sections were mounted with VECTASHIELD® medium containing DAPI and fluorescence detection of native EGFP expression and stained keratocan in eyeball samples was generated using the Leica DM5500 microscope. The embedded samples were stored at −80° C.

Two eyes from each group were fixed in 10% formalin and embedded in paraffin to be sectioned later at 4-µm thickness and stained with Haematoxylin and Eosin (H&E) for histological analysis. Images were obtained by the Leica DMC2900 microscope.

Quantification Analysis of EGFP Expression in Corneal Whole Mounts

Digital images of the corneal whole mounts were taken by Leica DM5500. EGFP positive area and fluorescence signal intensity was measured on these flat-mounts using ImageJ software. The total corneal area was outlined using the innermost vessels of the limbal arcade as the border. Total area containing EGFP expression was then normalized to the total corneal area, and the percentage of EGFP positive area was calculated. Mice treated with PBS were used as the negative control.

Quantification Analysis of EGFP Expression in Cryosections

Four eyeballs from each group were fixed and cryosectioned for keratocan immune-staining. For each sample, images of five corneal slides were captured. The EGFP cells and keratocan$^+$ cells on each image were counted separately, and the number of co-localized cells was then obtained using Imaris 8 software (Bitplane, Concord, MA, USA) to determine percentages of EGFP$^+$keratocan$^+$ cells among keratocan$^+$ cells.

Quantification analysis of rAAV genome copy number and RNA expression Corneas of three eyes in each group were harvested. Genomic DNA was isolated using QIAamp DNA kit (Qiagen, Hilden, Germany) following the manufacturer's instructions, and then digested with Mol Neurobiol SalI (NEB) at >10 U/µg of DNA under 37° C. for 1 hour. There are two SalI sites in the rAAV genome, and SalI digestion ensures single copies of EGFP transgene for droplet digital PCR (ddPCR) quantification. Multiplexed ddPCR was performed on a QX200 ddPCR system (Bio-Rad Laboratories, Hercules, CA, USA) using Taqman reagents targeting EGFP (Catalog #4400293, Life Technologies, Carlsbad, CA, USA) and the reference gene transferrin receptor (Tfrc) (Catalog #4458367, Invitrogen, Waltham, MA, USA). rAAV genome copy numbers per diploid genome were calculated as EGFP transgene copy numbers per two Tfrc gene copies. Liver DNA from mice with intravenous injection of rAAV9 EGFP vectors ($1 \times 10^{12}$ genomic copies) was used as a reference for a high vector genome copy number per cell.

Total RNA was extracted using the RNeasy 96 QIAcube HT kit with on-column DNase I digestion (Qiagen, Valencia, CA, USA), and then reverse transcribed into cDNA and subjected to multiplexed ddPCR using Taqman reagents targeting EGFP and Glyceraldehyde-3-Phosphate Dehydrogenase (GAPDH) (Catalog #4352339E, Life Technologies, Carlsbad, CA, USA). The quantity of EGFP mRNA was normalized to GAPDH mRNA and expressed as EGFP mRNA copy numbers per GAPDH mRNA copy.

Statistical Analysis

Results were expressed as mean±SD. Analysis was performed with one-way analysis of variance (ANOVA) for multiple variables and Bonfferoni's post-hoc multiple-comparison test was used for between-group differences using GraphPad Prism 6.0 (GraphPad Software, La Jolla, CA, USA), p values<0.05 were considered significant in all cases.

Figure 7A:
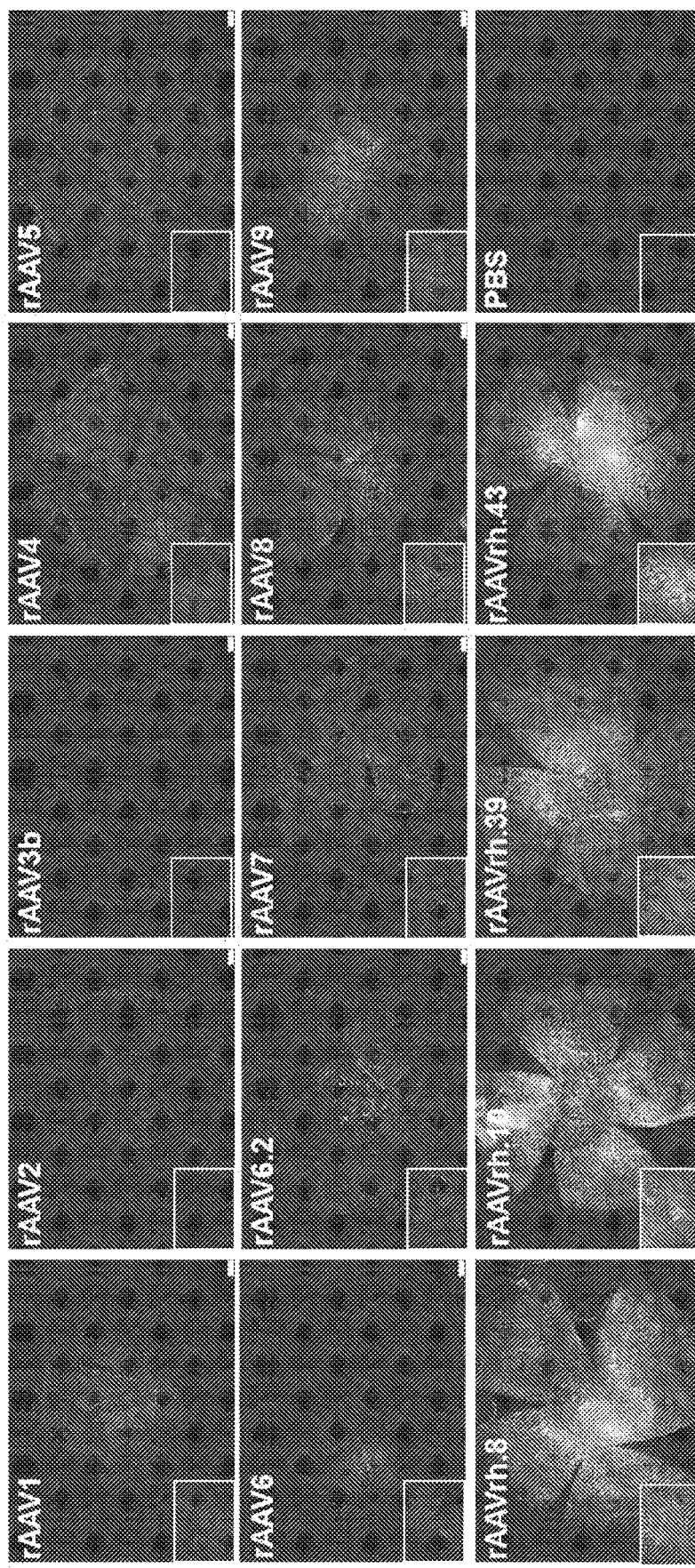
FIGS. 7A-7C show intra-stromal injection of rAAVrh.8, rAAVrh.10, rAAVrh.39 and rAAVrh.43 efficiently transduce mouse cornea.
Figure 7B:
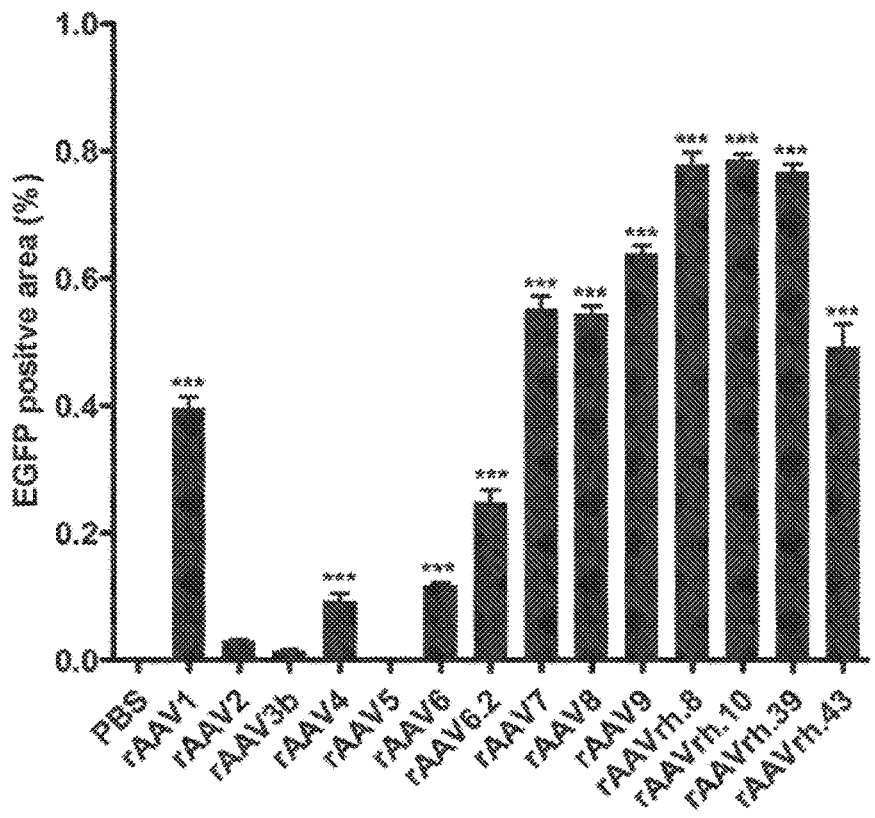
Figure 7C:
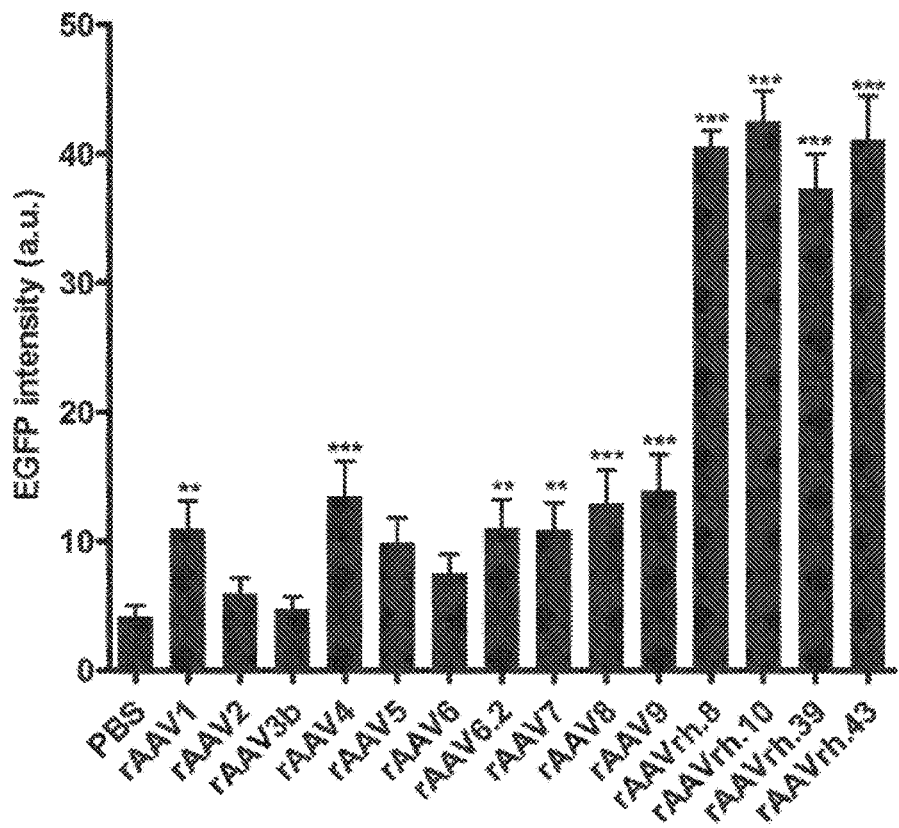

Intra-Stromal Injections of rAAVrh.8, rAAVrh.10, rAAVrh.39 and rAAVrh.43 Transduce the Cornea Efficiently The transduction efficiency of fourteen different rAAV serotypes was investigated. Mice were injected intra-stromally with rAAV1, rAAV2, rAAV3b, rAAV4, rAAV5, rAAV6, rAAV6.2, rAAV7, rAAV8, rAAV9, rAAVrh.8, rAAVrh.10, rAAVrh.39, or rAAVrh.43 expressing EGFP at a dose of $2.4 \times 10^{10}$ GCs per eye; PBS was injected as a negative control into normal mouse corneas (FIG. 6A). Compared to the PBS control, robust EGFP expression was observed in corneas at the fourth week after injection with rAAVrh.8, rAAVrh.10, rAAVrh.39 and rAAVrh.43 (FIG. 7A); the percentage of EGFP positive area and EGFP intensity in the corneal whole mounts of those four groups are presented in FIGS. 7B and 7C. Nearly 80% area of the whole corneas were efficiently transduced by rAAVrh.8, rh.10 and rh.39 vectors (FIG. 7B), while the EGFP intensity in the four rhesus serotype groups of rAAVrh.8, rh.10, rh.39 and rh.43 were approximately 4-fold stronger over those of other rAAV serotypes tested (FIG. 7C). These results demonstrated that rAAVrh.8, rAAVrh.10, rAAVrh.39 and rAAVrh.43 could transduce mouse cornea in a highly efficient manner.

Figure 8A:
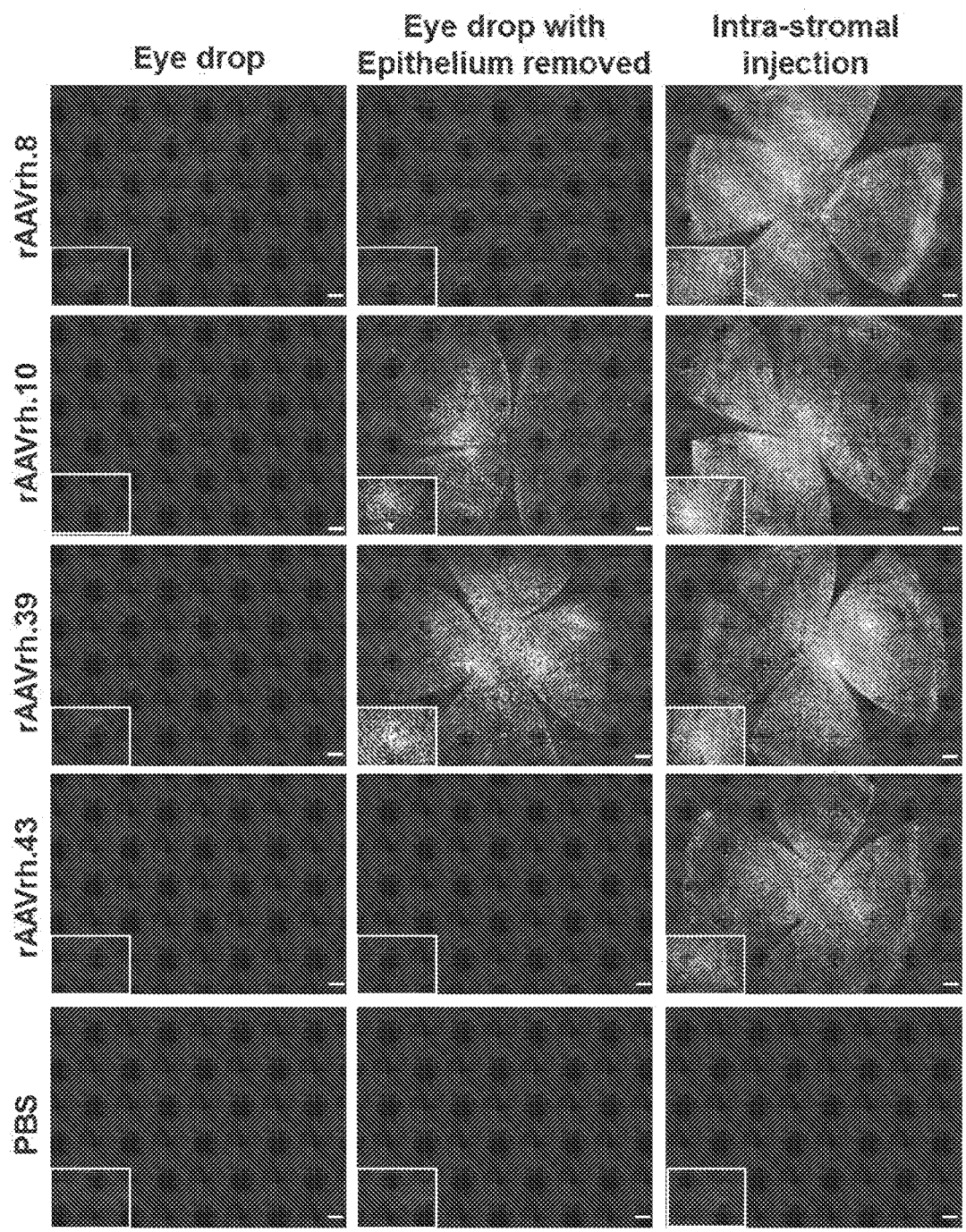
FIGS. 8A-8C show topical administration of rAAVrh.10 and rAAVrh.39 transduced mouse cornea when corneal epithelium was removed.
Figure 8B:
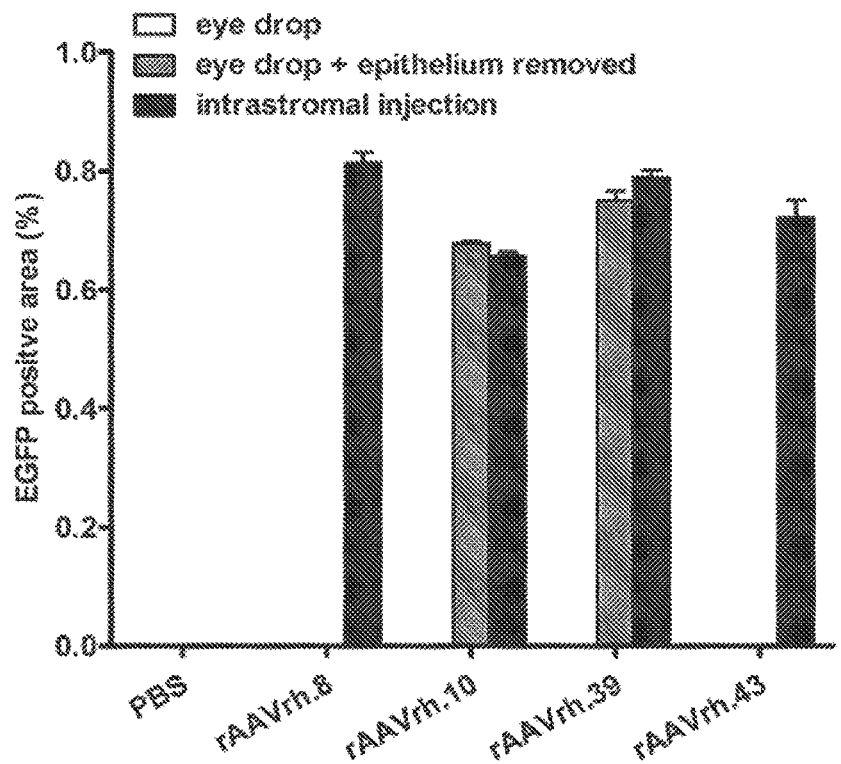
Figure 8C:
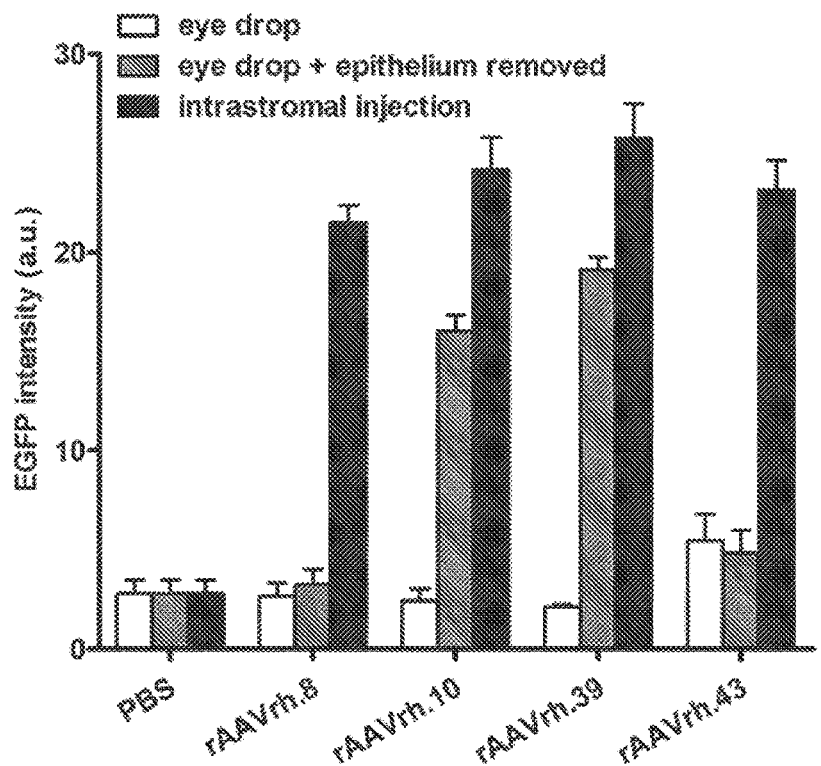

Topical Administrations of rAAVrh.10 and rAAVrh.39 Transduce the Cornea with Corneal Epithelium Removed To explore the feasibility of delivering certain rAAV serotypes to mouse cornea by an easy and noninvasive method, EGFP transduction of rAAVrh.8, rAAVrh.10, rAAVrh.39 and rAAVrh.43 was evaluated after topical administration to the corneas (FIG. 6B). Since the corneal epithelium is known to be a natural barrier for topical therapeutics to the corneal stroma, topical application of the four leading rAAV vectors were performed either with, or without, corneal epithelium scraping in comparison with intra-stromal injections of the same vectors at the same dose ($2.4 \times 10^{10}$ GCs per eye). Corneal whole mount imaging showed that all four serotypes were unable to transduce mouse cornea when the epithelium was present; however, rAAVrh.10 and rAAVrh.39 efficiently transduced corneal stroma when the epithelium was removed (FIG. 8A). In comparison to intra-stromal injections, topical administration of these two serotypes after epithelium removal produced similar percentages of EGFP positive area (FIG. 8B), but exhibited significantly lower EGFP intensity (p<0.001) (FIG. 8C).

rAAVrh.10 and rAAVrh.39 Achieve Sustained Corneal Transduction

Figure 9A:
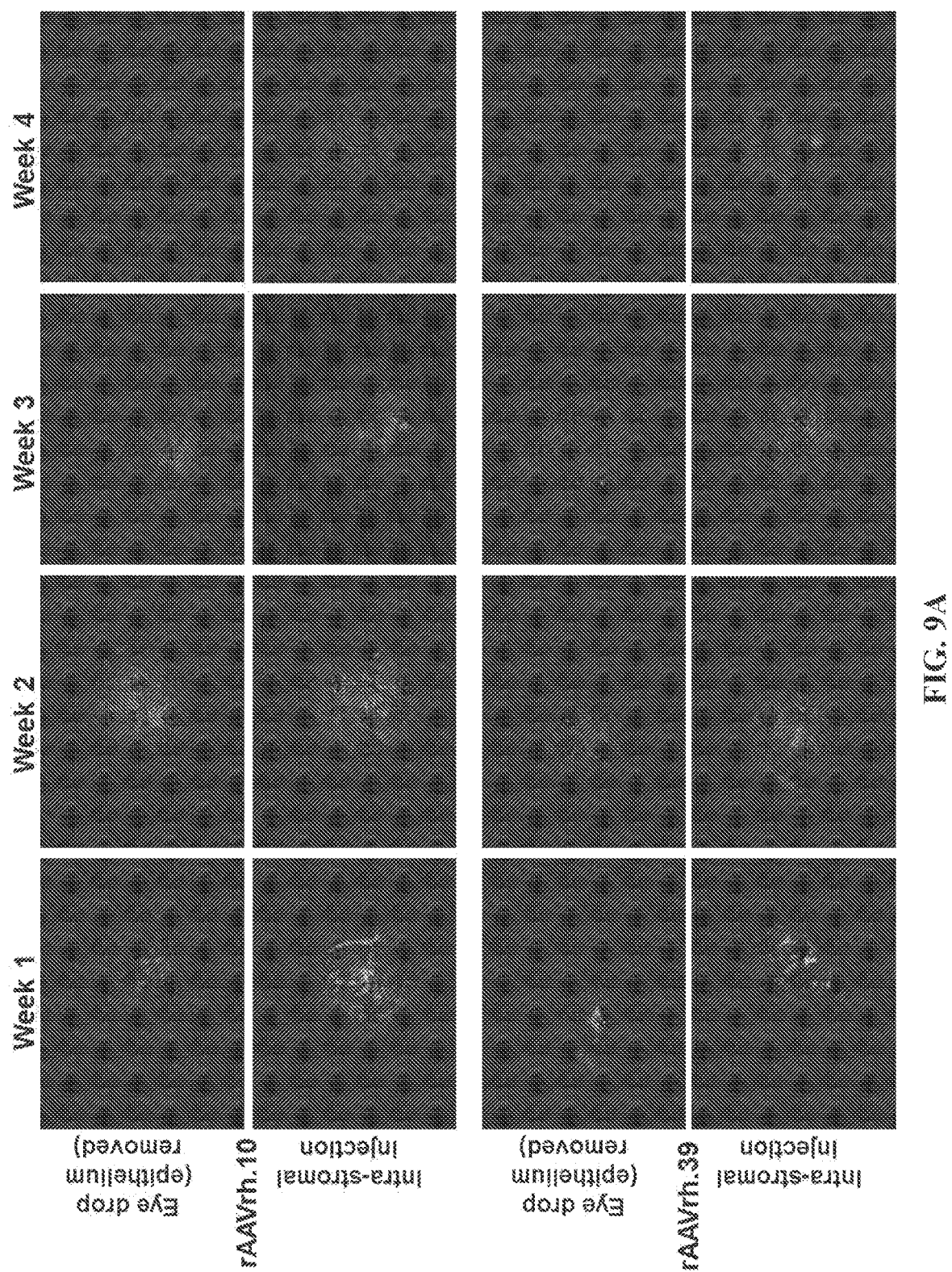
FIGS. 9A-9C show rAAVrh.10 and rAAVrh.39 transduction in mouse cornea continued at least for 4 weeks in vivo.
Figure 9B:
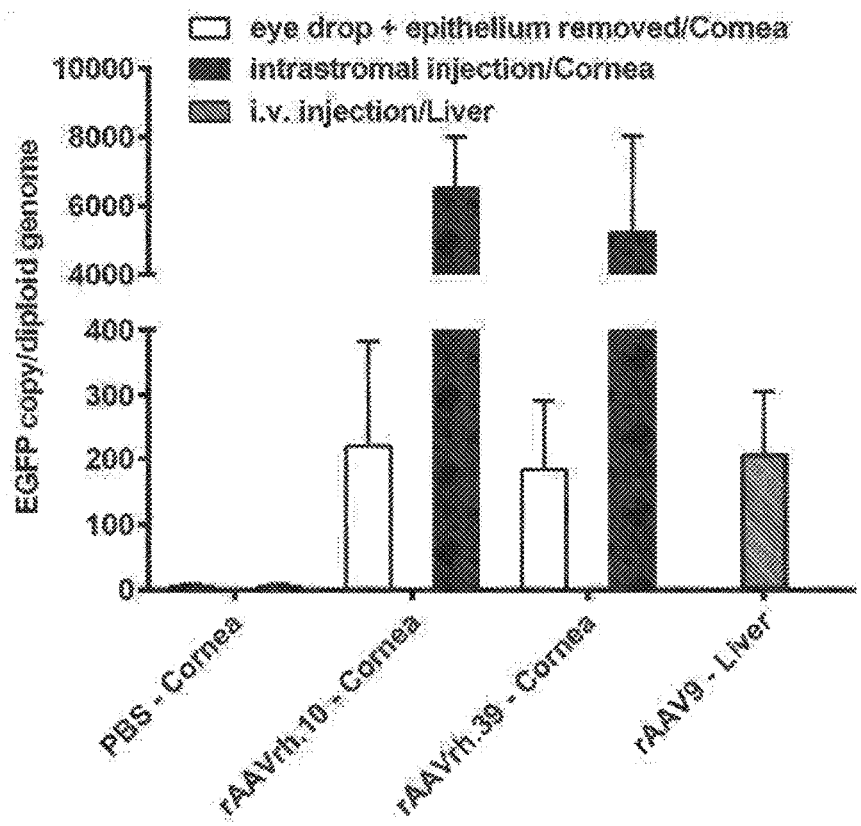
Figure 9C:
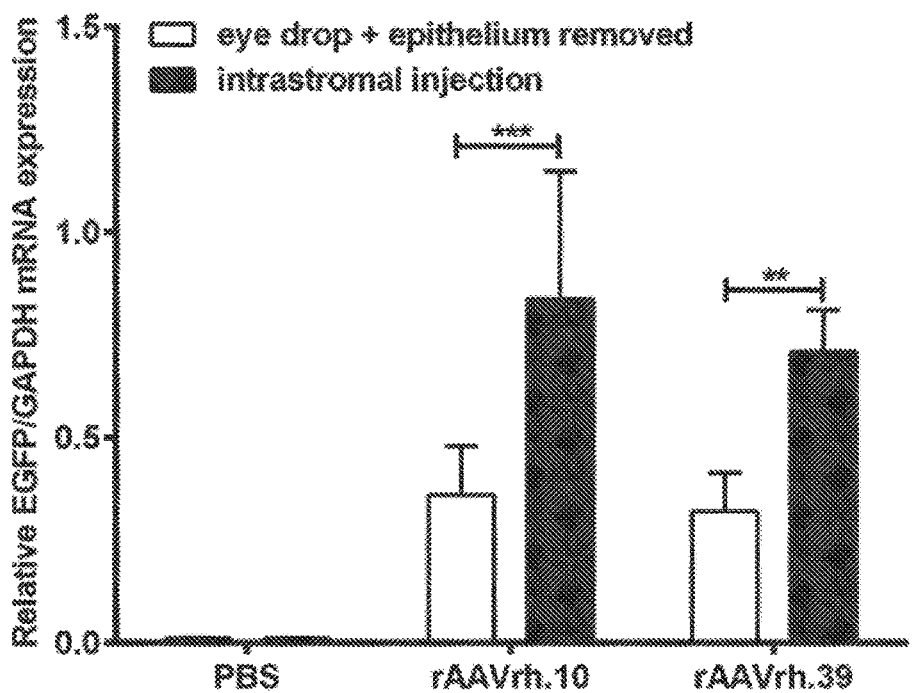

Following topical administration (eye drop with corneal epithelium removed) or intra-stromal injection, EGFP expression from rAAVrh.10 and rAAVrh.39 was apparent at 1-week post-treatment, reached peak expression around 2-weeks, and remained detectable at the 4-week study endpoint (FIG. 9A) when mouse corneas were harvested for ddPCR quantification of vector genome copies and EGFP mRNA levels. Data suggested that on average, more than 5,000 vector genomes per cell persisted at 4-weeks post-treatment for intra-stromally injected rAAVrh.10 and rh.39 serotypes and approximately 200 vector genome copies per cell detected for the topically administered two serotype vectors (FIG. 9B). The vector genome abundance in corneas that received rAAVs intra-stromally is 20- to 30-folds higher than that in mouse liver treated with an intravenous injection of rAAV9.EGFP at approximately 40-folds higher the dosage of rAAVrh.10 and rh.39 (FIG. 9B). This suggests that, at per genome basis, intra-stromal delivery of rAAVrh.10 and rAAVrh.39 to the cornea is much more efficient (800- to 1200-folds) than systemic delivery of a more concentrated highly liver tropic rAAV9 vector. In addition, EGFP mRNA expression levels in the rAAV treated corneas were well correlated with the abundance of vector genomes (FIG. 9C).

rAAVrh.10 and rAAVrh.39 Primarily Target Keratocytes in Corneal Stroma

Figure 10A:
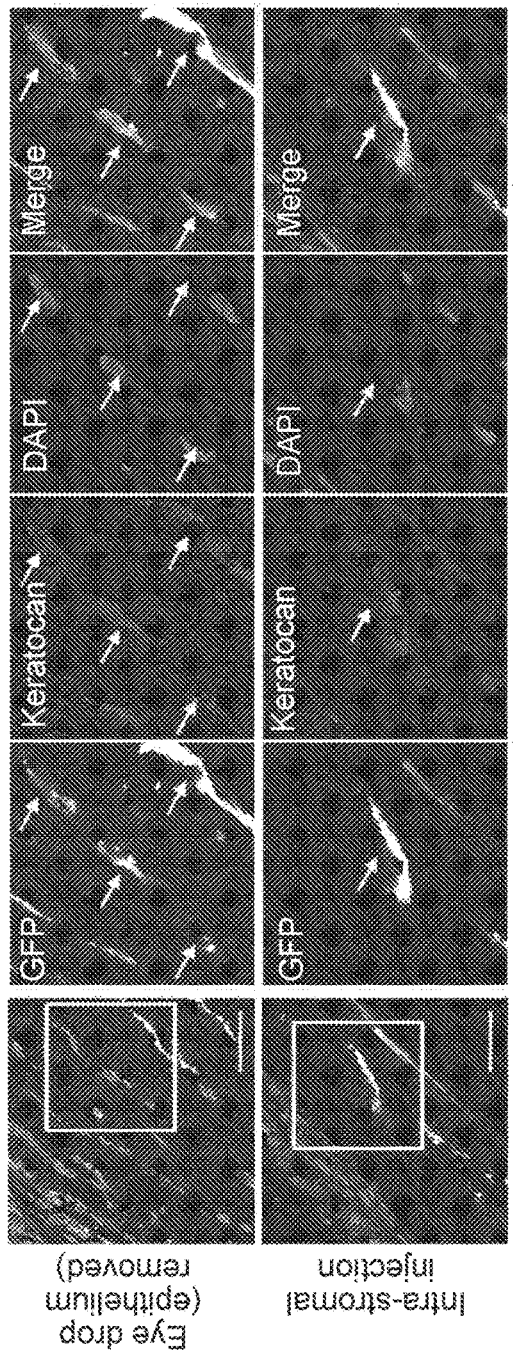
FIGS. 10A-10B show rAAVrh.10 and rAAVrh.39 could transduce mouse keratocytes in corneal stroma.
Figure 10A:
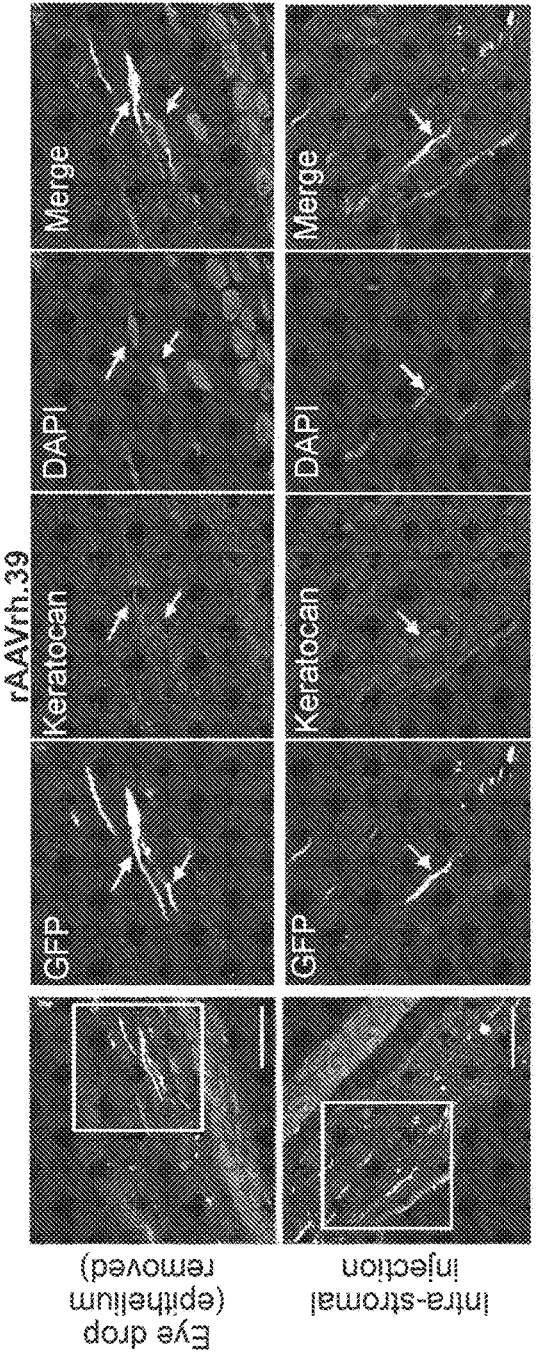
Figure 10B:
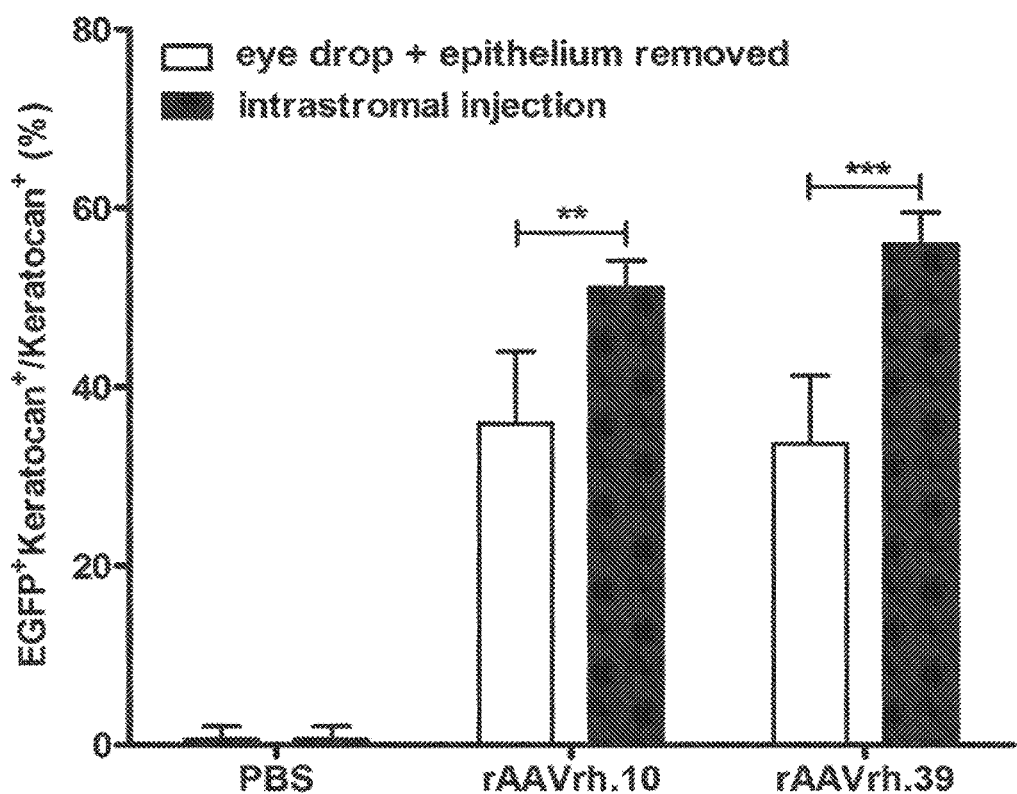

As keratocytes with characteristic interconnecting dendritic processes comprise 96% of the cornea in mice and humans, keratocytic tropism of rAAVrh.10 and rAAVrh.39 was characterized by using keratocan as a cell marker for keratocytes (FIG. 10A). Quantitative analysis of EGFP+/keratocan+ cells in the corneal stroma revealed that rAAVrh.10 and rAAVrh.39 transduced 51.1±3.0% and 55.97±3.5% of keratocytes respectively by intra-stromal injections, and 35.9±8.1% and 33.64±7.7% of keratocytes respectively by eye-drop applications to the epithelium-removed corneas (FIG. 10B). In other words, intra-stromal injection of rAAVrh.10 and rh.39 transduced 1.5- to 2-folds more keratocytes when compared to topical administration (FIG. 10B), which was aligned with results from the ddPCR quantification of EGFP mRNAs (FIG. 9C).

Figure 11:
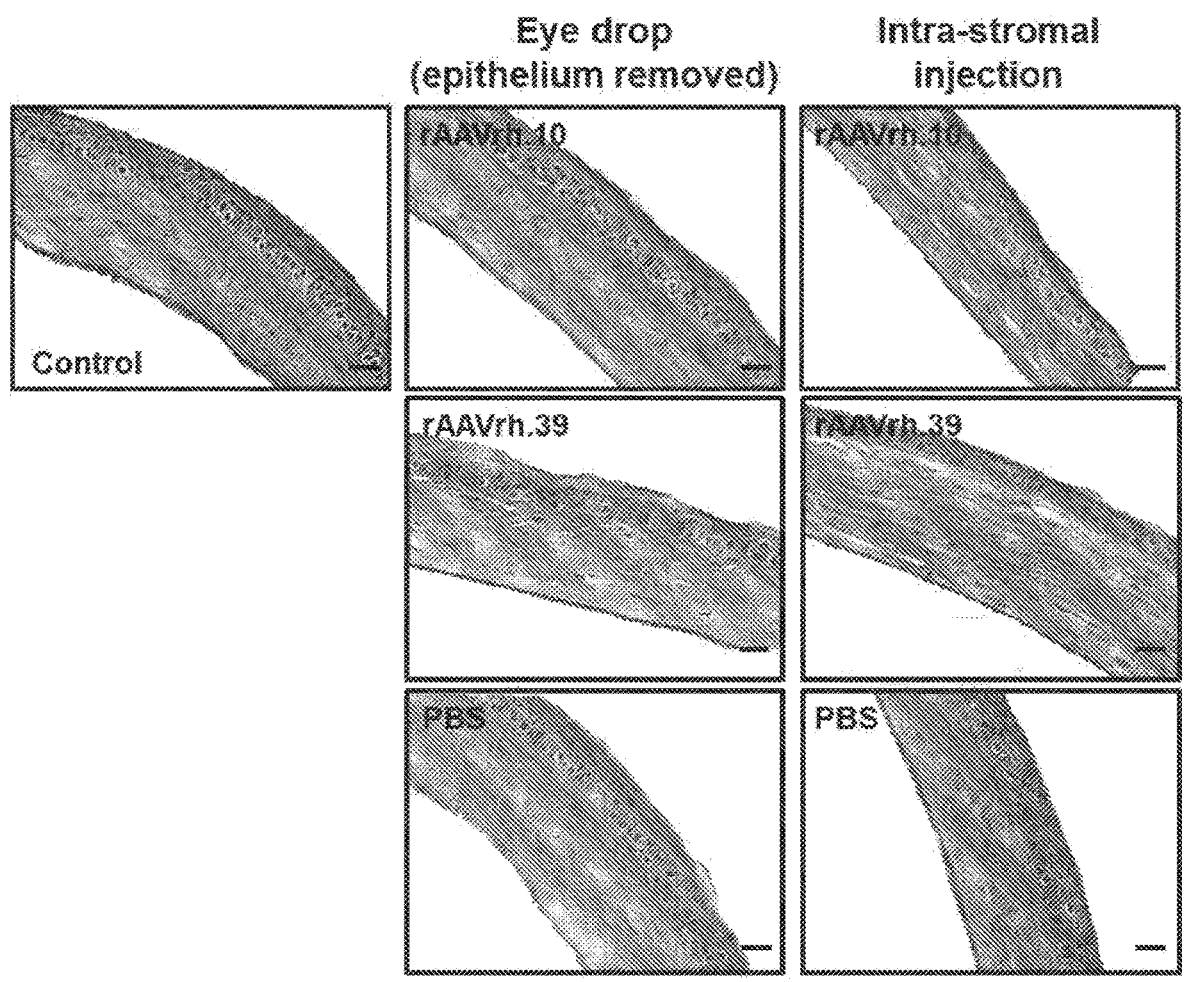
FIG. 11 shows transduction of rAAVrh.10 and rAAVrh.39 vectors had no adverse effect on cornea histology. Paraffin-embedded sections of the corneas stained with Haematoxylin and Eosin (H&E) displayed normal structures: all layers of the cornea were clear without obvious morphological changes compared to the control group or any other signs of inflammatory and immune reactions. Magnification: 200×, scale bar=50 µm.

Corneal Transduction by rAAVrh.10 and rAAVrh.39 Vectors Causes No Histopathology To evaluate possible vector-related toxicity caused by rAAV transduction in the corneal stroma, the histopathology of cornea tissues treated with rAAVrh.10 and rAAVrh.39 vectors at 4-weeks post-treatment was analyzed. Histological images of Haematoxylin and Eosin (H&E) stained tissue sections of corneas treated with rAAVrh.10 and rAAVrh.39 via either topical eye-drops or intra-stromal injections presented structures and morphologies similar to those that received PBS or no treatment; all corneal stromas remained organized into interweaving collagen lamellae with an even distribution of keratocytes (FIG. 11). These findings suggest that rAAV transduction of the corneas induced no adverse effects on corneal stromal morphology throughout the course of 4-weeks, implicating that rAAV did not deter overall health of the cornea tissue.

Figure 12A:
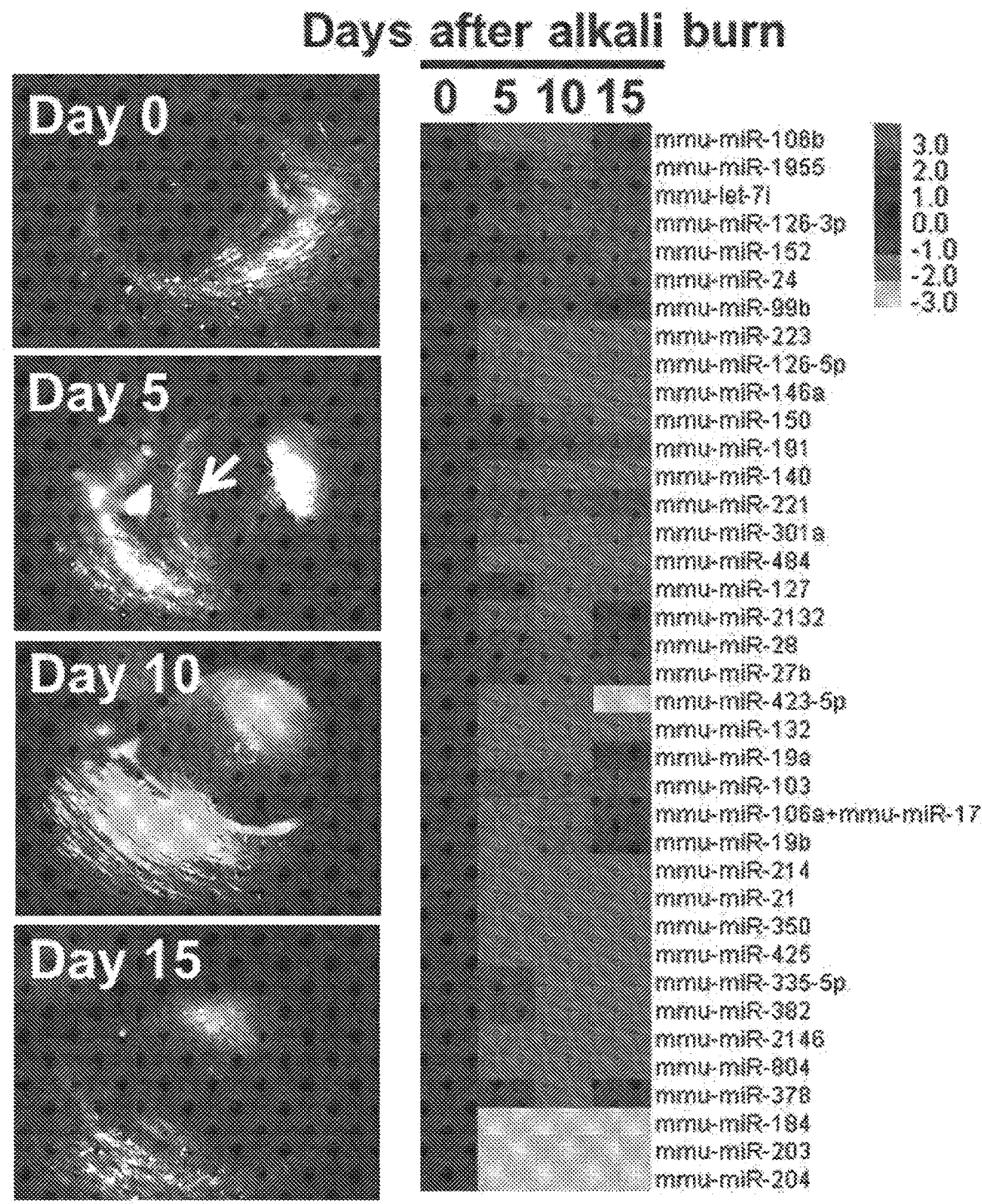
FIGS. 12A-12B show candidate miRNA selection.
Figure 12B:
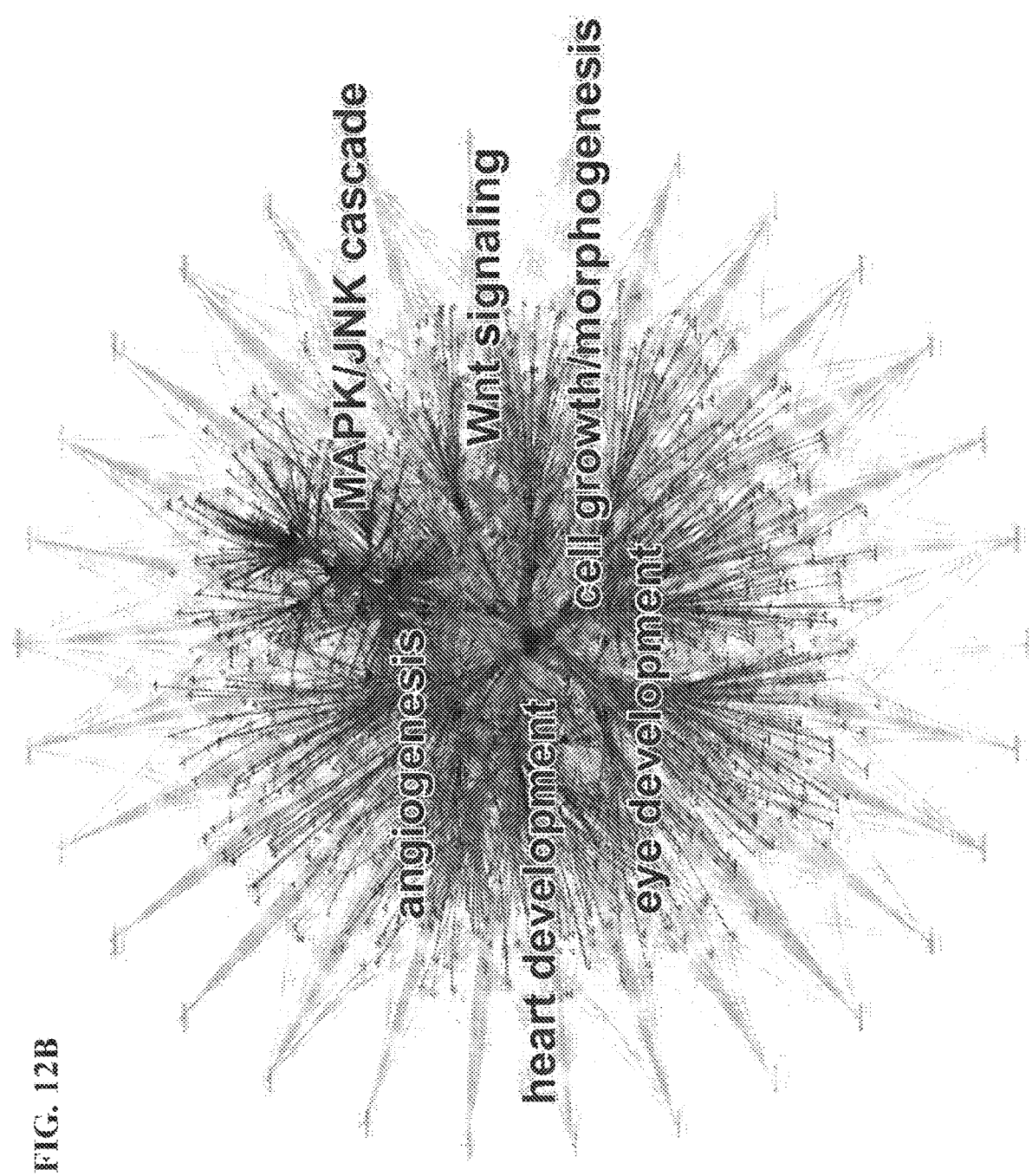

Example 3. rAAV Delivered MicroRNA Therapeutics Towards Efficacious Treatment of Corneal Neovascularization Candidate miRNA Selection FIG. 12 and Table 1 below show candidate miRNA selection and miRNA profiling of alkali-burn induced mouse corneal NV. Small RNAs prepared from corneal tissues harvested from of study mice were profiled for expression levels of 618 mouse miRNAs before and days 5, 10 and 15 after alkali injury.

Figure 13:
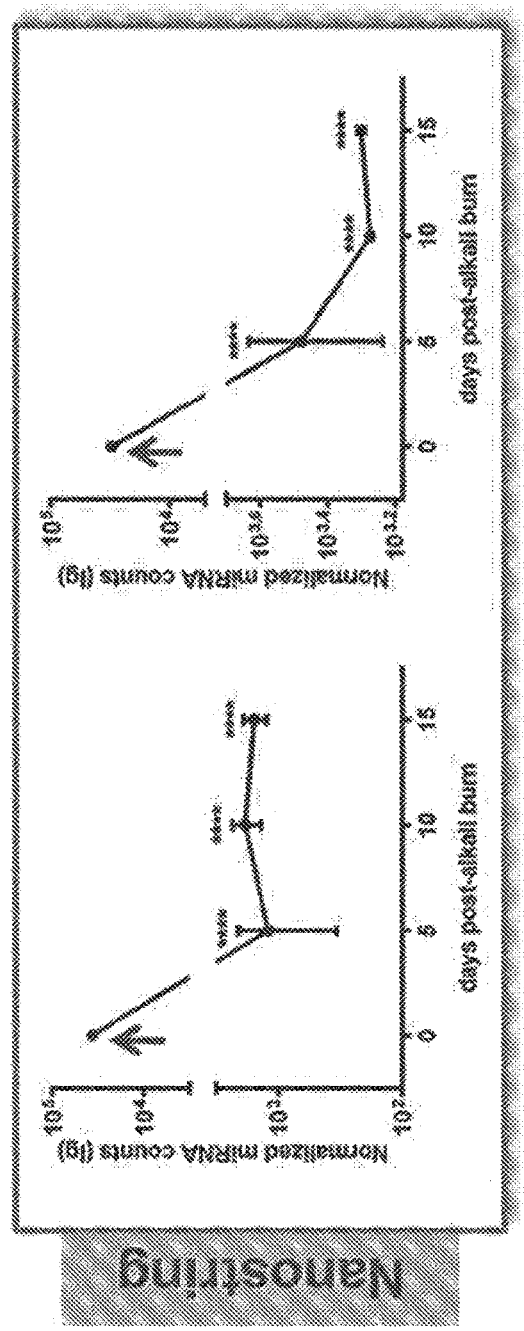
FIG. 13 shows candidate miRNA selection and qRT-PCR confirmation of miR-184 and miR-204. The arrow is the time point of alkali burn, ****: p<0001.
Figure 13:
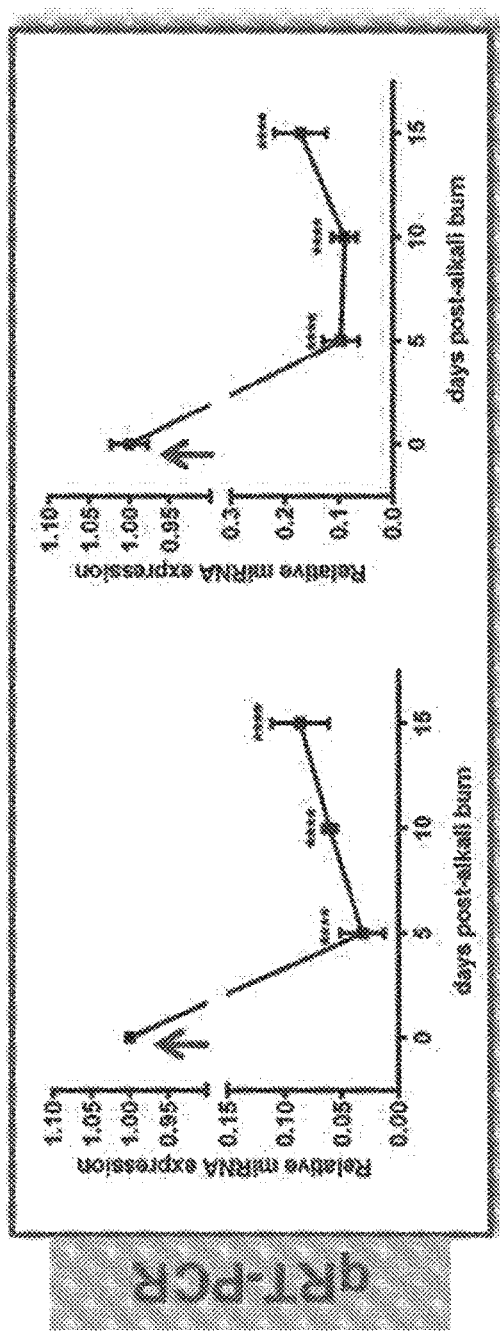

FIG. 13 shows candidate miRNA selection and qRT-PCR confirmation. miR-184 and miR-204 are significantly down-regulated post-alkali burn.

TABLE 1

| GO Term | Nr. Genes | % Associated Genes | Term Pvalue Corrected with Bonferroni step down |
|---|---|---|---|
| MAPK cascade | 449 | 63.328632 | 4.07E−10 |
| stress-activated MAPK cascade | 154 | 70.31963 | 1.58E−06 |
| regulation of MAPK cascade | 408 | 62.76923 | 3.20E−08 |
| positive regulation of MAPK cascade | 280 | 62.92135 | 4.03E−05 |
| JNK cascade | 126 | 71.18644 | 1.61E−05 |
| activation of MAPK activity | 77 | 75.4902 | 2.35E−04 |
| regulation of MAP kinase activity | 166 | 66.666664 | 1.59E−04 |
| positive regulation of MAP kinase activity | 123 | 70.68965 | 4.74E−05 |
| regulation of JNK cascade | 112 | 70.440254 | 2.66E−04 |
| regulation of epithelial cell proliferation | 196 | 63.843647 | 0.001112793 |
| regulation of cell growth | 238 | 66.111115 | 6.55E−07 |
| regulation of cell differentiation | 1005 | 62.61682 | 2.09E−23 |
| cell development | 1332 | 63.33809 | 5.20E−36 |
| cell morphogenesis | 830 | 68.31276 | 1.04E−37 |
| eye development | 249 | 64.010284 | 2.60E−05 |
| eye morphogenesis | 111 | 66.467064 | 0.025034129 |
| Wnt signaling pathway | 257 | 67.81003 | 1.99E−09 |
| regulation of Wnt signaling pathway | 173 | 70.04049 | 2.43E−07 |
| positive regulation of Wnt signaling pathway | 73 | 70.19231 | 0.044343167 |
| negative regulation of Wnt signaling pathway | 99 | 71.73913 | 3.33E−04 |
| canonical Wnt signaling pathway | 165 | 69.32773 | 2.25E−06 |
| negative regulation of canonical Wnt signaling pathway | 79 | 75.2381 | 2.08E−04 |
| regulation of canonical Wnt signaling pathway | 130 | 72.6257 | 1.11E−06 |
| vasculature development | 421 | 65.37267 | 1.40E−12 |
| blood vessel development | 403 | 65 | 2.25E−11 |
| blood vessel morphogenesis | 337 | 64.80769 | 7.68E−09 |
| angiogenesis | 279 | 64.73318 | 6.42E−07 |
| blood circulation | 257 | 61.778847 | 0.001406428 |
| heat development | 370 | 64.45993 | 1.58E−09 |
| cardiovascular system development | 645 | 63.988094 | 4.14E−17 |
| response to transforming growth factor beta | 132 | 65.67164 | 0.010692643 | rAAV Serotype Screening in Mouse Cornea

Figure 14:
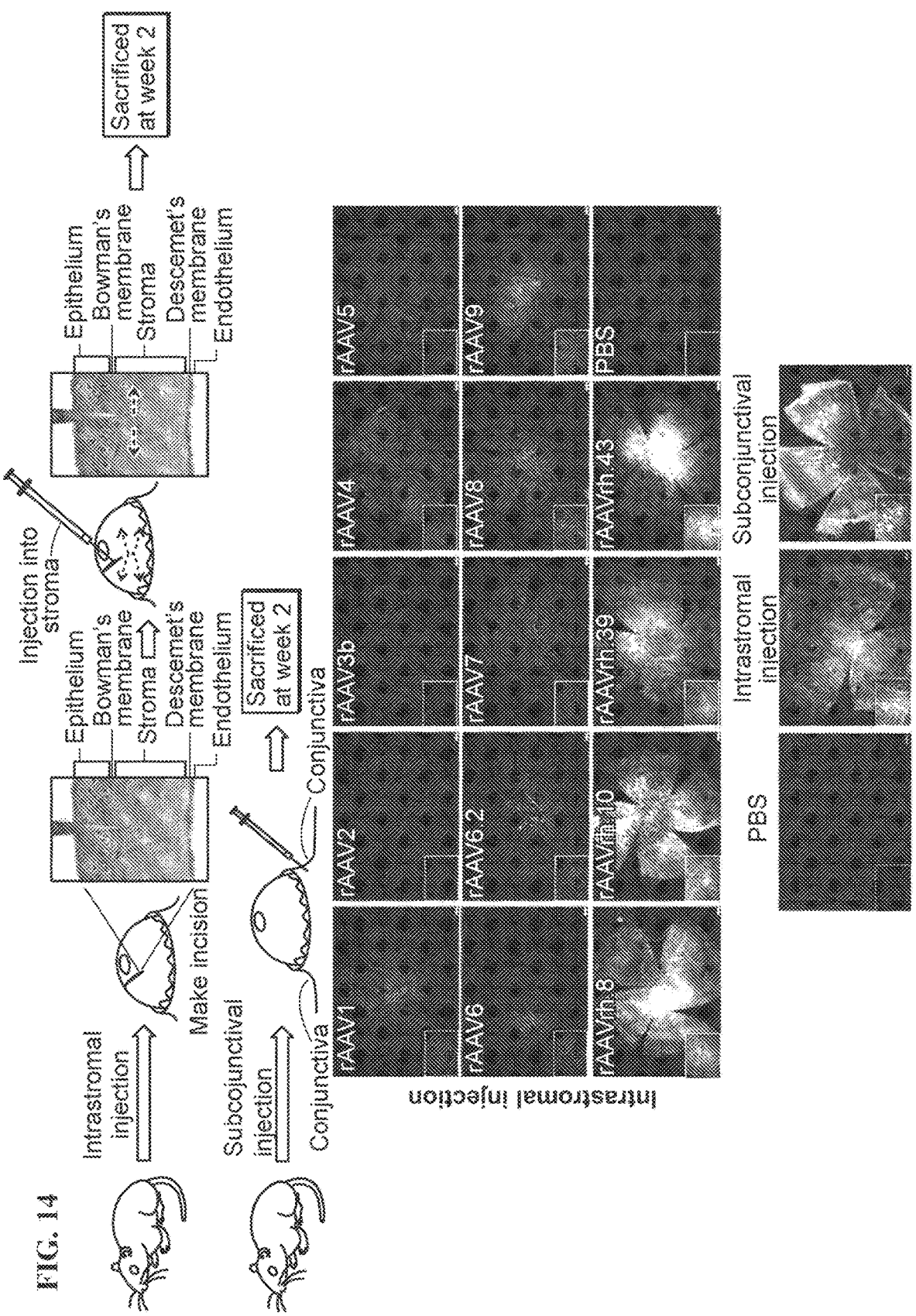
FIG. 14 shows rAAV serotype screening in mouse cornea of rAAV1, rAAV2, rAAV3b, rAAV4, rAAV5, rAAV6, rAAV6.2, rAAV7, rAAV8, rAAV9, rAAVrh.8, rAAVrh.10, rAAVrh.39, rAAVrh.43, and PBS.

FIG. 14 shows rAAV serotype screening in mouse cornea. Intra-stromal injection of rAAVrh.8, rAAVrh.10, rAAVrg.39 and rAAVrh.43 results in efficient transduction and EGFP expression.

rAAV.Rh10 Delivered EGFP Expression after Alkali Burn

Figure 15:
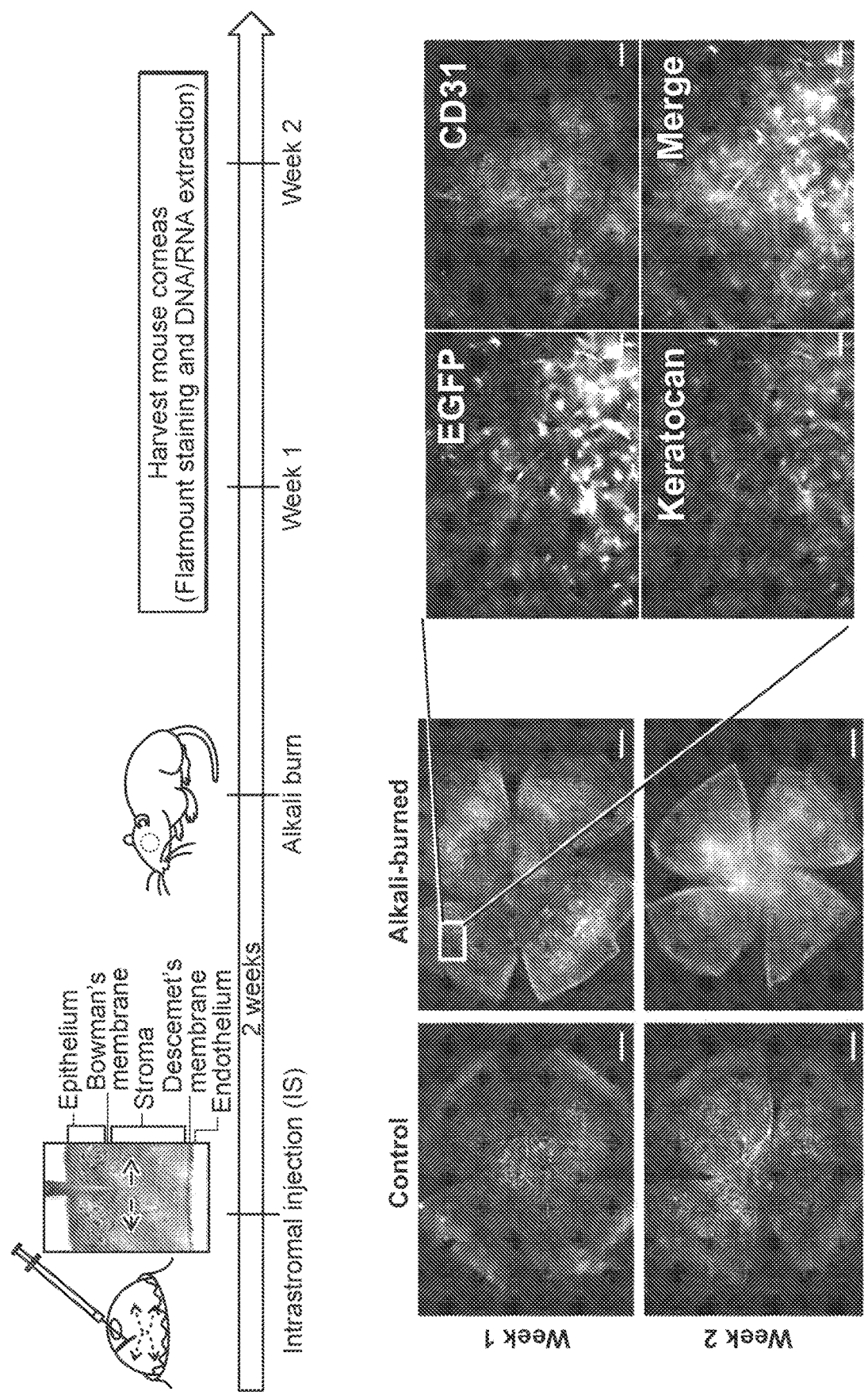
FIG. 15 shows rAAV.rh10 delivered EGFP expression after alkali burn and intrastromal injection (IS). Control and alkali-burned representative immunofluorescence images are shown after 1 and 2 weeks.
Figure 16:
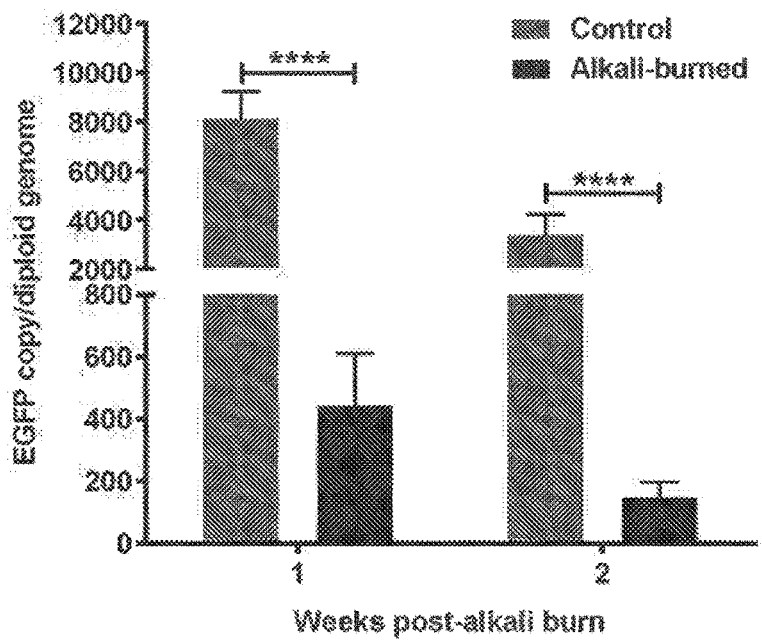
FIG. 16 graphically depicts rAAV.rh10 delivered EGFP expression after alkali burn and intrastromal injection (ddPCR). The left panel shows data regarding genomic copies and the right panel shows data regarding mRNA expression.
Figure 16:
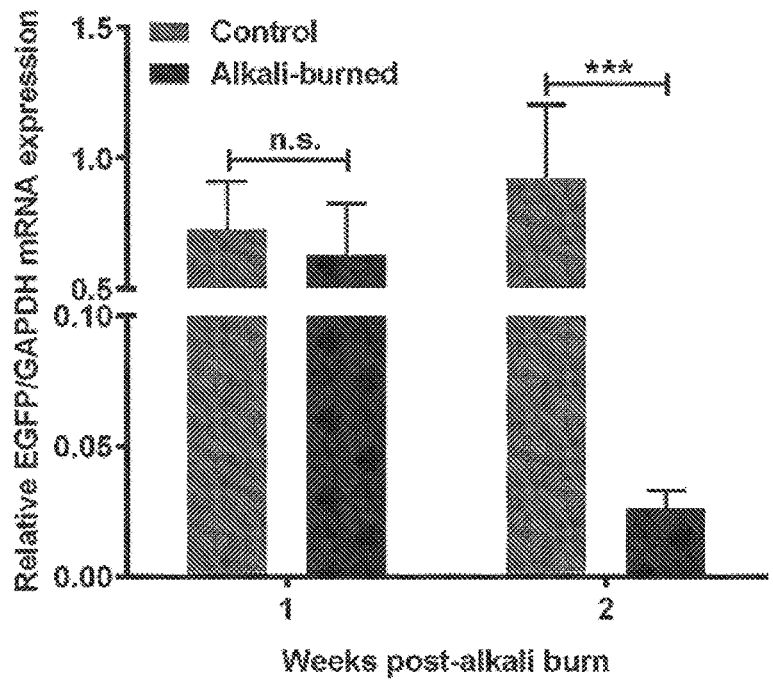
Figure 17:
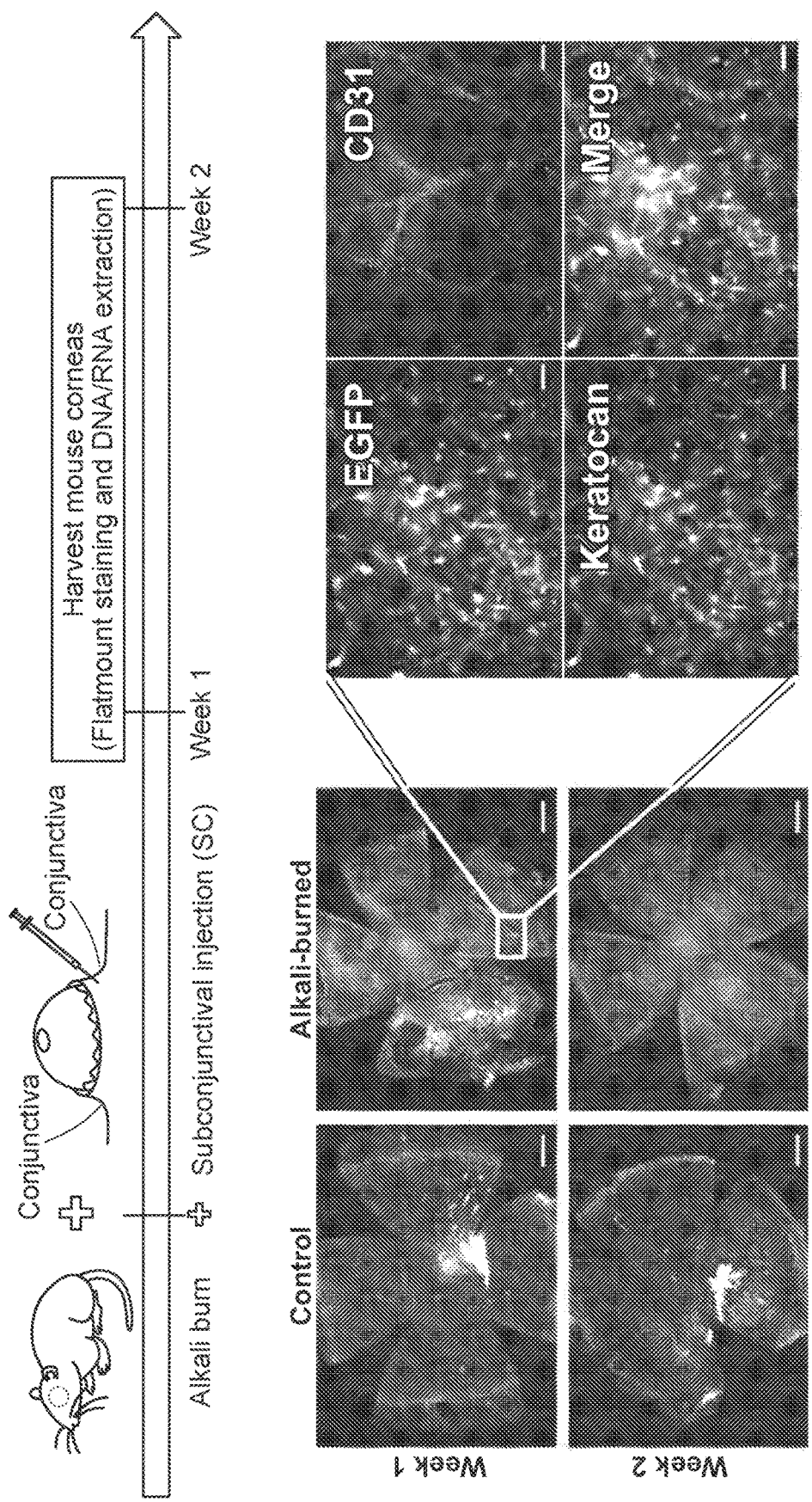
FIG. 17 shows rAAV.rh10 delivered EGFP expression after alkali burn and subconjunctival injection (SC). Control and alkali-burned representative immunofluorescence images are shown after 1 and 2 weeks.
Figure 18:
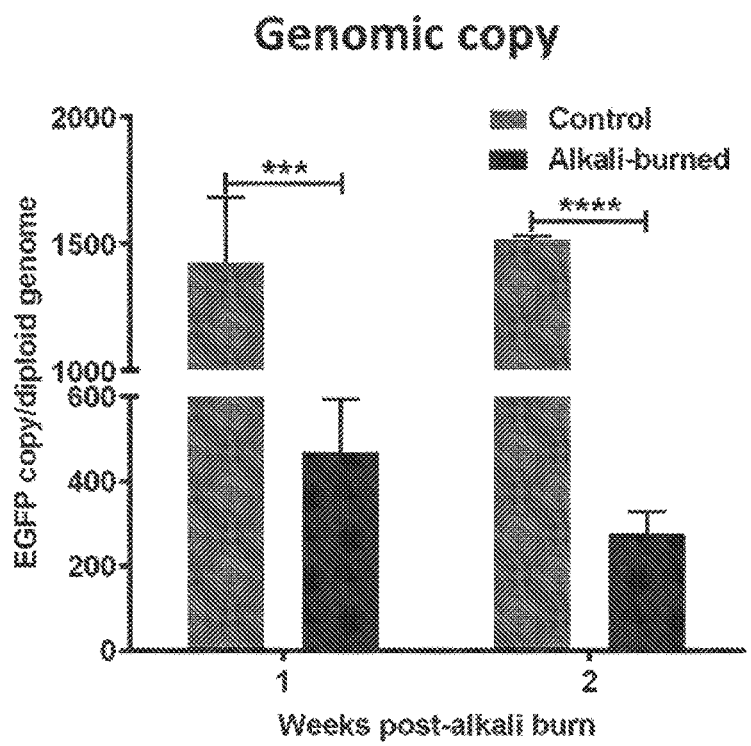
FIG. 18 graphically depicts rAAV.rh10 delivered EGFP expression after alkali burn and subconjunctival injection (ddPCR). The left panel shows data regarding genomic copies and the right panel shows data regarding mRNA expression.
Figure 18:
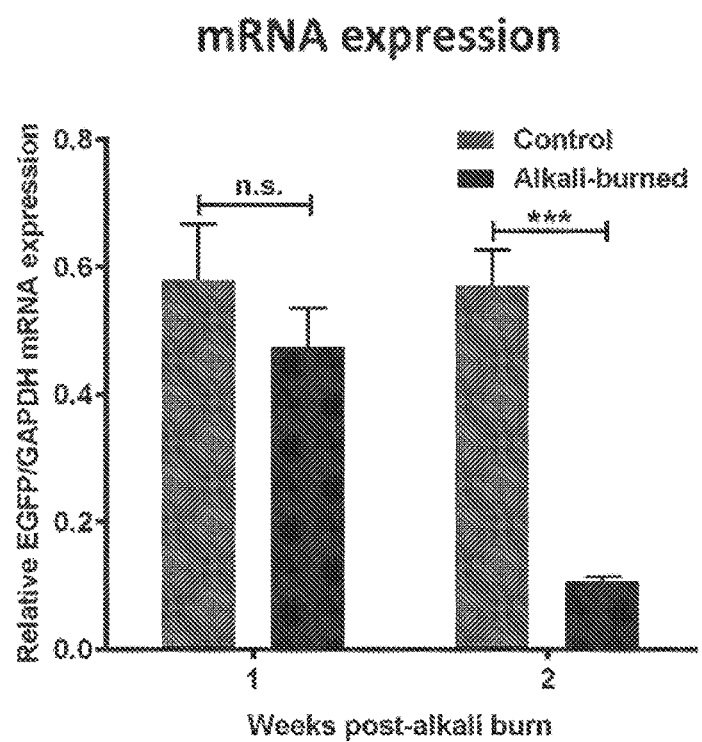

FIG. 15 shows rAAV.rh10 delivered EGFP expression after alkali burn; rAAVrh.10 was delivered via intrastromal injection. FIG. 16 graphically depicts rAAV.rh10 delivered EGFP expression administered via intrastromal injection after alkali burn, as measured by ddPCR. FIG. 17 shows rAAV.rh10 delivered EGFP expression after alkali burn and subconjunctival injection. FIG. 18 graphically depicts rAAV.rh10 delivered EGFP expression after alkali burn and subconjunctival injection (ddPCR).

rAAV.Rh10 Delivered Pri miR-184 & Pri miR-204 Inhibit Corneal Neovascularization (NV)

FIGS. 19A-19D show rAAV.rh10 delivered pri miR-184 and pri miR-204 inhibit corneal neovascularization (NV) as prevention through intrastromal injection (IS). FIGS. 20A-20D show rAAV.rh10 delivered pri miR-184 & pri miR-204 inhibit corneal NV as treatment through subconjunctival injection (SC).

Overexpression of miR-184 Inhibit Fzd4 Expression

Figure 21:
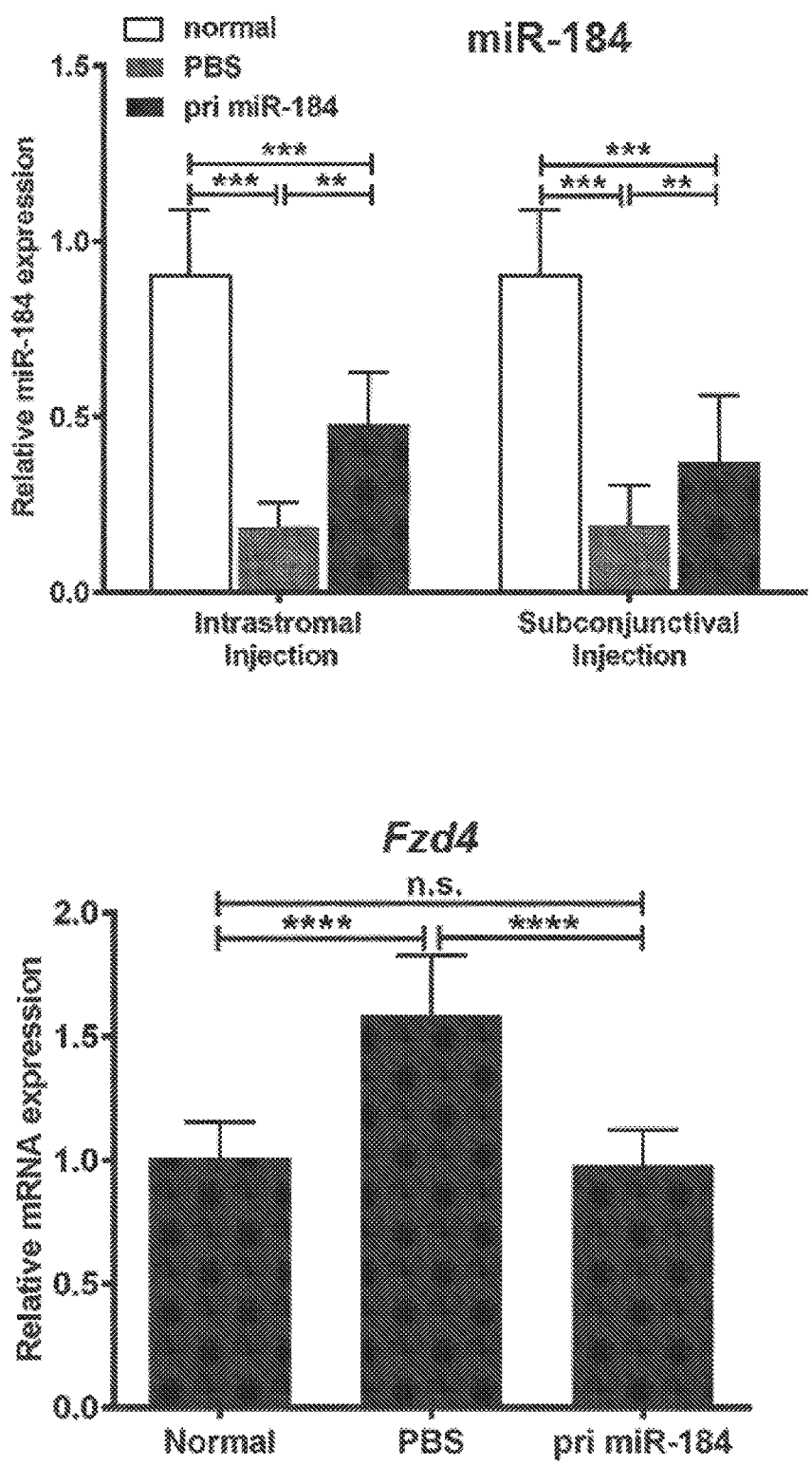
FIG. 21 shows overexpression of miR-184 inhibit Fzd4 expression (Wnt signaling).
Figure 21:
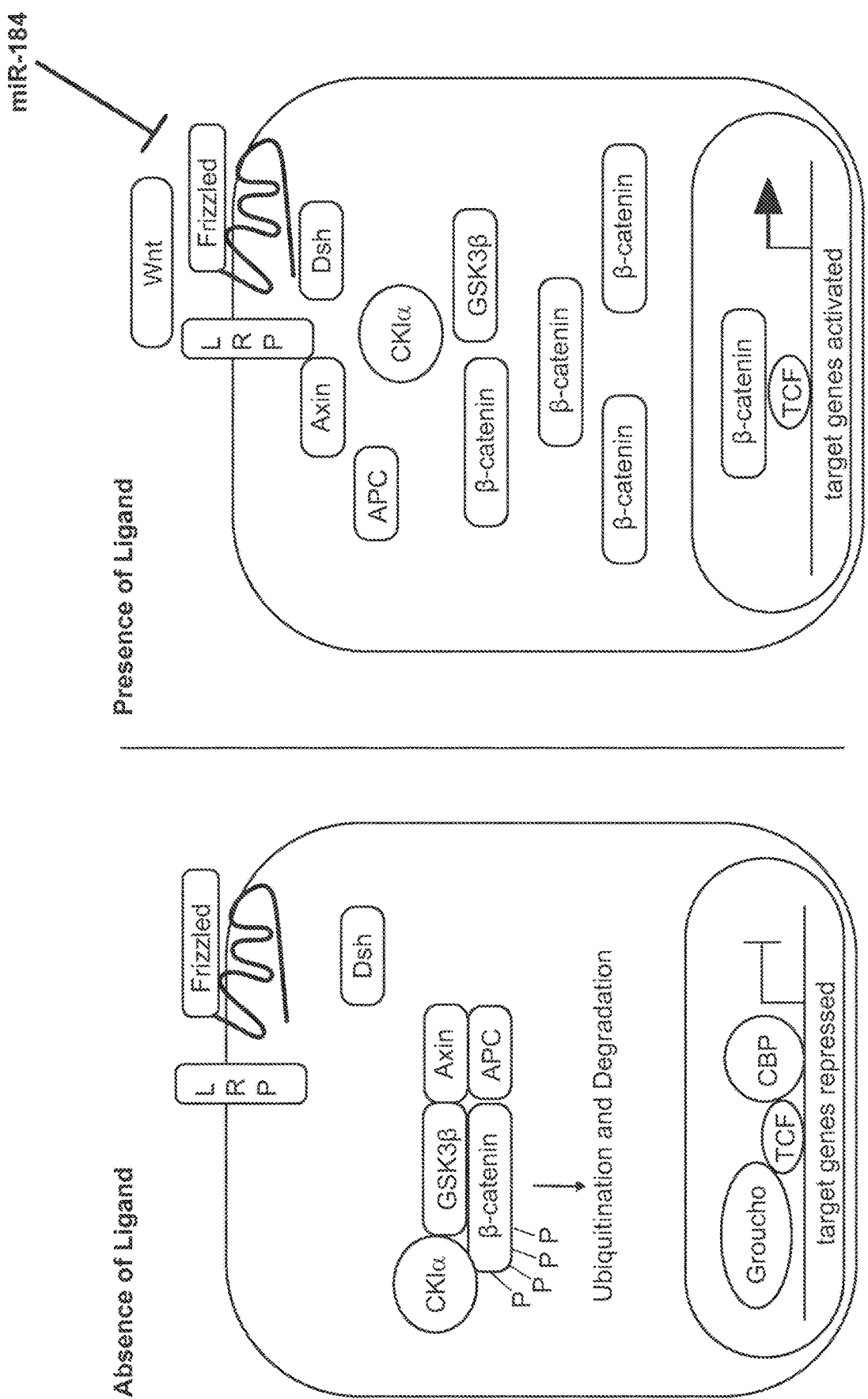
Figure 22:
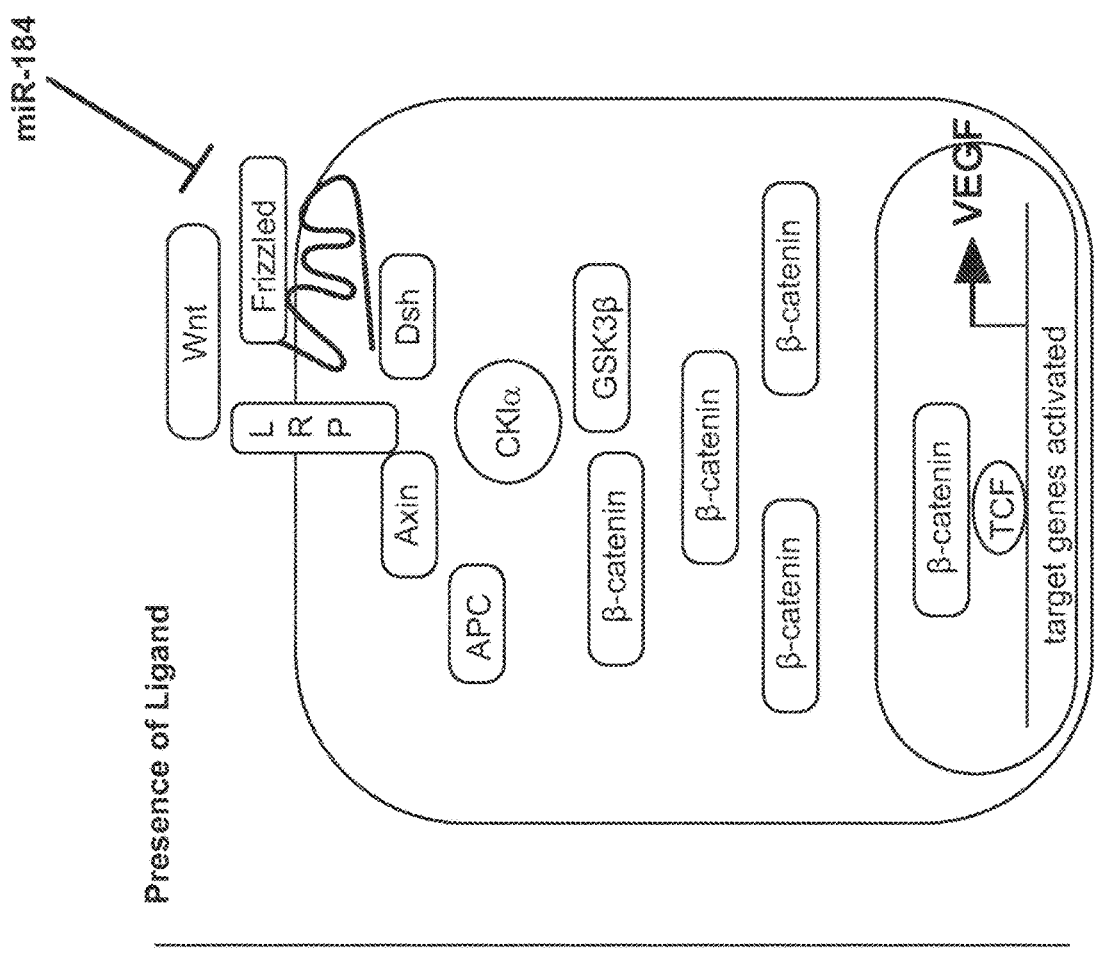
FIG. 22 shows overexpression of miR-184 inhibit Fzd4 expression (Wnt signaling).
Figure 22:
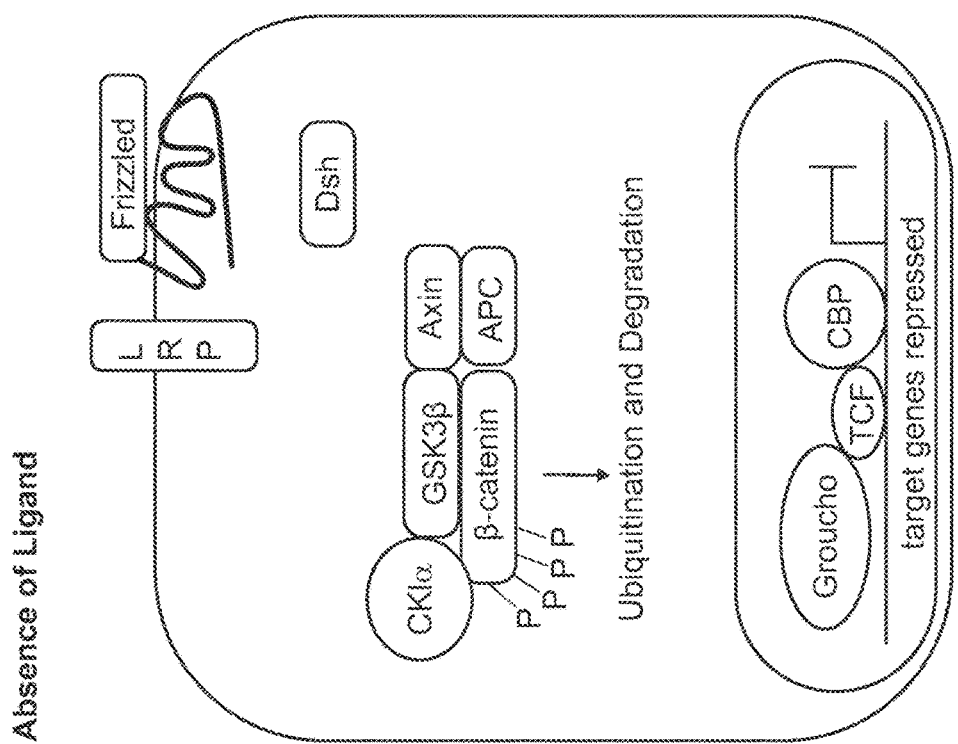
Figure 22:
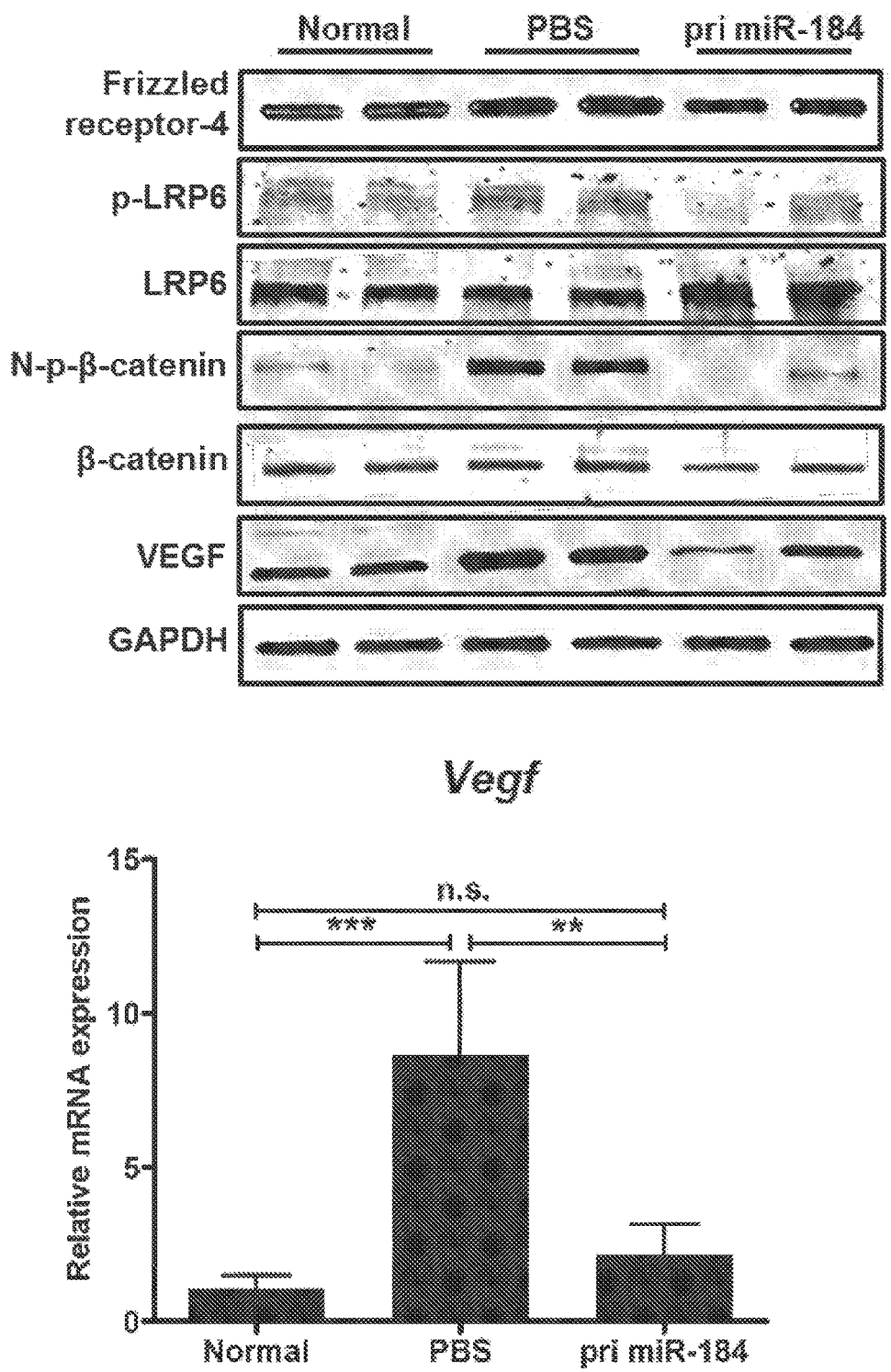
Figure 22:
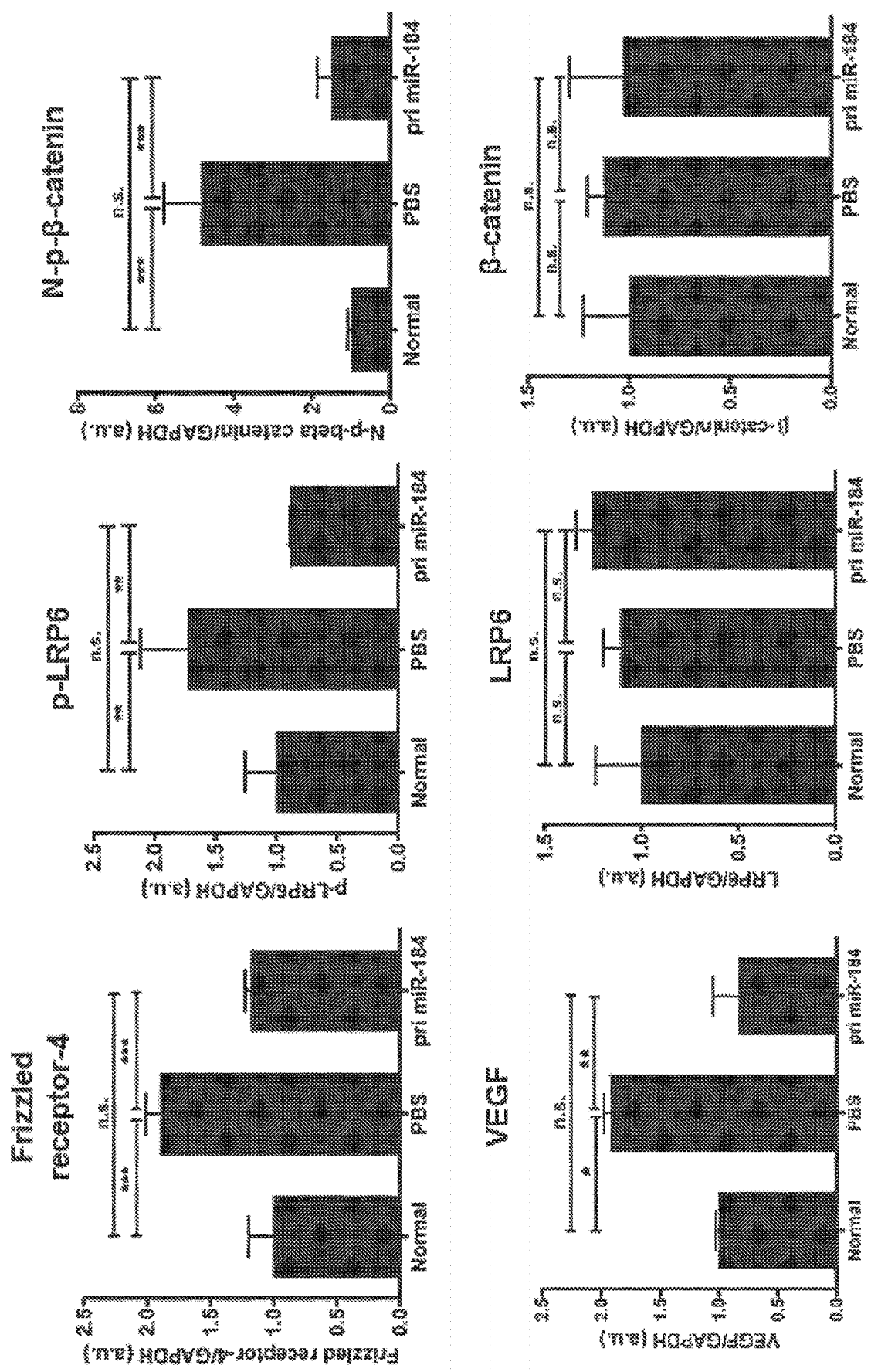

FIGS. 21-22 show overexpression of miR-184 inhibit Fzd4 expression (Wnt signaling). The diagram of the Wnt signaling pathway depicted on the right side of FIG. 21 is adapted from Shen et al., Mol Ther. 2008.

Overexpression of miR-204 Inhibit Angpt-1 Expression

Figure 23:
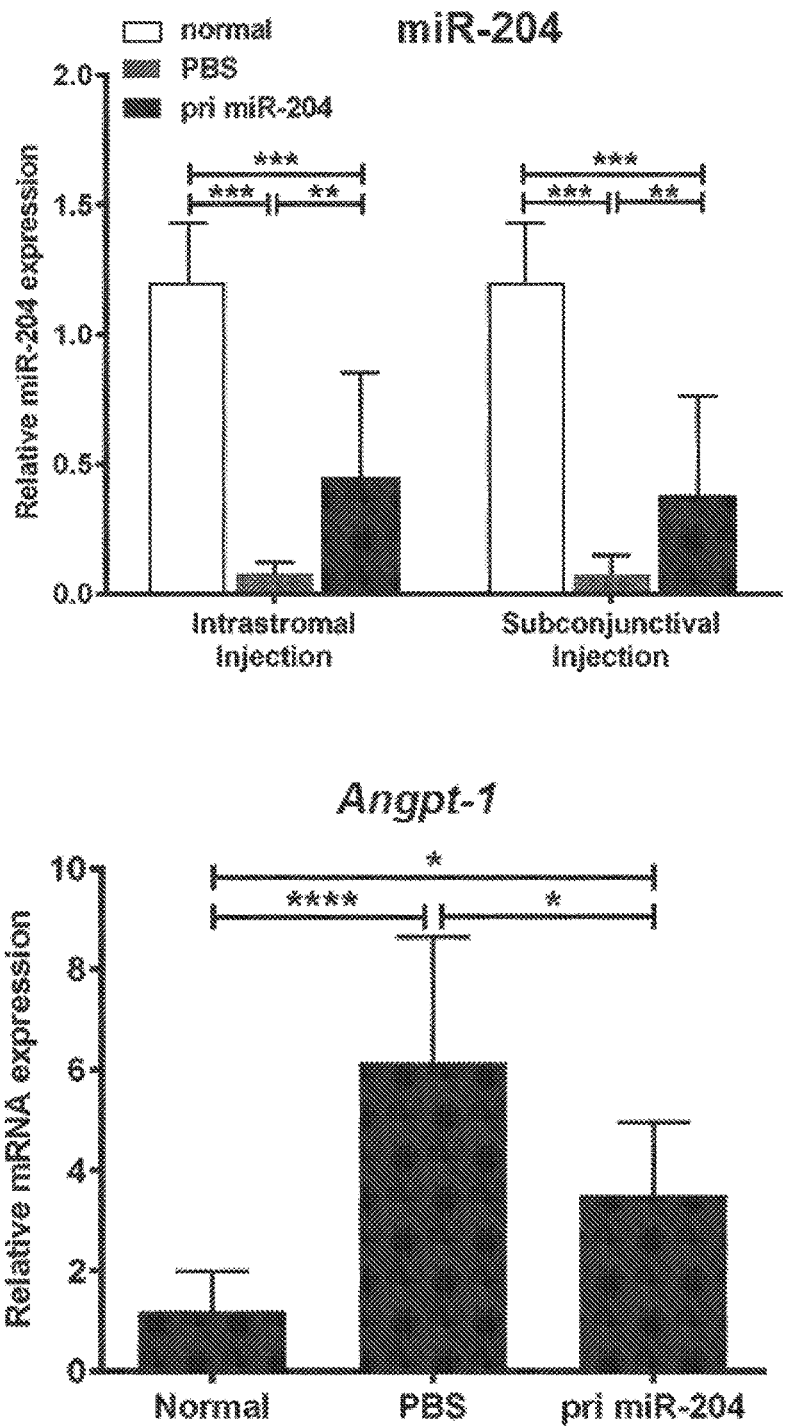
FIG. 23 shows overexpression of miR-204 inhibit Angpt-1 expression (Tie2-P13K-Akt pathway).
Figure 23:
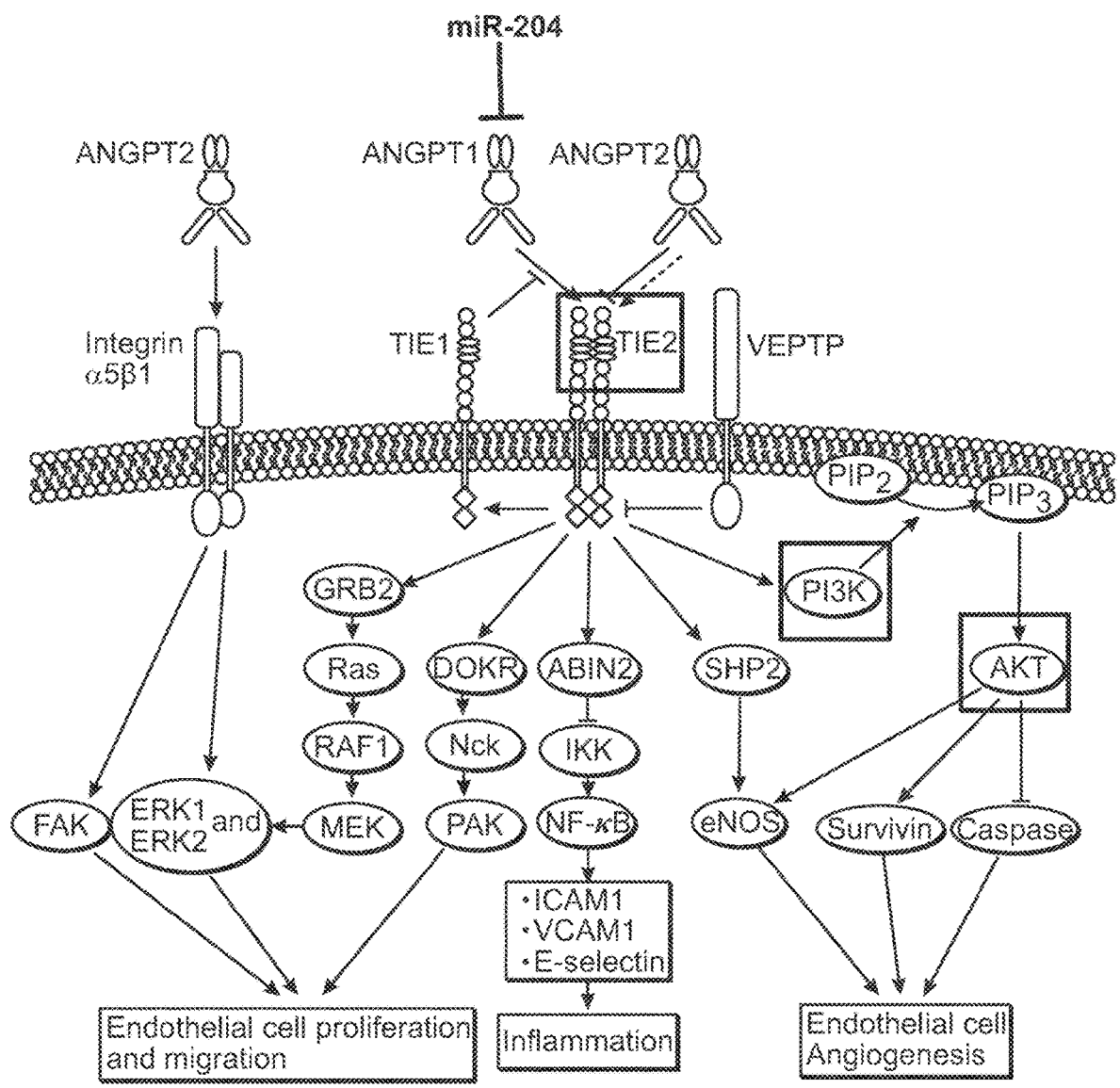
Figure 24:
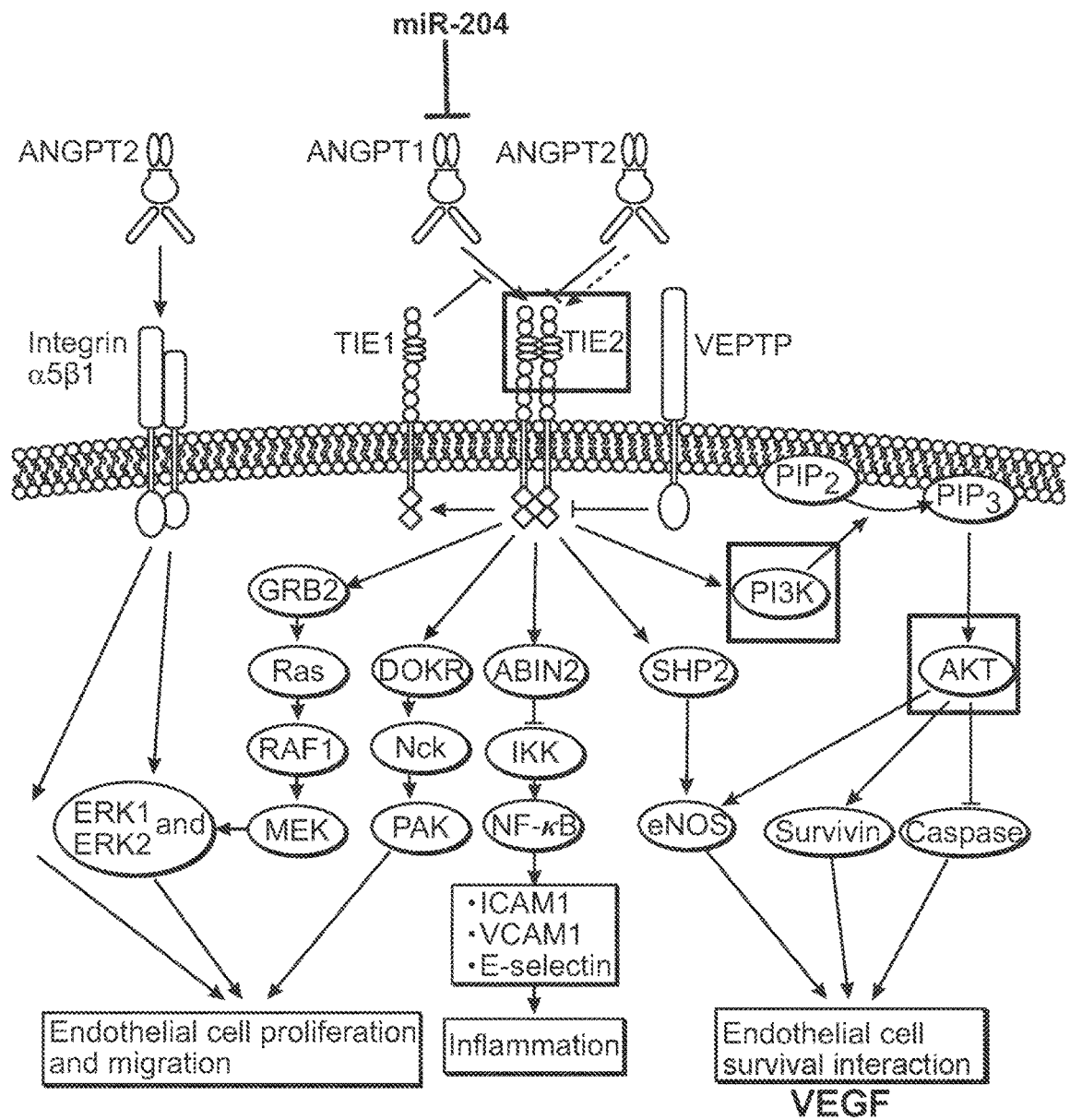
FIG. 24 shows overexpression of miR-204 inhibit Angpt-1 expression (Tie2-P13K-Akt pathway).
Figure 24:
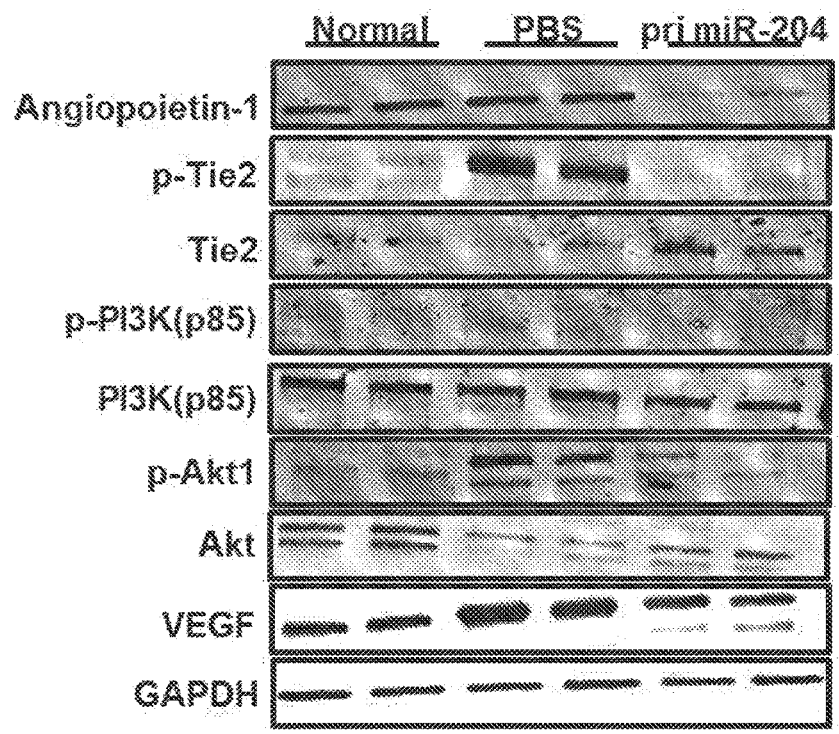
Figure 24:
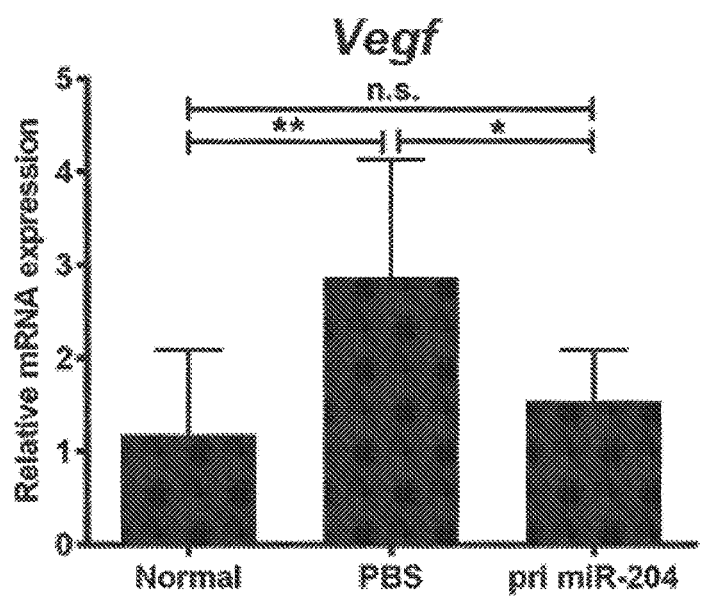
Figure 24:
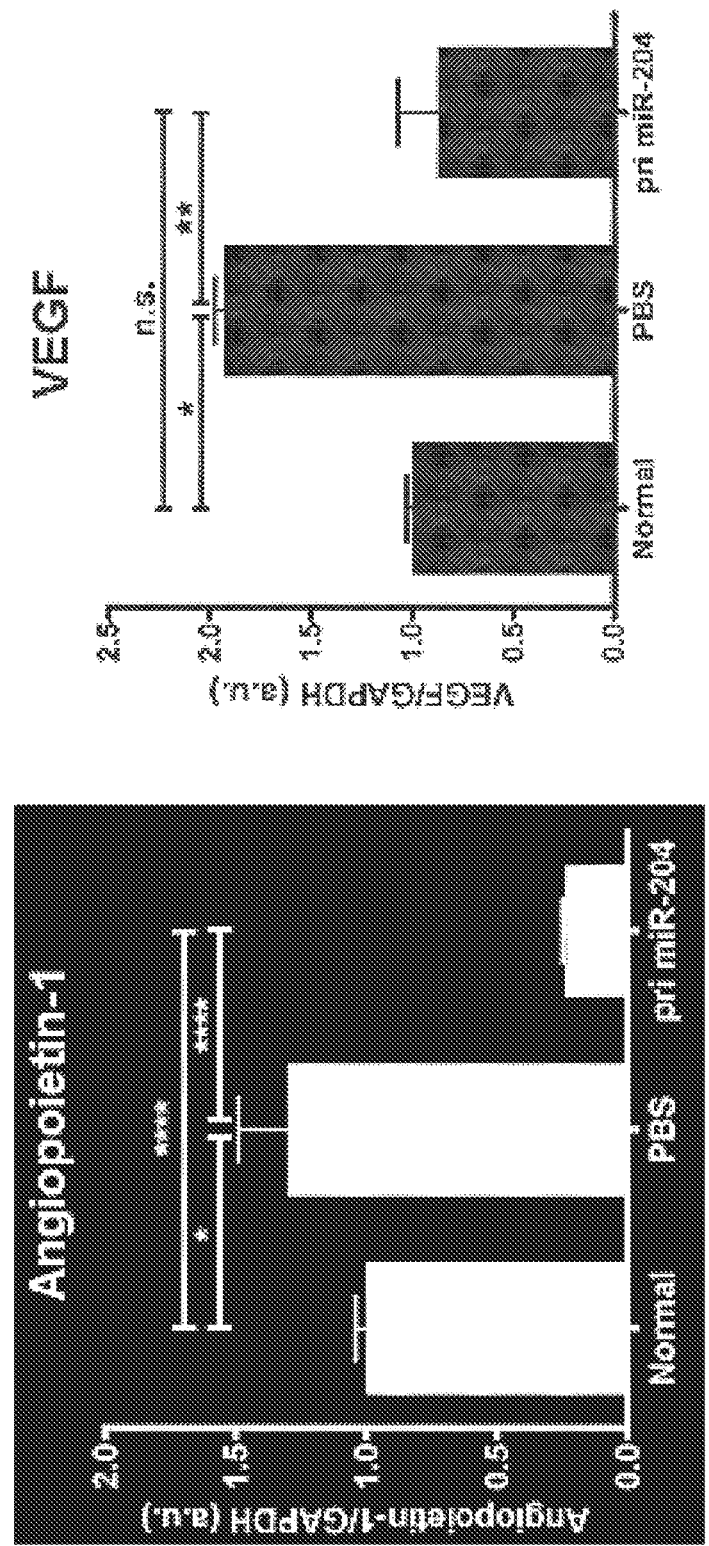
Figure 24:
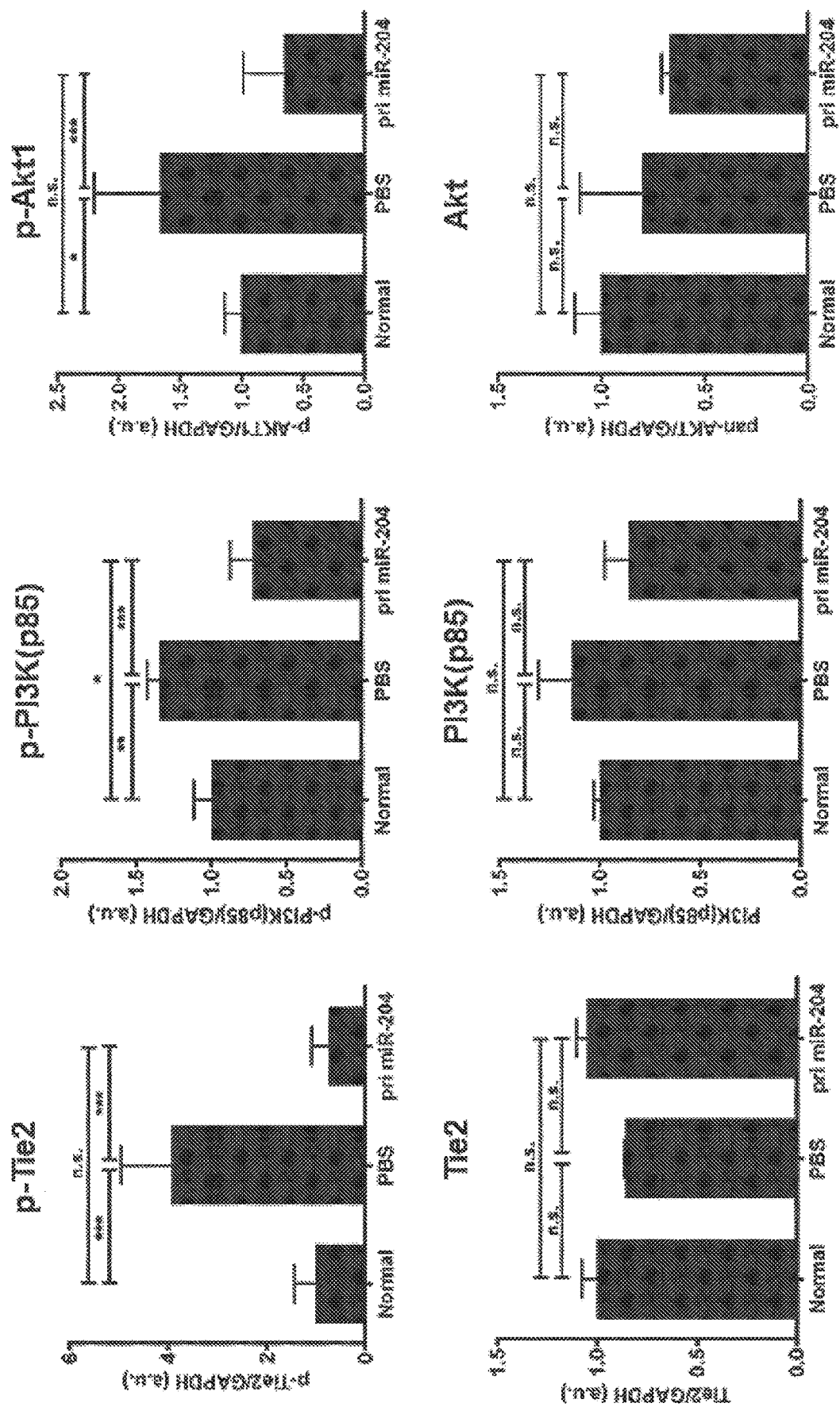
Figure 25A:
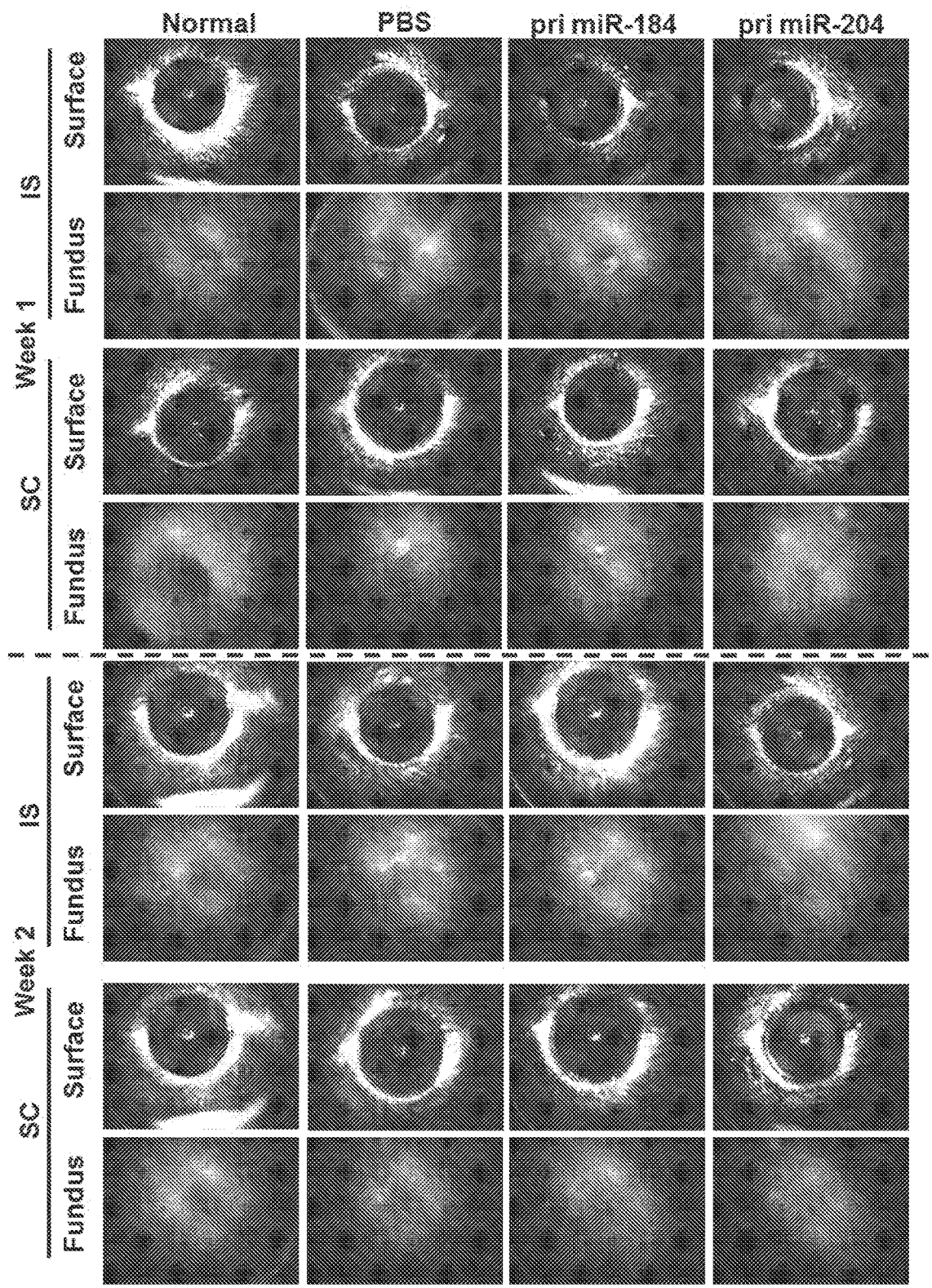
FIGS. 25A-25B show rAAVrh.10 delivered pri miR-184 and pri mir-204 did not induce obvious abnormality in normal mouse eyes.
Figure 25B:
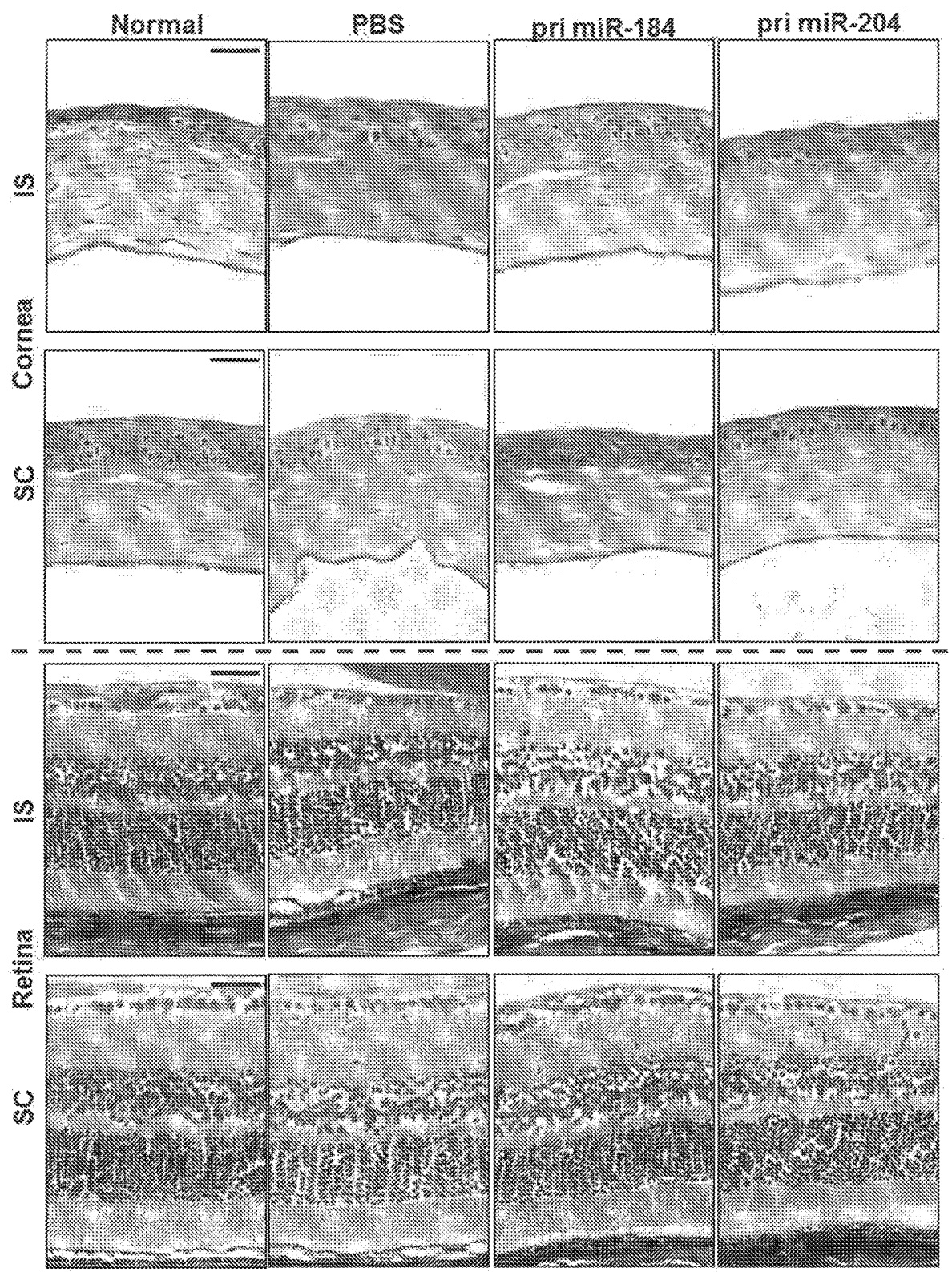

FIGS. 23-24 show overexpression of miR-204 inhibit Angpt-1 expression (e.g., Tie2-P13K-Akt pathway). The diagram of the miR-204 signaling pathway on the right side of FIG. 23 is adapted from Kather et al., Invest Opthalmol Vis Sci; 2004.

rAAVrh.10 Delivered Pri miR-184 & Pri Mir-204 Did not Induce Obvious Abnormality in Normal Mouse Eyes FIGS. 25A-25B show rAAVrh.10 delivered pri miR-184 & pri mir-204 do not induce obvious abnormality in normal mouse eyes.

Example 4. Ocular Delivery of miR-204 by rAAV

Materials and Methods
Mouse Corneal Neovascularization Induced by Alkali Burn

Alkali-burn treatments were conducted following previously published methods. Only the right eyes of mice were treated. Filter-paper discs (3-mm diameter) were pre-soaked in 1 M NaOH for 15 seconds, and applied to eyes in experimental groups for 20 seconds. The ocular surface was then washed with 15 mL of normal saline for 1 minute. Mouse corneas of anesthetized animals were imaged and acquired with a Micron III camera (PhoenixResearch Labs, Pleasanton, CA, USA). The area of corneal NV was calculated by using the following formula: Area $(mm^2)=CN/12 \times 3.1416 \times [R^2-(R-VL)^2]$, where CN is the clock hours of NV (1 clock hour equals 30 degrees of arc); R is the radius of the cornea; and VL is the maximal vessel length, extending from the limbal vasculature. Measurements of corneas in live animals were performed five times each under a Micron III microscope and the area of corneal NV was calculated accordingly.

Nanostring nCounter miRNA Assay for miRNA Profiling

A total of 100 ng of RNA was extracted from whole mouse corneas. Four corneas were pooled into one sample and profiled for miRNA expression using the nCounter miRNA Expression Assay Kit (NanoString Technologies, Inc., Seattle, WA, USA). The assay was performed according to the manufacturer's instructions, querying 578 mouse miRNA targets, 33 mouse-associated viral miRNA targets, and 6 negative control targets. The mean expression values of each miRNA were calculated by normalizing across our cohort to filter for expressed miRNAs. The 6 internal negative control probes served as the background threshold cutoff-point (set to 1.0).

RNA-Seq

Mouse corneas representing three treatment groups: non-treated (day 0), post-operative (day 5), and regression post-operative (day 15) were treated as above. Total RNA was extracted from tissues and processed for RNA-seq library preparation and high-throughput sequencing on a HiSeq2500 platform. Four corneas were pooled to represent a single sample library, and two libraries represent each treatment condition. Each biological condition therefore reflects eight individual mouse corneas. This strategy was employed to compensate for the low abundance of total RNA in an individual mouse cornea, and to limit the number of animals used for each condition. Primary bioinformatics analysis (Tophat/Cufflinks workflows, differential expression, and ontology enrichment analysis) was performed. Predicted miRNA target genes were selected from differentially expressed genes and analyzed with the CummeRbund (v2.12.1) software package.

Hierarchical Cluster Analysis

Hierarchical clustering was performed with average linkage using Cluster 3.0 (Eisen Lab, University of California at Berkeley, CA, USA). The clustered heat map was visualized using the interactive graphical software, TreeView. A limma algorithm was applied to filter the differentially expressed miRNAs from different experimental groups. After performing significance ($P<0.05$) and false discovery rate analysis (FDR<0.05), differentially expressed miRNAs with a ±2-fold change cut-off were selected. Selected miRNAs were ranked by fold-change.

miRNA Target Gene Prediction and Gene Ontology/Pathway Analysis

Differentially expressed miRNAs identified by nCounter Analysis were subjected to target gene prediction analysis using TargetScan and miRTarbase definitions. Gene ontology network maps and term enrichment analyses were performed using Cytoscape_v3.3.0 plug-in tools and ClueGO v2.2.332 with terms defined by GO_BiologicalProcess-GOA_07.12.2015 and KEGG pathways. Significance was defined by a Kappa score threshold of 0.4, with p-value cutoffs of 0.05 for pathway reporting. Genes and miRNAs enriching for terms related to vasculogenesis, JAK/STAT signaling, Ephrin signaling, eye development, epithelial cell homeostasis, BMP signaling, wound healing, and cell growth were reported.

rAAV Vector Production pri-miR-184 and pri-miR-204 were amplified using the PrimeSTAR Max DNA Polymerase kit (Takara, Japan) with the following primers:

```
pri-miR-184:
sense
                                    (SEQ ID NO: 30)
5'-CCGGAATTCTGTGCAGAAACATAAGTGACTCTCCAGGTG-3' antisense
                                    (SEQ ID NO: 31)
5'-ATCGGCGGCCGCGCAGAGAGCACATTTTGAATAAGCAAAGTG-3' pri-miR-204:
sense
                                    (SEQ ID NO: 32)
5'-CCGGAATTCTTTACCCACAGGACAGGGTGATGGAGAGGA-3' antisense
                                    (SEQ ID NO: 33)
5'-ATCGGCGGCCGCGTCACATGGTTTGGACCCAGAACTATTAGT-3'
```

PCR products were sub-cloned into the self-complementary (sc) pAAV-CB-PI-GaussiaLuc plasmid by conventional means using NotI and EcoRI restriction sites. The sc-pAAV-CB-PIEGFP plasmid and sc-pAAV-CB-PI-pri-miR184/204-GaussiaLuc plasmids were packaged with rAAVrh.10 capsids by triple plasmid transfection of HEK293 cells. Viruses were purified with CsCl gradient ultracentrifugation and titered by both quantitative polymerase chain reaction (qPCR) and silver staining of SDS-PAGE gels.

rAAV Transduction by Intrastromal or Subconjunctival Injection

Intrastromal injections were performed. Briefly, a 1.0 mm long incision using the tip of a 26-gauge needle was first created through the corneal epithelium, equidistant between the cornea-scleral junction and the corneal center. Then, $3.6 \times 10^{10}$ genomic copies (GC) of vector in 4 µL of PBS were injected through the incision into the corneal stroma using a 33-gauge needle and a 5 µL Hamilton syringe (Hamilton, Reno, NV, USA). Subconjunctival injections were performed using a 5 µL Hamilton syringe to deliver $3.6 \times 10^{10}$ GC of vector in 4 µL of PBS. Antibiotic ointment was applied after injections.

Quantitative Real-Time PCR (qRT-PCR) for microRNA and mRNA Expression Analyses

RNA extraction and qRT-PCR for miRNA (TaqMan miRNA assay, Life Technologies, Carlsbad, CA, USA: miR-184, miR-204) and mRNAs were performed. Primer sequences for fzd4, vegf-a, and angpt1 are reported in Table 2. U6 and β-actin were used as normalization transcripts for miRNAs and mRNAs, respectively.

TABLE 2

| Primer Name | Primer Sequence | SEQ ID NO: |
|---|---|---|
| Fzd4 Fwd | TGCCAGAACCTCGGCTACA | 34 |
| Fzd4 Rev | ATGAGCGGCGTGAAAGTTGT | 35 |
| Vegf-a Fwd | GCCAGCACATAGAGAGAATGAGC | 36 |
| Vegf-a Rev | CAAGGCTCACAGTGATTTTCTGG | 37 |
| Angpt1 Fwd | CACATAGGGTGCAGCAACCA | 38 |
| Angpt1 Rev | CGTCGTGTTCTGGAAGAATGA | 39 |

Droplet Digital PCR for rAAV Genome Copy Number and RNA Expression Analyses

Mouse cornea genomic DNA was isolated using the QIAamp DNA kit (Qiagen, Hilden, Germany), and then digested with >10 U/µg SalI (New England Biolabs, Ipswich, MA, USA) at 37° C. for 1 hour. There are two SalI sites in the rAAV genome, and SalI digestion ensures single copy emulsion for droplet digital PCR (ddPCR) quantification. Multiplexed ddPCR was performed on a QX200 ddPCR system (Bio-Rad Laboratories, Hercules, CA, USA) using Taqman reagents targeting EGFP (Catalog #4400293, Life Technologies) and the reference gene, transferrin receptor (Tfrc) (Catalog #4458367, Invitrogen, Waltham, MA, USA). rAAV genome copy numbers per diploid genome were calculated as EGFP transgene copy numbers per two Tfrc gene copies.

Total RNA was extracted using the RNeasy 96 QIAcube HT kit with on-column DNase I digestion (Qiagen, Valencia, CA, USA), reverse-transcribed into cDNA, and subjected to multiplexed ddPCR using TaqMan reagents targeting EGFP and Glyceraldehyde-3-Phosphate Dehydrogenase (gapdh) (Catalog #4352339E, LifeTechnologies). The quantity of EGFP was normalized to gapdh levels.

Western Blot

Total protein from corneas was extracted on ice with RIPA lysis buffer in the presence of freshly added protease and phosphatase inhibitors (Thermo Fisher Scientific, Waltham, MA, USA). A total of 10 µg/lane protein extract was loaded onto a 4-20% gradient SDS-polyacrylamide gel and transferred to nitrocellulose membranes (Bio-Rad Laboratories). Nonspecific binding was blocked with 5% nonfat milk or 5% BSA in TBST as recommended for each antibody. The membrane was incubated with rabbit anti-VEGF (ab46154, Abcam, Cambridge, MA, USA), anti-Angpt1 (ab95230, Abcam), anti-Tie2 (Cat. 7403, Cell Signaling, Danvers, MA, USA), anti-phospho-Tie2 (AF2720-SP, R&D Systems, Minneapolis, MN, USA), anti-PI3K (p85) (Cat. 4292, Cell Signaling), anti-phospho-PI3K (p85) (Cat. 4228, Cell Signaling), anti-Akt (ab8805, Abcam), anti-phospho-Akt1 (ab81283, Abcam), anti-Fzd4 (ab83042, Abcam), anti-LRP6 (Cat. 3395S, Cell Signaling), antiphospho-LRP6 (Cat. 2568S, Cell Signaling), anti-N-p-β-catenin (Cat. 4270, Cell Signaling), or anti-β-catenin (Cat. 8480S, Cell Signaling) antibodies overnight at 4° C. IRDye 800CWgoat anti-rabbit IgG (Cat. 926-32211, LI-COR, Lincoln, NE, USA) was used as the secondary antibody, and mouse anti-GAPDH antibody (ab8245, Abcam) was used as an internal standard.

Histological and Immunofluorescence-Histochemical Analyses

For rAAV transduction efficiency analysis, mouse eyes were enucleated and fixed in 4% paraformaldehyde. Corneas with limbi were then harvested for corneal flat-mounts, and blocked in 5% goat serum in PBS. For detecting EGFP expression in normal mouse corneas, flat-mounts were stained with rabbit anti-mouse GFP primary antibody (1:1000; Life Technologies), followed by goat anti-rabbit IgG-Alexa Fluor 488 secondary antibody (1:1500; Life Technologies). For corneas treated by alkali burn, flat-mounts were stained with rat anti-mouse CD31 (1:500; Abcam) and rabbit anti-mouse keratocan (1:50; SantaCruz Biotechnology, Dallas, TX, USA) primary antibodies, followed by goat anti-rat IgGAlexaFluor 568 and goat anti-rabbit IgG-Alexa Fluor 694 secondary antibodies (1:1500; Life Technologies). Corneal whole mounts were set with VECTASHIELD anti-fade mounting medium with DAPI (Vector Laboratories, Burlingame, CA, USA) for observation and imaging analysis. For corneal NV detection after alkali-burn treatment, flat-mounts were stained with the rat anti-mouse CD31 primary antibody (1:500; Abcam), followed by goat anti-rat IgG-Alexa Fluor 568 secondary antibody (1:1500).

To evaluate the safety of pri-miRNA vectors, mouse eyes from each group were fixed in 10% formalin, embedded in paraffin, sectioned at a thickness of 4 µm, and stained with Haematoxylin and Eosin (H&E) for histological analysis. Images were obtained using a Leica DMC2900 microscope (Leica Microsystems, Buffalo Grove, IL, USA).

miR-204 is Significantly Down-Regulated in Neovascularized Mouse Corneas

The expression of miRNAs in alkali-burn induced neovascularized mouse corneas was profiled by nCounter analysis. It was observed that among differentially expressed miRNAs, miR-204 is reduced more than 10-fold in response to alkali-burn injury. Whole-transcriptome analyses by RNA-seq and miRNA target prediction identified more than 200 corneal genes that are up-regulated in response to alkali-burn treatment and are predicted to be regulated by miR-204. Data indicate that overexpression of pri-miR-204 in injured corneas inhibited vascularization into the cornea.

Candidate therapeutic miRNAs that may function to inhibitor reverse corneal neovascularization (NV) when overexpressed were identified. First, neovascularized mouse corneas induced by alkali-burn treatment were characterized. Vascularization into the cornea was observed for 15 days following injury (FIG. 1A). Notably, corneal NV was observed to originate in the limbus by day 5, and fully expanded into the cornea by days 10 and 15. Untreated corneas and corneas following 5-, 10-, and 15-days after alkali-burn treatments were subjected to miRNA profiling using Nanostring nCounter analysis. 36 highly up-regulated and 3 strongly down-regulated miRNAs were observed in alkali-burn treated corneas (corneal NV miRNAs) compared to non-treated controls (FIG. 1A).

The range of angiogenesis-related genes that might be directly regulated by corneal NV miRNAs were investigated. Unbiased miRNA target prediction analysis was performed to identify genes with high likelihoods of being targeted by our panel of corneal NV miRNAs. TargetScan and miRTarbase target prediction yielded a list of 5,520 target genes. In this example, miR-204 was selected as the candidate therapeutic miRNA based on the observation that miR-204 exhibits >10-fold expression reduction in neovascularized corneas. Additionally, miR204 is conserved across several vertebrate species, making it an ideal candidate for translation into humans. The effect of miR-184 mimics on corneal NV was also observed. Differential miR-184 and miR-204 expression was verified by qRT-PCR (FIG. 13), confirming nCounter analysis results.

Differential Expression of miR-204 Target Genes in Alkali-Burn Treated Corneas Indicates that Multiple Pathways Promote Corneal Angiogenesis.

Figure 26A:
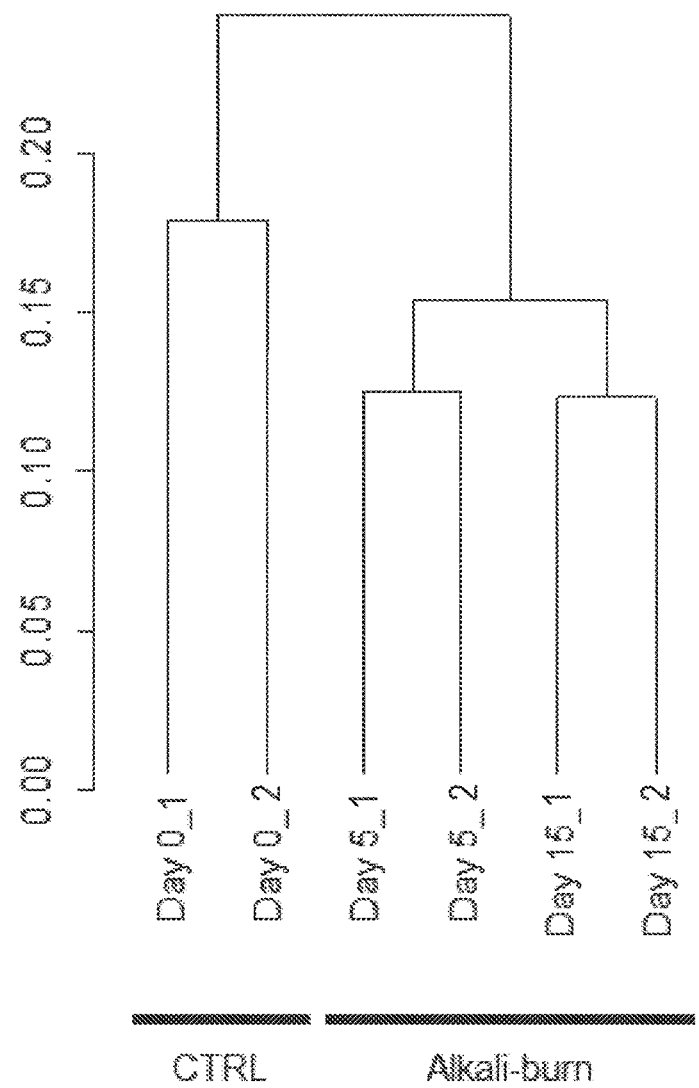
FIGS. 26A-26C show RNA-seq analysis reveals differential expression of miR target genes.
Figure 26B:
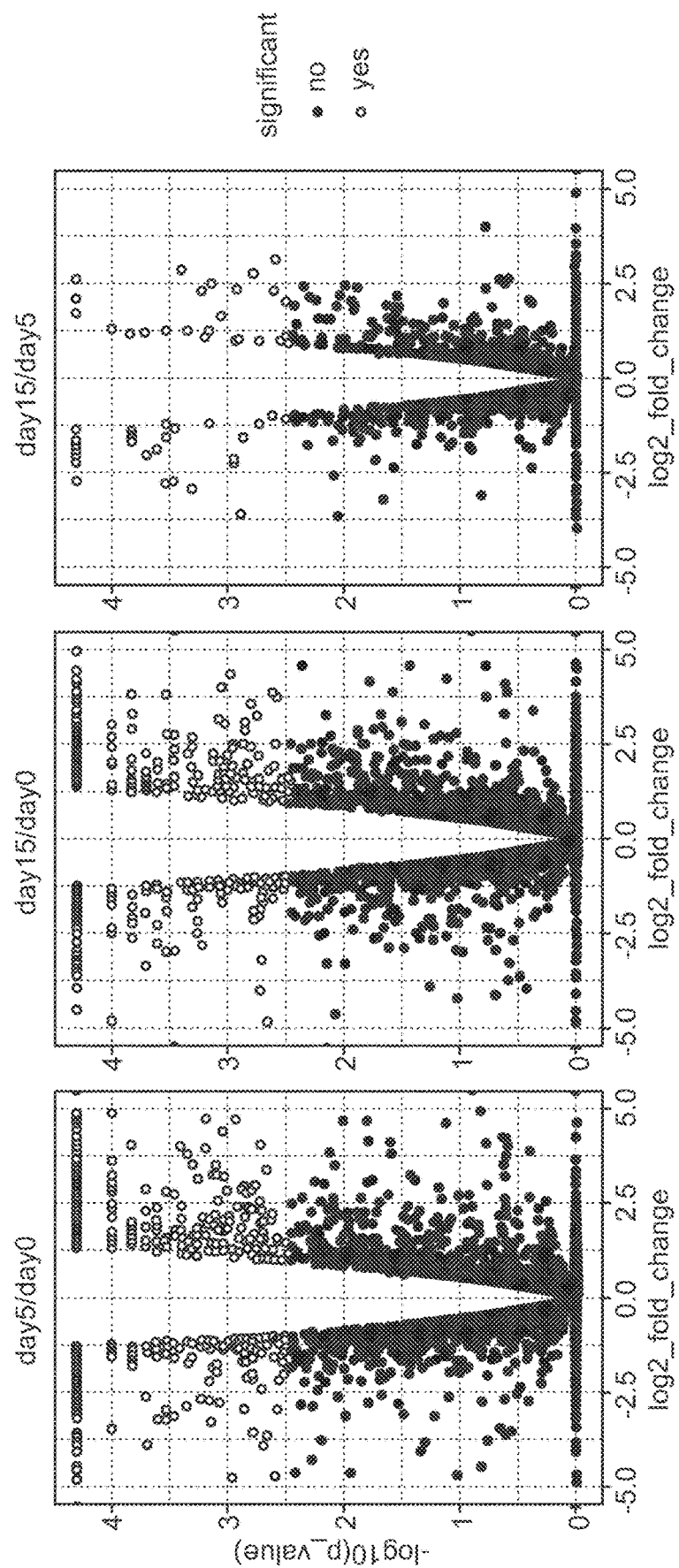
Figure 26C:
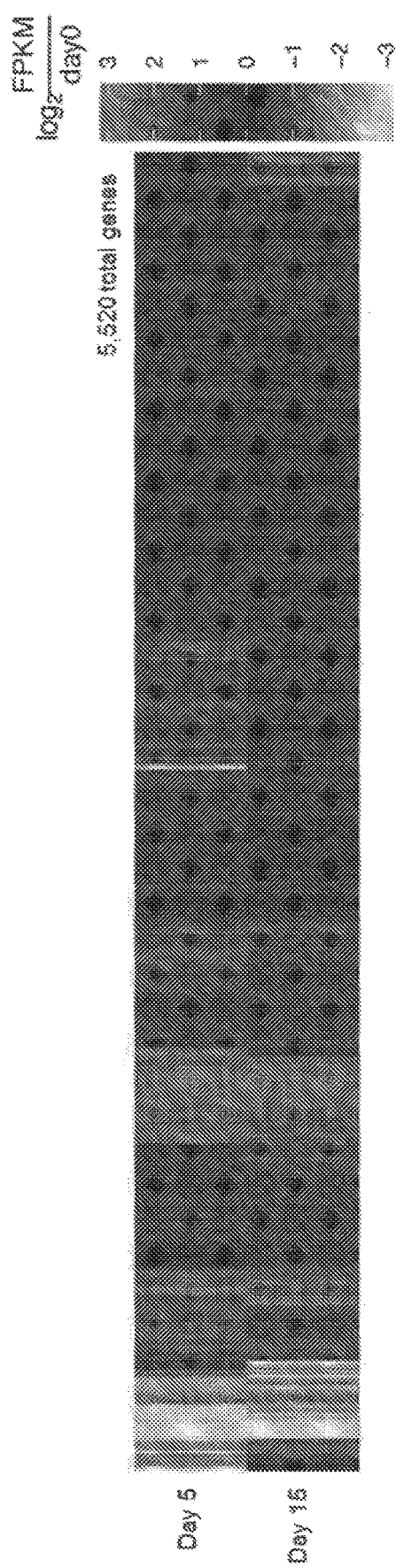

The extent that miR-204 may impact corneal angiogenesis was investigated. Specifically, whether miR-204 displays characteristics of a potent therapeutic miRNA for corneal NV by targeting multiple genes involved in angiogenesis, wound healing, and related signaling pathways was assessed. Targetscan and miRTarbase analysis indicate that miR-204 is targets 1,729 genes. Whole-transcriptome analysis of alkali-burn treated corneas by RNA-seq analysis was performed. Untreated corneas (day 0), and corneas 5-days and 15-days post-treatment (day 5 and day 15, respectively) were analyzed. Dendrograms reflecting the expression profile relationships across sample libraries indicate that day 5 and day 15 libraries share a higher degree of similarity than the day 0 corneas (FIG. 26A). The fold-change differences of the predicted target genes of all 39 corneal NV miRs were calculated. Volcano plots of differential miR target gene expression between day 0 and day 5 corneas, and day 0 and day 15 corneas (FIG. 26B) show an abundance of differentially expressed miR target genes, while comparison between day 5 and day 15 exhibit fewer differentially expressed miR target genes. This observation indicates that the majority of gene expression changes due to injury occur within the first five says of treatment. Heatmap analysis (FIG. 26C) further illustrates the range of miR target genes that are differentially expressed as a result of alkali-burn treatment.

Figure 27A:
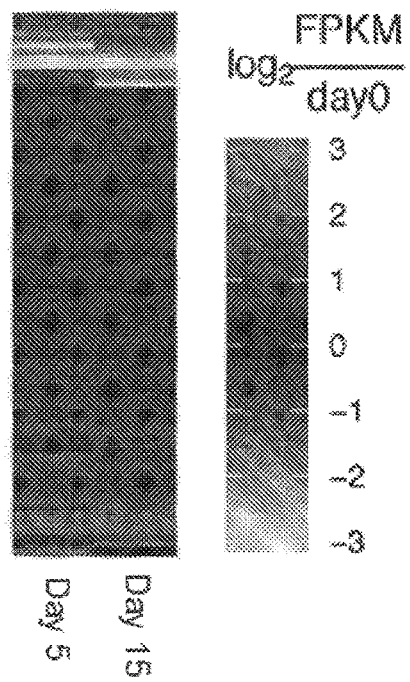
FIGS. 27A-27C show up-regulated miR-204-predicted targets are associated with multiple biological processes and pathways.
Figure 27B:
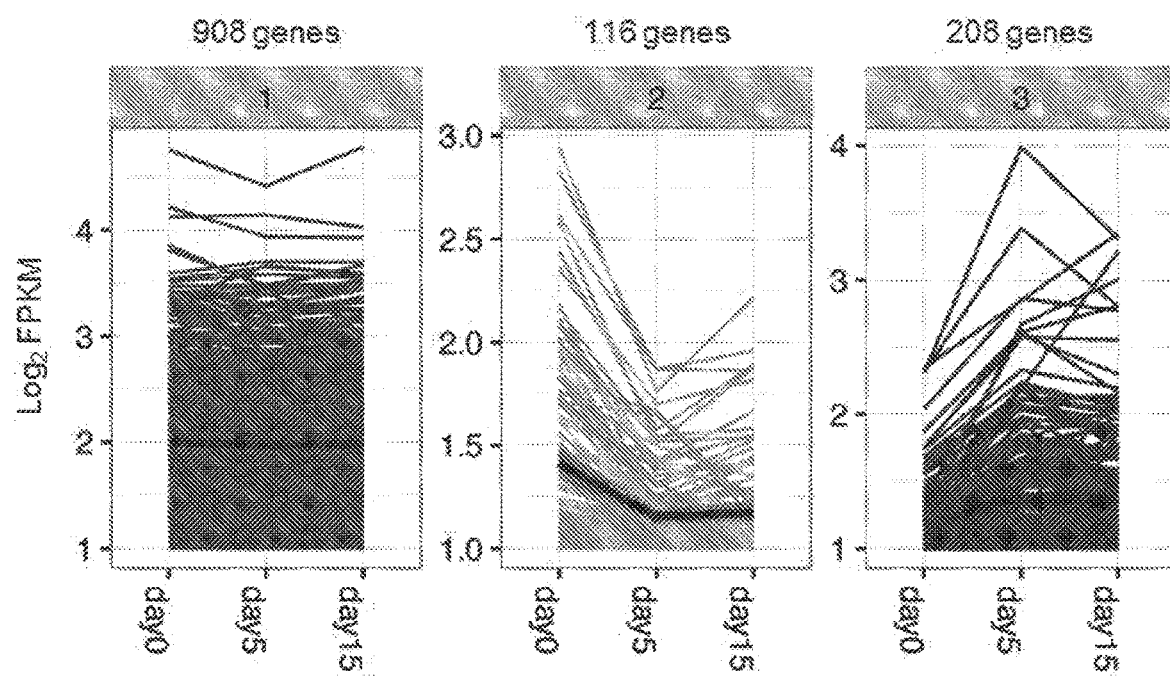
Figure 27C:
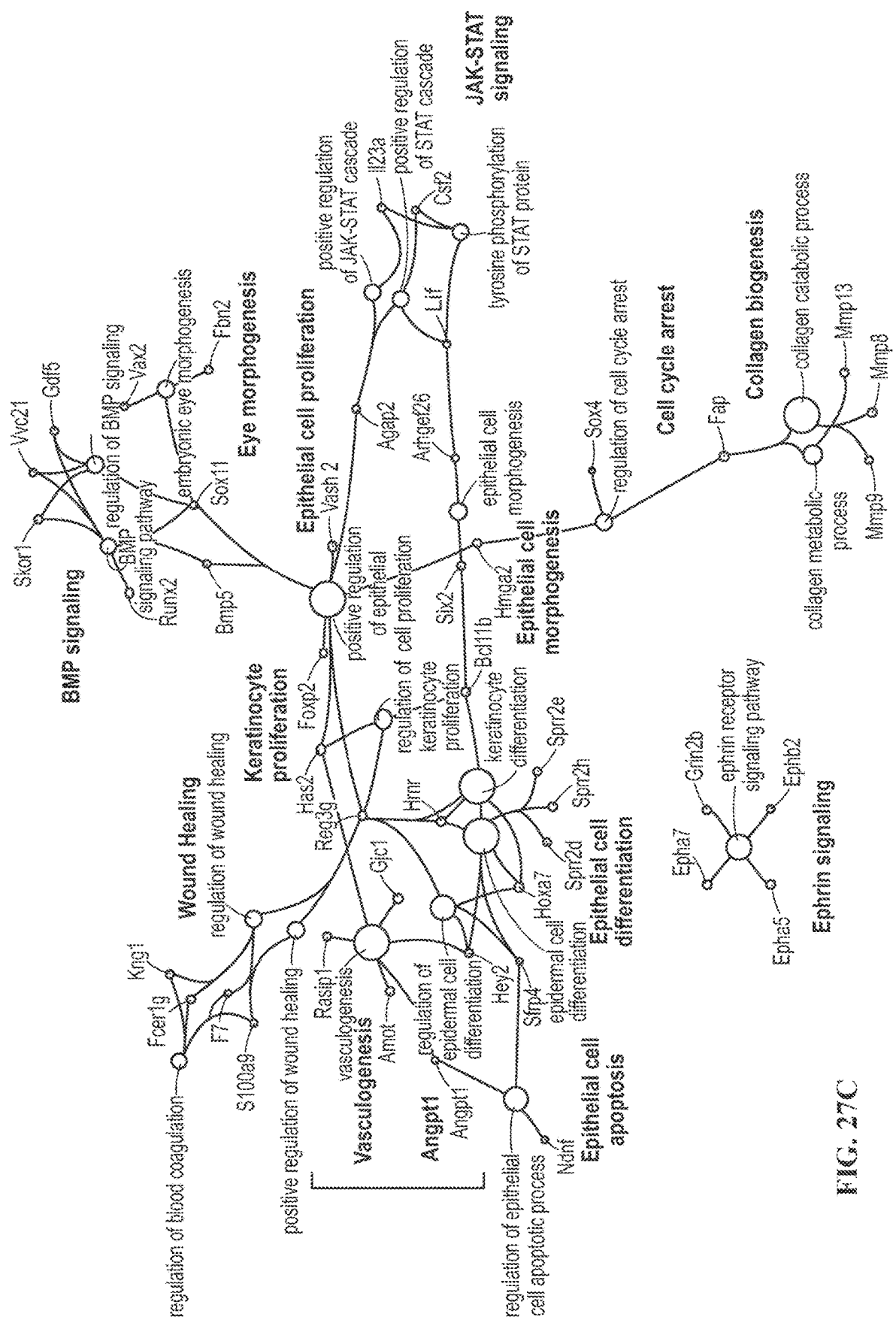
Figure 28:
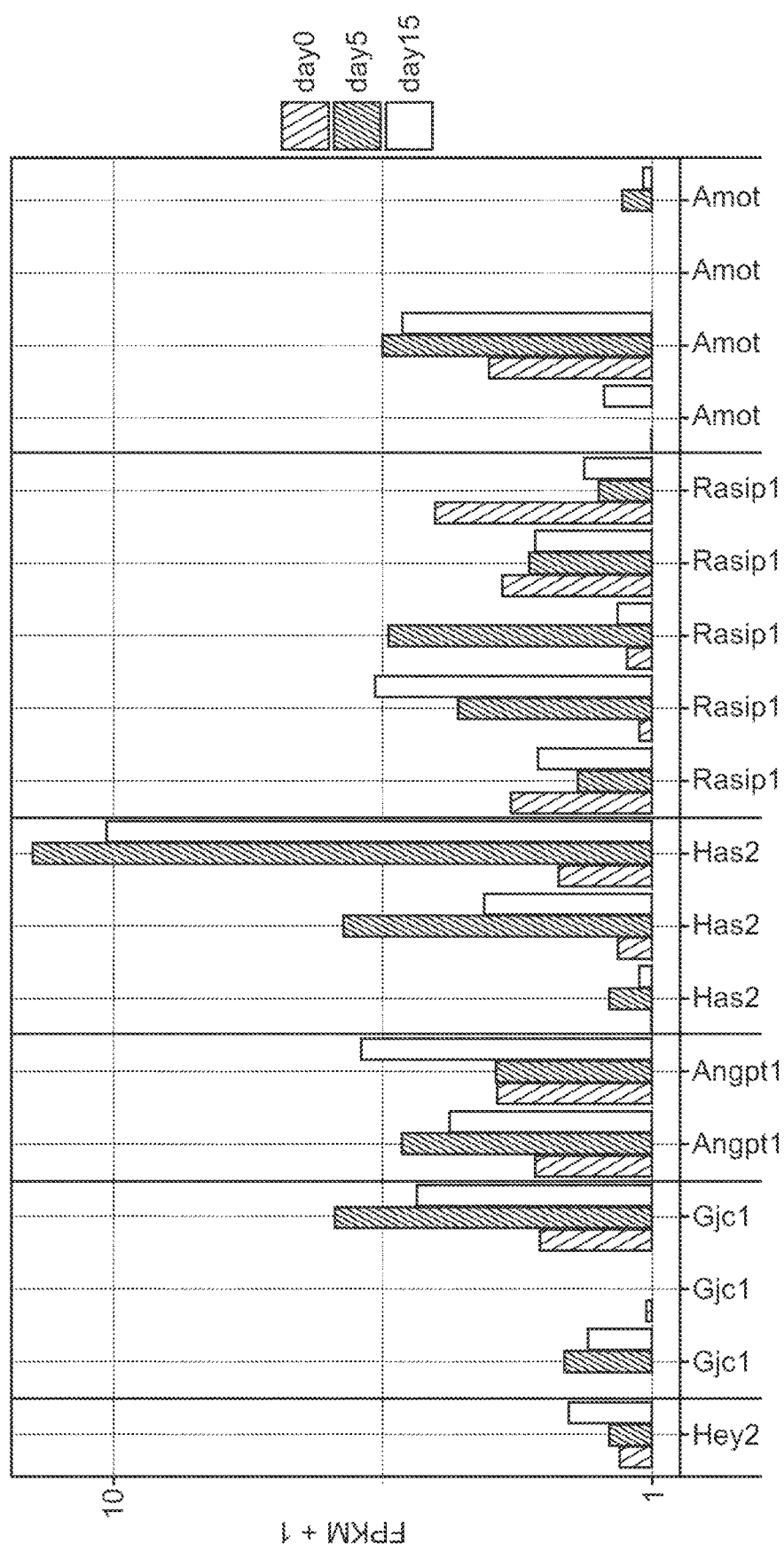
FIG. 28 shows expression of predicted miR-204 target genes that are related to vasculogenesis. Relative expression (FPKM) of predicted miR-204 target genes that are up-regulated after alkali-burn treatment of corneas. The six genes displayed, including their known isoforms, demonstrate an increase in mRNA expression as assessed by RNA-seq analysis. Data for untreated corneas (day 0), corneas 5 days post-treatment (day 5), and 15 days post-treatment (day 15) are shown.

Importantly, it was observed that among the 1,729 miR-204 gene targets, 1,232 are expressed in the cornea (FIG. 27A-27B). A set of genes that are up-regulated upon alkali-burn treatment was investigated. To this end, k-means clustering was performed to identify 208 genes that are exclusively up-regulated in corneas after 5 and 15 days post-alkali-burn treatment (FIG. 27B). These 208 miR-204 target genes were subjected to gene ontology (GO)-term enrichment analysis. By selecting on KEGG pathway and ontological terms closely related to angiogenesis and wound healing, several up-regulated miR-204 predicted targets were identified that demonstrate miR-204 as a potent anti-angiogenic effector (FIG. 27C). Specifically, the vasculogenesis-related genes: Hey2, Gjc1, Angpt1, Has2, and Amot were identified (FIG. 28). It was observed that Angpt1, Has2, and Hey2 also enrich for epithelial cell- and keratinocyte-related ontology terms, indicating that miR-204 directly regulates key genes with diverse roles in angiogenesis and cell proliferation in the cornea.

Both Intrastromal and Subconjunctival Delivery of rAAVrh.10 Efficiently Transduces Normal and Alkali-Burn Treated Corneas Delivery of therapeutic miRs into corneal tissues was investigated. It was observed that rAAVrh.10 exhibits the highest transduction efficiency in the corneal stroma by intrastromal injection. Two different routes of administration, intrastromal and subconjunctival, were investigated. Data for rAAVrh.10 transduction efficiency in normal mouse corneas by either intrastromal or subconjunctival injections indicate that both injection methods to deliver rAAVrh.10 EGFP vectors efficiently transduce the entire cornea (FIG. 14).

The effects of alkali-burn on the efficacy of corneal transduction by rAAVrh.10 vectors (schematized in FIG. 15 and FIG. 17) were investigated. Intrastromal injections were performed two weeks prior to alkali-burn induction. Subconjunctival injections were performed directly following alkali-burn. Whole flat-mount immunofluorescence analyses of eyes harvested one or two weeks post-alkali-burn show that EGFP transgene expression in non-alkali-burn treated corneas (control group) is strongly detected at weeks 1 and 2 with little change inexpression for both intrastromal and subconjunctival vector injections (FIG. 15 to FIG. 18). Alkali-burn treated corneas showed robust EGFP expression at week 1 following alkali-burn treatment, but exhibited an extreme loss of EGFP expression at week 2 (FIG. 15 and FIG. 17). EGFP was mainly expressed in kerotocytes and not in vascular endothelial cells.

The abundance of transduced rAAV genomes and EGFP mRNA expression following alkali-burn treatment was investigated. Quantitative analysis of vector genomes delivered by either intrastromal or subconjunctival injection indicated that rAAV genome copies in alkali-burn treated corneas were significantly lower than control corneas (FIG. 16 and FIG. 18). It was also observed that intrastromal delivery was more potent for transgene expression than subconjunctival delivery. In some embodiments, the relative loss between weeks 1 and 2 was ~50% in both delivery routes. Quantification of EGFP mRNA expression showed that there was no significant difference between alkali-burn and control groups at post-alkali-burn week 1; however, EGFP expression in alkali-burn treated corneas after 2 weeks were significantly lower than control corneas (FIG. 16). Data indicate that, in some embodiments, alkali-burn severely compromises the expression of rAAVrh.10 delivered transgenes following a two-week time course. In some embodiments, differences in transgene expression between normal corneas and treated corneas are negligible for at least one week after alkali burn following only a single treatment.

rAAVrh.10-Mediated miR-204 and miR-184 Overexpression by Subconjunctival Injection Inhibits Corneal NV A rAAVrh.10 vector that drives the expression of pri-miR-204 was produced. The efficacy of pri-miR-184 when delivered by rAAVrh.10 was also investigated.

Figure 19A:
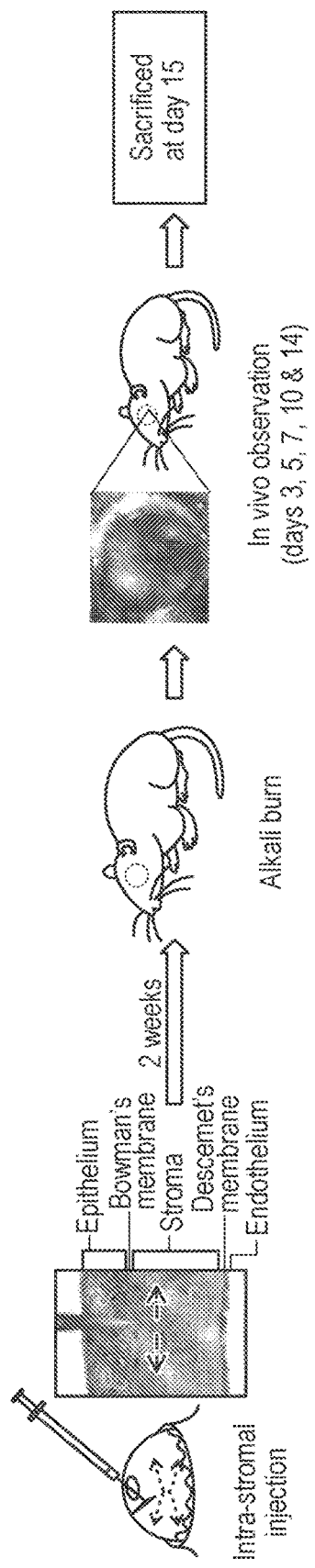
FIGS. 19A-19D show rAAV.rh10 delivered pri miR-184 and pri miR-204 could inhibit corneal NV as prevention through intrastromal injection (IS). The dashed circle represents avascular area, *: p<0.05, : p<0.01, *: p<0.001, ****: p<0.0001.
Figure 19B:
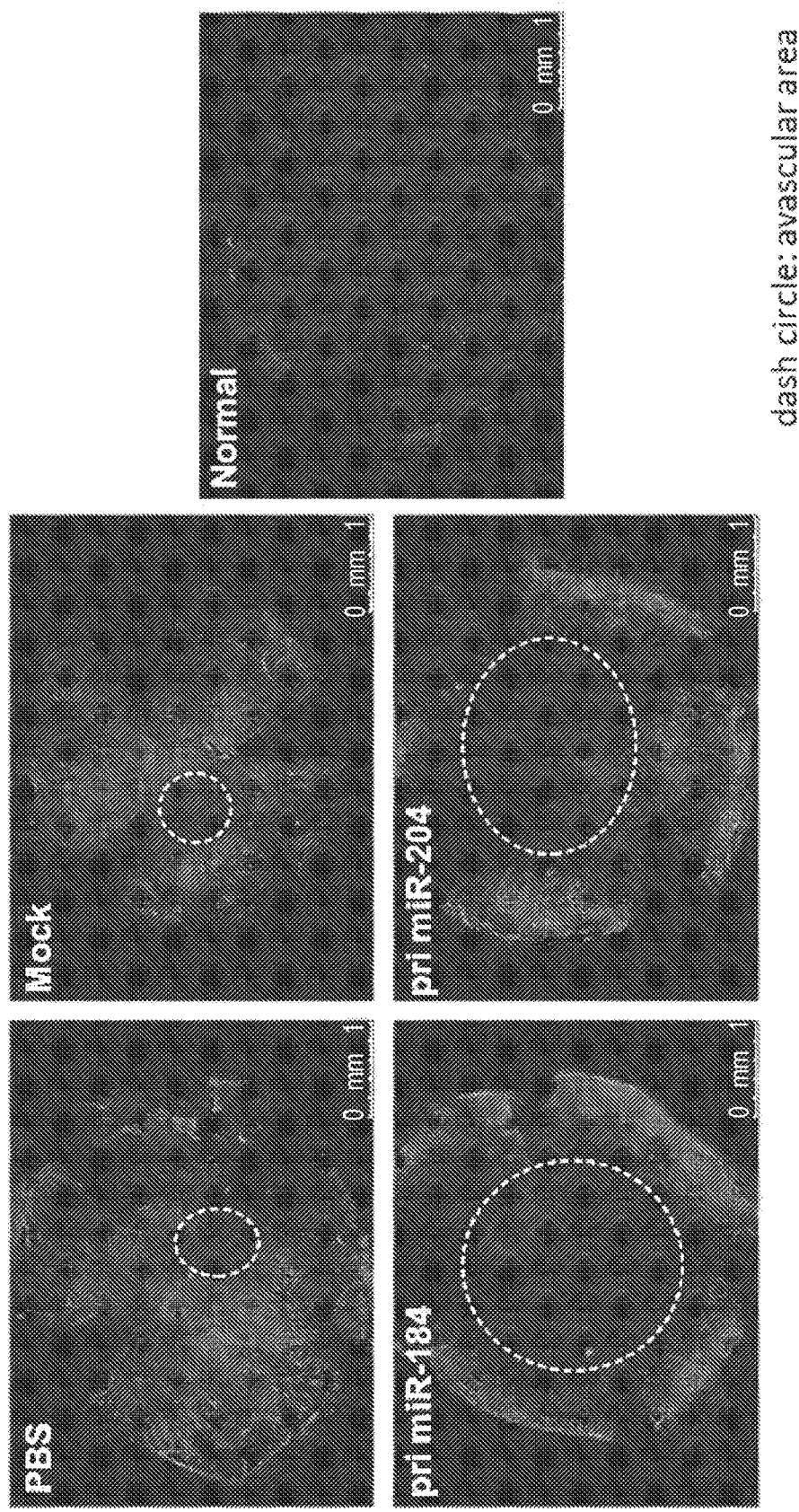
Figure 19C:
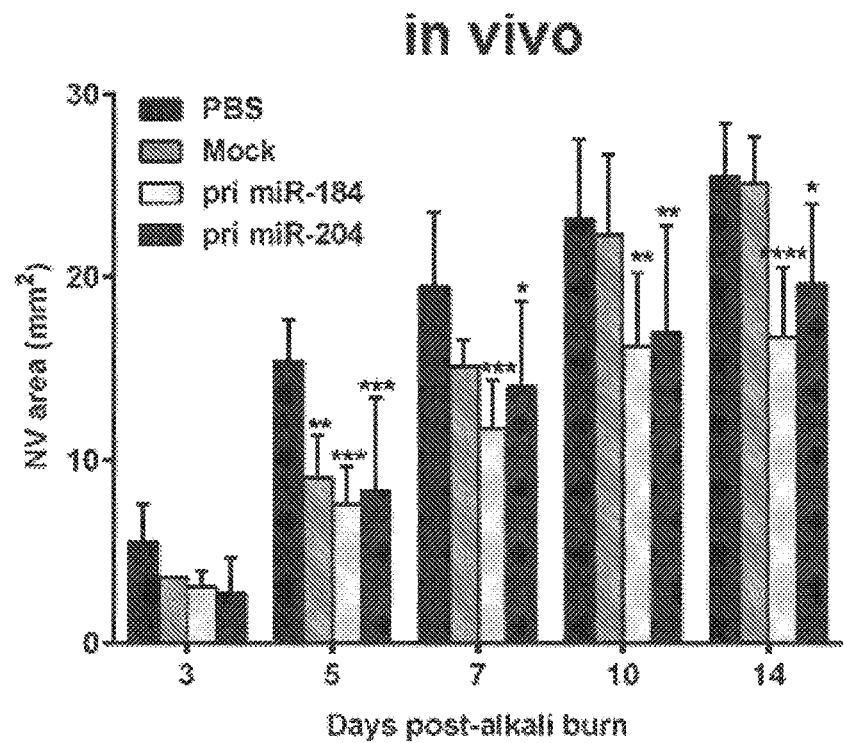
Figure 19D:
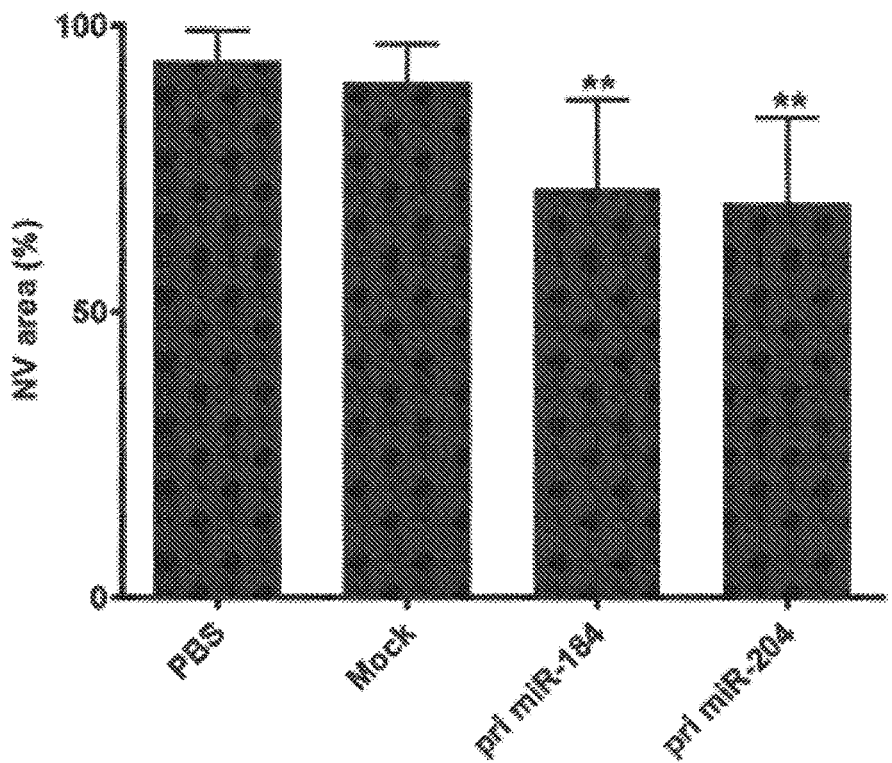
Figure 20A:
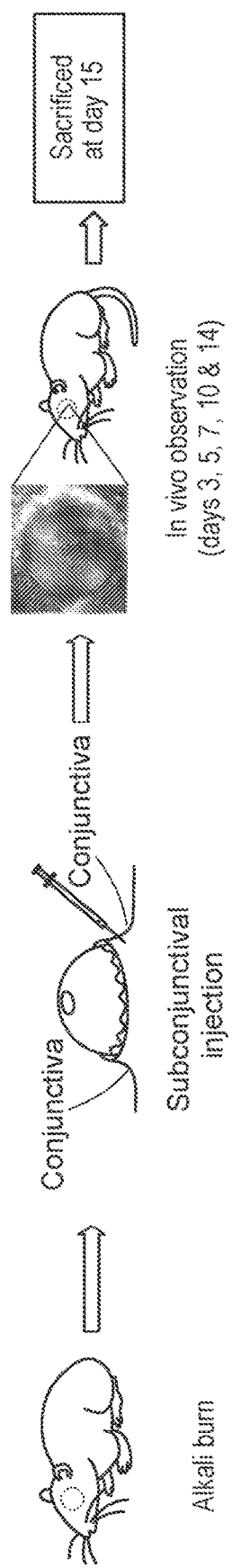
FIGS. 20A-20D show rAAV.rh10 delivered pri miR-184 and pri miR-204 could inhibit corneal NV as treatment through subconjunctival injection (SC). The dashed circle represents avascular area, *: p<0.05, : p<0.01, *: p<0.001, ****: p<0.0001.
Figure 20B:
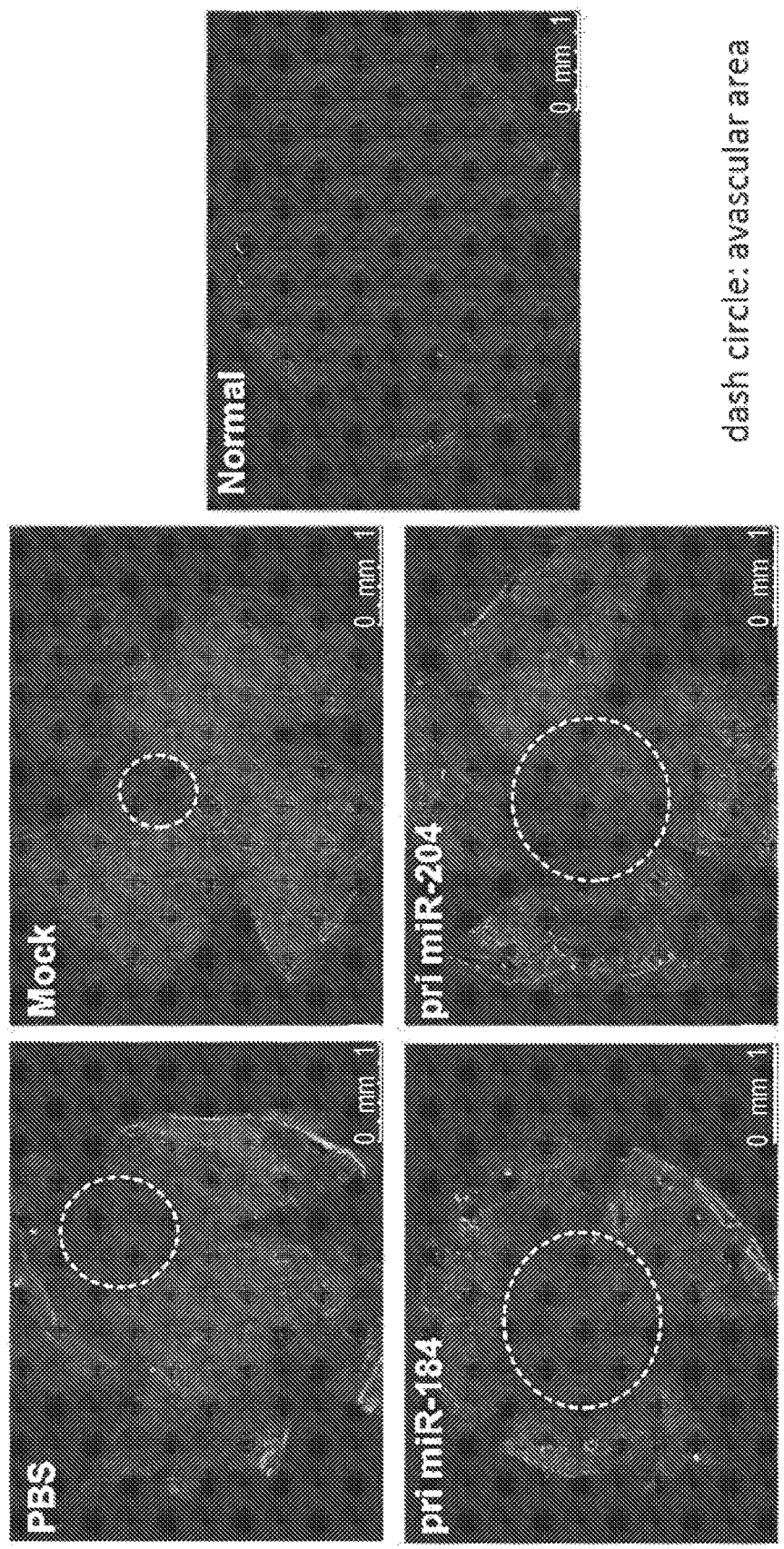
Figure 20C:
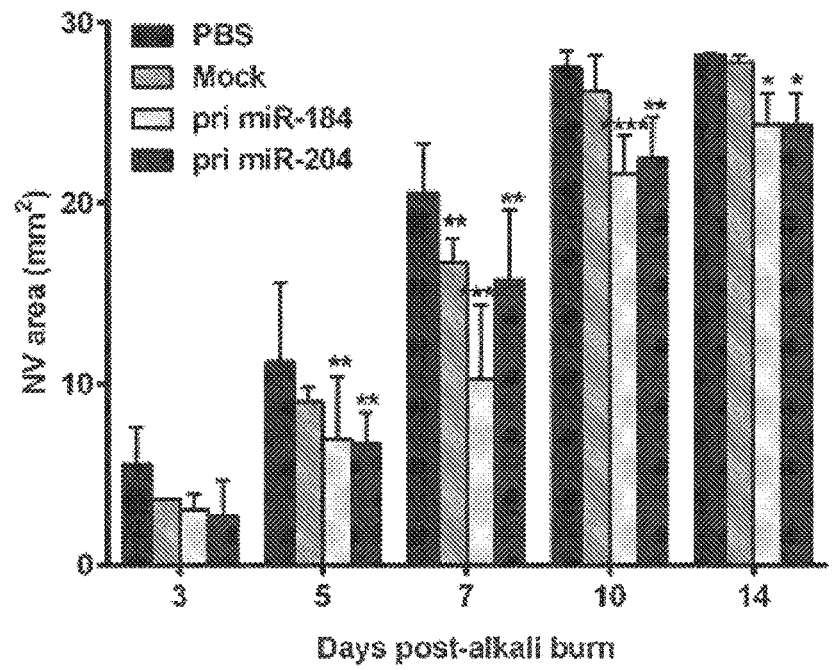
Figure 20D:
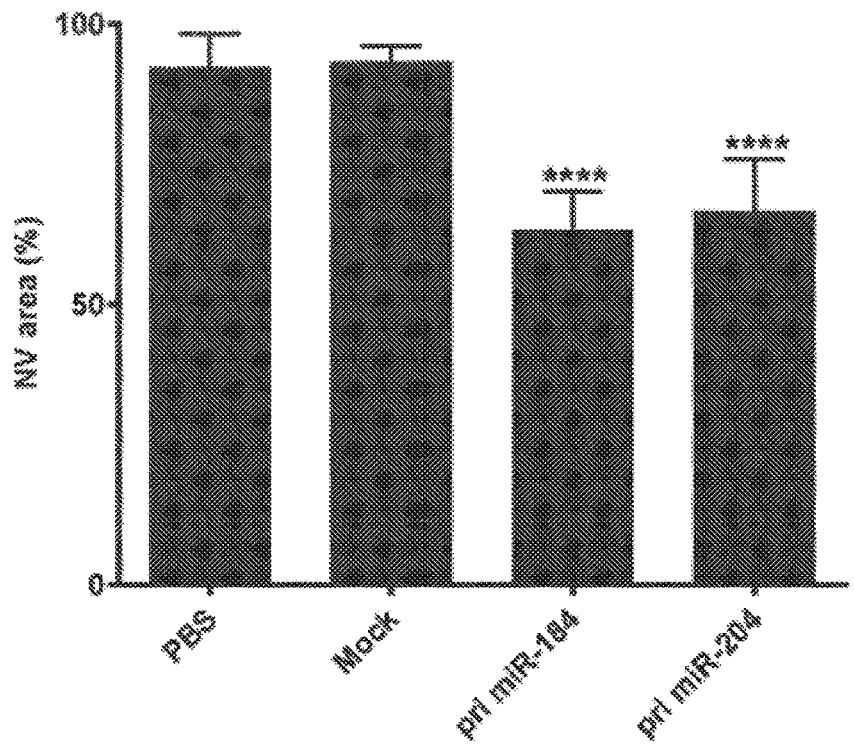

To evaluate the anti-angiogenic effects of pri-miR-204 or pri-miR-184 on corneal NV, miRNA vectors were delivered through subconjunctival injection immediately following alkali burn (FIG. 20A). In vivo tracking of corneal NV progression indicated an inhibition of NV areas after 7 days of mock (vector backbone), pri-miR-204, and pri-miR-184 treatments (FIG. 20C). The NV area in the mock treatment group recovered to those of PBS treatments by day 10, while pri-miR-204 and pri-miR-184 treatments resulted in significantly less NV. Differences in corneal NV after 15 days of treatment with pri-miR-204 or pri-miR-184 vectors as assessed by immunofluorescence analyses in flat-mounts were more definitive (FIG. 20B and FIG. 20D). Corneas immune-stained with anti-CD31 demonstrated that new blood vessels grew robustly in PBS and mock control groups, while corneas treated with pri-miR-204 and pri-miR-184 vectors effectively inhibited corneal NV.

rAAVrh.10-Mediated miR-204 and miR-184 Overexpression by Intrastromal Injection can Inhibit Corneal NV Mice were injected with pri-miR-204 vectors intrastromally, two weeks before alkali-burn treatment. Corneal NV was again observed for two weeks following treatment (FIG. 19A). Similar to subconjunctival injections that immediately followed alkali-burn treatment, a lag in NV in mock and pri-miR injections was observed. By day 10, the mock controls and PBS controls exhibited similar degrees of NV areas (FIG. 19C). Strikingly, NV area did not significantly increase between days 10 and 14 indicating that neovascularization can be halted by the exogenous expression of miR-204. Similar efficacies were also observed with pri-miR-184 treatments (FIG. 19C). Immunofluorescence and quantitative analysis of NV areas indicated that both miRNAs could effectively inhibit corneal NV, leading to a 20% reduction of NV area as compared to PBS and mock groups (FIG. 19B and FIG. 19D).

Delivery of the Anti-Angiogenic miR-204 Transgene Targets the Angpt1/Tie2/PI3K/Akt Pathway Whether blockage of corneal NV by rAAV delivery of primiR-204 directly impinges on neovascularization in the cornea was investigated. Angpt1 was selected as a marker for vasculogenesis, since it was identified as a predicted target for miR-204 and is significantly up-regulated upon alkali-burn treatment (FIG. 27C and FIG. 28). In some embodiments, Angpt1 has play a role in angiogenesis and wound healing in the cornea via activation of the PI3K/AKT signaling pathway. Alkali-burn treated mice were injected with rAAVrh.10 pri-miR-204 vectors either intrastromally or subconjunctivally.

Analysis of miR-204 expression in NV corneas indicated that miR-204 expression was significantly up-regulated in the pri-miR-204 treatment group compared to the PBS treatment group in both intrastromal and subconjunctival delivery routes (FIG. 23). The levels of exogenous miR-204 after vector injection and alkali-burn were still below those of normal control levels. Nevertheless, data indicate that angpt1 and vegf (a downstream target gene of PI3K/Akt pathway) messages were significantly down-regulated with rAAVrh.10-pri-miR-204 treatments compared to the PBS group (FIG. 24). Western blot analysis confirms that ANGPT-1 and VEGF are significantly reduced by exogenous expression of miR-204, while TIE2 (receptor for ANGPT1), PI3K, and AKT demonstrated a loss of phosphorylation without significant reduction in protein expression (FIG. 24). It was observed that delivery of the pri-miR-184 transgene via rAAV is able to perturb Fzd4/Wnt/β-catenin signaling in mouse corneas, and in turn, blocks corneal NV (FIG. 22). This finding is significant, as it provides in vivo support for miR-184's ability to down-regulate fzd-4, β-catenin, and vegf expression in the cornea, whereas previous evidence by others were resolved in human umbilical vein endothelial cells (HUVECs) and in transformed human corneal epithelial cells (HCEs).

Intrastromal or Subconjunctival Injection of rAAVrh.10 Pri-miR-204 and Pri-rniR-184 are Safe for Ocular Tissues The safety profile for the delivery of pri-miR-204 and pri-miR-184 vectors was investigated. Normal mouse eyes were treated with pri-miRNA vectors by intrastromal or subconjunctival injection, and the ocular surface and fundus were observed after two weeks. Gross in vivo observation showed no obvious abnormality in either pri-miRNA injected groups when compared to control groups (FIG. 25A). Eyes were then harvested for histopathologic analysis of corneas and retinas by H&E staining (FIG. 25B). No clear pathological outcomes were observed for the exogenous expression of pri-miRNA-184 and pri-miRNA-204 by rAAVrh.10 delivery. Together these results indicate that rAAV delivery and the exogenous expression of miRNAs do not elicit an inflammatory response and do not on their own drive tissue damage in the eye.

Sequences

```
>mmu-miR-21a (SEQ ID NO: 1)
UGUACCACCUUGUCGGAUAGCUUAUCAGACUGAUGUUGACUGUUGAAUCUCA
UGGCAACAGCAGUCGAUGGGCUGUCUGACAUUUUGGUAUC >mmu-miR-184 (SEQ ID NO: 2)
CCUUUCCUUAUCACUUUUCCAGCCAGCUUUGUGACUCUAAGUGUUGGACGGAG
AACUGAUAAGGGUAGG >mmu-miR-204 (SEQ ID NO: 3)
UGGACUUCCCUUUGUCAUCCUAUGCCUGAGAAUAUAUGAAGGAGGCUGGGAA
GGCAAAGGGACGUUCA >TuD miR-21 (SEQ ID NO: 4)
GACGGCGCTAGGATCATCAACTCAACATCAGTCATCTTGATAAGCTACAAGTATT
CTGGTCACAGAATACAACTCAACATCAGTCATCTTGATAAGCTACAAGATGATCC
TAGCGCCGTCTTTTT >pri miR-184 (SEQ ID NO: 5)
TGTGCAGAAACATAAGTGACTCTCCAGGTGTCAGAGGGAGAGACTGGGGCGAGA
GGCCAGAGCAAAGTAGAAGGGCACAGAGGGGCTTTGAATTTGAGGCAGAGGAG
GAACTGCAGAGAGGGGGCGGGAGGGCTCGCCGGGAAATCAAACGTCCATTTAC
ATCTTGTCCTGCAAAGCTTCATCAAAACTTCTTTGCCGGCCAGTCACGTCCCCTTA
TCACTTTTCCAGCCCAGCTTTGTGACTGTAAGTGTTGGACGGAGAACTGATAAGG
GTAGGTGATTGACACTCACAGCCTCCGGAACCCCGCGCCGCCTGCACTTGCGTG
ATGGGGAAAACCTGGCGTTCCCGCTCTGGGTGCCCGAGGACAGCAGGGGATTCC
AGGAGGAGACCTTGGGCATAGGGGGCCCAGGTATGCGCCCCCTGCCTGAGGATG
CTGGGGTAGCCTTTGTGTTTTGTCAGTGAGATCTCCACTTTGCTTATTCAAAATGT
GCTCTCTGC
```

Sequences pri miR-204 (SEQ ID NO: 6)
TTTACCCACAGGACAGGGTGATGGAGAGGAGGGTGAGGGTGGAGGCAAGCAGA
GGACCTCCTGATCATGTACCCATAGGACAGGGTGATGGAGAGGAGGGTGGGGGT
GGAGGCAAGCAGAGGACCTCCTGATCATGTACCCATAGGACAGGGTGATGGAAA
GGAGGGTGGGGGTGGAGGCAAGCAGAGGACTTCCTGATCGCGTACCCATGGCTA
CAGTCTTTCTTCATGTGACTCGTGACTTCCCTTTGTCATCCTATGCCTGAGAATA
TATGAAGGAGGCTGGGAAGGCAAAGGGACGTTCAATTGTCATCACTGGCATCTT
TTTTGATCATTGCACCATCATCAAATGCATTGGGATAACCATGACATGAAATTTT
CCATCATTGGGCCCATAACTGTCCCATAAGAGAGATGAAAAACACTGTATGTTAA
AGGTCATAGTAGAACTTCATCCAAGCAGCTCTGGAATTAGGAAGGAGTGAAATA
TACTCTCAAAGACTAATAGTTCTGGGTCCAAACCATGTGAC >AAV5 capsid protein amino acid sequence (SEQ ID NO: 7)
MSFVDHPPDWLEEVGEGLREFLGLEAGPPKPKPNQQHQDQARGLVLPGYNYLGPGN
GLDRGEPVNRADEVAREHDISYNEQLEAGDNPYLKYNHADAEFQEKLADDTSFGGN
LGKAVFQAKKRVLEPFGLVEEGAKTAPTGKRIDDHFPKRKKARTEEDSKPSTSSDAE
AGPSGSQQLQIPAQPASSLGADTMSAGGGGPLGDNNQGADGVGNASGDWHCDSTW
MGDRVVTKSTRTWVLPSYNNHQYREIKSGSVDGSNANAYFGYSTPWGYFDFNRFH
SHWSPRDWQRLINNYWGFRPRSLRVKIFNIQVKEVTVQDSTTTIANNLTSTVQVFTD
DDYQLPYVVGNGTEGCLPAFPPQVFTLPQYGYATLNRDNTENPTERSSFFCLEYFPS
KMLRTGNNFEFTYNFEEVPFHSSFAPSQNLFKLANPLVDQYLYRFVSTNNTGGVQFN
KNLAGRYANTYKNWFPGPMGRTQGWNLGSGVNRASVSAFATTNRMELEGASYQV
PPQPNGMTNNLQGSNTYALENTMIFNSQPANPGTTATYLEGNMLITSESETQPVNRV
AYNVGGQMATNNQSSTTAPATGTYNLQEIVPGSVWMERDVYLQGPIWAKIPETGAH
FHPSPAMGGFGLKHPPPMMLIKNTPVPGNITSFSDVPVSSFITQYSTGQVTVEMEWEL
KKENSKRWNPEIQYTNNYNDPQFVDFAPDSTGEYRTTRPIGTRYLTRPL >AAV6 capsid protein amino acid sequence (SEQ ID NO: 8)
MAADGYLPDWLEDNLSEGIREWWDLKPGAPKPKANQQKQDDGRGLVLPGYKYLG
PFNGLDKGEPVNAADAAALEHDKAYDQQLKAGDNPYLRYNHADAEFQERLQEDTS
FGGNLGRAVFQAKKRVLEPFGLVEEGAKTAPGKKRPVEQSPQEPDSSSGIGKTGQQP
AKKRLNFGQTGDSESVPDPQPLGEPPATPAAVGPTTMASGGGAPMADNNEGADGV
GNASGNWHCDSTWLGDRVITTSTRTWALPTYNNHLYKQISSASTGASNDNHYFGYS
TPWGYFDFNRFHCHFSPRDWQRLINNNWGFRPKRLNFKLFNIQVKEVTTNDGVTTIA
NNLTSTVQVFSDSEYQLPYVLGSAHQGCLPPFPADVFMIPQYGYLTLNNGSQAVGRS
SFYCLEYFPSQMLRTGNNFTFSYTFEDVPFHSSYAHSQSLDRLMNPLIDQYLYYLNRT
QNQSGSAQNKDLLFSRGSPAGMSVQPKNWLPGPCYRQQRVSKTKTDNNNSNFTWT
GASKYNLNGRESIINPGTAMASHKDDKDKFFPMSGVMIFGKESAGASNTALDNVMI
TDEEEIKATNPVATERFGTVAVNLQSSSTDPATGDVHVMGALPGMVWQDRDVYLQ
GPIWAKIPHTDGHFHPSPLMGGFGLKHPPPQILIKNTPVPANPPAEFSATKFASFITQYS
TGQVSVEIEWELQKENSKRWNPEVQYTSNYAKSANVDFTVDNNGLYTEPRPIGTRY
LTRPL >AAV6.2 capsid protein amino acid sequence (SEQ ID NO: 9)
MAADGYLPDWLEDNLSEGIREWWDLKPGAPKPKANQQKQDDGRGLVLPGYKYLG
PFNGLDKGEPVNAADAAALEHDKAYDQQLKAGDNPYLRYNHADAEFQERLQEDTS
FGGNLGRAVFQAKKRVLEPLGLVEEGAKTAPGKKRPVEQSPQEPDSSSGIGKTGQQP
AKKRLNFGQTGDSESVPDPQPLGEPPATPAAVGPTTMASGGGAPMADNNEGADGV
GNASGNWHCDSTWLGDRVITTSTRTWALPTYNNHLYKQISSASTGASNDNHYFGYS
TPWGYFDFNRFHCHFSPRDWQRLINNNWGFRPKRLNFKLFNIQVKEVTTNDGVTTIA
NNLTSTVQVFSDSEYQLPYVLGSAHQGCLPPFPADVFMIPQYGYLTLNNGSQAVGRS
SFYCLEYFPSQMLRTGNNFTFSYTFEDVPFHSSYAHSQSLDRLMNPLIDQYLYYLNRT
QNQSGSAQNKDLLFSRGSPAGMSVQPKNWLPGPCYRQQRVSKTKTDNNNSNFTWT
GASKYNLNGRESIINPGTAMASHKDDKDKFFPMSGVMIFGKESAGASNTALDNVMI
TDEEEIKATNPVATERFGTVAVNLQSSSTDPATGDVHVMGALPGMVWQDRDVYLQ
GPIWAKIPHTDGHFHPSPLMGGFGLKHPPPQILIKNTPVPANPPAEFSATKFASFITQYS
TGQVSVEIEWELQKENSKRWNPEVQYTSNYAKSANVDFTVDNNGLYTEPRPIGTRY
LTRPL >AAV7 capsid protein amino acid sequence (SEQ ID NO: 10)
MAADGYLPDWLEDNLSEGIREWWDLKPGAPKPKANQQKQDNGRGLVLPGYKYLG
PFNGLDKGEPVNAADAAALEHDKAYDQQLKAGDNPYLRYNHADAEFQERLQEDTS
FGGNLGRAVFQAKKRVLEPLGLVEEGAKTAPAKKRPVEPSPQRSPDSSTGIGKKGQQ
PARKRLNFGQTGDSESVPDPQPLGEPPAAPSSVGSGTVAAGGGAPMADNNEGADGV
GNASGNWHCDSTWLGDRVITTSTRTWALPTYNNHLYKQISSETAGSTNDNTYFGYS
TPWGYFDFNRFHCHFSPRDWQRLINNNWGFRPKKLRFKLFNIQVKEVTTNDGVTTIA
NNLTSTIQVFSDSEYQLPYVLGSAHQGCLPPFPADVFMIPQYGYLTLNNGSQSVGRSS
FYCLEYFPSQMLRTGNNFEFSYSFEDVPFHSSYAHSQSLDRLMNPLIDQYLYYLART
QSNPGGTAGNRELQFYQGGPSTMAEQAKNWLPGPCFRQQRVSKTLDQNNNSNFAW
TGATKYHLNGRNSLVNPGVAMATHKDDEDRFFPSSGVLIFGKTGATNKTTLENVLM
TNEEEIRPTNPVATEEYGIVSSNLQAANTAAQTQVVNNQGALPGMVWQNRDVYLQ
GPIWAKIPHTDGNFHPSPLMGGFGLKHPPPQILIKNTPVPANPPEVFTPAKFASFITQYS
TGQVSVEIEWELQKENSKRWNPEIQYTSNFEKQTGVDFAVDSQGVYSEPRPIGTRYL
TRNL

Sequences

>AAV8 capsid protein amino acid sequence (SEQ ID NO: 11)
MAADGYLPDWLEDNLSEGIREWWALKPGAPKPKANQQKQDDGRGLVLPGYKYLG
PFNGLDKGEPVNAADAAALEHDKAYDQQLQAGDNPYLRYNHADAEFQERLQEDTS
FGGNLGRAVFQAKKRVLEPLGLVEEGAKTAPGKKRPVEPSPQRSPDSSTGIGKKGQQ
PARKRLNFGQTGDSESVPDPQPLGEPPAAPSGVGPNTMAAGGGAPMADNNEGADG
VGSSSGNWHCDSTWLGDRVITTSTRTWALPTYNNHLYKQISNGTSGGATNDNTYFG
YSTPWGYFDFNRFHCHFSPRDWQRLINNNWGFRPKRLSFKLFNIQVKEVTQNEGTKT
IANNLTSTIQVFTDSEYQLPYVLGSAHQGCLPPFPADVFMIPQYGYLTLNNGSQAVGR
SSFYCLEYFPSQMLRTGNNFQFTYTFEDVPFHSSYAHSQSLDRLMNPLIDQYLYYLSR
TQTTGGTANTQTLGFSQGGPNTMANQAKNWLPGPCYRQQRVSTTTGQNNNSNFAW
TAGTKYHLNGRNSLANPGIAMATHKDDEERFFPSNGILIFGKQNAARDNADYSDVM
LTSEEEIKTTNPVATEEYGIVADNLQQQNTAPQIGTVNSQGALPGMVWQNRDVYLQ
GPIWAKIPHTDGNFHPSPLMGGFGLKHPPPQILIKNTPVPADPPTTFNQSKLNSFITQY
STGQVSVEIEWELQKENSKRWNPEIQYTSNYYKSTSVDFAVNTEGVYSEPRPIGTRYL
TRNL >AAV9 capsid protein amino acid sequence (SEQ ID NO: 12)
MAADGYLPDWLEDNLSEGIREWWALKPGAPQPKANQQHQDNARGLVLPGYKYLG
PGNGLDKGEPVNAADAAALEHDKAYDQQLKAGDNPYLKYNHADAEFQERLKEDTS
FGGNLGRAVFQAKKRLLEPLGLVEEAAKTAPGKKRPVEQSPQEPDSSAGIGKSGAQP
AKKRLNFGQTGDTESVPDPQPIGEPPAAPSGVGSLTMASGGGAPVADNNEGADGVG
SSSGNWHCDSQWLGDRVITTSTRTWALPTYNNHLYKQISNSTSGGSSNDNAYFGYS
TPWGYFDFNRFHCHFSPRDWQRLINNNWGFRPKRLNFKLFNIQVKEVTDNNGVKTI
ANNLTSTVQVFTDSDYQLPYVLGSAHEGCLPPFPADVFMIPQYGYLTLNDGSQAVG
RSSFYCLEYFPSQMLRTGNNFQFSYEFENVPFHSSYAHSQSLDRLMNPLIDQYLYYLS
KTINGSGQNQQTLKFSVAGPSNMAVQGRNYIPGPSYRQQRVSTTVTQNNNSEFAWP
GASSWALNGRNSLMNPGPAMASHKEGEDRFFPLSGSLIFGKQGTGRDNVDADKVMI
TNEEEIKTTNPVATESYGQVATNHQSAQAQAQTGWVQNQGILPGMVWQDRDVYLQ
GPIWAKIPHTDGNFHPSPLMGGFGMKHPPPQILIKNTPVPADPPTAFNKDKLNSFITQ
YSTGQVSVEIEWELQKENSKRWNPEIQYTSNYYKSNNVEFAVNTEGVYSEPRPIGTR
YLTRNL >AAVrh.8 capsid protein amino acid sequence (SEQ ID NO: 13)
MAADGYLPDWLEDNLSEGIREWWDLKPGAPKPKANQQKQDDGRGLVLPGYKYLG
PFNGLDKGEPVNAADAAALEHDKAYDQQLKAGDNPYLRYNHADAEFQERLQEDTS
FGGNLGRAVFQAKKRVLEPLGLVEEGAKTAPGKKRPVEQSPQEPDSSSGIGKTGQQP
AKKRLNFGQTGDSESVPDPQPLGEPPAAPSGLGPNTMASGGGAPMADNNEGADGV
GNSSGNWHCDSTWLGDRVITTSTRTWALPTYNNHLYKQISNGTSGGSTNDNTYFGY
STPWGYFDFNRFHCHFSPRDWQRLINNNWGFRPKRLNFKLFNIQVKEVTTNEGTKTI
ANNLTSTVQVFTDSEYQLPYVLGSAHQGCLPPFPADVFMVPQYGYLTLNNGSQALG
RSSFYCLEYFPSQMLRTGNNFQFSYTFEDVPFHSSYAHSQSLDRLMNPLIDQYLYYLV
RTQTTGTGGTQTLAFSQAGPSSMANQARNWVPGPCYRQQRVSTTTNQNNNSNFAW
TGAAKFKLNGRDSLMNPGVAMASHKDDDDRFFPSSGVLIFGKQGAGNDGVDYSQV
LITDEEEIKATNPVATEEYGAVAINNQAANTQAQTGLVHNQGVIPGMVWQNRDVYL
QGPIWAKIPHTDGNFHPSPLMGGFGLKHPPPQILIKNTPVPADPPLTFNQAKLNSFITQ
YSTGQVSVEIEWELQKENSKRWNPEIQYTSNYYKSTNVDFAVNTEGVYSEPRPIGTR
YLTRNL >AAVrh.10 capsid protein amino acid sequence (SEQ ID NO: 14)
MAADGYLPDWLEDNLSEGIREWWDLKPGAPKPKANQQKQDDGRGLVLPGYKYLG
PFNGLDKGEPVNAADAAALEHDKAYDQQLKAGDNPYLRYNHADAEFQERLQEDTS
FGGNLGRAVFQAKKRVLEPLGLVEEGAKTAPGKKRPVEPSPQRSPDSSTGIGKKGQQ
PAKKRLNFGQTGDSESVPDPQPIGEPPAGPSGLGSGTMAAGGGAPMADNNEGADGV
GSSSGNWHCDSTWLGDRVITTSTRTWALPTYNNHLYKQISNGTSGGSTNDNTYFGY
STPWGYFDFNRFHCHFSPRDWQRLINNNWGFRPKRLNFKLFNIQVKEVTQNEGTKTI
ANNLTSTIQVFTDSEYQLPYVLGSAHQGCLPPFPADVFMIPQYGYLTLNNGSQAVGR
SSFYCLEYFPSQMLRTGNNFEFSYQFEDVPFHSSYAHSQSLDRLMNPLIDQYLYYLSR
TQSTGGTAGTQQLLFSQAGPNNMSAQAKNWLPGPCYRQQRVSTTLSQNNNSNFAW
TGATKYHLNGRDSLVNPGVAMATHKDDEERFFPSSGVLMFGKQGAGKDNVDYSSV
MLTSEEEIKTTNPVATEQYGVVADNLQQQNAAPIVGAVNSQGALPGMVWQNRDVY
LQGPIWAKIPHTDGNFHPSPLMGGFGLKHPPPQILIKNTPVPADPPTTFSQAKLASFIT
QYSTGQVSVEIEWELQKENSKRWNPEIQYTSNYYKSTNVDFAVNTDGTYSEPRPIGT
RYLTRNL >AAVrh.39 capsid protein amino acid sequence (SEQ ID NO: 15)
MAADGYLPDWLEDNLSEGIREWWALKPGAPKPKANQQKQDDGRGLVLPGYKYLG
PFNGLDKGEPVNAADAAALEHDKAYDQQLKAGDNPYLRYNHADAEFQERLQEDTS
FGGNLGRAVFQAKKRVLEPLGLVEEAAKTAPGKKRPVEPSPQRSPDSSTGIGKKGQQ
PAKKRLNFGQTGDSESVPDPQPIGEPPAGPSGLGSGTMAAGGGAPMADNNEGADGV
GSSSGNWHCDSTWLGDRVITTSTRTWALPTYNNHLYKQISNGTSGGSTNDNTYFGY
STPWGYFDFNRFHCHFSPRDWQRLINNNWGFRPKRLSFKLFNIQVKEVTQNEGTKTI
ANNLTSTIQVFTDSEYQLPYVLGSAHQGCLPPFPADVFMIPQYGYLTLNNGSQAVGR
SSFYCLEYFPSQMLRTGNNFEFSYTFEDVPFHSSYAHSQSLDRLMNPLIDQYLYYLSR
TQSTGGTQGTQQLLFSQAGPANMSAQAKNWLPGPCYRQQRVSTTLSQNNNSNFAW
TGATKYHLNGRDSLVNPGVAMATHKDDEERFFPSSGVLMFGKQGAGRDNVDYSSV
MLTSEEEIKTTNPVATEQYGVVADNLQQTNTGPIVGNVNSQGALPGMVWQNRDVY

```
LQGPIWAKIPHTDGNFHPSPLMGGFGLKHPPPQILIKNTPVPADPPTTFSQAKLASFIT
QYSTGQVSVEIEWELQKENSKRWNPEIQYTSNYYKSTNVDFAVNTEGTYSEPRPIGT
RYLTRNL

>AAVrh.43 capsid protein amino acid sequence (SEQ ID NO: 16)
MAADGYLPDWLEDNLSEGIREWWDLKPGAPKPKANQQKQDDGRGLVLPGYKYLG
PFNGLDKGEPVNAADAAALEHDKAYDQQLEAGDNPYLRYNHADAEFQERLQEDTS
FGGNLGRAVFQAKKRVLEPLGLVEEGAKTAPGKKRPVEQSPQEPDSSSGIGKKGQQP
ARKRLNFGQTGDSESVPDPQPLGEPPAAPSGVGPNTMAAGGGAPMADNNEGADGV
GSSSGNWHCDSTWLGDRVITTSTRTWALPTYNNHLYKQISNGTSGGATNDNTYFGY
STPWGYFDFNRFHCHFSPRDWQRLINNNWGFRPKRLSFKLFNIQVKEVTQNEGTKTI
ANNLTSTIQVFTDSEYQLPYVLGSAHQGCLPPFPADVFMIPQYGYLTLNNGSQAVGR
SSFYCLEYFPSQMLRTGNNFQFTYTFEDVPFHSSYAHSQSLDRLMNPLIDQYLYYLSR
TQTTGGTANTQTLGFSQGGPNTMANQAKNWLPGPCYRQQRVSTTTGQNNNSNFAW
TAGTKYHLNGRNSLANPGIAMATHKDDEERFFPVTGSCFWQQNAARDNADYSDVM
LTSEEEIKTTNPVATEEYGIVADNLQQQNTAPQIGTVNSQGALPGMVWQNRDVYLQ
GPIWAKIPHTDGNFHPSPLMGGFGLKHPPPQILIKNTPVPADPPTTFNQSKLNSFITQY
STGQVSVEIEWELQKENSKRWNPEIQYTSNYYKSTSVDFAVNTEGVYSEPRPIGTRYL
TRNL >AAV5 capsid protein nucleic acid sequence (SEQ ID NO: 17)
ATGTCTTTTGTTGATCACCCTCCAGATTGGTTGGAAGAAGTTGGTGAAGGTCTTC
GCGAGTTTTTGGGCCTTGAAGCGGGCCCACCGAAACCAAAACCCAATCAGCAGC
ATCAAGATCAAGCCCGTGGTCTTGTGCTGCCTGGTTATAACTATCTCGGACCCGG
AAACGGTCTCGATCGAGGAGAGCCTGTCAACAGGGCAGACGAGGTCGCGCGAGA
GCACGACATCTCGTACAACGAGCAGCTTGAGGCGGGAGACAACCCCTACCTCAA
GTACAACCACGCGGACGCCGAGTTTCAGGAGAAGCTCGCCGACGACACATCCTT
CGGGGGAAACCTCGGAAAGGCAGTCTTTCAGGCCAAGAAAAGGGTTCTCGAACC
TTTTGGCCTGGTTGAAGAGGGTGCTAAGACGGCCCCTACCGGAAAGCGGATAGA
CGACCACTTTCCAAAAAGAAAGAAGGCCCGGACCGAAGAGGACTCCAAGCCTTC
CACCTCGTCAGACGCCGAAGCTGGACCCAGCGGATCCCAGCAGCTGCAAATCCC
AGCCCAACCAGCCTCAAGTTTGGGAGCTGATACAATGTCTGCGGGAGGTGGCGG
CCCATTGGGCGACAATAACCAAGGTGCCGATGGAGTGGGCAATGCCTCGGGAGA
TTGGCATTGCGATTCCACGTGGATGGGGACAGAGTCGTCACCAAGTCCACCCG
AACCTGGGTGCTGCCCAGCTACAACAACCACCAGTACCGAGAGATCAAAAGCGG
CTCCGTCGACGGAAGCAACGCCAACGCCTACTTTGGATACAGCACCCCCTGGGG
GTACTTTGACTTTAACCGCTTCCACAGCCACTGGAGCCCCGAGACTGGCAAAGA
CTCATCAACAACTACTGGGGCTTCAGACCCCGGTCCCTCAGAGTCAAAATCTTCA
ACATTCAAGTCAAAGAGGTCACGGTGCAGGACTCCACCACCACCATCGCCAACA
ACCTCACCTCCACCGTCCAAGTGTTTACGGACGACGACTACCAGCTGCCCTACGT
CGTCGGCAACGGGACCGAGGGATGCCTGCCGGCCTTCCCTCCGCAGGTCTTTACG
CTGCCGCAGTACGGTTACGCGACGCTGAACCGCGACAACACAGAAAATCCCACC
GAGAGGAGCAGCTTCTTCTGCCTAGAGTACTTTCCCAGCAAGATGCTGAGAACG
GGCAACAACTTTGAGTTTACCTACAACTTTGAGGAGGTGCCCTTCCACTCCAGCT
TCGCTCCCAGTCAGAACCTCTTCAAGCTGGCCAACCCGCTGGTGGACCAGTACTT
GTACCGCTTCGTGAGCACAAATAACACTGGCGGAGTCCAGTTCAACAAGAACCT
GGCCGGGAGATACGCCAACACCTACAAAAACTGGTTCCCGGGGCCCATGGGCCG
AACCCAGGGCTGGAACCTGGGCTCCGGGGTCAACCGCGCCAGTGTCAGCGCCTT
CGCCACGACCAATAGGATGGAGCTCGAGGGCGCGAGTTACCAGGTGCCCCCGCA
GCCGAACGGCATGACCAACAACCTCCAGGGCAGCAACACCTATGCCCTGGAGAA
CACTATGATCTTCAACAGCCAGCCGGCGAACCCGGGCACCACCGCCACGTACCT
CGAGGGCAACATGCTCATCACCAGCGAGAGCGAGACGCAGCCGGTGAACCGCGT
GGCGTACAACGTCGGCGGGCAGATGGCCACCAACAACCAGAGCTCCACCACTGC
CCCCGCGACCGGCACGTACAACCTCCAGGAAATCGTGCCCGGCAGCGTGTGGAT
GGAGAGGGACGTGTACCTCCAAGGACCCATCTGGGCAAGATCCCAGAGACGGG
GGCGCACTTTCACCCCTCTCCGGCCATGGGCGGATTCGGACTCAAACACCCACCG
CCCATGATGCTCATCAAGAACACGCCTGTGCCCGGAAATATCACCAGCTTCTCGG
ACGTGCCCGTCAGCAGCTTCATCACCCAGTACAGCACCGGGCAGGTCACCGTGG
AGATGGAGTGGGAGCTCAAGAAGGAAAACTCCAAGAGGTGGAACCCAGAGATC
CAGTACACAAACAACTACAACGACCCCCAGTTTGTGGACTTTGCCCCGGACAGC
ACCGGGGAATACAGAACCACCAGACCTATCGGAACCCGATACCTTACCCGACCC
CTT >AAV6 capsid nucleic acid sequence (SEQ ID NO: 18)
ATGGCTGCCGATGGTTATCTTCCAGATTGGCTCGAGGACAACCTCTCTGAGGGCA
TTCGCGAGTGGTGGGACTTGAAACCTGGAGCCCCGAAACCCAAAGCCAACCAGC
AAAAGCAGGACGACGGCCGGGGTCTGGTGCTTCCTGGCTACAAGTACCTCGGAC
CCTTCAACGGACTCGACAAGGGGGAGCCCGTCAACGCGGCGGATGCAGCGGCCC
TCGAGCACGACAAGGCCTACGACCAGCAGCTCAAAGCGGGTGACAATCCGTACC
TGCGGTATAACCACGCCGACGCCGAGTTTCAGGAGCGTCTGCAAGAAGATACGT
CTTTTGGGGGCAACCTCGGGCGAGCAGTCTTCCAGGCCAAGAAGAGGGTTCTCG
AACCTTTTGGTCTGGTTGAGGAAGGTGCTAAGACGGCTCCTGGAAAGAAACGTC
CGGTAGAGCAGTCGCCACAAGAGCCAGACTCCTCCTCGGGCATTGGCAAGACAG
GCCAGCAGCCCGCTAAAAAGAGACTCAATTTTGGTCAGACTGGCGACTCAGAGT
CAGTCCCCGACCCACAACCTCTCGGAGAACCTCCAGCAACCCCCGCTGCTGTGGG
ACCTACTACAATGGCTTCAGGCGGTGGCGCACCAATGGCAGACAATAACGAAGG
CGCCGACGGAGTGGGTAATGCCTCAGGAAATTGGCATTGCGATTCCACATGGCT
```

| Sequences |
| --- |
| GGGCGACAGAGTCATCACCACCAGCACCCGAACATGGGCCTTGCCCACCTATAA |
| CAACCACCTCTACAAGCAAATCTCCAGTGCTTCAACGGGGCCAGCAACGACAA |
| CCACTACTTCGGCTACAGCACCCCCTGGGGGTATTTTGATTTCAACAGATTCCAC |
| TGCCATTTCTCACCACGTGACTGGCAGCGACTCATCAACAACAATTGGGGATTCC |
| GGCCCAAGAGACTCAACTTCAAGCTCTTCAACATCCAAGTCAAGGAGGTCACGA |
| CGAATGATGGCGTCACGACCATCGCTAATAACCTTACCAGCACGGTTCAAGTCTT |
| CTCGGACTCGGAGTACCAGTTGCCGTACGTCCTCGGCTCTGCGCACCAGGGCTGC |
| CTCCCTCCGTTCCCGGCGGACGTGTTCATGATTCCGCAGTACGGCTACCTAACGC |
| TCAACAATGGCAGCCAGGCAGTGGGACGGTCATCCTTTTACTGCCTGGAATATTT |
| CCCATCGCAGATGCTGAGAACGGGCAATAACTTTACCTTCAGCTACACCTTCGAG |
| GACGTGCCTTTCCACAGCAGCTACGCGCACAGCCAGAGCCTGGACCGGCTGATG |
| AATCCTCTCATCGACCAGTACCTGTATTACCTGAACAGAACTCAGAATCAGTCCG |
| GAAGTGCCCAAAACAAGGACTTGCTGTTTAGCCGGGGGTCTCCAGCTGGCATGTC |
| TGTTCAGCCCAAAAACTGGCTACCTGGACCCTGTTACCGGCAGCAGCGCGTTTCT |
| AAAACAAAAACAGACAACAACAACAGCAACTTTACCTGGACTGGTGCTTCAAAA |
| TATAACCTTAATGGGCGTGAATCTATAATCAACCCTGGCACTGCTATGGCCTCAC |
| ACAAAGACGACAAAGACAAGTTCTTTCCCATGAGCGGTGTCATGATTTTTGGAAA |
| GGAGAGCGCCGGAGCTTCAAACACTGCATTGGACAATGTCATGATCACAGACGA |
| AGAGGAAATCAAAGCCACTAACCCCGTGGCCACCGAAAGATTTGGGACTGTGGC |
| AGTCAATCTCCAGAGCAGCAGCACAGACCCTGCGACCGGAGATGTGCATGTTAT |
| GGGAGCCTTACCTGGAATGGTGTGGCAAGACAGAGACGTATACCTGCAGGGTCC |
| TATTTGGGCCAAAATTCCTCACACGGATGGACACTTTCACCCGTCTCCTCTCATG |
| GGCGGCTTTGGACTTAAGCACCCGCCTCCTCAGATCCTCATCAAAAACACGCCTG |
| TTCCTGCGAATCCTCCGGCAGAGTTTTCGGCTACAAAGTTTGCTTCATTCATCACC |
| CAGTATTCCACAGGACAAGTGAGCGTGGAGATTGAATGGGAGCTGCAGAAAGAA |
| AACAGCAAACGCTGGAATCCCGAAGTGCAGTATACATCTAACTATGCAAAATCT |
| GCCAACGTTGATTTCACTGTGGACAACAATGGACTTTATACTGAGCCTCGCCCCA |
| TTGGCACCCGTTACCTCACCCGTCCCCTG |

>AAV6.2 capsid protein nucleic acid sequence (SEQ ID NO: 19)
ATGGCTGCCGATGGTTATCTTCCAGATTGGCTCGAGGACAACCTCTCTGAGGGCA
TTCGCGAGTGGTGGGACTTGAAACCTGGAGCCCCGAAACCCAAAGCCAACCAGC
AAAAGCAGGACGACGGCCGGGGTCTGGTGCTTCCTGGCTACAAGTACCTCGGAC
CCTTCAACGGACTCGACAAGGGGGAGCCCGTCAACGCGGCGGATGCAGCGGCCC
TCGAGCACGACAAGGCCTACGACCAGCAGCTCAAAGCGGGTGACAATCCGTACC
TGCGGTATAACCACGCGGACGCCGAGTTTCAGGAGCGTCTGCAAGAAGATACGT
CTTTTGGGGGCAACCTCGGGCGAGCAGTCTTCCAGGCCAAGAAGAGGGTTCTCG
AACCTCTTGGTCTGGTTGAGGAAGGTGCTAAGACGGCTCCTGGAAAGAAACGTC
CGGTAGAGCAGTCGCCACAAGAGCCAGACTCCTCCTCGGGCATTGGCAAGACAG
GCCAGCAGCCCGCTAAAAAGAGACTCAATTTTGGTCAGACTGGCGACTCAGAGT
CAGTCCCCGACCCACAACCTCTCGGAGAACCTCCAGCAACCCCGCTGCTGTGGG
ACCTACTACAATGGCTTCAGGCGGTGGCGCACCAATGGCAGACAATAACGAAGG
CGCCGACGGAGTGGGTAATGCCTCAGGAAATTGGCATTGCGATTCCACATGGCT
GGGCGACAGAGTCATCACCACCAGCACCCGAACATGGGCCTTGCCCACCTATAA
CAACCACCTCTACAAGCAAATCTCCAGTGCTTCAACGGGGCCAGCAACGACAA
CCACTACTTCGGCTACAGCACCCCCTGGGGGTATTTTGATTTCAACAGATTCCAC
TGCCATTTCTCACCACGTGACTGGCAGCGACTCATCAACAACAATTGGGGATTCC
GGCCCAAGAGACTCAACTTCAAGCTCTTCAACATCCAAGTCAAGGAGGTCACGA
CGAATGATGGCGTCACGACCATCGCTAATAACCTTACCAGCACGGTTCAAGTCTT
CTCGGACTCGGAGTACCAGTTGCCGTACGTCCTCGGCTCTGCGCACCAGGGCTGC
CTCCCTCCGTTCCCGGCGGACGTGTTCATGATTCCGCAGTACGGCTACCTAACGC
TCAACAATGGCAGCCAGGCAGTGGGACGGTCATCCTTTTACTGCCTGGAATATTT
CCCATCGCAGATGCTGAGAACGGGCAATAACTTTACCTTCAGCTACACCTTCGAG
GACGTGCCTTTCCACAGCAGCTACGCGCACAGCCAGAGCCTGGACCGGCTGATG
AATCCTCTCATCGACCAGTACCTGTATTACCTGAACAGAACTCAGAATCAGTCCG
GAAGTGCCCAAAACAAGGACTTGCTGTTTAGCCGGGGGTCTCCAGCTGGCATGTC
TGTTCAGCCCAAAAACTGGCTACCTGGACCCTGTTACCGGCAGCAGCGCGTTTCT
AAAACAAAAACAGACAACAACAACAGCAACTTTACCTGGACTGGTGCTTCAAAA
TATAACCTTAATGGGCGTGAATCTATAATCAACCCTGGCACTGCTATGGCCTCAC
ACAAAGACGACAAAGACAAGTTCTTTCCCATGAGCGGTGTCATGATTTTTGGAAA
GGAGAGCGCCGGAGCTTCAAACACTGCATTGGACAATGTCATGATCACAGACGA
AGAGGAAATCAAAGCCACTAACCCCGTGGCCACCGAAAGATTTGGGACTGTGGC
AGTCAATCTCCAGAGCAGCAGCACAGACCCTGCGACCGGAGATGTGCATGTTAT
GGGAGCCTTACCTGGAATGGTGTGGCAAGACAGAGACGTATACCTGCAGGGTCC
TATTTGGGCCAAAATTCCTCACACGGATGGACACTTTCACCCGTCTCCTCTCATG
GGCGGCTTTGGACTTAAGCACCCGCCTCCTCAGATCCTCATCAAAAACACGCCTG
TTCCTGCGAATCCTCCGGCAGAGTTTTCGGCTACAAAGTTTGCTTCATTCATCACC
CAGTATTCCACAGGACAAGTGAGCGTGGAGATTGAATGGGAGCTGCAGAAAGAA
AACAGCAAACGCTGGAATCCCGAAGTGCAGTATACATCTAACTATGCAAAATCT
GCCAACGTTGATTTCACTGTGGACAACAATGGACTTTATACTGAGCCTCGCCCCA
TTGGCACCCGTTACCTCACCCGTCCCCTG >AAV7 capsid protein nucleic acid sequence (SEQ ID NO: 20)
ATGGCTGCCGATGGTTATCTTCCAGATTGGCTCGAGGACAACCTCTCTGAGGGCA
TTCGCGAGTGGTGGGACCTGAAACCTGGAGCCCCGAAACCCAAAGCCAACCAGC
AAAAGCAGGACAACGGCCGGGGTCTGGTGCTTCCTGGCTACAAGTACCTCGGAC
CCTTCAACGGACTCGACAAGGGGGAGCCCGTCAACGCGGCGGACGCAGCGGCCC

```
TCGAGCACGACAAGGCCTACGACCAGCAGCTCAAAGCGGGTGACAATCCGTACC
TGCGGTATAACCACGCCGACGCCGAGTTTCAGGAGCGTCTGCAAGAAGATACGT
CATTTGGGGGCAACCTCGGGCGAGCAGTCTTCCAGGCCAAGAAGCGGGTTCTCG
AACCTCTCGGTCTGGTTGAGGAAGGCGCTAAGACGGCTCCTGCAAAGAAGAGAC
CGGTAGAGCCGTCACCTCAGCGTTCCCCCGACTCCTCCACGGGCATCGGCAAGA
AAGGCCAGCAGCCCGCCAGAAAGAGACTCAATTTCGGTCAGACTGGCGACTCAG
AGTCAGTCCCCGACCCTCAACCTCTCGGAGAACCTCCAGCAGCGCCCTCTAGTGT
GGGATCTGGTACAGTGGCTGCAGGCGGTGGCGCACCAATGGCAGACAATAACGA
AGGTGCCGACGGAGTGGGTAATGCCTCAGGAAATTGGCATTGCGATTCCACATG
GCTGGGCGACAGAGTCATTACCACCAGCACCCGAACCTGGGCCCTGCCCACCTA
CAACAACCACCTCTACAAGCAAATCTCCAGTGAAACTGCAGGTAGTACCAACGA
CAACACCTACTTCGGCTACAGCACCCCCTGGGGGTATTTTGACTTTAACAGATTC
CACTGCCACTTCTCACCACGTGACTGGCAGCGACTCATCAACAACAACTGGGGAT
TCCGGCCCAAGAAGCTGCGGTTCAAGCTCTTCAACATCCAGGTCAAGGAGGTCA
CGACGAATGACGGCGTTACGACCATCGCTAATAACCTTACCGACACGATTCAGGT
ATTCTCGGACTCGGAATACCAGCTGCCGTACGTCCTCGGCTCTGCGCACCAGGGC
TGCCTGCCTCCGTTCCCGGCGACGTCTTCATGATTCCTCAGTACGGCTACCTGA
CTCTCAACAATGGCAGTCAGTCTGTGGGACGTTCCTCCTTCTACTGCCTGGAGTA
CTTCCCCTCTCAGATGCTGAGAACGGGCAACAACTTTGAGTTCAGCTACAGCTTC
GAGGACGTGCCTTTCCACAGCAGCTACGCACACAGCCAGAGCCTGGACCGGCTG
ATGAATCCCCTCATCGACCAGTACTTGTACTACCTGGCCAGAACACAGAGTAACC
CAGGAGGCACAGCTGGCAATCGGGAACTGCAGTTTTACCAGGGCGGGCCTTCAA
CTATGGCCGAACAAGCCAAGAATTGGTTACCTGGACCTTGCTTCCGGCAACAAA
GAGTCTCCAAAACGCTGGATCAAAACAACAACAGCAACTTTGCTTGGACTGGTG
CCACCAAATATCACCTGAACGGCAGAAACTCGTTGGTTAATCCCGGCGTCGCCAT
GGCAACTCACAAGGACGACGAGGACCGCTTTTTCCCATCCAGCGGAGTCCTGATT
TTTGGAAAAACTGGAGCAACTAACAAAACTACATTGGAAAATGTGTTAATGACA
AATGAAGAAGAATTCGTCCTACTAATCCTGTAGCCACGGAAGAATACGGGATA
GTCAGCAGCAACTTACAAGCGGCTAATACTGCAGCCCAGACACAAGTTGTCAAC
AACCAGGGAGCCTTACCTGGCATGGTCTGGCAGAACCGGGACGTGTACCTGCAG
GGTCCCATCTGGGCCAAGATTCCTCACACGGATGGCAACTTTCACCCGTCTCCTT
TGATGGGCGGCTTTGGACTTAAACATCCGCCTCCTCAGATCCTGATCAAGAACAC
TCCCGTTCCCGCTAATCCTCCGGAGGTGTTTACTCCTGCCAAGTTTGCTTCGTTCA
TCACACAGTACAGCACCGGACAAGTCAGCGTGGAAATCGAGTGGGAGCTGCAGA
AGGAAAACAGCAAGCGCTGGAACCCGGAGATTCAGTACACCTCCAACTTTGAAA
AGCAGACTGGTGTGGACTTTGCCGTTGACAGCCAGGGTGTTTACTCTGAGCCTCG
CCCTATTGGCACTCGTTACCTCACCCGTAATCTG

>AAV8 capsid protein nucleic acid sequence (SEQ ID NO: 21)
ATGGCTGCCGATGGTTATCTTCCAGATTGGCTCGAGGACAACCTCTCTGAGGGCA
TTCGCGAGTGGTGGGCGCTGAAACCTGGAGCCCCGAAGCCCAAAGCCAACCAGC
AAAAGCAGGACGACGGCCGGGGTCTGGTGCTTCCTGGCTACAAGTACCTCGGAC
CCTTCAACGGACTCGACAAGGGGGAGCCCGTCAACGCGGCGGACGCAGCGGCC
TCGAGCACGACAAGGCCTACGACCAGCAGCTGCAGGCGGGTGACAATCCGTACC
TGCGGTATAACCACGCCGACGCCGAGTTTCAGGAGCGTCTGCAAGAAGATACGT
CTTTTGGGGGCAACCTCGGGCGAGCAGTCTTCCAGGCCAAGAAGCGGGTTCTCG
AACCTCTCGGTCTGGTTGAGGAAGGCGCTAAGACGGCTCCTGGAAAGAAGAGAC
CGGTAGAGCCATCACCCCAGCGTTCTCCAGACTCCTCTACGGGCATCGGCAAGA
AAGGCCAACAGCCCGCCAGAAAAGACTCAATTTGGTCAGACTGGCGACTCAG
AGTCAGTTCCAGACCCTCAACCTCTCGGAGAACCTCCAGCAGCGCCCTCTGGTGT
GGGACCTAATACAATGGCTGCAGGCGGTGGCGCACCAATGGCAGACAATAACGA
AGGCGCCGACGGAGTGGGTAGTTCCTCGGGAAATTGGCATTGCGATTCCACATG
GCTGGGCGACAGAGTCATCACCACCAGCACCCGAACCTGGGCCCTGCCCACCTA
CAACAACCACCTCTACAAGCAAATCTCCAACGGGACATCGGGAGGAGCCACCAA
CGACAACACCTACTTCGGCTACAGCACCCCCTGGGGGTATTTTGACTTTAACAGA
TTCCACTGCCACTTTTCACCACGTGACTGGCAGCGACTCATCAACAACAACTGGG
GATTCCGGCCCAAGAGACTCAGCTTCAAGCTCTTCAACATCCAGGTCAAGGAGGT
CACGCAGAATGAAGGCACCAAGACCATCGCCAATAACCTCACCAGCACCATCCA
GGTGTTTACGGACTCGGAGTACCAGCTGCCGTACGTTCTCGGCTCTGCCCACCAG
GGCTGCCTGCCTCCGTTCCCGGCGACGTGTTCATGATTCCCCAGTACGGCTACC
TAACACTCAACAACGGTAGTCAGGCCGTGGGACGCTCCTCCTTCTACTGCCTGGA
ATACTTTCCTTCGCAGATGCTGAGAACCGGCAACAACTTCCAGTTTACTTACACC
TTCGAGGACGTGCCTTTCCACAGCAGCTACGCCCACAGCCAGAGCTTGGACCGG
CTGATGAATCCTCTGATTGACCAGTACCTGTACTACTTGTCTCGGACTCAAACAA
CAGGAGGCACGGCAAATACGCAGACTCTGGGCTTCAGCCAAGGTGGGCCTAATA
CAATGGCCAATCAGGCAAAGAACTGGCTGCCAGGACCCTGTTACCGCCAACAAC
GCGTCTCAACGACAACCGGGCAAAACAACAATAGCAACTTTGCCTGGACTGCTG
GACCAAATACCATCTGAATGGAAGAAATTCATTGGCTAATCCTGGCATCGCTAT
GGCAACACACAAAGACGACGAGGAGCGTTTTTTTCCCAGTAACGGGATCCTGAT
TTTTGGCAAACAAAATGCTGCCAGAGACAATGCGGATTACAGCGATGTCATGCTC
ACCAGCGAGGAAGAAATCAAAACCACTAACCCTGTGGCTACAGAGGAATACGGT
ATCGTGGCAGATAACTTGCAGCAGCAAAACACGGCTCCTCAAATTGGAACTGTC
AACAGCCAGGGGGCCTTACCCGGTATGGTCTGGCAGAACCGGGACGTGTACCTG
CAGGGTCCCATCTGGGCCAAGATTCCTCACACGGACGGCAACTTCCACCCGTCTC
CGCTGATGGGCGGCTTTGGCCTGAAACATCCTCCGCCTCAGATCCTGATCAAGAA
CACGCCTGTACCTGCGGATCCTCCGACCACCTTCAACCAGTCAAAGCTGAACTCT
TTCATCACGCAATACAGCACCGGACAGGTCAGCGTGGAAATTGAATGGGAGCTG
```

```
CAGAAGGAAAACAGCAAGCGCTGGAACCCCGAGATCCAGTACACCTCCAACTAC
TACAAATCTACAAGTGTGGACTTTGCTGTTAATACAGAAGGCGTGTACTCTGAAC
CCCGCCCCATTGGCACCCGTTACCTCACCCGTAATCTG

>AAV9 capsid protein nucleic acid sequence (SEQ ID NO: 22)
ATGGCTGCCGATGGTTATCTTCCAGATTGGCTCGAGGACAACCTTAGTGAAGGAA
TTCGCGAGTGGTGGGCTTTGAAACCTGGAGCCCCTCAACCCAAGGCAAATCAAC
AACATCAAGACAACGCTCGAGGTCTTGTGCTTCCGGGTTACAAATACCTTGGACC
CGGCAACGGACTCGACAAGGGGGAGCCGGTCAACGCAGCAGACGCGGCGGCCC
TCGAGCACGACAAGGCCTACGACCAGCAGCTCAAGGCCGGAGACAACCCGTACC
TCAAGTACAACCACGCCGACGCCGAGTTCCAGGAGCGGCTCAAAGAAGATACGT
CTTTTGGGGGCAACCTCGGGCGAGCAGTCTTCCAGGCCAAAAAGAGGCTTCTTGA
ACCTCTTGGTCTGGTTGAGGAAGCGGCTAAGACGGCTCCTGGAAAGAAGAGGCC
TGTAGAGCAGTCTCCTCAGGAACCGGACTCCTCCGCGGGTATTGGCAAATCGGGT
GCACAGCCCGCTAAAAAGAGACTCAATTTCGGTCAGACTGGCGACAGAGTCA
GTCCCAGACCCTCAACCAATCGGAGAACCTCCCGCAGCCCCCTCAGGTGTGGGA
TCTCTTACAATGGCTTCAGGTGGTGGCGCACCCAGTGGCAGACAATAACGAAGGT
GCCGATGGAGTGGGTAGTTCCTCGGGAAATTGGCATTGCGATTCCCAATGGCTGG
GGGACAGAGTCATCACCACCAGCACCCGAACCTGGGCCTGCCCACCTACAACA
ATCACCTCTACAAGCAAATCTCCAACAGCACATCTGGAGGATCTTCAAATGACAA
CGCCTACTTCGGCTACAGCACCCCCTGGGGGTATTTTGACTTCAACAGATTCCAC
TGCCACTTCTCACCACGTGACTGGCAGCGACTCATCAACAACAACTGGGGATTCC
GGCCTAAGCGACTCAACTTCAAGCTCTTCAACATTCAGGTCAAAGAGGTTACGGA
CAACAATGGAGTCAAGACCATCGCCAATAACCTTACCAGCACGGTCCAGGTCTT
CACGGACTCAGACTATCAGCTCCCGTACGTGCTCGGGTCGGCTCACGAGGGCTGC
CTCCCGCCGTTCCCAGCGGACGTTTTCATGATTCCTCAGTACGGGTATCTGACGCT
TAATGATGGAAGCCAGGCCGTGGGTCGTTCGTCCTTTTACTGCCTGGAATATTTC
CCGTCGCAAATGCTAAGAACGGGTAACAACTTCCAGTTCAGCTACGAGTTTGAG
AACGTACCTTTCCATAGCAGCTACGCTCACAGCCAAAGCCTGGACCGACTAATG
AATCCACTCATCGACCAATACTTGTACTATCTCTCAAAGACTATTAACGGTTCTG
GACAGAATCAACAAACGCTAAAATTCAGTGTGGCCGGACCCAGCAACATGGCTG
TCCAGGGAAGAAACTATACCTGGACCCAGCTACCGACAACAACGTGTCTCAA
CCACTGTGACTCAAAACAACAACAGCGAATTTGCTTGGCCTGGAGCTTCTTCTTG
GGCTCTCAATGGACGTAATAGCTTGATGAATCCTGGACCTGCTATGGCCAGCCAC
AAAGAAGGAGAGGACCGTTTCTTTCCTTTGTCTGGATCTTTAATTTTTGGCAAAC
AAGGAACTGGAAGAGACAACGTGGATGCGGACAAAGTCATGATAACCAACGAA
GAAGAAATTAAAACTACTAACCCGGTAGCAACGGAGTCCTATGGACAAGTGGCC
ACAAACCACCAGAGTGCCCAAGCACAGGCGCAGACCGGCTGGGTTCAAAACCAA
GGAATACTTCCGGGTATGGTTTGGCAGGACAGAGATGTGTACCTGCAAGGACCC
ATTTGGGCCAAAATTCCTCACACGGACGGCAACTTTCACCCTTCTCCGCTGATGG
GAGGGTTTGGAATGAAGCACCCGCCTCCTCAGATCCTCATCAAAAACACACCTGT
ACCTGCGGATCCTCCAACGGCCTTCAACAAGGACAAGCTGAACTCTTTCATCACC
CAGTATTCTACTGGCCAAGTCAGCGTGGAGATCGAGTGGGAGCTGCAGAAGGAA
AACAGCAAGCGCTGGAACCCGGAGATCCAGTACACTTCCAACTATTACAAGTCT
AATAATGTTGAATTTGCTGTTAATACTGAAGGTGTATATAGTGAACCCCGCCCCA
TTGGCACCAGATACCTGACTCGTAATCTG >AAVrh.8 capsid protein nucleic acid sequence (SEQ ID NO: 23)
ATGGCTGCCGATGGTTATCTTCCAGATTGGCTCGAGGACAACCTCTCTGAGGGCA
TTCGCGAGTGGTGGGACTTGAAACCTGGAGCCCCGAAACCCAAAGCCAACCAGC
AAAAGCAGGACGACGGCCGGGGTCTGGTGCTTCCTGGCTACAAGTACCTCGGAC
CCTTCAACGGACTCGACAAGGGGGAGCCCGTCAACGCGGCGGACGCAGCGGCCC
TCGAGCACGACAAAGCCTACGACCAGCAGCTCAAAGCGGGTGACAATCCGTACC
TGCGGTATAATCACGCCGACGCCGAGTTTCAGGAGCGTCTGCAAGAAGATACGT
CTTTTGGGGGCAACCTCGGGCGAGCAGTCTTCCAGGCCAAGAAGCGGGTTCTCG
AACCTCTCGGTCTGGTTGAGGAAGGCGCTAAGACGGCTCCTGGAAAGAAGAGAC
CGGTAGAGCAGTCGCCACAAGAGCCAGACTCCTCCTCGGGCATCGGCAAGACAG
GCCAGCAGCCCGCTAAAAAGAGACTCAATTTTGGTCAGACTGGCGACTCAGAGT
CAGTCCCCGACCCACAACCTCTCGGAGAACCTCCAGCAGCCCCCTCAGGTCTGGG
ACCTAATACAATGGCTTCAGGCGGTGGCGCTCCAATGGCAGACAATAACGAAGG
CGCCGACGGAGTGGGTAATTCCTCGGGAAATTGGCATTGCGATTCCACATGGCTG
GGGGACAGAGTCATCACCACCAGCACCCGAACCTGGGCCTGCCCACCTACAAC
AACCACCTCTACAAGCAAATCTCCAACGGCACCTCGGGAGGAAGCACCAACGAC
AACACCTATTTTGGCTACAGCACCCCCTGGGGGTATTTTGACTTCAACAGATTCC
ACTGTCACTTTTCACCACGTGACTGGCAACGACTCATCAACAACAATTGGGGATT
CCGGCCCAAAAGACTCAACTTCAAGCTGTTCAACATCCAGGTCAAGGAAGTCAC
GACGAACGAAGGCACCAAGACCATCGCCAATAATCTCACCAGCACCGTGCAGGT
CTTTACGGACTCGGAGTACCAGTTACCGTACGTGCTAGGATCCGCTCACCAGGGA
TGTCTGCCTCCGTTCCCGGCGGACGTCTTCATGGTTCCTCAGTACGGCTATTTAAC
TTTAAACAATGGAAGCCAAGCCCTGGGACGTTCCTCCTTCTACTGTCTGGAGTAT
TTCCCATCGCAGATGCTGAGAACCGGCAACAACTTTCAGTTCAGCTACACCTTCG
AGGACGTGCCTTTCCACAGCAGCTACGCGCACAGCCAGAGCCTGGACAGGCTGA
TGAATCCCCTCATCGACCAGTACCTGTACTACCTGGTCAGAACGCAAACGACTGG
AACTGGAGGGACGCAGACTCTGGCATTCAGCCAAGCGGGTCCTAGCTCAATGGC
CAACCAGGCTAGAAATTGGGTGCCCGGACCTTGCTACCGGCAGCAGCGCGTCTC
CACGACAACCAACCAGAACAACAACAGCAACTTTGCCTGGACGGGAGCTGCCAA
GTTTAAGCTGAACGGCCGAGACTCTCTAATGAATCCGGGCGTGGCAATGGCTTCC
```

| Sequences |
|---|
| CACAAGGATGACGACGACCGCTTCTTCCCTTCGAGCGGGGTCCTGATTTTTGGCA<br>AGCAAGGAGCCGGGAACGATGGAGTGGATTACAGCCAAGTGCTGATTACAGATG<br>AGGAAGAAATCAAGGCTACCAACCCCGTGGCCACAGAAGAATATGGAGCAGTG<br>GCCATCAACAACCAGGCCGCCAATACGCAGGCGCAGACCGGACTCGTGCACAAC<br>CAGGGGGTGATTCCCGGCATGGTGTGGCAGAATAGAGACGTGTACCTGCAGGGT<br>CCCATCTGGGCCAAAATTCCTCACACGGACGGCAACTTTCACCCGTCTCCCCTGA<br>TGGGCGGCTTTGGACTGAAGCACCCGCCTCCTCAAATTCTCATCAAGAACACACC<br>GGTTCCAGCGGACCCGCCGCTTACCTTCAACCAGGCCAAGCTGAACTCTTTCATC<br>ACGCAGTACAGCACCGGACAGGTCAGCGTGGAAATCGAGTGGGAGCTGCAGAA<br>AGAAAACAGCAAACGCTGGAATCCAGAGATTCAATACACTTCCAACTACTACAA<br>ATCTACAAATGTGGACTTTGCTGTCAACACGGAGGGGGTTTATAGCGAGCCTCGC<br>CCCCATTGGCACCCGTTACCTCACCCGCAACCTGTAA |

>AAVrh.10 capsid protein nucleic acid sequence (SEQ ID NO: 24)
TCGAGGACAACCTCTCTGAGGGCATTCGCGAGTGGTGGGACTTGAAACCTGGAG
CCCCGAAACCCAAAGCCAACCAGCAAAAGCAGGACGACGGCCGGGGTCTGGTG
CTTCCTGGCTACAAGTACCTCGGACCCTTCAACGGACTCGACAAGGGGGAGCCC
GTCAACGCGGCGGACGCAGCGGCCCTCGAGCACGACAAGGCCTACGACCAGCAG
CTCAAAGCGGGTGACAATCCGTACCTGCGGTATAACCACGCCGACGCGGAGTTT
CAGGAGCGTCTGCAAGAAGATACGTCTTTTGGGGGCAACCTCGGGCGAGCAGTC
TTCCAGGCCAAGAAGCGGGTTCTCGAACCTCTCGGTCTGGTTGAGGAAGGCGCTA
AGACGGCTCCTGGAAAGAAGAGACCGGTAGAGCCATCACCCCAGCGTTCTCCAG
ACTCCTCTACGGGCATCGGCAAGAAAGGCCAGCAGCCCGCGAAAAAGAGACTCA
ACTTTGGGCAGACTGGCGACTCAGAGTCAGTGCCCGACCCTCAACCAATCGGAG
AACCCCCCGCAGGCCCCTCTGGTCTGGGATCTGGTACAATGGCTGCAGGCGGTG
GCGCTCCAATGGCAGACAATAACGAAGGCGCCGACGGAGTGGGTAGTTCCTCAG
GAAATTGGCATTGCGATTCCACATGGCTGGGCGACAGAGTCATCACCACCAGCA
CCCGAACCTGGGCCCTCCCCACCTACAACAACCACCTCTACAAGCAAATCTCCAA
CGGGACTTCGGGAGGAAGCACCAACGACAACACCTACTTCGGCTACAGCACCCC
CTGGGGGTATTTTGACTTTAACAGATTCCACTGCCACTTCTCACCACGTGACTGG
CAGCGACTCATCAACAACAACTGGGGATTCCGGCCCAAGAGACTCAACTTCAAG
CTCTTCAACATCCAGGTCAAGGAGGTCACGCAGAATGAAGGCACCAAGACCATC
GCCAATAACCTTACCAGCACGATTCAGGTCTTTACGGACTCGGAATACCAGCTCC
CGTACGTCCTCGGCTCTGCGCACCAGGGCTGCCTGCCTCCGTTCCCGGCGGACGT
CTTCATGATTCCTCAGTACGGGTACCTGACTCTGAACAATGGCAGTCAGGCCGTG
GGCCGTTCCTCCTTCTACTGCCTGGAGTACTTTCCTTCTCAAATGCTGAGAACGGG
CAACAACTTTGAGTTCAGCTACCAGTTTGAGGACGTGCCTTTTCACAGCAGCTAC
GCGCACAGCCAAAGCCTGGACCGGCTGATGAACCCCCTCATCGACCAGTACCTG
TACTACCTGTCTCGGACTCAGTCCACGGGAGGTACCGCAGGAACTCAGCAGTTGC
TATTTTCTCAGGCCGGGCCTAATAACATGTCGGCTCAGGCCAAAAACTGGCTACC
CGGGCCCTGCTACCGGCAGCAACGCGTCTCCACGACATCGTCGCAAAATAACAA
CAGCAACTTTGCCTGGACCGGTGCCACCAAGTATCATCTGAATGGCAGAGACTCT
CTGGTAAATCCCGGTGTCGCTATGGCAACCCACAAGGACGACGAAGAGCGATTT
TTTCCGTCCAGCGGAGTCTTAATGTTTGGGAAACAGGGAGCTGGAAAAGACAAC
GTGGACTATAGCAGCGTTATGCTAACCAGTGAGGAAGAAATTAAAACCACCAAC
CCAGTGGCCACAGAACAGTACGGCGTGGTGGCCGATAACCTGCAACAGCAAAAC
GCCGCTCCTATTGTAGGGGCCGTCAACAGTCAAGGAGCCTTACCTGGCATGGTCT
GGCAGAACCGGGACGTGTACCTGCAGGGTCCTATCTGGGCCAAGATTCCTCACA
CGGACGGAAACTTTCATCCCTCGCCGCTGATGGGAGGCTTTGGACTGAAACACCC
GCCTCCTCAGATCCTGATTAAGAATACACCTGTTCCCGCGGATCCTCCAACTACC
TTCAGTCAAGCTAAGCTGGCGTCGTTCATCACGCAGTACAGCACCGGACAGGTCA
GCGTGGAAATTGAATGGGAGCTGCAGAAAGAAAACAGCAAACGCTGGAACCCA
GAGATTCAATACACTTCCAACTACTACAAATCTACAAATGTGGACTTTGCTGTTA
ACACAGATGGCACTTATTCTGAGCCTCGCCCCATCGGCACCCGTTACCTCACCCG
TAATCTGTAATTGCTTGTTAATCAATAAACCGGTTGATTCGTTTCAGTTGAACTTT
GGTCTCTGCGAAGGGCGAATTCGTTT >AAVrh.39 capsid protein nucleic acid sequence (SEQ ID NO: 25)
ATGGCTGCCGATGGTTATCTTCCAGATTGGCTCGAGGACAACCTCTCTGAGGGCA
TTCGCGAGTGGTGGGCGCTGAAACCTGGAGCCCCGAAGCCCAAAGCCAACCAGC
AAAAGCAGGACGACGGCCGGGGTCTGGTGCTTCCTGGCTACAAGTACCTCGGAC
CCTTCAACGGACTCGACAAGGGGGAGCCCGTCAACGCGGCGGACGCAGCGGCCC
TCGAGCACGACAAGGCCTACGACCAGCAGCTCAAAGCGGGTGACAATCCGTACC
TGCGGTATAACCACGCCGACGCCGAGTTTCAGGAGCGTCTGCAAGAAGATACGT
CTTTTGGGGGCAACCTCGGGCGAGCAGTCTTCCAGGCCAAGAAGCGGGTTCTCG
AACCTCTCGGTCTGGTTGAGGAAGCTGCTAAGACGGCTCCTGGAAAGAAGAGAC
CGGTAGAACCGTCACCTCAGCGTTCCCCCGACTCCTCCACGGGCATCGGCAAGA
AAGGCCAGCAGCCCGCTAAAAAGAGACTGAACTTTGGTCAGACTGGCGACTCAG
AGTCAGTCCCCGACCCTCAACCAATCGGAGAACCACCAGCAGGCCCCTCTGGTCT
GGGATCTGGTACAATGGCTGCAGGCGGTGGCGCTCCAATGGCAGACAATAACGA
AGGCGCCGACGGAGTGGGTAGTTCCTCAGGAAATTGGCATTGCGATTCCACATG
GCTGGGCGACAGAGTCATCACCACCAGCACCCGAACCTGGGCCCTGCCCACCTA
CAACAACCACCTCTACAAGCAAATATCCAATGGGACATCGGAGGAAGCACCAA
CGACAACACCTACTTCGGCTACAGCACCCCCTGGGGGTATTTTGACTTCAACAGA
TTCCACTGCCACTTCTCACCACGTGACTGGCAGCGACTCATCAACAACAACTGGG
GATTCCGGCCCAAAAAGACTCAGCTTCAAGCTCTTCAACATCCAGGTCAAGGAGG
TCACGCAGAATGAAGGCACCAAGACCATCGCCAATAACCTTACCAGCACGATTC

```
AGGTATTTACGGACTCGGAATACCAGCTGCCGTACGTCCTCGGCTCCGCGCACCA
GGGCTGCCTGCCTCCGTTCCCGGCGGACGTCTTCATGATTCCCCAGTACGGCTAC
CTTACACTGAACAATGGAAGTCAAGCCGTAGGCCGTTCCTCCTTCTACTGCCTGG
AATATTTTCCATCTCAAATGCTGCGAACTGGAAACAATTTTGAATTCAGCTACAC
CTTCGAGGACGTGCCTTTCCACAGCAGCTACGCACACAGCCAGAGCTTGGACCG
ACTGATGAATCCTCTCATCGACCAGTACCTGTACTACTTATCCAGAACTCAGTCC
ACAGGAGGAACTCAAGGTACCCAGCAATTGTTATTTTCTCAAGCTGGGCCTGCAA
ACATGTCGGCTCAGGCTAAGAACTGGCTACCTGGACCTTGCTACCGGCAGCAGC
GAGTCTCTACGACACTGTCGCAAAACAACAACAGCAACTTTGCTTGGACTGGTGC
CACCAAATATCACCTGAACGGAAGAGACTCTTTGGTAAATCCCGGTGTCGCCATG
GCAACCCACAAGGACGACGAGGAACGCTTCTTCCCGTCGAGTGGAGTCCTGATG
TTTGGAAAACAGGGTGCTGGAAGAGACAATGTGGACTACAGCAGCGTTATGCTA
ACCAGCGAAGAAGAAATTAAAACCACTAACCCTGTAGCCACAGAACAATACGGT
GTGGTGGCTGATAACTTGCAGCAAACCAATACGGGGCCTATTGTGGGAAATGTC
AACAGCCAAGGAGCCTTACCTGGCATGGTCTGGCAGAACCGAGACGTGTACCTG
CAGGGTCCCATCTGGGCCAAGATTCCTCACACGGACGGCAACTTCCACCCTTCAC
CGCTAATGGGAGGATTTGGACTGAAGCACCCACCTCCTCAGATCCTGATCAAGA
ACACGCCGGTACCTGCGGATCCTCCAACAACGTTCAGCCAGGCGAAATTGGCTTC
CTTCATTACGCAGTACAGCACCGGACAGGTCAGCGTGGAAATCGAGTGGGAGCT
GCAGAAGGAGAACAGCAAACGCTGGAACCCAGAGATTCAGTACACTTCAAACTA
CTACAAATCTACAAATGTGGACTTTGCTGTCAATACAGAGGGAACTTATTCTGAG
CCTCGCCCCATTGGTACTCGTTACCTCACCCGTAATCTG

>AAVrh.43 capsid protein nucleic acid sequence (SEQ ID NO: 26)
ATGGCTGCCGATGGTTATCTTCCAGATTGGCTCGAGGACAACCTCTCTGAGGGCA
TTCGCGAGTGGTGGGACTTGAAACCTGGAGCCCCGAAACCCAAAGCCAACCAGC
AAAAGCAGGACGACGGCCGGGGCCTGGTGCTTCCTGGCTACAAGTACCTCGGAC
CCTTCAACGGACTCGACAAGGGGGAGCCCGTCAACGCGGCGGACGCAGCGGCCC
TCGAGCACGACAAGGCCTACGACCAGCAGCTCGAAGCGGGTGACAATCCGTACC
TGCGGTATAACCACGCCGACGCCGAGTTTCAGGAGCGTCTGCAAGAAGATACGT
CTTTTGGGGGCAACCTCGGGCGAGCAGTCTTCCAGGCCAAGAAGCGGGTTCTCG
AACCTCTCGGTCTGGTTGAGGAAGGCGCTAAGACGGCTCCTGGAAAGAAGAGAC
CAGTAGAGCAGTCACCCCAAGAACCAGACTCCTCCTCGGGCATCGGCAAGAAAG
GCCAACAGCCCGCCAGAAAAAGACTCAATTTTGGCCAGACTGGCGACTCAGAGT
CAGTTCCAGACCCTCAACCTCTCGGAGAACCTCCAGCAGCGCCCTCTGGTGTGGG
ACCTAATACAATGGCTGCAGGCGGTGGCGCACCAATGGCAGACAATAACGAAGG
CGCCGACGGAGTGGGTAGTTCCTCGGGAAATTGGCATTGCGATTCCACATGGCTG
GGCGACAGAGTCATCACCACCAGCACCCGAACCTGGGCCCTGCCCACCTACAAC
AACCACCTCTACAAGCAAATCTCCAACGGGACATCGGAGGAGCCACCAACGAC
AACACCTACTTCGGCTACAGCACCCCCTGGGGGTATTTTGACTTTAACAGATTCC
ACTGCCACTTTTCACCACGTGACTGGCAGCGACTCATCAACAACAACTGGGGATT
CCGGCCCAAGAGACTCAGCTTCAAGCTCTTCAACATCCAGGTCAAGGAGGTCAC
GCAGAATGAAGGCACCAAGACCATCGCCAATAACCTCACCAGCACCATCCAGGT
GTTTACGGACTCGGAGTACCAGCTGCCGTACGTTCTCGGCTCTGCCCACCAGGGC
TGCCTGCCTCCGTTCCCGGCGGACGTGTTCATGATTCCCCAGTACGGCTACCTAA
CACTCAACAACGGTAGTCAGGCCGTGGGACGCTCCTCCTTCTACTGCCTGGAATA
CTTTCCTTCGCAGATGCTGAGAACCGGCAACAACTTCCAGTTTACTTACACCTTC
GAGGACGTGCCTTTCCACAGCAGCTACGCCCACAGCCAGAGCTTGGACCGGCTG
ATGAATCCTCTGATTGACCAGTACCTGTACTACTTGTCTCGGACTCAAACAACAG
GAGGCACGGCAAATACGCAGACTCTGGGCTTCAGCCAAGGTGGGCCTAATACAA
TGGCCAATCAGGCAAAGAACTGGCTGCCAGGACCCTGTTACCGCCAACAACGCG
TCTCAACGACAACCGGGCAAAACAACAATAGCAACTTTGCCTGGACTGCTGGGA
CCAAATACCATCTGAATGGAAGAAATTCATTGGCTAATCCTGGCATCGCTATGGC
AACACACAAAGACGACGAGGAGCGTTTTTTCCCAGTAACGGGATCCTGTTTTTGG
CAACAAAATGCTGCCAGAGACAATGCGGATTACAGCGATGTCATGCTCACCAGC
GAGGAAGAAATCAAAACCACTAACCCTGTGGCTACAGAGGAATACGGTATCGTG
GCAGATAACTTGCAGCAGCAAAACACGGCTCCTCAAATTGGAACTGTCAACAGC
CAGGGGGCCTTACCCGGTATGGTCTGGCAGAACCGGGACGTGTACCTGCAGGGT
CCCATCTGGGCAAGATTCCTCACACGGACGGCAACTTCCACCCGTCTCCGCTGA
TGGGCGGCTTTGGCCTGAAACATCCTCCGCCTCAGATCCTGATCAAGAACACGCC
TGTACCTGCGGATCCTCCGACCACCTTCAACCAGTCAAAGCTGAACTCTTTCATC
ACGCAATACAGCACCGGACAGGTCAGCGTGGAAATTGAATGGGAGCTACAGAAG
GAAAACAGCAAGCGCTGGAACCCCGAGATCCAGTACACCTCCAACTACTACAAA
TCTACAAGTGTGGACTTTGCTGTTAATACAGAAGGCGTGTACTCTGAACCCCGCC
CCATTGGCACCCGTTACCTCACCCGTAATCTGTAA >Frizzled 4 (Fzd4) Nucleic Acid Sequence (SEQ ID NO: 27)
AGCGCTGGGGCGGTGAGAACAGCGCGGCGTAGAGTGCAGGCGGGCTTCGCCGAA
AAGCCGGACTCGGCCGGCGCCGAGTTCTGGGATCGCGCCTGCAGCCATGACCC
TAGCAGTCCATCCCTCGGCCCGGGCTCCGGACGTCTGATATCCCGCACATTCTCG
TACAACTGCTGGAGAGGCGACTGCTGCCCCCTTGTCGCCCTTGGCGCTTACCGC
ATTCCCTATCCGGAGTTGGGAGCAGCGCGGCCACCGGCGCCCTGTGCAAACTG
GGGGTGTCTGCTAGATCAGCCTCTGCCGCTGCTGCCCGCAGCTCTGGCCATGGCC
TGGCCGGGCACAGGGCCGAGCAGCCGGGGGGCGCTGGAGGCGTCGGGCTCAG
GCTGGGGCTGCTGCTGCAGTTCCTCCTGCTCCTGCGGCCGACACTGGGGTTCGGG
GACGAGGAGGAGCGGCGCTGCGACCCCATCCGCATCGCCATGTGCCAGAACCTC
GGCTACAACGTGACCAAGATGCCCAACTTAGTGGGACACGAGCTGCAGACAGAC
```

| Sequences |
| --- |
| GCCGAGCTGCAGCTGACAACTTTCACGCCGCTCATCCAGTACGGCTGCTCCAGCC
AGCTGCAGTTCTTCCTTTGTTCGGTTTATGTGCCAATGTGCACAGAGAAGATCAA
CATCCCCATCGGCCCGTGCGGTGGCATGTGCCTTTCAGTCAAGAGACGCTGTGAA
CCAGTCCTGAGAGAATTTGGGTTTGCCTGGCCCGACACCCTGAACTGCAGCAAGT
TCCCGCCCCAGAACGACCACAACCACATGTGCATGGAAGGACCAGGTGATGAAG
AGGTTCCCTTGCCCCACAAGACTCCCATCCAGCCCGGGGAAGAGTGCCACTCCGT
GGGAAGCAATTCTGATCAGTACATCTGGGTGAAGAGGAGCCTGAACTGTGTTCTC
AAGTGTGGCTACGATGCTGGCTTGTACAGCCGCTCAGCTAAGGAGTTCACGGATA
TTTGGATGGCTGTGTGGGCCAGCCTCTGCTTCATCTCCACCACCTTCACCGTGCTG
ACCTTCCTGATTGATTCATCCAGGTTTTCTTACCCTGAGCGCCCCATCATATTTCT
CAGTATGTGCTATAATATTTATAGCATTGCTTATATTGTTCGGCTGACTGTAGGCC
GGGAAAGGATATCCTGTGATTTTGAAGAGGCGGCAGAGCCCGTTCTCATCCAAG
AAGGACTTAAGAACACAGGATGTGCAATAATTTTCTTGCTGATGTACTTTTTTGG
AATGGCCAGCTCCATTTGGTGGGTTATTCTGACACTCACTTGGTTTTTGGCAGCCG
GACTCAAGTGGGGTCATGAAGCCATTGAAATGCACAGTTCTTATTTCCACATCGC
AGCCTGGGCTATTCCCGCAGTGAAAACCATTGTCATCTTGATTATGAGACTAGTG
GATGCCGATGAACTGACTGGCTTGTGCTATGTTGGGAACCAAAATCTAGATGCCC
TCACTGGCTTTGTGGTGGCTCCTCTCTTTACGTATTTGGTGATTGGAACGCTGTTC
ATTGCGGCGGGTTTGGTGGCCTTATTCAAAATCCGGTCCAATCTTCAAAAAGACG
GGACAAAGACAGACAAGTTGGAAAGGCTAATGGTCAAGATCGGGGTCTTCTCAG
TACTGTACACGGTTCCTGCAACCTGTGTGATTGCCTGTTATTTCTATGAAATCTCA
AACTGGGCACTCTTTCGATATTCTGCAGATGACTCAAACATGGCAGTTGAAATGT
TGAAAATTTTTATGTCTTTGCTCGTGGGCATCACTTCAGGCATGTGGATTTGGTCT
GCCAAAACTCTTCACACGTGGCAAAAGTGTTCTAACCGATTGGTGAATTCTGGGA
AGGTAAAGAGAGAGAAGAGGGGGAATGGTTGGGTGAAGCCAGGAAAAGGCAAC
GAGACTGTGGTATAAGACTAGCCGGCTTCCTCGTTCCTCATTGTGAAGGAAGTGA
TGCAGGGAATCTCAGTTTGAACAAACTTAGAAACACTTCAGCCCACACACACCC
ACGTCAGCCCACCACCACTCACCCAACTCAGCATCAGAAGACCAATGGCTTCACT
GCAGACTTTGGAATGGTCCAAAATGGAAAAGCCAGTTAGAGGTTTTCAAAGCTG
TGAAAAATCAAATGTTGATCACTTTAGCAGGTCACAGCTTGGAGTCCGTGGAG
GTCCCGCCTAGATTCCTGAAGCCCAGGGTGATAGTGTTTGCTCCTACTGGGTGGG
ATTTCAACTGTGAGTTGATAACATGCAAGGAGAAAGATTAATTTTTAAAACCCTT
TTAAATTTTAAATAGTAACTAGGTCTTGCAGATAGCAAAGTGATCTATAAACACT
GGAAATGCTGGGTTGGGAGACGTGTTGCAGAGTTTTATAGTTTGGCTGGTCTAAC
ATAAACATCTTCTGGCCTACACTGTCTGCTGTTTAGAACTCTGTAGCGCACTCCCA
AGAGGTGGTGTCAAAATCCTTCAGTGCCTTTGTCGTAAAACAGAATTGTTTGAGC
AAACAAAAGTACTGTACTAACACACGTAAGGTATCCAGTGGATTTCTCTCTCCTG
AAATTTCAACATCCCTAATTCTAGGCAGCCCCTGTTTTCTTCACTTTAAACTAATG
ACTCAAAAAAAAAAAAGGTTATTTTTATAGGATTTTTTTTTTTGCACTGCAGCAT
GCCTAATGAGAGGAAAAGGGAAGGTGATTCACTTTCTGACAATCACTTAATTCA
GAGAAAAATGAGATTTGCTAAGTTGACTTACCTTACCGACCCTAGAGACCTATTG
CATTAAGCAATGTTAAGCAATTGGGACTTAAAATATTTTAGTTTGTGTGATTGCA
TCTAGGCAGACGCCAGTCTGGAAGAACTGAAATGTTAAATTTCTTGGCAACTTTG
CATTCACACAGATTAACTGTGTAATTTGTGTGTGTCAATTACAATTAAAAGCACA
TTCTTGGACCATGACATAGTATACTCAATTGACTTTAAAACTGTGGTCAACTTGC
ATTCTTAGTGTGATAGTGCCTTTCCCCCCTGTAGCATAAGAATGTTATCGGAGTTT
GGTCTACTTGCCACAATGGAGACTTATTCAGCTTTGCAAAGGCAACTAAGGACAG
CAGATCCAAATACGTGGTGCATAATTGTTCCTTAGTAATGGACAAAGGTTCTTAT
AAGATTTCACTGGAGGCAGTGTGGCCTGGAGTATTTATATGATGCCTAATGAACC
TCCAGAATGCTGGCCAGAGGCTGGATTGGTTAGCAGGGGATATGGTGTAGACGG
AGTGAAATGAGCTGCAAAGTCTAACAGCACGAGTCTTAATTGCCTTTGCTGGGGT
ATCCAAAGCCTTTAAAATTTATGCTTTAAGTCCCTCACAAGGGGGTACCCGCTA
GCAACCTATCAAAAGTTGAAGTTCTTTTAAAATTGTGACTGGCCTTTTCTTAACC
TGCCTTAGGCCTTTTAATCACCAGATCTCTGGGACAAAACATTGTACATGTCACA
GGTTGCTCTCCTTGTATTTCATGCCTGTCTGCTTCAGCAACTTCAGTTATTTATTG
ATTCATGCTTTTAGTAAGAGCCCTTAATGTTTTGTCCAATCCTACTTTGTGGAG
AAACATTTCATGGATTCCAAATCCCAAATAGGCAAATAGGTGTTCAAATTCTGGA
AAT |
| >Angiopoietin-1 Nucleic Acid Sequence (SEQ ID NOs: 28 and 29)
Isoform 1 (SEQ ID NO: 28)
AATTTGTAAGCCGATCCGCCGCCCAAAGCCATCAGCAATCCTTAGCATAGGGGC
ACACTCATGCATTCCTGTCAAGTCATCTTGTGAAGGCTGCCTGCTTCCAGCTTGGC
TTGGATGTGCAACCTTAATAAAACTCACTGAGGTCTGGGAGAAAATAGCAGATC
TGCTGCAGATAGGGTAGAGGAAAGGGGCTAGAATATGTACTCGCAGCTGACGCG
GGCAGGCTCCACGCTGAACGGTTACACAGAGAGGAAACAATAAATCTAAGCTAC
TATTGCAATAAATATCTCAAGTTTTAACGAAGGAAACTATCATTACAGTTAAAAT
TTTTTAAAGTAACGCTTTTTTAGAACAAAGCTAACAAATGGCTAGTTTTCTGTGG
ATCTTCTTCAAACGCTTTCTTTAACGGGGAAAGAGTCAAACAAGCAGTTTTACCT
GAAATAAAGAACTAGTTTAAAGGTCAGAAGAGAAGAGCAAGCTTTGCAGGAGG
CACGGAAGGCAAGCGCTGGCAGTACAATGACAGTTTTCCTTTCCTTTGCATTCTT
CGCTGCCATTCTGACTCACATAGGGTGCAGCAACCAGCGCCGAAATCCAGAAAA
CGGAGGGAGAAGATATAACCGGATTCAACATGGGCAATGTGCCTACACTTTCAT
TCTTCCAGAACACGACGGGAACTGCCGTGAGAGTGCGACAGAGCAGTACAACAC
CAACGCTCTGCAAAGGGATGCTCCACACGTGGAGCCGGATTTCTCTTCCCAGAAA
CTTCAGCATCTGGAGCATGTGATGAAAATTATACTCAGTGGCTGCAAAAACTTG
AGAATTACATTGTGGAAAATATGAAGTCGGAGATGGCCCAGATACAACAGAATG |

| Sequences |
| --- |
| CTGTTCAAAACCACACGGCCACCATGCTTGAGATAGGAACCAGTCTCTTATCTCA |
| GACTGCAGAGCAGACCCGAAAGCTGACAGATGTTGAGACCCAGGTACTAAATCA |
| AACATCCCGACTTGAAATACAACTGCTAGAGAATTCATTATCAACATACAAGCTA |
| GAGAAGCAACTTCTCCAACAGACAAATGAAATTCTGAAGATTCACGAAAAAAAC |
| AGTTTACTAGAGCACAAAATCTTAGAAATGGAGGGAAAACACAAAGAAGAATTG |
| GACACCTTGAAGGAGGAGAAAGAAAACCTTCAAGGCTTGGTTTCTCGTCAGACA |
| TTCATCATCCAGGAGTTGGAGAAGCAACTTAGTAGAGCTACCAACAACAACAGC |
| ATCCTGCAGAAGCAACAACTGGAGCTCATGGACACAGTTCATAACCTTATCAGCC |
| TTTGCACTAAAGAAGGTGTTTTGCTAAAGGGAGGAAAAAGAGAAGAAGAGAAA |
| CCATTTCGAGACTGTGCAGATGTATATCAAGCTGGTTTTAATAAAAGTGGAATCT |
| ACACTATTTATTTTAATAATATGCCAGAACCCAAAAAGGTATTTTGCAATATGGA |
| TGTGAATGGGGGAGGTTGGACAGTAATACAACACCGGGAAGATGGAAGCCTGGA |
| TTTCCAGAGGGGCTGGAAGGAGTATAAAATGGGTTTTGGGAATCCCTCTGGTGA |
| ATATTGGCTTGGGAACGAGTTCATTTTTGCAATAACCAGTCAGAGGCAGTACATG |
| CTGAGGATTGAGCTGATGGACTGGGAAGGGAACCGAGCCTACTCACAGTACGAC |
| AGATTCCACATAGGAAATGAAAAGCAGAACTATAGGTTATATTTAAAAGGTCAC |
| ACAGGGACAGCAGGCAAACAGAGCAGCTTGATCTTACACGGTGCCGATTTCAGC |
| ACGAAGGATGCTGATAACGACAACTGTATGTGCAAATGCGCTCTCATGCTAACA |
| GGAGGTTGGTGGTTCGATGCCTGTGGCCCTTCCAATCTAAATGGAATGTTCTACA |
| CTGCGGGACAAAATCATGGAAAACTGAATGGGATAAAGTGGCACTACTTCAAAG |
| GGCCCAGTTACTCCTTACGTTCCACCACCATGATGATCCGGCCCTTGGACTTTTGA |
| AGGTGCTCTGCCAGTATTAGAAAGCTGCAAAGAAAGCTGGGCATGTTCCCAGAT |
| GAGAAGCTAGTCAGAGGCTTCAGAAACAACCAACATTGTCTCCATTCCAGCAGC |
| AAGTGGTTATGTCATGTCACCTGGGTTTGGAGCCTTCTGAGGTCAACAGAATCGC |
| CACTTGGGTCCAGAGAATGCCACTCACAATCATGTTTAAAAGGGAAGAAACTTCT |
| CAGCTTGCTGCACTTCAAAGTGCTACTGGATCACATTCTGAACTTATAACATCCT |
| GATGCTGAATGCAACTTGTTTCATGTAAAAGCAAAAGAAGAAGAAACAGCAAAT |
| GGGAACAGGCTTTCCAGAATCTGTTGAAGATGGATTGTGGAGGTGACCTGGTATC |
| ACTGTAGGAAATCCTGCTAACAATACATCACTGCCCAAAAGAGACATAAAGAAA |
| AGTTTTGTCTACTGAGTTGGCTAAAAGTTAGTGGAGTTCACCTGCCCATTTCCAGT |
| ATCATATTTACTAGCTGATTTCAGGTTTCCTGTGTTCAAATGTAAACTCTGTTCTT |
| GTAAGCCATGATACAATATAGTACATGGAGGATAAGAGTTGGGCTGGGGGTAGAAGGTG |
| CCTAAAGACTCTTGAGTTTCTGGGGATTCAGTTTTCAAAAGATATAAAATATAAT |
| CAAGAATGGATAAAACAGGTGAAAATCACACTCATGCTACAGTGTTCCTTTACAT |
| GAAATTTGATTAACTGATCCACAAGAATGTTTAGAGCCTGAGTATATATAAAGAC |
| TGGAAGTGTTATCACCCAGTTCTCAAAACAATAAGCAGGCAGTTAACATTCTCAT |
| TGACAGTATGTAGGAGAGCAATATGTGGAGTACTTGAGTTGGAACAGCCCATTG |
| TACAGATCTTGCATGTATTTGCATATGTATGGCATTATTATTTTTAAAGTGTTCGT |
| AGGCCTTCAATTCTTCATACAGATTTTTCATGCTAATTTAATTTTTGTTAATTAAC |
| TGCAATGTACTTACTAAATATATCCTACTCCAGTTTTTTATGAGTTATACTTTAAA |
| GTCTACAAATAATAGAAGAATTTTAAATATCATTGTACATAATATCTTATACCTG |
| TCCATGCTAAACTCAATAATTGTTTAGTCTGGAATATATGATGCTGTCCACAACT |
| GATGACTATAAATATGATTGTTTAAAGACAGTTACCATACTATTGATTAAATATA |
| TTACTCTGCATAGTTTTTCTCCTCCAGGATCTGTTTCTTCAAGCAATTTCTACCTTG |
| TAAAATAATGGTAGTAGAGAAAATTGACATAACTCCTTGTACAAAAGAATTATA |
| GAAAAAATTACAGTCATTTGACTAGGAAGTTTCTGATTGTTAGCTGCTATAAGTG |
| CCTTAGTTAAGATGCCCCTGTGTTATAATATGTAGTAAATGAAGTTTTGGACACA |
| GGATTCTGTGATAACCTGATGTGACTGCAGTATTCTATCAAGTTCTCTTTGTTGTT |
| AAATGTTCAAGGTTATAGTAGAAAAAAAACATTCAATCAAACACAATTTGCCAT |
| GAAAGGAGAGAACTAAATGTAGGCACCAGTTCTGTTTTCTCAGAGAAGGAGAAG |
| ACTTTCTGGGACGTACATGTACCAAAATATAAATCTTGATAACCGCAGCCACAAA |
| GCCTTAGTGACTTTCCTCTACCTGGTAAGACAGAGCTCTTCATGCTTTTAAGAAA |
| AGATTCTGAATGCTTCCCACCACATCTTTCTTATATTTTATATGTGTTCATAAAGTA |
| CTATTTTGCCTTACAAGAGGTATGTGCCGACATTACAGGATTTTTCTACTATAGTG |
| ACTCCTTCACAGCTTTCTTAAGCCTAGCCCTCTAAAAGCTTCCTTCTCATTTAGAT |
| GAAAGAAAATGAGTATTTTGTGATTCTGGTGATTGTGGTGGTTGTTGTTGTTGTT |
| GTTGTTGTTCCCACAGATGTTCGAAAACTCATCTTGGGTAAATTGTTTTTCAATCC |
| ACATTACAAAAATAAAGCGAAACAAGGAGAAAAAAAAGCATGGAATTTACTGA |
| TTTGTTATGTGGGTTTGAAAAATAAGATATTGTTTTCAGTTATTTATAATAAAGCA |
| GTATAATGTGTACATTGTATAATGCCAACATGTGTGTAGCAATTTGATACGCATA |
| GCTTTTTGCATTTAATTAATGCAGGGCAGAAAAATTAGATAACTCGAACTTTGTC |
| TTGAAGTTTCTATTTCAATAAAAGCTGTGTCATTTCTATGAAAATGTCTTCATAAG |
| ATTACATTATTTCATTTAAATAAAATTGAAAATAATGTGGGCAA |

Isoform 2 (SEQ ID NO: 29):
AATTTGTAAGCCGATCCGCCGCCCAAAGCCATCAGCAATCCTTAGCATAGGGGC
ACACTCATGCATTCCTGTCAAGTCATCTTGTGAAGGCTGCCTGCTTCCAGCTTGGC
TTGGATGTGCAACCTTAATAAAACTCACTGAGGTCTGGGAGAAAATAGCAGATC
TGCTGCAGATAGGGTAGAGGAAGGGGCTAGAATATGTACTCGCAGCTGACGCG
GGCAGGCTCCACGCTGAACGGTTACACAGAGAGGAAACAATAAATCTAAGCTAC
TATTGCAATAAATATCTCAAGTTTTAACGAAGGAAACTATCATTACAGTTAAAAT
TTTTTAAAGTAACGCTTTTTTAGAACAAAGCTAACAAATGGCTAGTTTTCTGTGG
ATCTTCTTCAAACGCTTTCTTTAACGGGGAAAGAGTCAAACAAGCAGTTTTACCT
GAAATAAAGAACTAGTTTAAAGGTCAGAAGAGAAGAGCAAGCTTTGCAGGAGG
CACGGAAGGCAAGCGCTGGCAGTACAATGACAGTTTTCCTTTCCTTTGCATTCTT
CGCTGCCATTCTGACTCACATAGGGTGCAGCAACCAGCGCCGAAATCCAGAAAA
CGGAGGGAGAAGATATAACCGGATTCAACATGGGCAATGTGCCTACACTTTCAT -continued

| Sequences |
|---|
| TCTTCCAGAACACGACGGGAACTGCCGTGAGAGTGCGACAGAGCAGTACAACAC |
| CAACGCTCTGCAAAGGGATGCTCCACACGTGGAGCCGGATTTCTCTTCCCAGAAA |
| CTTCAGCATCTGGAGCATGTGATGAAAATTATACTCAGTGGCTGCAAAAACTTG |
| AGAATTACATTGTGGAAAATATGAAGTCGGAGATGGCCCAGATACAACAGAATG |
| CTGTTCAAAACCACACGGCCACCATGCTTGAGATAGGAACCAGTCTCTTATCTCA |
| GACTGCAGAGCAGACCCGAAAGCTGACAGATGTTGAGACCCAGGTACTAAATCA |
| AACATCCCGACTTGAAATACAACTGCTAGAGAATTCATTATCAACATACAAGCTA |
| GAGAAGCAACTTCTCCAACAGACAAATGAAATTCTGAAGATTCACGAAAAAAAC |
| AGTTTACTAGAGCACAAATCTTAGAAATGGAGGGAAAACACAAAGAAGAATTG |
| GACACCTTGAAGGAGGAGAAAGAAAACCTTCAAGGCTTGGTTTCTCGTCAGACA |
| TTCATCATCCAGGAGTTGGAGAAGCAACTTAGTAGAGCTACCAACAACAACAGC |
| ATCCTGCAGAAGCAACAACTGGAGCTCATGGACACAGTTCATAACCTTATCAGCC |
| TTTGCACTAAAGAAGTTTTGCTAAAGGGAGGAAAAAGAGAAGAAGAGAAACCAT |
| TTCGAGACTGTGCAGATGTATATCAAGCTGGTTTTAATAAAAGTGGAATCTACAC |
| TATTTATTTTAATAATATGCCAGAACCCAAAAAGGTATTTTGCAATATGGATGTG |
| AATGGGGGAGGTTGGACAGTAATACAACACCGGGAAGATGGAAGCCTGGATTTC |
| CAGAGGGGCTGGAAGGAGTATAAAATGGGTTTTGGGAATCCCTCTGGTGAATAT |
| TGGCTTGGGAACGAGTTCATTTTTGCAATAACCAGTCAGAGGCAGTACATGCTGA |
| GGATTGAGCTGATGGACTGGGAAGGGAACCGAGCCTACTCACAGTACGACAGAT |
| TCCACATAGGAAATGAAAAGCAGAACTATAGGTTATATTTAAAAGGTCACACAG |
| GGACAGCAGGCAAACAGAGCAGCTTGATCTTACACGGTGCCGATTTCAGCACGA |
| AGGATGCTGATAACGACAACTGTATGTGCAAATGCGCTCTCATGCTAACAGGAG |
| GTTGGTGGTTCGATGCCTGTGGCCCTTCCAATCTAAATGGAATGTTCTACACTGC |
| GGGACAAAATCATGGAAAACTGAATGGGATAAAGTGGCACTACTTCAAAGGGCC |
| CAGTTACTCCTTACGTTCCACCACCATGATGATCCGCCCTTGGACTTTTGAAGGT |
| GCTCTGCCAGTATTAGAAAGCTGCAAAGAAAGCTGGGCATGTTCCCAGATGAGA |
| AGCTAGTCAGAGGCTTCAGAAACAACCAACATTGTCTCCATTCCAGCAGCAAGT |
| GGTTATGTCATGTCACCTGGGTTTGGAGCCTTCTGAGGTCAACAGAATCGCCACT |
| TGGGTCCAGAGAATGCCACTCACAATCATGTTTAAAAGGGAAGAAACTTCTCAG |
| CTTGCTGCACTTCAAAGTGCTACTGGATCACATTCTGAACTTATAACATCCTGAT |
| GCTGAATGCAACTTGTTTCATGTAAAAGCAAAAGAAGAAGAAACAGCAAATGGG |
| AACAGGCTTTCCAGAATCTGTTGAAGATGGATTGTGGAGGTGACCTGGTATCACT |
| GTAGGAAATCCTGCTAACAATACATCACTGCCCAAAAGAGACATAAAGAAAAGT |
| TTTGTCTACTGAGTTGGCTAAAAGTTAGTGGAGTTCACCTGCCCATTTCCAGTATC |
| ATATTTACTAGCTGATTTCAGGTTTCCTGTGTTCAAATGTAAACTCTGTTCTTGTA |
| AGCCATGATACAATATAGTACATGGAGGATAAGAGTTGGGGGTAGAAGGTGCCT |
| AAAGACTCTTGAGTTTCTGGGGATTCAGTTTTCAAAAGATATAAAATATAATCAA |
| GAATGGATAAAACAGGTGAAAATCACACTCATGCTACAGTGTTCCTTTACATGAA |
| ATTTGATTAACTGATCCACAAGAATGTTTAGAGCCTGAGTATATATAAAGACTGG |
| AAGTGTTATCACCCAGTTCTCAAAACAATAAGCAGGCAGTTAACATTCTCATTGA |
| CAGTATGTAGGAGAGCAATATGTGGAGTACTTGAGTTGGAACAGCCCATTGTAC |
| AGATCTTGCATGTATTTGCATATGTATGGCATTATTATTTTAAAGTGTTCGTAGG |
| CCTTCAATTCTTCATACAGATTTTTCATGCTAATTTAATTTTTGTTAATTAACTGCA |
| ATGTACTTACTAAATATATCCTACTCCAGTTTTTTATGAGTTATACTTTAAAGTCT |
| ACAAATAATAGAAGAATTTTAAATATCATTGTACATAATATCTTATACCTGTCCA |
| TGCTAAACTCAATAATTGTTTAGTCTGGAATATATGATGCTGTCCAACAACTGATG |
| ACTATAAATATGATTGTTTAAAGACAGTTACCATACTATTGATTAAATATATTAC |
| TCTGCATAGTTTTTCTCCTCCAGGATCTGTTTCTTCAAGCAATTTCTACCTTGTAA |
| AATAATGGTAGTAGAGAAAATTGACATAACTCCTTGTACAAAAGAATTATAGAA |
| AAAATTACAGTCATTTGACTAGGAAGTTTCTGATTGTTAGCTGCTATAAGTGCCT |
| TAGTTAAGATGCCCCTGTGTTATAATATGTAGTAAATGAAGTTTTGGACACAGGA |
| TTCTGTGATAACCTGATGTGACTGCAGTATTCTATCAAGTTCTCTTTGTTGTTAAA |
| TGTTCAAGGTTATAGTAGAAAAAAAACATTCAATCAAACACAATTTGCCATGAA |
| AGGAGAGAACTAAATGTAGGCACCAGTTCTGTTTTCTCAGAGAAGGAGAAGACT |
| TTCTGGGACGTACATGTACCAAAATATAAATCTTGATAACCGCAGCCACAAAGCC |
| TTAGTGACTTTCCTCTACCTGGTAAGACAGAGCTCTTCATGCTTTTAAGAAAAGA |
| TTCTGAATGCTTCCCACCACATCTTTCTTATATTTATATGTGTTCATAAAGTACTA |
| TTTTGCCTTACAAGAGGTATGTGCCGACATTACAGGATTTTTCTACTATAGTGACT |
| CCTTCACAGCTTTCTTAAGCCTAGCCCTCTAAAAGCTTCCTTCTCATTTAGATGAA |
| AGAAAATGAGTATTTTTGTGATTCTGGTGATTGTGGTGGTGTTGTTGTTGTTGTT |
| GTTGTTCCCACAGATGTTCGAAAACTCATCTTGGGTAAATTGTTTTTCAATCCACA |
| TTACAAAAATAAAGCGAAACAAGGAGAAAAAAAAGCATGAATTTACTGATTTG |
| TTATGTGGGTTTGAAAAATAAGATATTGTTTTCAGTTATTTATAATAAAGCAGTA |
| TAATGTGTACATTGTATAATGCCAACATGTGTGTAGCAATTTGATACGCATAGCT |
| TTTTGCATTTAATTAATGCAGGGCAGAAAATTAGATAACTCGAACTTTGTCTTG |
| AAGTTTCTATTTCAATAAAAGCTGTGTCATTTCTATGAAAATGTCTTCATAAGATT |
| ACATTATTTCATTTAAATAAAATTGAAAATAATGTGGGCAA |

What is claimed is:

1. A recombinant adeno-associated virus (rAAV) comprising:
   (i) a capsid protein having a serotype of AAVrh.10 encoded by the amino acid sequence set forth in SEQ ID NO: 14; and,
   (ii) a nucleic acid comprising a promoter operably linked to a transgene encoding a protein associated with an ocular disease, wherein the transgene comprises a tough decoy (TuD) miRNA having a region of complementarity to SEQ ID NO:1.

2. The rAAV of claim 1, wherein the TuD miRNA comprises SEQ ID NO: 4.

3. The rAAV of claim 1, wherein the rAAV further comprises two AAV inverted terminal repeats (ITRs), wherein the ITRs flank the transgene.

4. The rAAV of claim 1, wherein the protein associated with an ocular disease is Frizzled 4, angiopoietin 1, angiopoietin 2, transforming growth factor beta (TGFβ), mitogen-activated protein kinase (MAPK), IL-1α, IL-1β, IL-6, TNFα, IFNγ, CD4, protein p27, cytokeratin 13, ILGF2, junB, metallothionein hMT-Ie, keratin 6 (KRT6), beta-2 microglobulin, CTGF, or VEGF.

* * * * *

UNITED STATES PATENT AND TRADEMARK OFFICE
CERTIFICATE OF CORRECTION

| | |
|---|---|
| PATENT NO. | : 11,851,657 B2 |
| APPLICATION NO. | : 17/342587 |
| DATED | : December 26, 2023 |
| INVENTOR(S) | : Guangping Gao et al. |

It is certified that error appears in the above-identified patent and that said Letters Patent is hereby corrected as shown below:

In the Claims

In Claim 4, Column 138, Line 15 the text "IL-1(3" should read --IL-1β--

Signed and Sealed this
Thirtieth Day of January, 2024

Katherine Kelly Vidal
*Director of the United States Patent and Trademark Office*

SEQUENCE LISTING

<160> NUMBER OF SEQ ID NOS: 39

<210> SEQ ID NO 1

-continued

```
<211> LENGTH: 92
<212> TYPE: RNA
<213> ORGANISM: Artificial Sequence
<220> FEATURE:
<223> OTHER INFORMATION: Synthetic Polynucleotide

<400> SEQUENCE: 1
uguaccaccu ugucggauag cuuaucagac ugauguugac uguugaaucu cauggcaaca    60
gcagucgaug ggcugucuga cauuuuggua uc                                 92

<210> SEQ ID NO 2
<211> LENGTH: 69
<212> TYPE: RNA
<213> ORGANISM: Artificial Sequence
<220> FEATURE:
<223> OTHER INFORMATION: Synthetic Polynucleotide

<400> SEQUENCE: 2 ccuuccuua ucacuuuucc agccagcuuu gugacucuaa guguuggacg agaacugau     60 aaggguagg                                                            69

<210> SEQ ID NO 3
<211> LENGTH: 68
<212> TYPE: RNA
<213> ORGANISM: Artificial Sequence
<220> FEATURE:
<223> OTHER INFORMATION: Synthetic Polynucleotide

<400> SEQUENCE: 3
uggacuuccc uuugucaucc uaugccugag aauauaugaa ggaggcuggg aaggcaaagg   60
gacguuca                                                             68

<210> SEQ ID NO 4
<211> LENGTH: 125
<212> TYPE: DNA
<213> ORGANISM: Artificial Sequence
<220> FEATURE:
<223> OTHER INFORMATION: Synthetic Polynucleotide

<400> SEQUENCE: 4
gacggcgcta ggatcatcaa ctcaacatca gtcatcttga taagctacaa gtattctggt   60
cacagaatac aactcaacat cagtcatctt gataagctac aagatgatcc tagcgccgtc  120
ttttt                                                               125

<210> SEQ ID NO 5
<211> LENGTH: 500
<212> TYPE: DNA
<213> ORGANISM: Artificial Sequence
<220> FEATURE:
<223> OTHER INFORMATION: Synthetic Polynucleotide

<400> SEQUENCE: 5
tgtgcagaaa cataagtgac tctccaggtg tcagagggag agactggggc gagaggccag   60
agcaaagtag aagggcacag aggggctttg aatttgaggc agaggaggaa ctgcagagag  120
ggggcgggga gggctcgccg ggaaatcaaa cgtccattta catcttgtcc tgcaaagctt  180
catcaaaact tctttgccgg ccagtcacgt ccccttatca cttttccagc ccagctttgt  240
gactgtaagt gttggacgga gaactgataa gggtaggtga ttgacactca cagcctccgg  300 aaccccccgcg ccgcctgcac ttgcgtgatg gggaaaacct ggcgttcccg ctctgggtgc  360
ccgaggacag caggggattc caggaggaga ccttgggcat aggggccca ggtatgcgcc  420
```

```
ccctgcctga ggatgctggg gtagcctttg tgttttgtca gtgagatctc cactttgctt    480
attcaaaatg tgctctctgc                                                500
```

<210> SEQ ID NO 6
<211> LENGTH: 530
<212> TYPE: DNA
<213> ORGANISM: Artificial Sequence
<220> FEATURE:
<223> OTHER INFORMATION: Synthetic Polynucleotide

<400> SEQUENCE: 6

```
tttacccaca ggacagggtg atggagagga gggtgagggt ggaggcaagc agaggacctc     60
ctgatcatgt acccatagga cagggtgatg gagaggaggg tgggggtgga ggcaagcaga    120
ggacctcctg atcatgtacc cataggacag ggtgatggaa aggagggtgg gggtggaggc    180
aagcagagga cttcctgatc gcgtacccat ggctacagtc tttcttcatg tgactcgtgg    240
acttcccttt gtcatcctat gcctgagaat atatgaagga ggctgggaag caaagggac     300 gttcaattgt catcactggc atcttttttg atcattgcac catcatcaaa tgcattggga    360
taaccatgac atgaaatttt ccatcattgg gcccataact gtcccataag agagatgaaa    420
aacactgtat gttaaaggtc atagtagaac ttcatccaag cagctctgga attaggaagg    480
agtgaaatat actctcaaag actaatagtt ctgggtccaa accatgtgac              530
```

<210> SEQ ID NO 7
<211> LENGTH: 724
<212> TYPE: PRT
<213> ORGANISM: Artificial Sequence
<220> FEATURE:
<223> OTHER INFORMATION: Synthetic Polypeptide

<400> SEQUENCE: 7

```
Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190
```

```
Met Ser Ala Gly Gly Gly Gly Pro Leu Gly Asp Asn Gln Gly Ala
            195                 200                 205
Asp Gly Val Gly Asn Ala Ser Gly Asp Trp His Cys Asp Ser Thr Trp
    210                 215                 220
Met Gly Asp Arg Val Val Thr Lys Ser Thr Arg Thr Trp Val Leu Pro
225                 230                 235                 240
Ser Tyr Asn Asn His Gln Tyr Arg Glu Ile Lys Ser Gly Ser Val Asp
                245                 250                 255
Gly Ser Asn Ala Asn Ala Tyr Phe Gly Tyr Ser Thr Pro Trp Gly Tyr
            260                 265                 270
Phe Asp Phe Asn Arg Phe His Ser His Trp Ser Pro Arg Asp Trp Gln
        275                 280                 285
Arg Leu Ile Asn Asn Tyr Trp Gly Phe Arg Pro Arg Ser Leu Arg Val
    290                 295                 300
Lys Ile Phe Asn Ile Gln Val Lys Glu Val Thr Val Gln Asp Ser Thr
305                 310                 315                 320
Thr Thr Ile Ala Asn Asn Leu Thr Ser Thr Val Gln Val Phe Thr Asp
                325                 330                 335
Asp Asp Tyr Gln Leu Pro Tyr Val Val Gly Asn Gly Thr Glu Gly Cys
            340                 345                 350
Leu Pro Ala Phe Pro Pro Gln Val Phe Thr Leu Pro Gln Tyr Gly Tyr
        355                 360                 365
Ala Thr Leu Asn Arg Asp Asn Thr Glu Asn Pro Thr Glu Arg Ser Ser
    370                 375                 380
Phe Phe Cys Leu Glu Tyr Phe Pro Ser Lys Met Leu Arg Thr Gly Asn
385                 390                 395                 400
Asn Phe Glu Phe Thr Tyr Asn Phe Glu Glu Val Pro Phe His Ser Ser
                405                 410                 415
Phe Ala Pro Ser Gln Asn Leu Phe Lys Leu Ala Asn Pro Leu Val Asp
            420                 425                 430
Gln Tyr Leu Tyr Arg Phe Val Ser Thr Asn Asn Thr Gly Gly Val Gln
        435                 440                 445
Phe Asn Lys Asn Leu Ala Gly Arg Tyr Ala Asn Thr Tyr Lys Asn Trp
    450                 455                 460
Phe Pro Gly Pro Met Gly Arg Thr Gln Gly Trp Asn Leu Gly Ser Gly
465                 470                 475                 480
Val Asn Arg Ala Ser Val Ser Ala Phe Ala Thr Thr Asn Arg Met Glu
                485                 490                 495
Leu Glu Gly Ala Ser Tyr Gln Val Pro Pro Gln Pro Asn Gly Met Thr
            500                 505                 510
Asn Asn Leu Gln Gly Ser Asn Thr Tyr Ala Leu Glu Asn Thr Met Ile
        515                 520                 525
Phe Asn Ser Gln Pro Ala Asn Pro Gly Thr Thr Ala Thr Tyr Leu Glu
    530                 535                 540
Gly Asn Met Leu Ile Thr Ser Glu Ser Glu Thr Gln Pro Val Asn Arg
545                 550                 555                 560
Val Ala Tyr Asn Val Gly Gly Gln Met Ala Thr Asn Asn Gln Ser Ser
                565                 570                 575
Thr Thr Ala Pro Ala Thr Gly Thr Tyr Asn Leu Gln Glu Ile Val Pro
            580                 585                 590
Gly Ser Val Trp Met Glu Arg Asp Val Tyr Leu Gln Gly Pro Ile Trp
        595                 600                 605
Ala Lys Ile Pro Glu Thr Gly Ala His Phe His Pro Ser Pro Ala Met
```

```
                    610                 615                 620
Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                    645                 650                 655

Ser Phe Ile Thr Gln Tyr Ser Thr Gly Gln Val Thr Val Glu Met Glu
                    660                 665                 670

Trp Glu Leu Lys Lys Glu Asn Ser Lys Arg Trp Asn Pro Glu Ile Gln
                    675                 680                 685

Tyr Thr Asn Asn Tyr Asn Asp Pro Gln Phe Val Asp Phe Ala Pro Asp
                    690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 8
<211> LENGTH: 736
<212> TYPE: PRT
<213> ORGANISM: Artificial Sequence
<220> FEATURE:
<223> OTHER INFORMATION: Synthetic Polypeptide

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                    20                  25                  30

Lys Ala Asn Gln Gln Lys Gln Asp Asp Gly Arg Gly Leu Val Leu Pro
                    35                  40                  45

Gly Tyr Lys Tyr Leu Gly Pro Phe Asn Gly Leu Asp Lys Gly Glu Pro
            50                  55                  60

Val Asn Ala Ala Asp Ala Ala Ala Leu Glu His Asp Lys Ala Tyr Asp
65              70                  75                  80

Gln Gln Leu Lys Ala Gly Asp Asn Pro Tyr Leu Arg Tyr Asn His Ala
                    85                  90                  95

Asp Ala Glu Phe Gln Glu Arg Leu Gln Glu Asp Thr Ser Phe Gly Gly
                    100                 105                 110

Asn Leu Gly Arg Ala Val Phe Gln Ala Lys Lys Arg Val Leu Glu Pro
                    115                 120                 125

Phe Gly Leu Val Glu Glu Gly Ala Lys Thr Ala Pro Gly Lys Lys Arg
            130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                    165                 170                 175

Gly Asp Ser Glu Ser Val Pro Asp Pro Gln Pro Leu Gly Glu Pro Pro
                    180                 185                 190

Ala Thr Pro Ala Ala Val Gly Pro Thr Thr Met Ala Ser Gly Gly Gly
                    195                 200                 205

Ala Pro Met Ala Asp Asn Asn Glu Gly Ala Asp Gly Val Gly Asn Ala
            210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                    245                 250                 255
```

```
Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670
```

```
Gln Tyr Ser Thr Gly Gln Val Ser Val Glu Ile Glu Trp Glu Leu Gln
            675                 680                 685
Lys Glu Asn Ser Lys Arg Trp Asn Pro Glu Val Gln Tyr Thr Ser Asn
        690                 695                 700
Tyr Ala Lys Ser Ala Asn Val Asp Phe Thr Val Asp Asn Asn Gly Leu
705                 710                 715                 720
Tyr Thr Glu Pro Arg Pro Ile Gly Thr Arg Tyr Leu Thr Arg Pro Leu
                725                 730                 735

<210> SEQ ID NO 9
<211> LENGTH: 736
<212> TYPE: PRT
<213> ORGANISM: Artificial Sequence
<220> FEATURE:
<223> OTHER INFORMATION: Synthetic Polypeptide

<400> SEQUENCE: 9

Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Leu Glu His Asp Lys Ala Tyr Asp Gln
65                  70                  75                  80
Gln Leu Lys Ala Gly Asp Asn Pro Tyr Leu Arg Tyr Asn His Ala Asp
                85                  90                  95
Ala Glu Phe Gln Glu Arg Leu Gln Glu Asp Thr Ser Phe Gly Gly Asn
            100                 105                 110
Leu Gly Arg Ala Val Phe Gln Ala Lys Lys Arg Val Leu Glu Pro Leu
        115                 120                 125
Gly Leu Val Glu Glu Gly Ala Lys Thr Ala Pro Gly Lys Lys Arg Pro
    130                 135                 140
Val Glu Gln Ser Pro Gln Glu Pro Asp Ser Ser Ser Gly Ile Gly Lys
145                 150                 155                 160
Thr Gly Gln Gln Pro Ala Lys Lys Arg Leu Asn Phe Gly Gln Thr Gly
                165                 170                 175
Asp Ser Glu Ser Val Pro Asp Pro Gln Pro Leu Gly Glu Pro Pro Ala
            180                 185                 190
Thr Pro Ala Ala Val Gly Pro Thr Thr Met Ala Ser Gly Gly Gly Ala
        195                 200                 205
Pro Met Ala Asp Asn Asn Glu Gly Ala Asp Gly Val Gly Asn Ala Ser
    210                 215                 220
Gly Asn Trp His Cys Asp Ser Thr Trp Leu Gly Asp Arg Val Ile Thr
225                 230                 235                 240
Thr Ser Thr Arg Thr Trp Ala Leu Pro Thr Tyr Asn Asn His Leu Tyr
                245                 250                 255
Lys Gln Ile Ser Ser Ala Ser Thr Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn
    290                 295                 300
```

-continued

```
Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
            325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
            565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
            645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
```

725                 730                 735

<210> SEQ ID NO 10
<211> LENGTH: 737
<212> TYPE: PRT
<213> ORGANISM: Artificial Sequence
<220> FEATURE:
<223> OTHER INFORMATION: Synthetic Polypeptide

<400> SEQUENCE: 10

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro
    115                 120                 125

Leu Gly Leu Val Glu Glu Gly Ala Lys Thr Ala Pro Ala Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
            165                 170                 175

Thr Gly Asp Ser Glu Ser Val Pro Asp Pro Gln Pro Leu Gly Glu Pro
        180                 185                 190

Pro Ala Ala Pro Ser Ser Val Gly Ser Gly Thr Val Ala Ala Gly Gly
    195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Ser Glu Thr Ala Gly Ser Thr Asn Asp Asn
        260                 265                 270

Thr Tyr Phe Gly Tyr Ser Thr Pro Trp Gly Tyr Phe Asp Phe Asn Arg
    275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
            325                 330                 335

Asn Leu Thr Ser Thr Ile Gln Val Phe Ser Asp Ser Glu Tyr Gln Leu
        340                 345                 350

Pro Tyr Val Leu Gly Ser Ala His Gln Gly Cys Leu Pro Pro Phe Pro

```
                355                 360                 365
Ala Asp Val Phe Met Ile Pro Gln Tyr Gly Tyr Leu Thr Leu Asn Asn
370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
        435                 440                 445

Arg Thr Gln Ser Asn Pro Gly Gly Thr Ala Gly Asn Arg Glu Leu Gln
    450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
        515                 520                 525

His Lys Asp Asp Glu Asp Arg Phe Phe Pro Ser Ser Gly Val Leu Ile
    530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 11
<211> LENGTH: 738
<212> TYPE: PRT
<213> ORGANISM: Artificial Sequence
<220> FEATURE:
```

<223> OTHER INFORMATION: Synthetic Polypeptide

<400> SEQUENCE: 11

```
Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Leu Glu His Asp Lys Ala Tyr Asp
65                  70                  75                  80
Gln Gln Leu Gln Ala Gly Asp Asn Pro Tyr Leu Arg Tyr Asn His Ala
            85                  90                  95
Asp Ala Glu Phe Gln Glu Arg Leu Gln Glu Asp Thr Ser Phe Gly Gly
        100                 105                 110
Asn Leu Gly Arg Ala Val Phe Gln Ala Lys Lys Arg Val Leu Glu Pro
    115                 120                 125
Leu Gly Leu Val Glu Glu Gly Ala Lys Thr Ala Pro Gly Lys Lys Arg
130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Arg Lys Arg Leu Asn Phe Gly Gln
            165                 170                 175
Thr Gly Asp Ser Glu Ser Val Pro Asp Pro Gln Pro Leu Gly Glu Pro
        180                 185                 190
Pro Ala Ala Pro Ser Gly Val Gly Pro Asn Thr Met Ala Ala Gly Gly
    195                 200                 205
Gly Ala Pro Met Ala Asp Asn Asn Glu Gly Ala Asp Gly Val Gly Ser
    210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
            245                 250                 255
Leu Tyr Lys Gln Ile Ser Asn Gly Thr Ser Gly Gly Ala Thr Asn Asp
        260                 265                 270
Asn Thr Tyr Phe Gly Tyr Ser Thr Pro Trp Gly Tyr Phe Asp Phe Asn
    275                 280                 285
Arg Phe His Cys His Phe Ser Pro Arg Asp Trp Gln Arg Leu Ile Asn
    290                 295                 300
Asn Asn Trp Gly Phe Arg Pro Lys Arg Leu Ser Phe Lys Leu Phe Asn
305                 310                 315                 320
Ile Gln Val Lys Glu Val Thr Gln Asn Glu Gly Thr Lys Thr Ile Ala
            325                 330                 335
Asn Asn Leu Thr Ser Thr Ile Gln Val Phe Thr Asp Ser Glu Tyr Gln
        340                 345                 350
Leu Pro Tyr Val Leu Gly Ser Ala His Gln Gly Cys Leu Pro Pro Phe
    355                 360                 365
Pro Ala Asp Val Phe Met Ile Pro Gln Tyr Gly Tyr Leu Thr Leu Asn
    370                 375                 380
Asn Gly Ser Gln Ala Val Gly Arg Ser Ser Phe Tyr Cys Leu Glu Tyr
385                 390                 395                 400
```

```
Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
                565                 570                 575

Glu Glu Tyr Gly Ile Val Ala Asp Asn Leu Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 12
<211> LENGTH: 736
<212> TYPE: PRT
<213> ORGANISM: Artificial Sequence
<220> FEATURE:
<223> OTHER INFORMATION: Synthetic Polypeptide

<400> SEQUENCE: 12

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
```

```
            20                  25                  30
Lys Ala Asn Gln Gln His Gln Asp Asn Ala Arg Gly Leu Val Leu Pro
            35                  40                  45
Gly Tyr Lys Tyr Leu Gly Pro Gly Asn Gly Leu Asp Lys Gly Glu Pro
 50                  55                  60
Val Asn Ala Ala Asp Ala Ala Leu Glu His Asp Lys Ala Tyr Asp
 65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
                100                 105                 110
Asn Leu Gly Arg Ala Val Phe Gln Ala Lys Lys Arg Leu Leu Glu Pro
                115                 120                 125
Leu Gly Leu Val Glu Glu Ala Ala Lys Thr Ala Pro Gly Lys Lys Arg
                130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
                180                 185                 190
Ala Ala Pro Ser Gly Val Gly Ser Leu Thr Met Ala Ser Gly Gly Gly
                195                 200                 205
Ala Pro Val Ala Asp Asn Asn Glu Gly Ala Asp Gly Val Gly Ser Ser
                210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
                260                 265                 270
Ala Tyr Phe Gly Tyr Ser Thr Pro Trp Gly Tyr Phe Asp Phe Asn Arg
                275                 280                 285
Phe His Cys His Phe Ser Pro Arg Asp Trp Gln Arg Leu Ile Asn Asn
                290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
                340                 345                 350
Pro Tyr Val Leu Gly Ser Ala His Glu Gly Cys Leu Pro Pro Phe Pro
                355                 360                 365
Ala Asp Val Phe Met Ile Pro Gln Tyr Gly Tyr Leu Thr Leu Asn Asp
                370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
                435                 440                 445
```

Lys Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 13
<211> LENGTH: 736
<212> TYPE: PRT
<213> ORGANISM: Artificial Sequence
<220> FEATURE:
<223> OTHER INFORMATION: Synthetic Polypeptide

<400> SEQUENCE: 13

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

```
Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Leu Gly Pro Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Val Pro Gln Tyr Gly Tyr Leu Thr Leu Asn Asn
    370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Val
        435                 440                 445

Arg Thr Gln Thr Thr Gly Thr Gly Gly Thr Gln Thr Leu Ala Phe Ser
    450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Asn Gln Asn
                485                 490                 495
```

```
Asn Asn Ser Asn Phe Ala Trp Thr Gly Ala Ala Lys Phe Lys Leu Asn
                500                 505                 510

Gly Arg Asp Ser Leu Met Asn Pro Gly Val Ala Met Ala Ser His Lys
            515                 520                 525

Asp Asp Asp Asp Arg Phe Phe Pro Ser Ser Gly Val Leu Ile Phe Gly
        530                 535                 540

Lys Gln Gly Ala Gly Asn Asp Gly Val Asp Tyr Ser Gln Val Leu Ile
545                 550                 555                 560

Thr Asp Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
            580                 585                 590

Thr Gly Leu Val His Asn Gln Gly Val Ile Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Leu Thr Phe Asn Gln Ala Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 14
<211> LENGTH: 738
<212> TYPE: PRT
<213> ORGANISM: Artificial Sequence
<220> FEATURE:
<223> OTHER INFORMATION: Synthetic Polypeptide

<400> SEQUENCE: 14

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125
```

-continued

```
Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
```

```
                545                 550                 555                 560
Met Leu Thr Ser Glu Glu Ile Lys Thr Thr Asn Pro Val Ala Thr
                    565                 570                 575
Glu Gln Tyr Gly Val Ala Asp Asn Leu Gln Gln Gln Asn Ala Ala
                580                 585                 590
Pro Ile Val Gly Ala Val Asn Ser Gln Gly Ala Leu Pro Gly Met Val
            595                 600                 605
Trp Gln Asn Arg Asp Val Tyr Leu Gln Gly Pro Ile Trp Ala Lys Ile
        610                 615                 620
Pro His Thr Asp Gly Asn Phe His Pro Ser Pro Leu Met Gly Gly Phe
625                 630                 635                 640
Gly Leu Lys His Pro Pro Gln Ile Leu Ile Lys Asn Thr Pro Val
                    645                 650                 655
Pro Ala Asp Pro Pro Thr Thr Phe Ser Gln Ala Lys Leu Ala Ser Phe
                660                 665                 670
Ile Thr Gln Tyr Ser Thr Gly Gln Val Ser Val Glu Ile Glu Trp Glu
            675                 680                 685
Leu Gln Lys Glu Asn Ser Lys Arg Trp Asn Pro Glu Ile Gln Tyr Thr
        690                 695                 700
Ser Asn Tyr Tyr Lys Ser Thr Asn Val Asp Phe Ala Val Asn Thr Asp
705                 710                 715                 720
Gly Thr Tyr Ser Glu Pro Arg Pro Ile Gly Thr Arg Tyr Leu Thr Arg
                    725                 730                 735
Asn Leu

<210> SEQ ID NO 15
<211> LENGTH: 738
<212> TYPE: PRT
<213> ORGANISM: Artificial Sequence
<220> FEATURE:
<223> OTHER INFORMATION: Synthetic Polypeptide

<400> SEQUENCE: 15

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Lys Pro
                20                  25                  30
Lys Ala Asn Gln Gln Lys Gln Asp Asp Gly Arg Gly Leu Val Leu Pro
            35                  40                  45
Gly Tyr Lys Tyr Leu Gly Pro Phe Asn Gly Leu Asp Lys Gly Glu Pro
        50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
                100                 105                 110
Asn Leu Gly Arg Ala Val Phe Gln Ala Lys Lys Arg Val Leu Glu Pro
            115                 120                 125
Leu Gly Leu Val Glu Glu Ala Ala Lys Thr Ala Pro Gly Lys Lys Arg
        130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Lys Lys Arg Leu Asn Phe Gly Gln
                165                 170                 175
```

```
Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Gln Gly Thr Gln Gln Leu Leu
    450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Arg Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Thr Asn Thr Gly
            580                 585                 590
```

```
Pro Ile Val Gly Asn Val Asn Ser Gln Gly Ala Leu Pro Gly Met Val
            595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 16
<211> LENGTH: 736
<212> TYPE: PRT
<213> ORGANISM: Artificial Sequence
<220> FEATURE:
<223> OTHER INFORMATION: Synthetic Polypeptide

<400> SEQUENCE: 16

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Glu Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro
    115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Gly Ile Gly
145                 150                 155                 160

Lys Lys Gly Gln Gln Pro Ala Arg Lys Arg Leu Asn Phe Gly Gln Thr
            165                 170                 175

Gly Asp Ser Glu Ser Val Pro Asp Pro Gln Pro Leu Gly Glu Pro Pro
        180                 185                 190

Ala Ala Pro Ser Gly Val Gly Pro Asn Thr Met Ala Ala Gly Gly Gly
    195                 200                 205

Ala Pro Met Ala Asp Asn Asn Glu Gly Ala Asp Gly Val Gly Ser Ser
```

```
              210                 215                 220
Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Ala Thr Asn Asp Asn
                260                 265                 270

Thr Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
                290                 295                 300

Asn Trp Gly Phe Arg Pro Lys Arg Leu Ser Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Glu Tyr Gln Leu
                340                 345                 350

Pro Tyr Val Leu Gly Ser Ala His Gln Gly Cys Leu Pro Pro Phe Pro
                355                 360                 365

Ala Asp Val Phe Met Ile Pro Gln Tyr Gly Tyr Leu Thr Leu Asn Asn
                370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Thr Tyr Thr
                405                 410                 415

Phe Glu Asp Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Arg Thr Gln Thr Thr Gly Gly Thr Ala Asn Thr Gln Thr Leu Gly Phe
                450                 455                 460

Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Thr Thr Thr Gly Gln
                485                 490                 495

Asn Asn Asn Ser Asn Phe Ala Trp Thr Ala Gly Thr Lys Tyr His Leu
                500                 505                 510

Asn Gly Arg Asn Ser Leu Ala Asn Pro Gly Ile Ala Met Ala Thr His
                515                 520                 525

Lys Asp Asp Glu Glu Arg Phe Phe Pro Val Thr Gly Ser Cys Phe Trp
530                 535                 540

Gln Gln Asn Ala Ala Arg Asp Asn Ala Asp Tyr Ser Asp Val Met Leu
545                 550                 555                 560

Thr Ser Glu Glu Glu Ile Lys Thr Thr Asn Pro Val Ala Thr Glu Glu
                565                 570                 575

Tyr Gly Ile Val Ala Asp Asn Leu Gln Gln Gln Asn Thr Ala Pro Gln
                580                 585                 590

Ile Gly Thr Val Asn Ser Gln Gly Ala Leu Pro Gly Met Val Trp Gln
                595                 600                 605

Asn Arg Asp Val Tyr Leu Gln Gly Pro Ile Trp Ala Lys Ile Pro His
                610                 615                 620

Thr Asp Gly Asn Phe His Pro Ser Pro Leu Met Gly Gly Phe Gly Leu
625                 630                 635                 640
```

```
Lys His Pro Pro Gln Ile Leu Ile Lys Asn Thr Pro Val Pro Ala
            645                 650                 655
Asp Pro Pro Thr Thr Phe Asn Gln Ser Lys Leu Asn Ser Phe Ile Thr
        660                 665                 670
Gln Tyr Ser Thr Gly Gln Val Ser Val Glu Ile Glu Trp Glu Leu Gln
    675                 680                 685
Lys Glu Asn Ser Lys Arg Trp Asn Pro Glu Ile Gln Tyr Thr Ser Asn
690                 695                 700
Tyr Tyr Lys Ser Thr Ser Val Asp Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735
```

<210> SEQ ID NO 17
<211> LENGTH: 2172
<212> TYPE: DNA
<213> ORGANISM: Artificial Sequence
<220> FEATURE:
<223> OTHER INFORMATION: Synthetic Polynucleotide

<400> SEQUENCE: 17

```
atgtcttttg ttgatcaccc tccagattgg ttggaagaag ttggtgaagg tcttcgcgag      60
ttttgggcc ttgaagcggg cccaccgaaa ccaaaaccca atcagcagca tcaagatcaa      120
gcccgtggtc ttgtgctgcc tggttataac tatctcggac ccggaaacgg tctcgatcga      180
ggagagcctg tcaacagggc agacgaggtc gcgcgagagc acgacatctc gtacaacgag      240
cagcttgagg cgggagacaa ccctacctc aagtacaacc acgcggacgc cgagtttcag       300
gagaagctcg ccgacgacac atccttcggg ggaaacctcg aaaggcagt ctttcaggcc       360
aagaaaaggg ttctcgaacc ttttggcctg gttgaagagg gtgctaagac ggcccctacc      420
ggaaagcgga tagacgacca cttccaaaa agaaagaagg cccggaccga agaggactcc       480
aagccttcca cctcgtcaga cgccgaagct ggacccagcg atcccagca gctgcaaatc       540
ccagcccaac cagcctcaag tttgggagct gatacaatgt ctgcgggagg tgcggccca       600
ttgggcgaca ataaccaagg tgccgatgga gtgggcaatg cctcgggaga ttggcattgc      660
gattccacgt ggatggggga cagagtcgtc accaagtcca cccgaacctg ggtgctgccc      720
agctacaaca accaccagta ccgagagatc aaaagcggct ccgtcgacgg aagcaacgcc      780
aacgcctact ttggatacag caccccctgg gggtactttg actttaaccg cttccacagc      840
cactggagcc cccgagactg gcaaagactc atcaacaact actgggggctt cagacccccgg     900
tccctcagag tcaaaatctt caacattcaa gtcaagagg tcacggtgca ggactccacc       960
accaccatcg ccaacaacct cacctccacc gtccaagtgt ttacgacga cgactaccag      1020
ctgcccctacg tcgtcggcaa cgggaccgag ggatgcctgc cggccttccc tccgcaggtc      1080
tttacgctgc cgcagtacgg ttacgcgacg ctgaaccgcg acaacacaga aaatcccacc      1140
gagaggagca gcttcttctg cctagagtac tttcccagca agatgctgag aacgggcaac      1200
aactttgagt ttacctacaa ctttgaggag gtgccttcc actccagctt cgctcccagt      1260
cagaacctct tcaagctggc caacccgctg gtggaccagt acttgtaccg cttcgtgagc      1320
acaaataaca ctggcggagt ccagttcaac aagaacctgg ccgggagata cgccaacacc      1380
tacaaaaact ggttcccggg gcccatgggc cgaacccagg ctggaacct gggctccggg      1440
gtcaaccgcg ccagtgtcag cgccttcgcc acgaccaata ggatggagct cgagggcgcg      1500
```

| | |
|---|---:|
| agttaccagg tgcccccgca gccgaacggc atgaccaaca acctccaggg cagcaacacc | 1560 |
| tatgccctgg agaacactat gatcttcaac agccagccgg cgaacccggg caccaccgcc | 1620 |
| acgtacctcg agggcaacat gctcatcacc agcgagagcg agacgcagcc ggtgaaccgc | 1680 |
| gtggcgtaca acgtcggcgg gcagatggcc accaacaacc agagctccac cactgccccc | 1740 |
| gcgaccggca cgtacaacct ccaggaaatc gtgcccggca gcgtgtggat ggagagggac | 1800 |
| gtgtacctcc aaggacccat ctgggccaag atcccagaga cggggcgca ctttcaccc | 1860 |
| tctccggcca tgggcggatt cggactcaaa cacccaccgc ccatgatgct catcaagaac | 1920 |
| acgcctgtgc ccggaaatat caccagcttc tcggacgtgc ccgtcagcag cttcatcacc | 1980 |
| cagtacagca ccgggcaggt caccgtggag atggagtggg agctcaagaa ggaaaactcc | 2040 |
| aagaggtgga acccagagat ccagtacaca aacaactaca cgacccccca gtttgtggac | 2100 |
| tttgccccgg acagcaccgg ggaatacaga accaccagac ctatcggaac ccgatacctt | 2160 |
| acccgacccc tt | 2172 |

<210> SEQ ID NO 18
<211> LENGTH: 2208
<212> TYPE: DNA
<213> ORGANISM: Artificial Sequence
<220> FEATURE:
<223> OTHER INFORMATION: Synthetic Polynucleotide

<400> SEQUENCE: 18

| | |
|---|---:|
| atggctgccg atggttatct tccagattgg ctcgaggaca acctctctga gggcattcgc | 60 |
| gagtggtggg acttgaaacc tggagccccg aaacccaaag ccaaccagca aaagcaggac | 120 |
| gacggccggg gtctggtgct tcctggctac aagtacctcg gacccttcaa cggactcgac | 180 |
| aagggggagc ccgtcaacgc ggcggatgca gcggccctcg agcacgacaa ggcctacgac | 240 |
| cagcagctca agcgggtga caatccgtac ctgcggtata ccacgccga cgccgagttt | 300 |
| caggagcgtc tgcaagaaga tacgtctttt gggggcaacc tcgggcgagc agtcttccag | 360 |
| gccaagaaga gggttctcga accttttggt ctggttgagg aaggtgctaa gacggctcct | 420 |
| ggaaagaaac gtccggtaga gcagtcgcca aagagccag actcctcctc gggcattggc | 480 |
| aagacaggcc agcagcccgc taaaaagaga ctcaattttg gtcagactgg cgactcagag | 540 |
| tcagtccccg acccacaacc tctcggagaa cctccagcaa cccccgctgc tgtgggacct | 600 |
| actacaatgg cttcaggcgg tggcgcacca atggcagaca taacgaagg cgccgacgga | 660 |
| gtgggtaatg cctcaggaaa ttggcattgc gattccacat ggctgggcga cagagtcatc | 720 |
| accaccagca cccgaacatg gccttgccc acctataaca accacctcta caagcaaatc | 780 |
| tccagtgctt caacggggc cagcaacgac aaccactact cggctacag cacccctgg | 840 |
| gggtattttg atttcaacag attccactgc catttctcac acgtgactg gcagcgactc | 900 |
| atcaacaaca attggggatt ccggcccaag agactcaact tcaagctctt caacatccaa | 960 |
| gtcaaggagg tcacgacgaa tgatggcgtc acgaccatcg ctaataacct taccagcacg | 1020 |
| gttcaagtct ctcggactc ggagtaccag ttgccgtacg tcctcggctc tgcgcaccag | 1080 |
| ggctgcctcc ctccgttccc ggcggacgtg ttcatgattc cgcagtacgg ctacctaacg | 1140 |
| ctcaacaatg gcagccaggc agtgggacgg tcatcctttt actgcctgga atatttccca | 1200 |
| tcgcagatgc tgagaacggg caataacttt accttcagct acaccttcga ggacgtgcct | 1260 |
| ttccacagca gctacgcgca cagccagagc ctggaccggc tgatgaatcc tctcatcgac | 1320 |
| cagtacctgt attacctgaa cagaactcag aatcagtccg gaagtgccca aaacaaggac | 1380 |

```
ttgctgttta gccggggtc tccagctggc atgtctgttc agcccaaaaa ctggctacct    1440
ggaccctgtt accggcagca gcgcgtttct aaaacaaaaa cagacaacaa caacagcaac    1500
tttacctgga ctggtgcttc aaaatataac cttaatgggc gtgaatctat aatcaaccct    1560
ggcactgcta tggcctcaca caaagacgac aaagacaagt tctttcccat gagcggtgtc    1620 atgattttg gaaaggagag cgccggagct tcaaacactg cattggacaa tgtcatgatc    1680
acagacgaag aggaaatcaa agccactaac cccgtggcca ccgaaagatt tgggactgtg    1740
gcagtcaatc tccagagcag cagcacagac cctgcgaccg agatgtgca tgttatggga    1800 gccttacctg gaatggtgtg caagacaga gacgtatacc tgcagggtcc tatttgggcc    1860
aaaattcctc acacggatgg acactttcac ccgtctcctc tcatgggcgg ctttggactt    1920
aagcacccgc ctcctcagat cctcatcaaa aacacgcctg ttcctgcgaa tcctccggca    1980
gagttttcgg ctacaaagtt tgcttcattc atcacccagt attccacagg acaagtgagc    2040
gtggagattg aatgggagct gcagaaagaa acagcaaac gctggaatcc cgaagtgcag    2100
tatacatcta actatgcaaa atctgccaac gttgatttca ctgtggacaa caatggactt    2160
tatactgagc ctcgccccat tggcacccgt tacctcaccc gtccctg              2208

<210> SEQ ID NO 19
<211> LENGTH: 2208
<212> TYPE: DNA
<213> ORGANISM: Artificial Sequence
<220> FEATURE:
<223> OTHER INFORMATION: Synthetic Polynucleotide

<400> SEQUENCE: 19
atggctgccg atggttatct tccagattgg ctcgaggaca acctctctga gggcattcgc      60
gagtggtggg acttgaaacc tggagccccg aaacccaaag ccaaccagca aaagcaggac     120
gacggccggg gtctggtgct tcctggctac aagtacctcg gacccttcaa cggactcgac     180
aagggggagc ccgtcaacgc ggcggatgca gcggccctcg agcacgacaa ggcctacgac     240
cagcagctca aagcgggtga caatccgtac ctgcggtata accacgccga cgccgagttt     300
caggagcgtc tgcaagaaga tacgtctttt ggggcaacc tcgggcgagc agtcttccag     360
gccaagaaga gggttctcga acctcttggt ctggttgagg aaggtgctaa gacggctcct     420
ggaaagaaac gtccggtaga gcagtcgcca aagagccag actcctcctc gggcattggc     480
aagacaggcc agcagcccgc taaaaagaga ctcaattttg gtcagactgg cgactcagag     540
tcagtccccg acccacaacc tctcggagaa cctccagcaa cccccgctgc tgtgggacct     600
actacaatgg cttcaggcgg tggcgcacca atggcagaca taacgaaggg cgccgacgga     660
gtgggtaatg cctcaggaaa ttggcattgc gattccacat ggctgggcga cagagtcatc     720
accaccagca cccgaacatg ggccttgccc acctataaca accacctcta caagcaaatc     780
tccagtgctt caacggggc cagcaacgac aaccactact cggctacag caccccctgg     840 gggtattttg atttcaacag attccactgc catttctcac cacgtgactg cagcgactc     900 atcaacaaca ttggggatt ccggcccaag agactcaact tcaagctctt caacatccaa     960
gtcaaggagg tcacgacgaa tgatggcgtc acgaccatcg ctaataacct taccagcacg    1020
gttcaagtct tctcggactc ggagtaccag ttgccgtacg tcctcggctc tgcgcaccag    1080
ggctgcctcc ctccgttccc ggcggacgtg ttcatgattc cgcagtacgg ctacctaacg    1140
ctcaacaatg gcagccaggc agtgggacgg tcatcctttt actgcctgga atatttccca    1200
```

| | |
|---|---|
| tcgcagatgc tgagaacggg caataacttt accttcagct acaccttcga ggacgtgcct | 1260 |
| ttccacagca gctacgcgca cagccagagc ctggaccggc tgatgaatcc tctcatcgac | 1320 |
| cagtacctgt attacctgaa cagaactcag aatcagtccg gaagtgccca aaacaaggac | 1380 |
| ttgctgttta gccgggggtc tccagctggc atgtctgttc agcccaaaaa ctggctacct | 1440 |
| ggaccctgtt accggcagca gcgcgtttct aaaacaaaaa cagacaacaa caacagcaac | 1500 |
| tttacctgga ctggtgcttc aaaatataac cttaatgggc gtgaatctat aatcaaccct | 1560 |
| ggcactgcta tggcctcaca caaagacgac aaagacaagt tctttcccat gagcggtgtc | 1620 |
| atgattttg gaaaggagag cgccggagct caaacactg cattggacaa tgtcatgatc | 1680 |
| acagacgaag aggaaatcaa agccactaac cccgtggcca ccgaaagatt tgggactgtg | 1740 |
| gcagtcaatc tccagagcag cagcacagac cctgcgaccg agatgtgca tgttatggga | 1800 |
| gccttacctg gaatggtgtg caagacaga gacgtatacc tgcagggtcc tatttgggcc | 1860 |
| aaaattcctc acacggatgg acactttcac ccgtctcctc tcatgggcgg ctttggactt | 1920 |
| aagcacccgc ctcctcagat cctcatcaaa aacacgcctt tcctgcgaa tcctccggca | 1980 |
| gagttttcgg ctacaaagtt tgcttcattc atcacccagt attccacagg acaagtgagc | 2040 |
| gtggagattg aatgggagct gcagaaagaa acagcaaac gctggaatcc gaagtgcag | 2100 |
| tatacatcta actatgcaaa atctgccaac gttgatttca ctgtggacaa caatggactt | 2160 |
| tatactgagc ctcgccccat ggcacccgt tacctcaccc gtccctg | 2208 |

<210> SEQ ID NO 20
<211> LENGTH: 2211
<212> TYPE: DNA
<213> ORGANISM: Artificial Sequence
<220> FEATURE:
<223> OTHER INFORMATION: Synthetic Polynucleotide

<400> SEQUENCE: 20

| | |
|---|---|
| atggctgccg atggttatct tccagattgg ctcgaggaca acctctctga gggcattcgc | 60 |
| gagtggtggg aacctgaaacc tggagccccg aaacccaaag ccaaccagca aaagcaggac | 120 |
| aacggccggg tctggtgct tcctggctac aagtacctcg gacccttcaa cggactcgac | 180 |
| aaggggagc ccgtcaacgc ggcggacgca gcggccctcg agcacgacaa ggcctacgac | 240 |
| cagcagctca aagcgggtga caatccgtac ctgcggtata accacgccga cgccgagttt | 300 |
| caggagcgtc tgcaagaaga tacgtcattt ggggcaacc tcgggcgagc agtcttccag | 360 |
| gccaagaagc gggttctcga acctctcggt ctggttgagg aaggcgctaa gacggctcct | 420 |
| gcaaagaaga gaccggtaga gccgtcacct cagcgttccc ccgactcctc cacgggcatc | 480 |
| ggcaagaaag ccagcagcc cgccagaaag agactcaatt tcggtcagac tggcgactca | 540 |
| gagtcagtcc ccgacccctca acctctcgga gaacctccag cagcgccctc tagtgtggga | 600 |
| tctggtacag tggctgcagg cggtggcgca ccaatggcag acaataacga aggtgccgac | 660 |
| ggagtgggta atgcctcagg aaattggcat tgcgattcca catggctggg cgacagagtc | 720 |
| attaccacca gcacccgaac ctgggccctg cccacctaca acaaccacct ctacaagcaa | 780 |
| atctccagtg aaactgcagg tagtaccaac gacaacacct acttcggcta cagcacccc | 840 |
| tgggggtatt ttgactttaa cagattccac tgccacttct caccacgtga ctggcagcga | 900 |
| ctcatcaaca caactgggg attccggccc aagaagctgc ggttcaagct cttcaacatc | 960 |
| caggtcaagg aggtcacgac gaatgacggc gttacgacca tcgctaataa ccttaccagc | 1020 |
| acgattcagg tattctcgga ctcggaatac cagctgccgt acgtcctcgg ctctgcgcac | 1080 |

```
cagggctgcc tgcctccgtt cccggcggac gtcttcatga ttcctcagta cggctacctg    1140
actctcaaca atggcagtca gtctgtggga cgttcctcct tctactgcct ggagtacttc    1200
ccctctcaga tgctgagaac gggcaacaac tttgagttca gctacagctt cgaggacgtg    1260
cctttccaca gcagctacgc acacagccag agcctggacc ggctgatgaa tcccctcatc    1320
gaccagtact tgtactacct ggccagaaca cagagtaacc caggaggcac agctggcaat    1380
cgggaactgc agttttacca gggcgggcct tcaactatgg ccgaacaagc caagaattgg    1440
ttacctggac cttgcttccg gcaacaaaga gtctccaaaa cgctggatca aacaacaac    1500 agcaactttg cttggactgg tgccaccaaa tatcacctga acggcagaaa ctcgttggtt    1560
aatcccggcg tcgccatggc aactcacaag gacgacgagg accgcttttt cccatccagc    1620
ggagtcctga ttttggaaa actggagca actaacaaaa ctacattgga aaatgtgtta    1680
atgacaaatg aagaagaaat tcgtcctact aatcctgtag ccacggaaga atacgggata    1740
gtcagcagca acttacaagc ggctaatact gcagcccaga cacaagttgt caacaaccag    1800
ggagccttac ctggcatggt ctggcagaac cgggacgtgt acctgcaggg tcccatctgg    1860
gccaagattc ctcacacgga tggcaacttt cacccgtctc ctttgatggg cggctttgga    1920
cttaaacatc cgcctcctca gatcctgatc aagaacactc ccgttcccgc taatcctccg    1980
gaggtgttta ctcctgccaa gtttgcttcg ttcatcacac agtacagcac cggacaagtc    2040
agcgtggaaa tcgagtggga gctgcagaag gaaaacagca gcgctggaa cccggagatt    2100 cagtacacct ccaactttga aaagcagact ggtgtggact ttgccgttga cagccagggt    2160
gtttactctg agcctcgccc tattggcact cgttacctca cccgtaatct g             2211
```

<210> SEQ ID NO 21
<211> LENGTH: 2214
<212> TYPE: DNA
<213> ORGANISM: Artificial Sequence
<220> FEATURE:
<223> OTHER INFORMATION: Synthetic Polynucleotide

<400> SEQUENCE: 21

```
atggctgccg atggttatct tccagattgg ctcgaggaca acctctctga gggcattcgc     60
gagtggtggg cgctgaaacc tggagccccg aagcccaaag ccaaccagca aaagcaggac    120
gacggccggg tctggtgct tcctggctac aagtacctcg acccttcaa cggactcgac    180 aaggggagc ccgtcaacgc ggcggacgca gcggccctcg agcacgacaa ggcctacgac    240
cagcagctgc aggcgggtga caatccgtac ctgcggtata ccacgccga cgccgagttt    300 caggagcgtc tgcaagaaga tacgtctttt gggggcaacc tcgggcgagc agtcttccag    360
gccaagaagc gggttctcga acctctcggt ctggttgagg aaggcgctaa gacggctcct    420
ggaaagaaga gaccggtaga gccatcaccc cagcgttctc cagactcctc tacgggcatc    480
ggcaagaaag ccaacagcc cgccagaaaa gactcaatt ttggtcagac tggcgactca    540
gagtcagttc cagaccctca acctctcgga gaacctccag cagcgccctc tggtgtggga    600
cctaatacaa tggctgcagg cggtggcgca ccaatggcag acaataacga aggcgccgac    660
ggagtgggta gttcctcggg aaattggcat tgcgattcca catggctggg cgacagagtc    720
atcaccacca gcacccgaac ctgggccctg cccacctaca acaaccacct ctacaagcaa    780
atctccaacg gacatcggg aggagccacc aacgacaaca cctacttcgg ctacagcacc    840
ccctgggggt attttgactt taacagattc cactgccact ttcaccacg tgactggcag    900
```

```
cgactcatca acaacaactg gggattccgg cccaagagac tcagcttcaa gctcttcaac    960
atccaggtca aggaggtcac gcagaatgaa ggcaccaaga ccatcgccaa taacctcacc   1020
agcaccatcc aggtgtttac ggactcggag taccagctgc cgtacgttct cggctctgcc   1080
caccagggct gcctgcctcc gttcccggcg gacgtgttca tgattcccca gtacggctac   1140
ctaacactca acaacggtag tcaggccgtg gacgctcct ccttctactg cctggaatac     1200
tttccttcgc agatgctgag aaccggcaac aacttccagt ttacttacac cttcgaggac   1260
gtgcctttcc acagcagcta cgcccacagc cagagcttgg accggctgat gaatcctctg   1320
attgaccagt acctgtacta cttgtctcgg actcaaacaa caggaggcac ggcaaatacg   1380
cagactctgg gcttcagcca aggtgggcct aatacaatgg ccaatcaggc aaagaactgg   1440
ctgccaggac cctgttaccg ccaacaacgc gtctcaacga caaccgggca aaacaacaat   1500
agcaactttg cctggactgc tgggaccaaa taccatctga atggaagaaa ttcattggct   1560
aatcctggca tcgctatggc aacacacaaa gacgacgagg agcgtttttt tcccagtaac   1620
gggatcctga ttttggcaa acaaaatgct gccagagaca atgcggatta cagcgatgtc      1680
atgctcacca gcgaggaaga aatcaaaacc actaaccctg tggctacaga ggaatacggt   1740
atcgtggcag ataacttgca gcagcaaaac acggctcctc aaattggaac tgtcaacagc   1800
cagggggcct acccggtat ggtctggcag aaccgggacg tgtacctgca gggtcccatc     1860
tgggccaaga ttcctcacac ggacggcaac ttccacccgt ctccgctgat gggcggcttt   1920
ggcctgaaac atcctccgcc tcagatcctg atcaagaaca cgcctgtacc tgcggatcct   1980
ccgaccacct tcaaccagtc aaagctgaac tctttcatca cgcaatacag caccggacag   2040
gtcagcgtgg aaattgaatg ggagctgcag aaggaaaaca gcaagcgctg gaaccccgag   2100
atccagtaca cctccaacta ctacaaatct acaagtgtgg actttgctgt taatacagaa   2160
ggcgtgtact ctgaaccccg ccccattggc accgttacc tcacccgtaa tctg          2214
```

<210> SEQ ID NO 22
<211> LENGTH: 2208
<212> TYPE: DNA
<213> ORGANISM: Artificial Sequence
<220> FEATURE:
<223> OTHER INFORMATION: Synthetic Polynucleotide

<400> SEQUENCE: 22

```
atggctgccg atggttatct tccagattgg ctcgaggaca accttagtga aggaattcgc     60
gagtggtggg cttttgaaacc tggagcccct caacccaagg caaatcaaca acatcaagac   120
aacgctcgag gtcttgtgct tccgggttac aaataccttg acccggcaa cggactcgac      180 aagggggagc cggtcaacgc agcagacgcg gcggccctcg agcacgacaa ggcctacgac    240
cagcagctca aggccggaga caacccgtac ctcaagtaca ccacgccga cgccgagttc     300 caggagcggc tcaaagaaga tacgtctttt ggggcaacc tcgggcgagc agtcttccag     360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag   540
tcagtcccag accctcaacc aatcggagaa cctcccgcag ccccctcagg tgtgggatct   600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggcccctgcc acctacaaca atcacctcta caagcaaatc   780
```

```
tccaacagca catctggagg atcttcaaat gacaacgcct acttcggcta cagcacccccc   840 tgggggtatt ttgacttcaa cagattccac tgccacttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caagaaggaa gaggaccgtt tctttccttt gtctggatct  1620 ttaattttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgcagaccg gctgggttca aaaccaagga  1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa acagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctg              2208
```

<210> SEQ ID NO 23
<211> LENGTH: 2211
<212> TYPE: DNA
<213> ORGANISM: Artificial Sequence
<220> FEATURE:
<223> OTHER INFORMATION: Synthetic Polynucleotide

<400> SEQUENCE: 23

```
atggctgccg atggttatct tccagattgg ctcgaggaca acctctctga gggcattcgc    60
gagtggtggg acttgaaacc tggagccccg aaacccaaag ccaaccagca aaagcaggac   120
gacggccggg gtctggtgct tcctggctac aagtacctcg gacccttcaa cggactcgac   180
aagggggagc ccgtcaacgc ggcggacgca gcggcccctcg agcacgacaa agcctacgac   240
cagcagctca agcgggtga caatccgtac ctgcggtata atcacgccga cgccgagttt   300
caggagcgtc tgcaagaaga tacgtctttt gggggcaacc tcgggcgagc agtcttccag   360
gccaagaagc gggttctcga acctctcggt ctggttgagg aaggcgctaa gacggctcct   420
ggaaagaaga gaccggtaga gcagtcgcca caagagccag actcctcctc gggcatcggc   480
aagacaggcc agcagcccgc taaaagaga ctcaattttg gtcagactgg cgactcagag   540
tcagtccccg acccacaacc tctcggagaa cctccagcag ccccctcagg tctgggacct   600
```

| aatacaatgg cttcaggcgg tgcgctcca atggcagaca ataacgaagg cgccgacgga | 660 |
| gtgggtaatt cctcgggaaa ttggcattgc gattccacat ggctgggggga cagagtcatc | 720 |
| accaccagca cccgaacctg ggccctgccc acctacaaca accacctcta caagcaaatc | 780 |
| tccaacggca cctcgggagg aagcaccaac gacaacacct attttggcta cagcaccccc | 840 |
| tgggggtatt ttgacttcaa cagattccac tgtcactttt caccacgtga ctggcaacga | 900 |
| ctcatcaaca acaattgggg attccggccc aaaagactca acttcaagct gttcaacatc | 960 |
| caggtcaagg aagtcacgac gaacgaaggc accaagacca tcgccaataa tctcaccagc | 1020 |
| accgtgcagg tctttacgga ctcggagtac cagttaccgt acgtgctagg atccgctcac | 1080 |
| cagggatgtc tgcctccgtt cccggcggac gtcttcatgg ttcctcagta cggctattta | 1140 |
| actttaaaca atggaagcca agccctggga cgttcctcct tctactgtct ggagtatttc | 1200 |
| ccatcgcaga tgctgagaac cggcaacaac tttcagttca gctacacctt cgaggacgtg | 1260 |
| cctttccaca gcagctacgc gcacagccag agcctggaca ggctgatgaa tccccctcatc | 1320 |
| gaccagtacc tgtactacct ggtcagaacg caaacgactg gaactggagg gacgcagact | 1380 |
| ctggcattca gccaagcggg tcctagctca atggccaacc aggctagaaa ttgggtgccc | 1440 |
| ggaccttgct accggcagca gcgcgtctcc acgacaacca accagaacaa caacagcaac | 1500 |
| tttgcctgga cgggagctgc caagtttaag ctgaacggcc gagactctct aatgaatccg | 1560 |
| ggcgtggcaa tggcttccca caaggatgac gacgaccgct tcttcccttc gagcggggtc | 1620 |
| ctgattttg gcaagcaagg agccgggaac gatggagtgg attacagcca agtgctgatt | 1680 |
| acagatgagg aagaaatcaa ggctaccaac cccgtggcca cagaagaata tggagcagtg | 1740 |
| gccatcaaca accaggccgc caatacgcag gcgcagaccg gactcgtgca accaggggg | 1800 |
| gtgattcccg gcatggtgtg gcagaataga gacgtgtacc tgcagggtcc catctgggcc | 1860 |
| aaaattcctc acacggacgg caactttcac ccgtctcccc tgatgggcgg ctttggactg | 1920 |
| aagcacccgc ctcctcaaat tctcatcaag aacacaccgg ttccagcgga cccgccgctt | 1980 |
| accttcaacc aggccaagct gaactctttc atcacgcagt acagcaccgg acaggtcagc | 2040 |
| gtggaaatcg agtgggagct gcagaaagaa aacagcaaac gctggaatcc agagattcaa | 2100 |
| tacacttcca actactacaa atctacaaat gtggactttg ctgtcaacac ggaggggtt | 2160 |
| tatagcgagc ctcgcccccat tggcacccgt tacctcaccc gcaacctgta a | 2211 |

```
<210> SEQ ID NO 24
<211> LENGTH: 2258
<212> TYPE: DNA
<213> ORGANISM: Artificial Sequence
<220> FEATURE:
<223> OTHER INFORMATION: Synthetic Polynucleotide

<400> SEQUENCE: 24
```

| tcgaggacaa cctctctgag ggcattcgcg agtggtggga cttgaaacct ggagccccga | 60 |
| aacccaaagc caaccagcaa aagcaggacg acggccgggg tctggtgctt cctggctaca | 120 |
| agtacctcgg acccttcaac ggactcgaca aggggagcc cgtcaacgcg gcggacgcag | 180 |
| cggccctcga gcacgacaag gcctacgacc agcagctcaa agcgggtgac aatccgtacc | 240 |
| tgcggtataa ccacgccgac gccgagtttc aggagcgtct gcaagaagat acgtcttttg | 300 |
| ggggcaacct cgggcgagca gtcttccagg ccaagaagcg ggttctcgaa cctctcggtc | 360 |
| tggttgagga aggcgctaag acggctcctg gaaagaagag accggtagag ccatcacccc | 420 |
| agcgttctcc agactcctct acgggcatcg gcaagaaagg ccagcagccc gcgaaaaaga | 480 |

```
gactcaactt tgggcagact ggcgactcag agtcagtgcc cgaccctcaa ccaatcggag    540
aaccccccgc aggcccctct ggtctgggat ctggtacaat ggctgcaggc ggtggcgctc    600
caatggcaga caataacgaa ggcgccgacg gagtgggtag ttcctcagga aattggcatt    660
gcgattccac atggctgggc gacagagtca tcaccaccag cacccgaacc tgggccctcc    720
ccacctacaa caaccacctc tacaagcaaa tctccaacgg gacttcggga ggaagcacca    780 acgacaaac ctacttcggc tacagcaccc cctgggggta ttttgactt aacagattcc     840 actgccactt ctcaccacgt gactggcagc gactcatcaa caacaactgg ggattccggc    900
ccaagagact caacttcaag ctcttcaaca tccaggtcaa ggaggtcacg cagaatgaag    960
gcaccaagac catcgccaat aaccttacca gcacgattca ggtctttacg gactcggaat   1020
accagctccc gtacgtcctc ggctctgcgc accaggctg cctgcctccg ttcccggcgg    1080
acgtcttcat gattcctcag tacgggtacc tgactctgaa caatggcagt caggccgtgg   1140
gccgttcctc cttctactgc ctggagtact ttccttctca aatgctgaga cgggcaaca    1200 actttgagtt cagctaccag tttgaggacg tgccttttca cagcagctac gcgcacagcc   1260
aaagcctgga ccggctgatg aacccctca tcgaccagta cctgtactac ctgtctcgga    1320
ctcagtccac gggaggtacc gcaggaactc agcagttgct attttctcag gccgggccta   1380
ataacatgtc ggctcaggcc aaaaactggc tacccgggcc ctgctaccgg cagcaacgcg   1440
tctccacgac actgtcgcaa aataacaaca gcaactttgc ctggaccggt gccaccaagt   1500
atcatctgaa tggcagagac tctctggtaa atcccggtgt cgctatggca acccacaagg   1560
acgacgaaga gcgattttt ccgtccagcg gagtcttaat gtttgggaaa cagggagctg    1620
gaaaagacaa cgtggactat agcagcgtta tgctaaccag tgaggaagaa attaaaacca   1680
ccaacccagt ggccacagaa cagtacggcg tggtggccga taacctgcaa cagcaaaacg   1740
ccgctcctat tgtaggggcc gtcaacagtc aaggagcctt acctggcatg gtctggcaga   1800
accgggacgt gtacctgcag ggtcctatct gggccaagat tcctcacacg gacggaaact   1860
ttcatccctc gccgctgatg ggaggctttg gactgaaaca cccgcctcct cagatcctga   1920
ttaagaatac acctgttccc gcggatcctc caactacctt cagtcaagct aagctggcgt   1980
cgttcatcac gcagtacagc accggacagg tcagcgtgga aattgaatgg gagctgcaga   2040
aagaaaacag caaacgctgg aacccagaga ttcaatacac ttccaactac tacaaatcta   2100
caaatgtgga ctttgctgtt aacacagatg gcacttattc tgagcctcgc cccatcggca   2160
cccgttacct cacccgtaat ctgtaattgc ttgttaatca ataaaccggt tgattcgttt   2220
cagttgaact ttggtctctg cgaagggcga attcgttt                           2258
```

<210> SEQ ID NO 25
<211> LENGTH: 2214
<212> TYPE: DNA
<213> ORGANISM: Artificial Sequence
<220> FEATURE:
<223> OTHER INFORMATION: Synthetic Polynucleotide

<400> SEQUENCE: 25

```
atggctgccg atggttatct tccagattgg ctcgaggaca acctctctga gggcattcgc     60
gagtggtggg cgctgaaacc tggagccccg aagcccaaag ccaaccagca aaagcaggac    120 gacgccggg gtctggtgct tcctggctac aagtacctcg acccttcaa cggactcgac      180 aaggggagc ccgtcaacgc ggcggacgca gcggcccctcg agcacgacaa ggcctacgac    240
```

```
cagcagctca aagcgggtga caatccgtac ctgcggtata accacgccga cgccgagttt    300
caggagcgtc tgcaagaaga tacgtctttt gggggcaacc tcgggcgagc agtcttccag    360
gccaagaagc gggttctcga acctctcggt ctggttgagg aagctgctaa gacggctcct    420
ggaaagaaga gaccggtaga accgtcacct cagcgttccc ccgactcctc cacgggcatc    480
ggcaagaaag gccagcagcc cgctaaaaag agactgaact ttggtcagac tggcgactca    540
gagtcagtcc ccgaccctca accaatcgga gaaccaccag caggcccctc tggtctggga    600
tctggtacaa tggctgcagg cggtggcgct ccaatggcag acaataacga aggcgccgac    660
ggagtgggta gttcctcagg aaattggcat tgcgattcca catggctggg cgacagagtc    720
atcaccacca gcacccgaac ctgggccctg cccacctaca caaccacct ctacaagcaa    780 atatccaatg ggacatcggg aggaagcacc aacgacaaca cctacttcgg ctacagcacc    840
ccctgggggt attttgactt caacagattc cactgccact tctcaccacg tgactggcag    900
cgactcatca caacaactg gggattccgg ccaaaaagac tcagcttcaa gctcttcaac    960
atccaggtca aggaggtcac gcagaatgaa ggcaccaaga ccatcgccaa taaccttacc   1020
agcacgattc aggtatttac ggactcggaa taccagctgc cgtacgtcct cggctccgcg   1080
caccagggct gcctgcctcc gttcccggcg gacgtcttca tgattcccca gtacggctac   1140
cttacactga caatggaagt caagccgta ggccgttcct ccttctactg cctggaatat   1200
tttccatctc aaatgctgcg aactggaaac aatttttgaat tcagctacac cttcgaggac   1260 gtgccttttcc acagcagcta cgcacacagc cagagcttgg accgactgat gaatcctctc   1320
atcgaccagt acctgtacta cttatccaga actcagtcca caggaggaac tcaaggtacc   1380
cagcaattgt tattttctca agctgggcct gcaaacatgt cggctcaggc taagaactgg   1440
ctacctggac cttgctaccg gcagcagcga gtctctacga cactgtcgca aaacaacaac   1500
agcaactttg cttggactgg tgccaccaaa tatcacctga cggaagaga ctctttggta    1560 aatcccggtg tcgccatggc aacccacaag gacgacgagg aacgcttctt cccgtcgagt   1620
ggagtcctga tgtttggaaa acagggtgct ggaagagaca atgtggacta cagcagcgtt   1680
atgctaacca gcgaagaaga aattaaaacc actaaccctg tagccacaga acaatacggt   1740
gtggtggctg ataacttgca gcaaaccaat acggggccta ttgtgggaaa tgtcaacagc   1800
caaggagcct tacctggcat ggtctggcag aaccgagacg tgtacctgca gggtcccatc   1860
tgggccaaga ttcctcacac ggacggcaac ttccacccct taccgctaat gggaggattt   1920
ggactgaagc acccacctcc tcagatcctg atcaagaaca cgccggtacc tgcggatcct   1980
ccaacaacgt tcagccaggc gaaattggct tccttcatta cgcagtacag caccggacag   2040
gtcagcgtgg aaatcgagtg ggagctgcag aaggagaaca gcaaacgctg gaacccagag   2100
attcagtaca cttcaaacta ctacaaatct acaaatgtgg actttgctgt caatacagag   2160
ggaacttatt ctgagcctcg ccccattggt actcgttacc tcacccgtaa tctg          2214
```

<210> SEQ ID NO 26
<211> LENGTH: 2211
<212> TYPE: DNA
<213> ORGANISM: Artificial Sequence
<220> FEATURE:
<223> OTHER INFORMATION: Synthetic Polynucleotide

<400> SEQUENCE: 26

```
atggctgccg atggttatct tccagattgg ctcgaggaca acctctctga gggcattcgc     60
gagtggtggg acttgaaacc tggagccccg aaacccaaag ccaaccagca aaagcaggac    120
```

```
gacggccggg gcctggtgct tcctggctac aagtacctcg gacccttcaa cggactcgac      180 aaggggggagc ccgtcaacgc ggcggacgca gcggccctcg agcacgacaa ggcctacgac      240
cagcagctcg aagcgggtga caatccgtac ctgcggtata accacgccga cgccgagttt      300
caggagcgtc tgcaagaaga tacgtctttt gggggcaacc tcgggcgagc agtcttccag      360
gccaagaagc gggttctcga acctctcggt ctggttgagg aaggcgctaa gacggctcct      420
ggaaagaaga gaccagtaga gcagtcaccc caagaaccag actcctcctc gggcatcggc      480
aagaaaggcc aacagcccgc cagaaaaaga ctcaattttg gccagactgg cgactcagag      540
tcagttccag accctcaacc tctcggagaa cctccagcag cgccctctgg tgtgggacct      600
aatacaatgg ctgcaggcgg tggcgcacca atggcagaca ataacgaagg cgccgacgga      660
gtgggtagtt cctcgggaaa ttggcattgc gattccacat ggctgggcga cagagtcatc      720
accaccagca cccgaacctg ggccctgccc acctacaaca accacctcta caagcaaatc      780
tccaacggga catcgggagg agccaccaac gacaacacct acttcggcta cagcaccccc      840
tgggggtatt ttgactttaa cagattccac tgccactttt caccacgtga ctggcagcga      900
ctcatcaaca caactgggg attccggccc aagagactca gcttcaagct cttcaacatc      960
caggtcaagg aggtcacgca gaatgaaggc accaagacca tcgccaataa cctcaccagc     1020
accatccagg tgtttacgga ctcggagtac cagctgccgt acgttctcgg ctctgcccac     1080
cagggctgcc tgcctccgtt cccggcggac gtgttcatga ttccccagta cggctaccta     1140
acactcaaca acgtagtcca ggccgtggga cgctcctcct tctactgcct ggaatacttt     1200
ccttcgcaga tgctgagaac cggcaacaac ttccagttta cttacacctt cgaggacgtg     1260
cctttccaca gcagctacgc ccacagccag agcttggacc ggctgatgaa tcctctgatt     1320
gaccagtacc tgtactactt gtctcggact caaacaacag gaggcacggc aaatacgcag     1380
actctgggct tcagccaagg tgggcctaat acaatggcca atcaggcaaa gaactggctg     1440
ccaggaccct gttaccgcca acaacgcgtc tcaacgacaa ccgggcaaaa caacaatagc     1500
aactttgcct ggactgctgg gaccaaatac catctgaatg gaagaaattc attggctaat     1560
cctggcatcg ctatggcaac acacaaagac gacgaggagc gttttttccc agtaacggga     1620
tcctgttttt ggcaacaaaa tgctgccaga gacaatgcgg attacagcga tgtcatgctc     1680
accagcgagg aagaaatcaa aaccactaac cctgtggcta cagaggaata cggtatcgtg     1740
gcagataact tgcagcagca aaacacggct cctcaaattg gaactgtcaa cagccagggg     1800
gccttacccg gtatggtctg gcagaaccgg gacgtgtacc tgcagggtcc catctgggcc     1860
aagattcctc acacggacgg caacttccac ccgtctccgc tgatgggcgg ctttggcctg     1920
aaacatcctc cgcctcagat cctgatcaag aacacgcctg tacctgcgga tcctccgacc     1980
accttcaacc agtcaaagct gaactctttc atcacgcaat acagcaccgg acaggtcagc     2040
gtggaaattg aatgggagct acagaaggaa aacagcaagc gctggaaccc cgagatccag     2100
tacacctcca actactacaa atctacaagt gtggactttg ctgttaatac agaaggcgtg     2160
tactctgaac ccgcccccat ggcacccgt tacctcaccc gtaatctgta a              2211
```

<210> SEQ ID NO 27  
<211> LENGTH: 3685  
<212> TYPE: DNA  
<213> ORGANISM: Artificial Sequence  
<220> FEATURE:  
<223> OTHER INFORMATION: Synthetic Polynucleotide

```
<400> SEQUENCE: 27
agcgctgggg cggtgagaac agcgcggcgt agagtgcagg cgggcttcgc cgaaaagccg      60
gactcggccg gcgccgagtt ctgggatcgc cgcctgcagc catgacccta gcagtccatc     120
cctcggcccg ggctccggac gtctgatatc ccgcacattc tcgtacaact gctggagagg     180
cgactgctgc ccccttgtcg cccttggcgc cttaccgcat tccctatccg gagttgggag     240
cagcgcggcc accggcgccc ctgtgcaaac tgggggtgtc tgctagatca gcctctgccg     300
ctgctgcccg cagctctggc catggcctgg ccgggcacag ggccgagcag ccgggggggcg     360
cctggaggcg tcgggctcag gctgggctg ctgctgcagt tcctcctgct cctgcggccg       420
acactggggt tcggggacga ggaggagcgg cgctgcgacc ccatccgcat cgccatgtgc     480
cagaacctcg gctacaacgt gaccaagatg cccaacttag tgggacacga gctgcagaca     540
gacgccgagc tgcagctgac aactttcacg ccgctcatcc agtacggctg ctccagccag     600
ctgcagttct cctttgttc ggtttatgtg ccaatgtgca cagagaagat caacatcccc      660
atcggcccgt gcggtggcat gtgcctttca gtcaagagac gctgtgaacc agtcctgaga     720
gaatttgggt ttgcctggcc cgacaccctg aactgcagca gttcccgcc ccagaacgac      780
cacaaccaca tgtgcatgga aggaccaggt gatgaagagg ttcccttgcc ccacaagact     840
cccatccagc ccggggaaga gtgccactcc gtgggaagca attctgatca gtacatctgg     900
gtgaagagga gcctgaactg tgttctcaag tgtggctacg atgctggctt gtacagccgc     960
tcagctaagg agttcacgga tatttggatg gctgtgtggg ccagcctctg cttcatctcc    1020
accaccttca ccgtgctgac cttcctgatt gattcatcca ggttttctta ccctgagcgc    1080
cccatcatat ttctcagtat gtgctataat atttatagca ttgcttatat tgttcggctg    1140
actgtaggcc gggaaaggat atcctgtgat tttgaagagg cggcagagcc cgttctcatc    1200
caagaaggac ttaagaacac aggatgtgca ataatttttct tgctgatgta ctttttttgga   1260
atggccagct ccatttggtg ggttattctg acactcactt ggtttttggc agccggactc    1320
aagtgggtc atgaagccat tgaaatgcac agttcttatt ccacatcgc agcctgggct       1380
attcccgcag tgaaaaccat tgtcatcttg attatgagac tagtggatgc cgatgaactg    1440
actggcttgt gctatgttgg gaaccaaaat ctagatgccc tcactggctt tgtggtggct    1500
cctctcttta cgtatttggt gattggaacg ctgttcattg cggcgggttt ggtggcctta    1560
ttcaaaatcc ggtccaatct tcaaaaagac gggacaaaga cagacaagtt ggaaaggcta    1620
atggtcaaga tcggggtctt ctcagtactg tacacggttc ctgcaacctg tgtgattgcc    1680
tgttattct atgaaatctc aaactgggca ctctttcgat attctgcaga tgactcaaac    1740
atggcagttg aaatgttgaa aatttttatg tctttgctcg tgggcatcac ttcaggcatg    1800
tggatttggt ctgccaaaac tcttcacacg tggcaaaagt gttctaaccg attggtgaat    1860
tctgggaagg taaagagaga gaagaggggg aatggttggg tgaagccagg aaaaggcaac    1920
gagactgtgg tataagacta gccggcttcc tcgttcctca ttgtgaagga agtgatgcag    1980
ggaatctcag tttgaacaaa cttagaaaca cttcagccca cacacaccca cgtcagccca    2040
ccaccactca cccaactcag catcagaaga ccaatggctt cactgcagac tttggaatgg    2100
tccaaaatgg aaaagccagt tagaggtttt caaagctgtg aaaaatcaaa atgttgatca    2160
ctttagcagg tcacagcttg gagtccgtgg aggtcccgcc tagattcctg aagcccaggg    2220
tgatagtgtt tgctccctact gggtgggatt tcaactgtga gttgataaca tgcaggagaa    2280
aagattaatt tttaaaaccc ttttaaattt taaatagtaa ctaggtcttg cagatagcaa    2340
```

```
agtgatctat aaacactgga aatgctgggt tgggagacgt gttgcagagt tttatagttt    2400
ggctggtcta acataaacat cttctggcct acactgtctg ctgtttagaa ctctgtagcg    2460
cactcccaag aggtggtgtc aaaatccttc agtgcctttg tcgtaaaaca gaattgtttg    2520
agcaaacaaa agtactgtac taacacacgt aaggtatcca gtggatttct ctctcctgaa    2580
atttcaacat ccctaattct aggcagcccc tgttttcttc actttaaact aatgactcaa    2640
aaaaaaaaaa ggttattttt ataggatttt ttttttttgc actgcagcat gcctaatgag    2700
aggaaaaggg aaggtgattc actttctgac aatcacttaa ttcagagaaa aatgagattt    2760
gctaagttga cttaccttac cgaccctaga gacctattgc attaagcaat gttaagcaat    2820
tgggacttaa aatattttag tttgtgtgat tgcatctagg cagacgccag tctggaagaa    2880
ctgaaatgtt aaatttcttg gcaactttgc attcacacag attaactgtg taatttgtgt    2940
gtgtcaatta caattaaaag cacattcttg gaccatgaca tagtatactc aattgacttt    3000
aaaactgtgg tcaacttgca ttcttagtgt gatagtgcct ttcccccctg tagcataaga    3060
atgttatcgg agtttggtct acttgccaca atggagactt attcagcttt gcaaaggcaa    3120
ctaaggacag cagatccaaa tacgtggtgc ataattgttc cttagtaatg gacaaaggtt    3180
cttataagat ttcactggag gcagtgtggc ctggagtatt tatatgatgc ctaatgaacc    3240
tccagaatgc tggccagagg ctggattggt tagcagggga tatggtgtag acggagtgaa    3300
atgagctgca aagtctaaca gcacgagtct taattgcctt tgctggggta tccaaagcct    3360
ttaaaattta tgctttaagt ccctcacaag gggggtaccc gctagcaacc tatcaaaagt    3420
tgaagttctt ttaaaattgt gactggcctt tttcttaacc tgccttaggc cttttaatca    3480
ccagatctct gggacaaaac attgtacatg tcacaggttg ctctccttgt atttcatgcc    3540
tgtctgcttc agcaacttca gttatttatt gattcatgct tttagtaaga gagcccttaa    3600
tgttttgtcc aatcctactt tgtggagaaa catttcatgg attccaaatc ccaaataggc    3660
aaataggtgt tcaaattctg gaaat                                         3685
```

<210> SEQ ID NO 28
<211> LENGTH: 4316
<212> TYPE: DNA
<213> ORGANISM: Artificial Sequence
<220> FEATURE:
<223> OTHER INFORMATION: Synthetic Polynucleotide

<400> SEQUENCE: 28

```
aatttgtaag ccgatccgcc gcccaaagcc atcagcaatc cttagcatag gggcacactc      60
atgcattcct gtcaagtcat cttgtgaagg ctgcctgctt ccagcttggc ttggatgtgc     120
aaccttaata aaactcactg aggtctggga gaaaatagca gatctgctgc agataggta     180 gaggaaaggg gctagaatat gtactcgcag ctgacgcggg caggctccac gctgaacggt     240
tacacagaga ggaaacaata aatctaagct actattgcaa taaatatctc aagttttaac     300
gaaggaaact atcattacag ttaaaatttt ttaaagtaac gcttttttag aacaaagcta     360
acaaatggct agttttctgt ggatcttctt caaacgcttt cttttaacggg gaaagagtca     420 aacaagcagt tttacctgaa ataaagaact agtttaaagg tcagaagaga agagcaagct     480
ttgcaggagg cacggaaggc aagcgctggc agtacaatga cagttttcct ttcctttgca     540
ttcttcgctg ccattctgac tcacataggg tgcagcaacc agcgccgaaa tccagaaaac     600
ggagggagaa gatataaccg gattcaacat gggcaatgtg cctacacttt cattcttcca     660
```

```
gaacacgacg ggaactgccg tgagagtgcg acagagcagt acaacaccaa cgctctgcaa      720
agggatgctc cacacgtgga gccggatttc tcttcccaga aacttcagca tctggagcat      780
gtgatggaaa attatactca gtggctgcaa aaacttgaga attacattgt ggaaaatatg      840
aagtcggaga tggcccagat acaacagaat gctgttcaaa accacacggc caccatgctt      900
gagataggaa ccagtctctt atctcagact gcagagcaga cccgaaagct gacagatgtt      960
gagacccagg tactaaatca acatcccga cttgaaatac aactgctaga gaattcatta      1020
tcaacataca agctagagaa gcaacttctc caacagacaa atgaaattct gaagattcac      1080
gaaaaaaaca gtttactaga gcacaaaatc ttagaaatgg agggaaaaca caaagaagaa      1140
ttggacacct tgaaggagga gaaagaaaac cttcaaggct tggtttctcg tcagacattc      1200
atcatccagg agttggagaa gcaacttagt agagctacca acaacaacag catcctgcag      1260
aagcaacaac tggagctcat ggacacagtt cataaccttta tcagcctttg cactaaagaa      1320
ggtgttttgc taaagggagg aaaaagagaa gaagagaaac catttcgaga ctgtgcagat      1380
gtatatcaag ctggttttaa taaaagtgga atctacacta tttatttaa taatatgcca      1440 gaacccaaaa aggtattttg caatatggat gtgaatgggg gaggttggac agtaatacaa      1500
caccgggaag atgaagcct ggattccag aggggctgga aggagtataa aatgggtttt      1560
gggaatccct ctggtgaata ttggcttggg aacgagttca tttttgcaat aaccagtcag      1620
aggcagtaca tgctgaggat tgagctgatg gactgggaag ggaaccgagc ctactcacag      1680
tacgacagat tccacatagg aaatgaaaag cagaactata ggttatattt aaaaggtcac      1740
acagggacag caggcaaaca gagcagcttg atcttacacg gtgccgattt cagcacgaag      1800
gatgctgata acgacaactg tatgtgcaaa tgcgctctca tgctaacagg aggttggtgg      1860
ttcgatgcct gtggccctc caatctaaat ggaatgttct acactgcggg acaaaatcat      1920
ggaaaactga atgggataaa gtggcactac ttcaaagggc ccagttactc cttacgttcc      1980
accaccatga tgatccggcc cttggacttt tgaaggtgct ctgccagtat tagaaagctg      2040
caaagaaagc tgggcatgtt cccagatgag aagctagtca gaggcttcag aaacaaccaa      2100
cattgtctcc attccagcag caagtggtta tgtcatgtca cctgggtttg gagccttctg      2160
aggtcaacag aatcgccact tgggtccaga gaatgccact cacaatcatg tttaaaaggg      2220
aagaaacttc tcagcttgct gcacttcaaa gtgctactgg atcacattct gaacttataa      2280
catcctgatg ctgaatgcaa cttgtttcat gtaaaagcaa aagaagaaga aacagcaaat      2340
gggaacaggc tttccagaat ctgttgaaga tggattgtgg aggtgacctg gtatcactgt      2400
aggaaatcct gctaacaata catcactgcc caaaagagac ataagaaaaa gttttgtcta      2460
ctgagttggc taaagttag tggagttcac ctgcccattt ccagtatcat atttactagc      2520
tgatttcagg tttcctgtgt tcaaatgtaa actctgttct tgtaagccat gatacaatat      2580
agtacatgga ggataagagt tgggggtaga aggtgcctaa agactcttga gtttctgggg      2640 attcagttttt caaagatat aaaatataat caagaatgga taaaacaggt gaaaatcaca      2700
ctcatgctac agtgttcctt tacatgaaat ttgattaact gatccacaag aatgtttaga      2760
gcctgagtat atataaagac tggaagtgtt atcacccagt tctcaaaaca ataagcaggc      2820
agttaacatt ctcattgaca gtatgtagga gagcaatatg tggagtactt gagttggaac      2880
agcccattgt acagatcttg catgtatttg catatgtatg gcattattat ttttaaagtg      2940
ttcgtaggcc ttcaattctt catacagatt tttcatgcta atttaattttt tgttaattaa      3000 ctgcaatgta cttactaaat atatcctact ccagtttttt atgagttata ctttaaagtc      3060
```

| | |
|---|---|
| tacaaataat agaagaattt taaatatcat tgtacataat atcttatacc tgtccatgct | 3120 |
| aaactcaata attgtttagt ctggaatata tgatgctgtc cacaactgat gactataaat | 3180 |
| atgattgttt aaagacagtt accatactat tgattaaata tattactctg catagttttt | 3240 |
| ctcctccagg atctgtttct tcaagcaatt tctaccttgt aaaataatgg tagtagagaa | 3300 |
| aattgacata actccttgta caaaagaatt atagaaaaaa ttacagtcat ttgactagga | 3360 |
| agtttctgat tgttagctgc tataagtgcc ttagttaaga tgcccctgtg ttataatatg | 3420 |
| tagtaaatga agttttggac acaggattct gtgataacct gatgtgactg cagtattcta | 3480 |
| tcaagttctc tttgttgtta aatgttcaag gttatagtag aaaaaaaaca ttcaatcaaa | 3540 |
| cacaatttgc catgaaagga gagaactaaa tgtaggcacc agttctgttt tctcagagaa | 3600 |
| ggagaagact ttctgggacg tacatgtacc aaaatataaa tcttgataac cgcagccaca | 3660 |
| aagccttagt gacttttcctc tacctggtaa gacagagctc ttcatgcttt taagaaaaga | 3720 |
| ttctgaatgc ttcccaccac atctttctta tatttatatg tgttcataaa gtactatttt | 3780 |
| gccttacaag aggtatgtgc cgacattaca ggattttttct actatagtga ctccttcaca | 3840 |
| gctttcttaa gcctagccct ctaaaagctt ccttctcatt tagatgaaag aaaatgagta | 3900 |
| tttttgtgat tctggtgatt gtggtggttg ttgttgttgt tgttgttgtt cccacagatg | 3960 |
| ttcgaaaact catcttgggt aaattgtttt tcaatccaca ttacaaaaat aaagcgaaac | 4020 |
| aaggagaaaa aaaagcatgg aatttactga tttgttatgt gggtttgaaa ataagatat | 4080 |
| tgttttcagt tatttataat aaagcagtat aatgtgtaca ttgtataatg ccaacatgtg | 4140 |
| tgtagcaatt tgatacgcat agcttttttgc atttaattaa tgcagggcag aaaaattaga | 4200 |
| taactcgaac tttgtcttga agtttctatt tcaataaaag ctgtgtcatt tctatgaaaa | 4260 |
| tgtcttcata agattacatt atttcattta aataaaattg aaaataatgt gggcaa | 4316 |

<210> SEQ ID NO 29
<211> LENGTH: 4313
<212> TYPE: DNA
<213> ORGANISM: Artificial Sequence
<220> FEATURE:
<223> OTHER INFORMATION: Synthetic Polynucleotide

<400> SEQUENCE: 29

| | |
|---|---|
| aatttgtaag ccgatccgcc gcccaaagcc atcagcaatc cttagcatag ggcacactc | 60 |
| atgcattcct gtcaagtcat cttgtgaagg ctgcctgctt ccagcttggc ttggatgtgc | 120 |
| aaccttaata aaactcactg aggtctggga gaaaatagca gatctgctgc agatagggta | 180 |
| gaggaaaggg gctagaatat gtactcgcag ctgacgcggg caggctccac gctgaacggt | 240 |
| tacacagaga ggaaacaata aatctaagct actattgcaa taaatatctc aagttttaac | 300 |
| gaaggaaact atcattacag ttaaaatttt ttaaagtaac gcttttttag aacaaagcta | 360 |
| acaaatggct agttttctgt ggatcttctt caaacgcttt ctttaacggg gaagagtca | 420 |
| aacaagcagt tttacctgaa ataaagaact agtttaaagg tcagaagaga agagcaagct | 480 |
| ttgcaggagg cacggaaggc aagcgctggc agtacaatga cagttttcct ttcctttgca | 540 |
| ttcttcgctg ccattctgac tcacataggg tgcagcaacc agcgccgaaa tccagaaaac | 600 |
| ggagggagaa gatataaccg gattcaacat gggcaatgtg cctacacttt cattcttcca | 660 |
| gaacacgacg ggaactgccg tgagagtgcg acagagcagt acaacaccaa cgctctgcaa | 720 |
| agggatgctc cacacgtgga gccggatttc tcttcccaga aacttcagca tctggagcat | 780 |

```
gtgatggaaa attatactca gtggctgcaa aaacttgaga attacattgt ggaaaatatg    840
aagtcggaga tggcccagat acaacagaat gctgttcaaa accacacggc caccatgctt    900
gagataggaa ccagtctctt atctcagact gcagagcaga cccgaaagct gacagatgtt    960
gagacccagg tactaaatca acatcccga cttgaaatac aactgctaga gaattcatta    1020
tcaacataca agctagagaa gcaacttctc aacagacaa atgaaattct gaagattcac     1080
gaaaaaaaca gtttactaga gcacaaaatc ttagaaatgg agggaaaaca caaagaagaa    1140
ttggacacct tgaaggagga gaaagaaaac cttcaaggct tggtttctcg tcagacattc    1200
atcatccagg agttggagaa gcaacttagt agagctacca acaacaacag catcctgcag    1260
aagcaacaac tggagctcat ggacacagtt cataacctta tcagcctttg cactaaagaa    1320
gttttgctaa agggaggaaa aagagaagaa gagaaaccat ttcgagactg tgcagatgta    1380
tatcaagctg gttttaataa aagtggaatc tacactattt attttaataa tatgccagaa    1440
cccaaaaagg tattttgcaa tatggatgtg aatgggggag gttggacagt aatacaacac    1500
cgggaagatg gaagcctgga tttccagagg ggctggaagg agtataaaat gggttttggg    1560
aatccctctg gtgaatattg gcttgggaac gagttcattt ttgcaataac cagtcagagg    1620
cagtacatgc tgaggattga gctgatggac tgggaaggga accgagccta ctcacagtac    1680
gacagattcc acataggaaa tgaaaagcag aactataggt tatatttaaa aggtcacaca    1740
gggacagcag gcaaacagag cagcttgatc ttacacggtg ccgatttcag cacgaaggat    1800
gctgataacg acaactgtat gtgcaaatgc gctctcatgc taacaggagg ttggtggttc    1860
gatgcctgtg gcccttccaa tctaaatgga atgttctaca ctgcgggaca aaatcatgga    1920
aaactgaatg ggataaagtg gcactacttc aaagggccca gttactcctt acgttccacc    1980
accatgatga tccggccctt ggactttgta aggtgctctg ccagtattag aaagctgcaa    2040
agaaagctgg gcatgttccc agatgagaag ctagtcagag gcttcagaaa caaccaacat    2100
tgtctccatt ccagcagcaa gtggttatgt catgtcacct gggtttggag ccttctgagg    2160
tcaacagaat cgccacttgg gtccagagaa tgccactcac aatcatgttt aaaagggaag    2220
aaacttctca gcttgctgca cttcaaagtg ctactggatc acattctgaa cttataacat    2280
cctgatgctg aatgcaactt gtttcatgta aaagcaaaag aagaagaaac agcaaatggg    2340
aacaggcttt ccagaatctg ttgaagatgg attgtggagg tgacctggta tcactgtagg    2400
aaatcctgct aacaatacat cactgcccaa aagagacata aagaaaagtt ttgtctactg    2460
agttggctaa aagttagtgg agttcacctg cccatttcca gtatcatatt tactagctga    2520
tttcaggttt cctgtgttca aatgtaaact ctgttcttgt aagccatgat acaatatagt    2580
acatggagga taagagttgg gggtagaagg tgcctaaaga ctcttgagtt tctggggatt    2640
cagttttcaa aagatataaa atataatcaa gaatggataa acaggtgaa aatcacactc     2700 atgctacagt gttcctttac atgaaatttg attaactgat ccacaagaat gtttagagcc    2760
tgagtatata taaagactgg aagtgttatc acccagttct caaaacaata agcaggcagt    2820
taacattctc attgacagta tgtaggagag caatatgtgg agtacttgag ttggaacagc    2880
ccattgtaca gatcttgcat gtatttgcat atgtatggca ttattatttt taaagtgttc    2940
gtaggccttc aattcttcat acagattttt catgctaatt taattttgt taattaactg      3000 caatgtactt actaaatata tcctactcca gttttttatg agttatactt taaagtctac    3060
aaataataga agaattttaa atatcattgt acataatatc ttatacctgt ccatgctaaa    3120
ctcaataatt gtttagtctg gaatatatga tgctgtccac aactgatgac tataaatatg    3180
```

```
attgtttaaa gacagttacc atactattga ttaaatatat tactctgcat agttttctc    3240 ctccaggatc tgtttcttca agcaatttct accttgtaaa ataatggtag tagagaaaat    3300
tgacataact ccttgtacaa aagaattata gaaaaatta cagtcatttg actaggaagt     3360
ttctgattgt tagctgctat aagtgcctta gttaagatgc ccctgtgtta taatatgtag    3420
taaatgaagt tttggacaca ggattctgtg ataacctgat gtgactgcag tattctatca    3480
agttctcttt gttgttaaat gttcaaggtt atagtagaaa aaaacattc aatcaaacac     3540 aatttgccat gaaaggagag aactaaatgt aggcaccagt tctgttttct cagagaagga    3600
gaagactttc tgggacgtac atgtaccaaa atataaatct tgataaccgc agccacaaag    3660
ccttagtgac tttcctctac ctggtaagac agagctcttc atgcttttaa gaaaagattc    3720
tgaatgcttc ccaccacatc tttcttatat ttatatgtgt tcataaagta ctatttgcc    3780 ttacaagagg tatgtgccga cattacagga ttttctact atagtgactc cttcacagct     3840
ttcttaagcc tagccctcta aaagcttcct tctcatttag atgaaagaaa atgagtattt    3900
ttgtgattct ggtgattgtg gtggttgttg ttgttgttgt tgttgttccc acagatgttc    3960
gaaaactcat cttgggtaaa ttgttttca atccacatta caaaaataaa gcgaaacaag    4020 gagaaaaaa agcatggaat ttactgattt gttatgtggg tttgaaaaat aagatattgt     4080
tttcagttat ttataataaa gcagtataat gtgtacattg taataagcca acatgtgtgt    4140
agcaatttga tacgcatagc ttttgcatt taattaatgc agggcagaaa aattagataa     4200 ctcgaactt gtcttgaagt ttctatttca ataaaagctg tgtcatttct atgaaaatgt    4260
cttcataaga ttacattatt tcatttaaat aaaattgaaa ataatgtggg caa           4313
```

<210> SEQ ID NO 30
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 30
ccggaattct gtgcagaaac ataagtgact ctccaggtg                          39

<210> SEQ ID NO 31
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 31
atcggcggcc gcgcagagag cacattttga ataagcaaag tg                      42

<210> SEQ ID NO 32
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 32
ccggaattct ttacccacag gacagggtga tggagagga                          39

<210> SEQ ID NO 33
<211> LENGTH: 42
<212> TYPE: DNA

<213> ORGANISM: Artificial Sequence
<220> FEATURE:
<223> OTHER INFORMATION: Synthetic Polynucleotide

<400> SEQUENCE: 33
atcggcggcc gcgtcacatg gtttggaccc agaactatta gt                42

<210> SEQ ID NO 34
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 34
tgccagaacc tcggctaca                                           19

<210> SEQ ID NO 35
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 35
atgagcggcg tgaaagttgt                                          20

<210> SEQ ID NO 36
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 36
gccagcacat agagagaatg agc                                      23

<210> SEQ ID NO 37
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 37
caaggctcac agtgattttc tgg                                      23

<210> SEQ ID NO 38
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 38
cacatagggt gcagcaacca                                          20

<210> SEQ ID NO 39
<211> LENGTH: 21
<212> TYPE: DNA
<213> ORGANISM: Artificial Sequence
<220> FEATURE:
<223> OTHER INFORMATION: Synthetic Polynucleotide

```
<400> SEQUENCE: 39
cgtcgtgttc tggaagaatg a                                          21
```